US012742175B2

(12) United States Patent
Navarro et al.

(10) Patent No.: US 12,742,175 B2
(45) Date of Patent: Sep. 22, 2026

(54) CHLORELLA-BASED PRODUCTION OF EXTRACELLULAR VESICLE-EMBEDDED SMALL RNAS FOR PROPHYLACTIC OR THERAPEUTIC APPLICATIONS

(71) Applicants: IMMUNRISE, Paris (FR); CENTRE NATIONAL DE LA RECHERCHE SCIENTIFIQUE (CNRS), Paris (FR)

(72) Inventors: Lionel Navarro, Antony (FR); Khadeeja Adam Sy, Bobigny (FR); Magali Charvin, Paris (FR); Antonio Emidio Fortunato, Bagnolet (FR)

(73) Assignees: ENGREEN, Bordeaux (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 629 days.

(21) Appl. No.: 18/044,868

(22) PCT Filed: Sep. 13, 2021

(86) PCT No.: PCT/EP2021/075119

§ 371 (c)(1),
(2) Date: Mar. 10, 2023

(87) PCT Pub. No.: WO2022/053687

PCT Pub. Date: Mar. 17, 2022

(65) Prior Publication Data

US 2024/0218387 A1 Jul. 4, 2024

(30) Foreign Application Priority Data

Sep. 11, 2020 (EP) .................................... 20306018

(51) Int. Cl.

| | |
|---|---|
| ***C12N 15/82*** | (2006.01) |
| ***A61K 36/05*** | (2006.01) |
| ***C12N 1/125*** | (2026.01) |
| ***C12N 15/113*** | (2010.01) |
| ***C12R 1/89*** | (2006.01) |

(52) U.S. Cl.
CPC .......... *C12N 15/8257* (2013.01); *A61K 36/05* (2013.01); *C12N 1/125* (2021.05); *C12N 15/113* (2013.01); *C12N 2310/141* (2013.01); *C12R 2001/89* (2021.05)

(58) Field of Classification Search
CPC .. C12N 15/8257; C12N 1/125; C12N 15/113; C12N 2310/141; A61K 36/05; C12R 1/89
See application file for complete search history.

(56) References Cited

FOREIGN PATENT DOCUMENTS

WO 2020/035620 A1 2/2020

OTHER PUBLICATIONS

Yang et al. (Biotechnology Journal, vol. 10 No. 10, pp. 1244-1261).*
Navarro et al. The transcriptional innate immune response to flg22. Interplay and overlap with Avr gene-dependent defense responses and bacterial pathogenesis. Plant Physiol. 2004, 135(2), 1113-1128.
Niu et al. A new inducible expression system in a transformed green alga, *Chlorella vulgaris*. Genetics and molecular research: GMR, 2011, 10(4), 3427-3434.
Noble et al. Direct comparison of optical and electron microscopy methods for structural characterization of extracellular vesicles. J Struct Biol. 2020, 210(1), 107474, 1-8.
O'Brien, et al. RNA delivery by extracellular vesicles in mammalian cells and its applications. Nature reviews. Molecular cell biology, 2020, 21, 1-22.
Ostrowski et al. Rab27a and Rab27b control different steps of the exosome secretion pathway. Nature cell biology, 2010, 12(1), 19-30.
Run et al. Stable nuclear transformation of the industrial alga *Chlorella pyrenoidosa,* Algal Research 17, 2016, 17, 196-201.
Rutter and Innes. Extracellular Vesicles Isolated from the Leaf Apoplast Carry Stress-Response Proteins. Plant physiology, 2017, 173(1), 728-741.
Safi et al. Morphology, composition, production, processing and applications of Chlorella vulgaris: A review. Renewable and Sustainable Energy Reviews, 2014, 35, 265-278.
Schatz et al. Communication via extracellular vesicles enhances viral infection of a cosmopolitan alga. Nat Microbiol. 2017, 2(11), 1485-1492.

(Continued)

*Primary Examiner* — Robert A Zeman
(74) *Attorney, Agent, or Firm* — Arrigo, Lee, Guttman & Mouta-Bellum LLP

(57) ABSTRACT

The invention relates to a novel method to produce small RNAs targeting pathogenicity factors, essential genes and/or antimicrobial resistance genes of animal pathogens. This method also includes the production of small RNAs directed against host susceptibility factors, whose silencing, inactivation, or deletion, is known to enhance resistance towards the targeted pathogen(s). More specifically, the invention involves the expression of exogenous RNA interference (RNAi) precursor(s) in *Chlorella* cells, which in turn express and release Extracellular Vesicle (EV)-embedded antimicrobial small RNAs. Importantly, *Chlorella* EVs protect antimicrobial small RNAs from ribonuclease-mediated digestion. They are also rapidly and efficiently internalized by human alveolar epithelial cells, highlighting their potential for delivering antimicrobial small RNAs in these cells, and for controlling respiratory infections. The invention can thus be used for prophylactic or therapeutic treatments, to reduce various infectious diseases in animals, including humans. Furthermore, because the integrity and functionality of *Chlorella* EVs remain unaltered when produced in photobioreactors, and when stored frozen, this novel method has the potential to be further exploited for the industrialization of EV-based anti-infective products.

8 Claims, 31 Drawing Sheets

Figure 1:
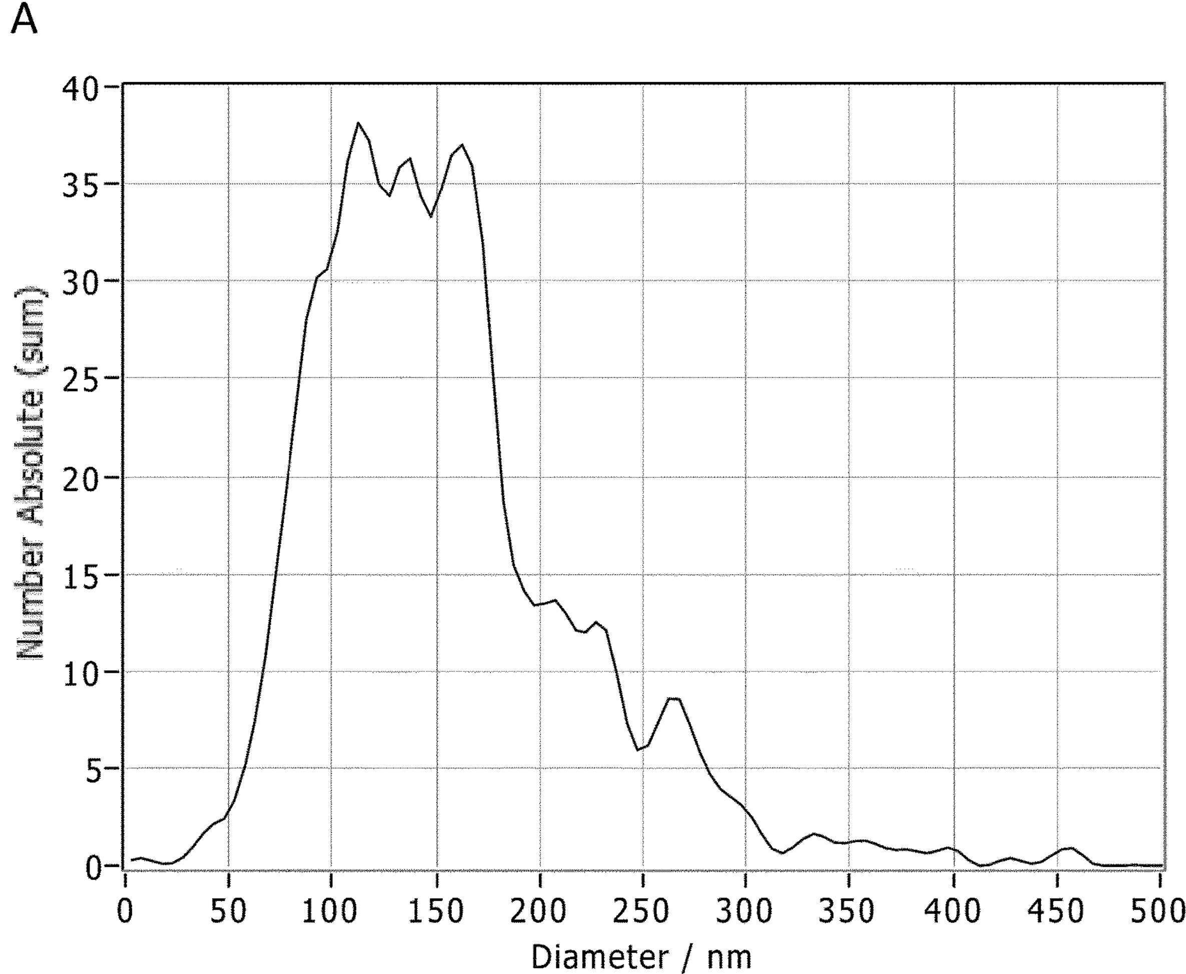

Specification includes a Sequence Listing.

(56) References Cited

OTHER PUBLICATIONS

Siddiqi, et al. COVID-19 illness in native and immunosuppressed states: A clinical-therapeutic staging proposal. The Journal of heart and lung transplantation, 2020, 39(5), 405-407.
Sreedharan et al. CorR regulates multiple components of virulence in *Pseudomonas syringae* pv. tomato DC3000. Molecular plant-microbe interactions:MPMI, 2006, 19(7), 768-779.
Strasfeld and Chou. Antiviral drug resistance: mechanisms and clinical implications. Infectious disease clinics of North America, 2010, 24(2), 413-437.
Teng et al. Plant-Derived Exosomal MicroRNAs Shape the Gut Microbiota. Cell Host Microbe, 2018, 24, 637-652.
Tompkins et al. Protection against lethal influenza virus challenge by RNA interference in vivo. Proceedings of the National Academy of Sciences of the United States of America, 2004, 101(23), 8682-8686.
V'Kovski et al. Determination of host proteins composing the microenvironment of coronavirus replicase complexes by proximity-labeling, eLife, 2019, 8, e42037, 1-30.
Wang and Jin. Spray-Induced Gene Silencing: a Powerful Innovative Strategy for Crop Protection. Trends in microbiology, 2017, 25(1), 4-6.
Wang et al. Cross-kingdom RNA trafficking and environmental RNAi for powerful innovative pre- and post-harvest plant protection. Current opinion in plant biology, 2017, 38, 133-141.
Wang et al. Tetraspanin genes in plants. Plant Sci. 2012, 19, 9-15.
Wang et al. Bidirectional cross-kingdom RNAi and fungal uptake of external RNAs confer plant protection. Nature plants, 2016, 2, 16151, 1-10.
Wang, et al. Delivery of therapeutic agents by nanoparticles made of grapefruit-derived lipids. Nature communications, 2013, 4, 1867, 1-13.
Whangbo and Hunter. Environmental RNA interference. Trends in genetics: TIG, 2008, 24(6), 297-305.
Yang et al. Development of a stable genetic system for Chlorella vulgaris—a promising green alga for CO2 biomitigation, Algal Res., 2015, 12, 134-141.
Yang and Merlin. Can naturally occurring nanoparticle-based targeted drug delivery effectively treat inflammatory bowel disease? Expert opinion on drug delivery, 2020, 17(1), 1-4.
Zhang et al. Characterization of GFP-AtPEN1 as a marker protein for extracellular vesicles isolated from Nicotiana benthamiana leaves. Plant signaling & behavior, 2020, 15(9), e1791519, 1-5.
Zhang et al. Plant derived edible nanoparticles as a new therapeutic approach against diseases. Tissue barriers, 2016, 4(2), e1134415, 1-9.
Zuniga et al. Genome-Scale Metabolic Model for the Green Alga *Chlorella vulgaris* UTEX 395 Accurately Predicts Phenotypes under Autotrophic, Heterotrophic, and Mixotrophic Growth Conditions. Plant physiology, 2016, 172(1), 589-602.
Zhang et al. Single processing center models for human Dicer and bacterial RNase III. Cell. 2004, 118(1), 57-68.
Zipfel et al. Bacterial disease resistance in Arabidopsis through flagellin perception. Nature. 2004, 428 (6984):764-767.
Kuruvinashetti et al, Algal Extracellular vesicles for therapeutic applications,2020 IEEE 20th international conference on nanotechnology (IEEE NANO) Virtual Conference, Jul. 2020, 1-4.
Park et al, Antiviral effects of miRNAs in extracellular vesicles against severe acute respiratory syndrome coronavirus 2 and mutations in SARS-COV-2 RNA Virus, bioRxiv, 2020, 1-47.
De Assis et al, Development and characterization of nanovesicles containing phenolic compounds of microalgae spirulina strain Leb-18 and chlorella pyrenoidosa, Advances in Materials Physics and Chemistry, 2014, 4, 6-12.
Andersen, et al. New unstable variants of green fluorescent protein for studies of transient gene expression in bacteria. Applied and environmental microbiology, 1998, 64(6), 2240-2246.
Asha et al., Advancements in Nucleic Acid Based Therapeutics against Respiratory Viral Infections. Journal of Clinical Medicine, 2018, 8(1), 6, 1-24.
Akenasy et al. Optical imaging of PKH-labeled hematopoietic cells in recipient bone marrow in vivo. Stem cells, 2002, 20(6), 501-513.
Bai et al. A new strategy to produce a defensin: stable production of mutated NP-1 in nitrate reductase-deficient Chlorella ellipsoidea. PloS one, 2013, 8(1), e54966, 1-9.
Bally et al. The Rise and Rise of Nicotiana benthamiana: A Plant for All Reasons. Annual review of phytopathology, 2018, 56, 405-426.
Bewicke-Copley et al. Extracellular vesicles released following heat stress induce bystander effect in unstressed populations. Journal of extracellular vesicles, 2017, 6(1), 1340746, 1-10.
Bitko, et al. Inhibition of respiratory viruses by nasally administered siRNA. Nature medicine, 2005, 11(1), 50-55.
Blanc et al. The Chlorella variabilis NC64A genome reveals adaptation to photosymbiosis, coevolution with viruses, and cryptic sex. The Plant cell, 2010, 22(9), 2943-2955.
Bolognesi et al. Characterizing the mechanism of action of double-stranded RNA activity against western corn rootworm (*Diabrotica virgifera virgifera* LeConte). PloS one, 2012, 7(10), e47534, 1-11.
Brooks et al. Identification and characterization of a well-defined series of coronatine biosynthetic mutants of *Pseudomonas syringae* pv. tomato DC3000. Molecular Plant-Microbe Interactions, 2004, 17(2), 162-174.
Cai et al. Plants send small RNAs in extracellular vesicles to fungal path-ogen to silence virulence genes. Science, 2018, 360(6393), 1126-112.
Campbell-Valois, et al. A fluorescent reporter reveals on/off regulation of the Shigella type III secretion apparatus during entry and cell-to-cell spread. Cell host & microbe, 2014, 15(2), 177-189.
Cerutti, et al. RNA-mediated silencing in Algae: biological roles and tools for analysis of gene function. Eukaryotic cell, 2011, 10(9), 1164-1172.
Cha et al. Assessment of factors affecting Agrobacterium-mediated genetic transformation of the unicellular green alga, *Chlorella vulgaris*. World journal of microbiology & biotechnology, 2012, 28(4), 1771-1779.
Chien et al. Solar-to-bioH(2) production enhanced by homologous overexpression of hydrogenase in green alga *Chlorella* sp. DT, Int. J. Hydrog. Energy, 2012, 37, 17738-17748.
Chuo et al. Imaging extracellular vesicles: current and emerging methods. Journal of biomedical science, 2018, 25(1), 91, 1-10.
Colao et al. Manufacturing Exosomes: A Promising Therapeutic Platform. Trends in molecular medicine, 2018, 24(3), 242-256.
Collett et al. Endoplasmic reticulum stress stimulates the release of extracellular vesicles carrying danger-associated molecular pattern (DAMP) molecules. Oncotarget. 2018, 9(6), 6707-6717.
De Andrade and De Andrade. An overview on the application of genus *Chlorella* in bio-technological processes. J Adv Res Biotech, 2017, 2(1), 1-9.
Devincenzo et al. A randomized, double-blind, placebo-controlled study of an RNAi-based therapy directed against respiratory syncytial virus. Proceedings of the National Academy of Sciences of the United States of America, 2010, 107(19), 8800-8805.
Durrant and Dong. Systemic acquired resistance. Annu Rev Phytopathol. 2004, 42, 185-209.
Elowitz and Leibler. A synthetic oscillatory network of transcriptional regulators. Nature, 2000, 403(6767), 335-338.
Fan, & Jin. Structures of RIG-I-Like Receptors and Insights into Viral RNA Sensing. Advances in experimental medicine and biology, 2019, 1172, 157-188.
Fick et al. The extent of heterocellular communication mediated by gap junctions is predictive of bystander tumor cytotoxicity in vitro. Proceedings of the National Academy of Sciences of the United States of America, 1995, 92(24), 11071-11075.
Fouts et al. Genomewide identification of *Pseudomonas syringae* pv. tomato DC3000 promoters controlled by the HrpL alternative sigma factor. Proceedings of the National Academy of Sciences of the United States of America, 2002, 99(4), 2275-2280.
Gao, et al. Phylogenetic analysis of the endoribonuclease Dicer family. PloS one, 2014, 9(4), e95350, 1-7.
Garaeva et al. Delivery of functional exogenous proteins by plant-derived vesicles to human cells in vitro. Sci Rep, 2021, 11, 6489, 1-12.

(56) References Cited

OTHER PUBLICATIONS

Ge et al. Inhibition of influenza virus production in virus-infected mice by RNA interference. Proc Natl Acad Sci USA. 2004, 101(23), 8676-8681.
Gomez-Gomez et al. FLS2: an LRR receptor-like kinase involved in the perception of the bacterial elicitor flagellin in *Arabidopsis*. Mol Cell, 2000, 5(6), 1003-1011.
Gordon et al. A SARS-CoV-2-Human Protein-Protein Interaction Map Reveals Drug Targets and Potential Drug-Repurposing. Nature, 2020, 583, 459-488.
Guarnieri, et al. Genome Sequence of the Oleaginous Green Alga, *Chlorella vulgaris* UTEX 395. Frontiers in bioengineering and biotechnology, 2018, 6(37), 1-2.
Guo et al. Small RNA-based antimicrobial immunity. Nature reviews. Immunology, 2019, 19(1), 31-44.
Hoffmann et al. SARS-CoV-2 Cell Entry Depends on ACE2 and TMPRSS2 and Is Blocked by a Clinically Proven Protease Inhibitor. Cell, 2020, 181(2), 271-280.
Hou et al. A Phytophthora Effector SuppressesTrans-Kingdom RNAi to Promote Disease Susceptibility. Cell Host Microbe, 2018, 25, 153-165.
Howard, et al. Emerging virus diseases: can we ever expect the unexpected?. Emerging microbes & infections, 2012, 1(12), e46, 1-11.
Ivashuta et al. Environmental RNAi in herbivorous insects. RNA, 2015, 21(5), 840-850.
Kaner and Shaack. Understanding Ebola: the 2014 epidemic. Globalization and health, 2016, 12(1), 53, 1-7.
Kim et al. Stable integration and functional expression of flounder growth hormone gene in transformed microalga, Chlorella ellipsoidea. Marine biotechnology, 2002, 4(1), 63-73.
Koch, A. et al. Host-induced gene silencing of cytochrome P450 lanosterol C14alpha-demethylase-encoding genes confers strong resistance to *Fusarium* species. Proc Natl Acad Sci USA, 2013,110(48), 19324-19239.
Koch et al. An RNAi-Based Control of Fusarium graminearum Infections Through Spraying of Long dsRNAs Involves a Plant Passage and Is Controlled by the Fungal Silencing Machinery. PLoS pathogens, 2016, 12(10), e1005901, 1-22.
Kolb, et al. FYVE1 is essential for vacuole biogenesis and intracellular trafficking in *Arabidopsis*. Plant physiology, 2015, 167(4), 1361-1373.
Langmead, et al. Ultrafast and memory-efficient alignment of short DNA sequences to the human genome. Genome Biol., 2009, 10, R25, 1-10.
Li et al. Using siRNA in prophylactic and therapeutic regimens against SARS coronavirus in Rhesus macaque. Nature medicine, 2005, 11(9), 944-951.
Lin, et al. Knockdown of PsbO leads to induction of HydA and production of photobiological H2 in the green alga *Chlorella* sp. DT. Bioresource technology, 2013, 143, 154-162.
Maji et al. In vitro toxicology studies of extracellular vesicles. J Appl Toxicol. 2017, 37(3), 310-318.
Meighen. Molecular biology of bacterial bioluminescence. Microbiological reviews, 1991, 55(1), 123-142.
Melotto et al. Plant stomata function in innate immunity against bacterial invasion. Cell, 2006, 126(5), 969-980.
Mukherjee et al. Evolution of animal and plant dicers: early parallel duplications and recurrent adaptation of antiviral RNA binding in plants. Molecular biology and evolution, 2013, 30(3), 627-641.
Murphy et al. The evolution of core proteins involved in microRNA biogenesis. BMC Evol. Biol. 2008, 8(92), 1-18.
Nakase et al. Environmental pH stress influences cellular secretion and uptake of extracellular vesicles. FEBS Open Bio, 2021, 11, 753-767.

* cited by examiner

A

FIGURE 1 (continuation)
B
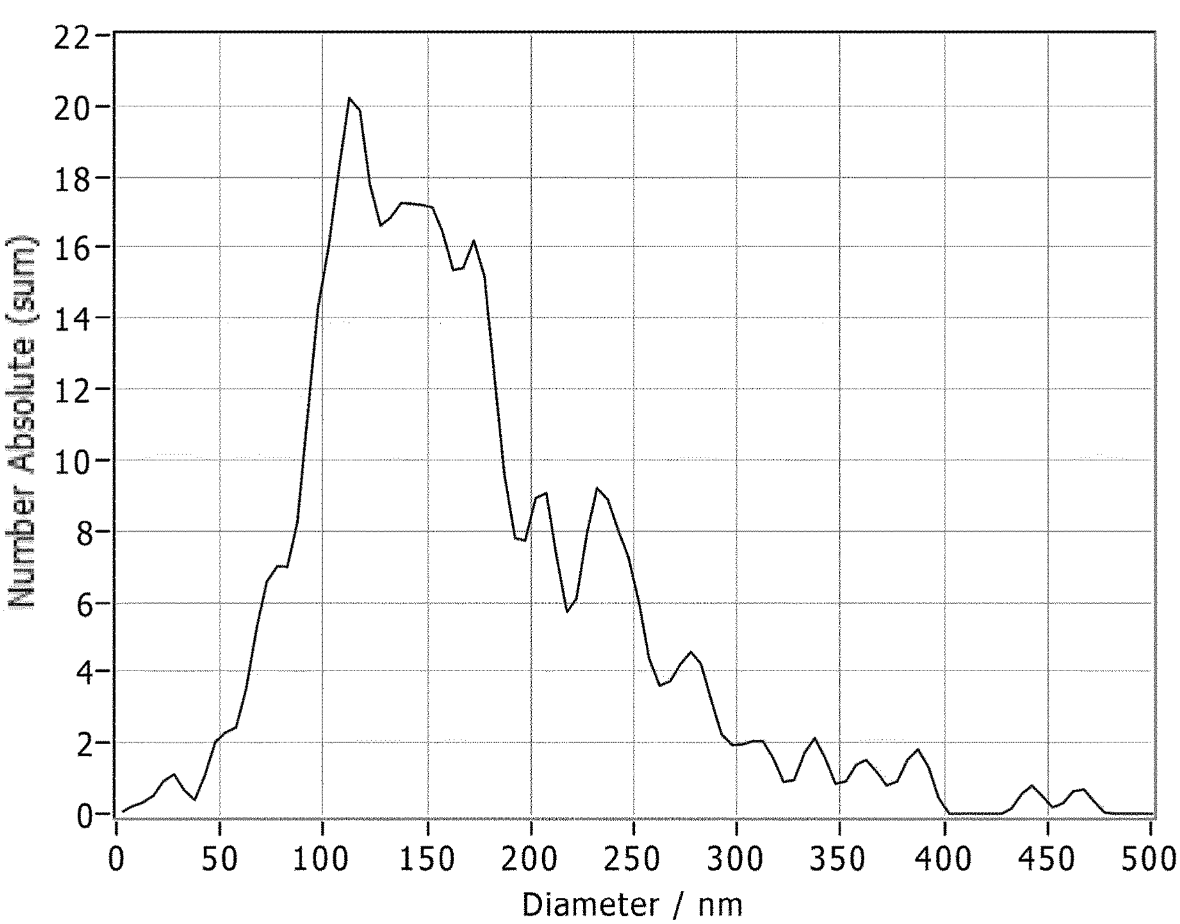
C
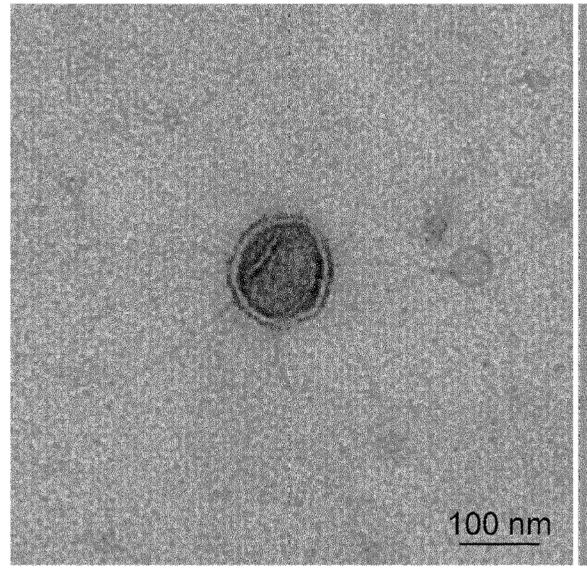
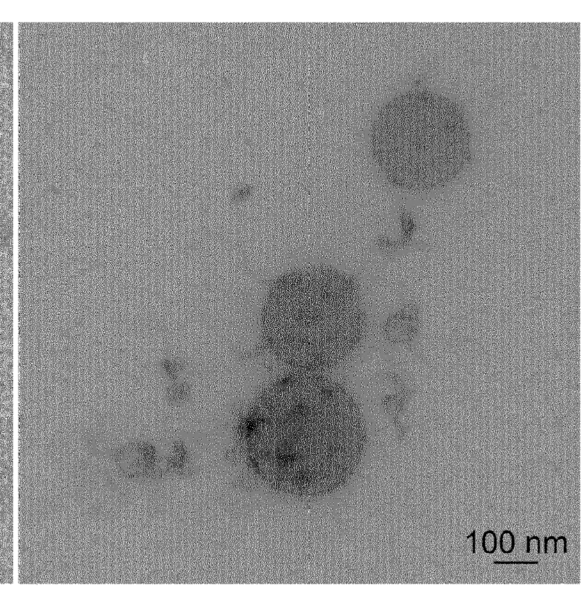

FIGURE 1 (continuation)
D
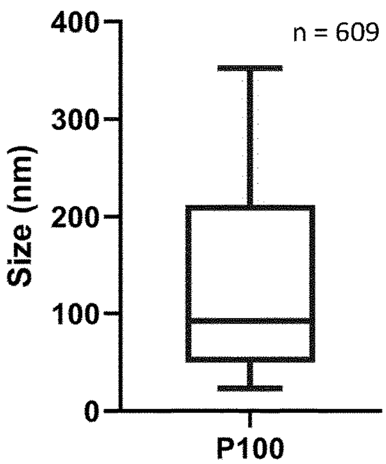
E
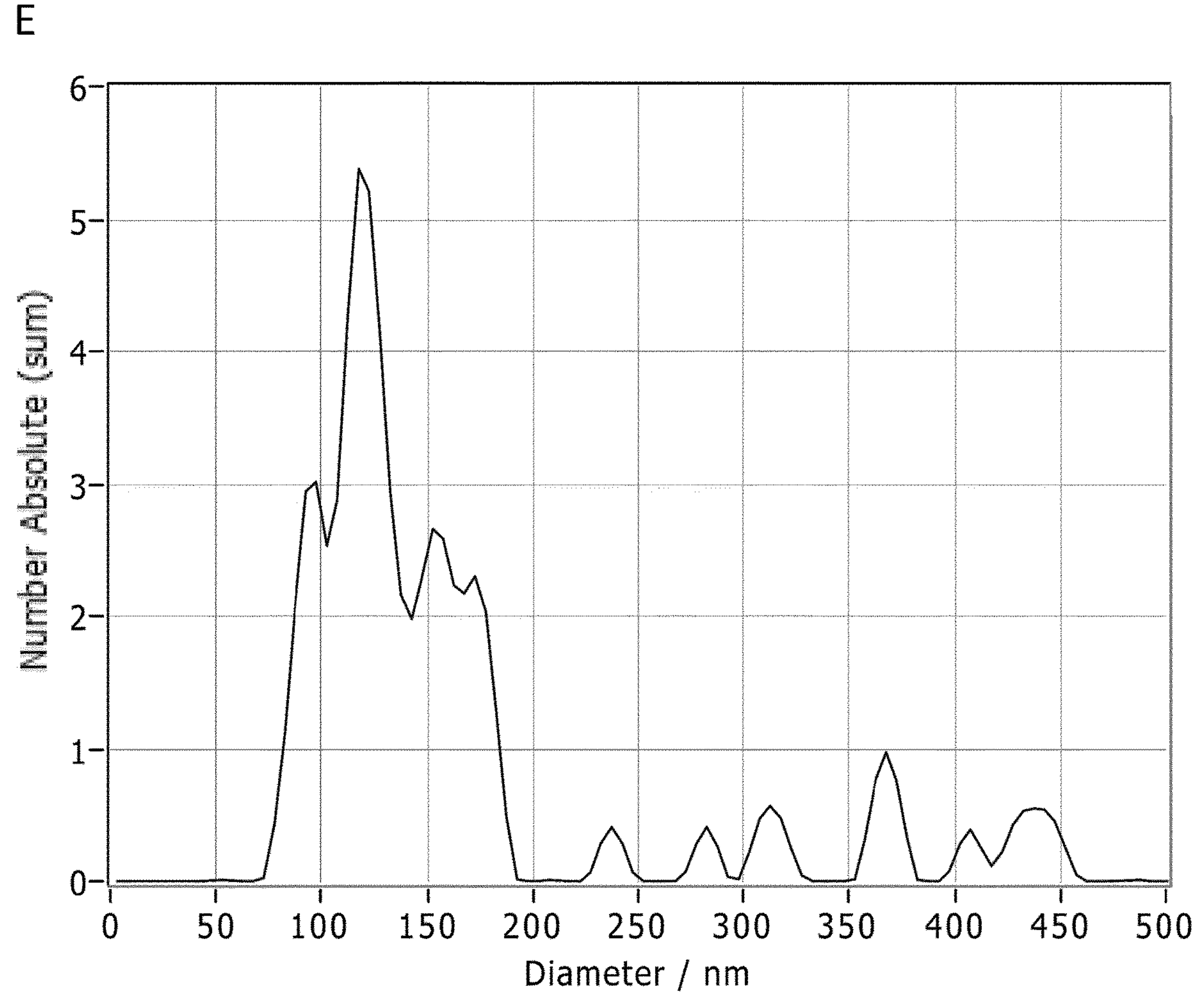

Figure 2:
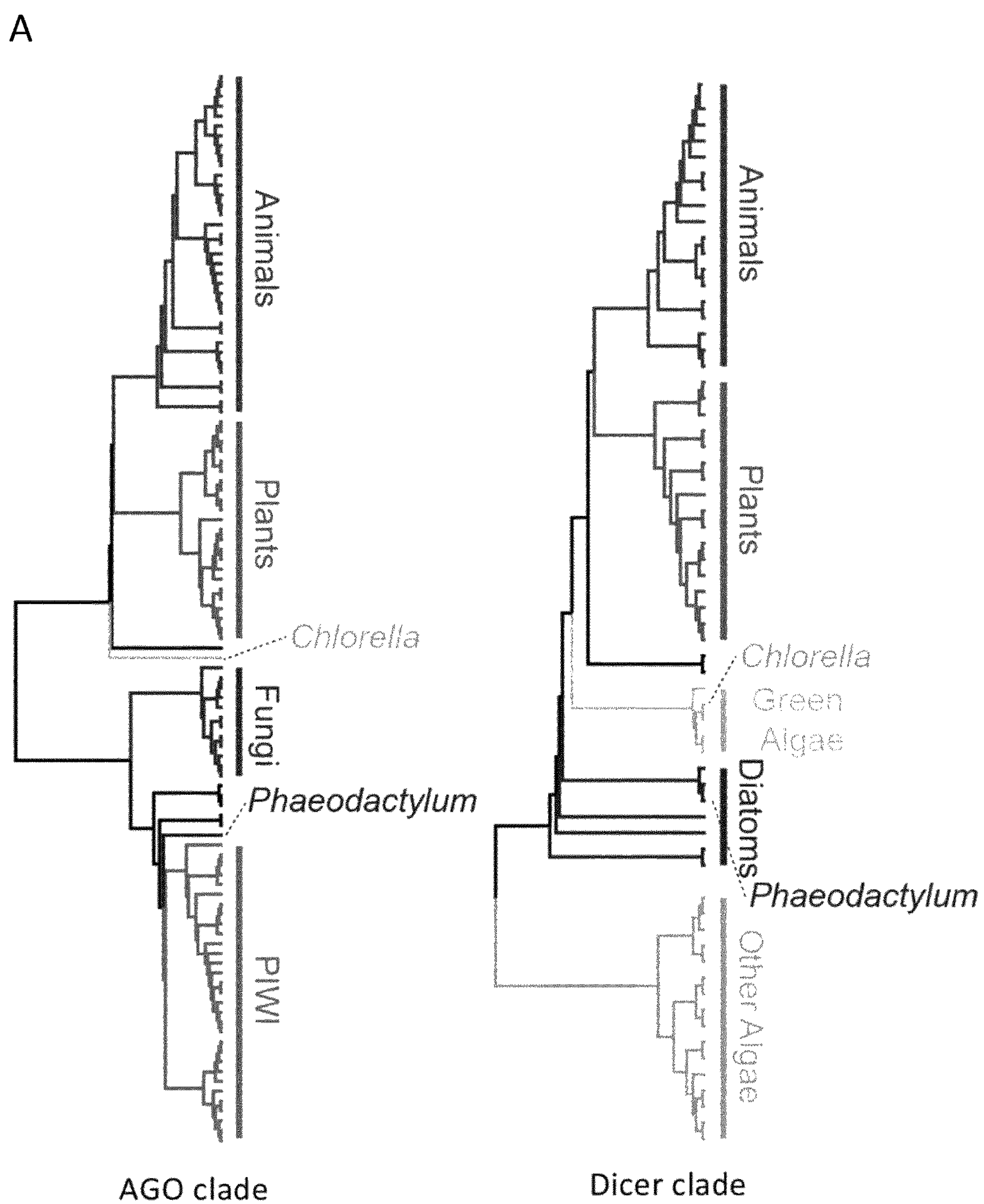

FIGURE 2 (continuation)
B
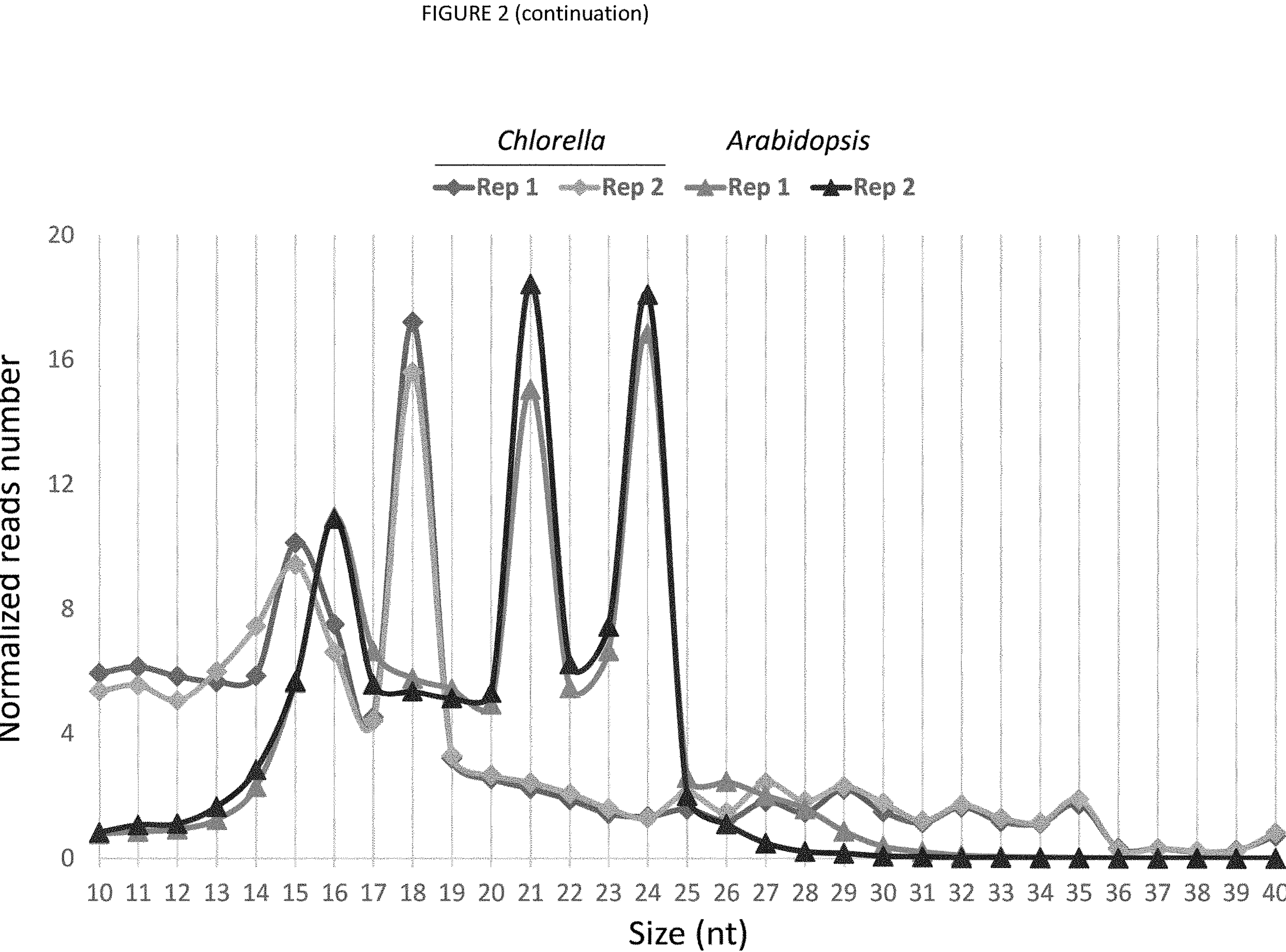

Figure 3:
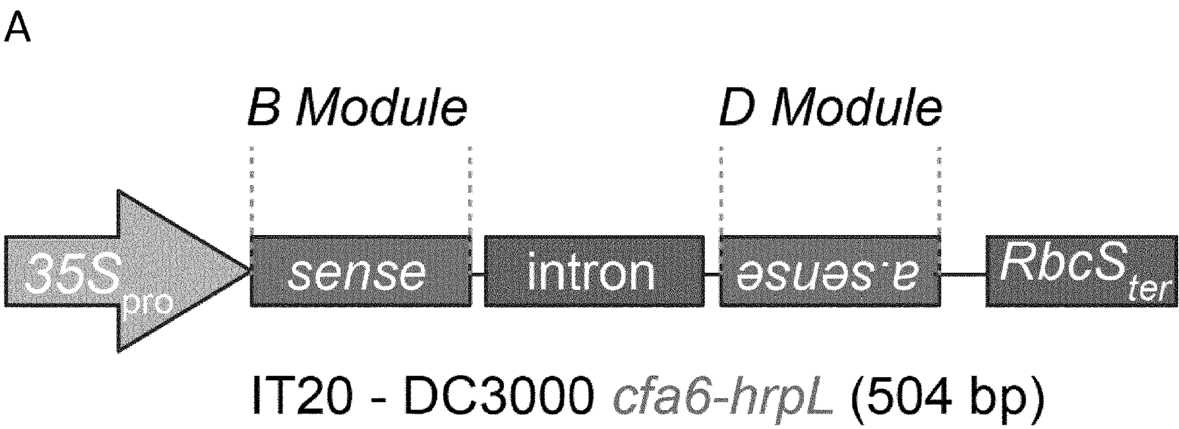

FIGURE 3 (continuation)
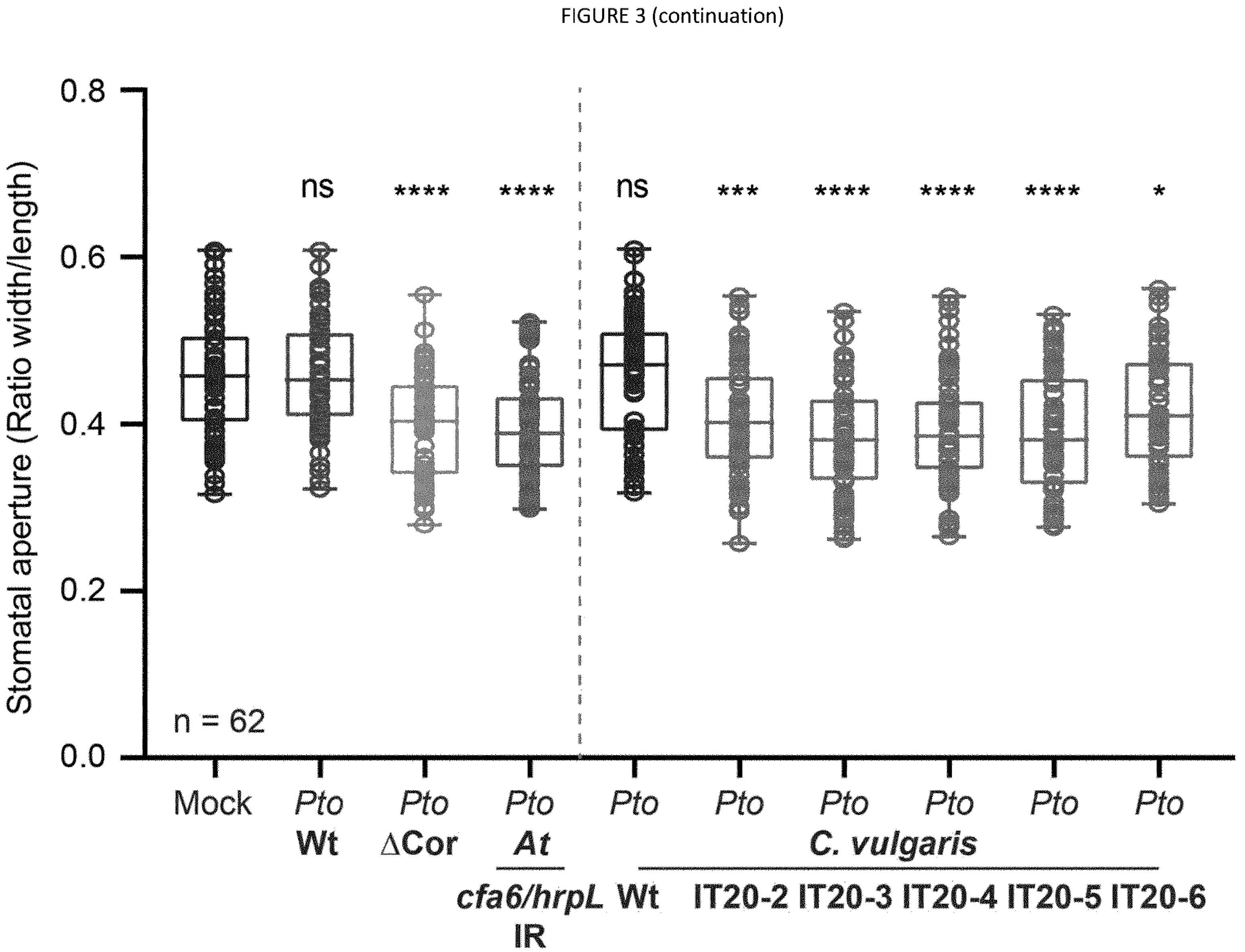

FIGURE 3 (continuation)
C
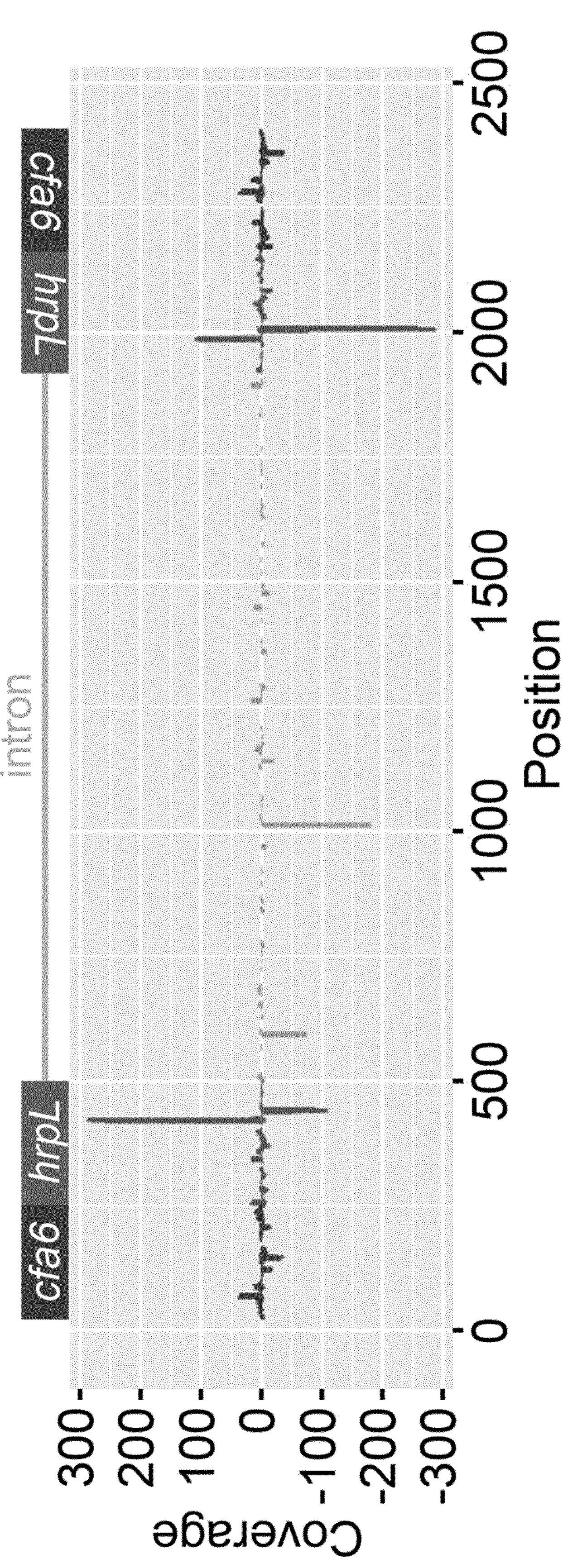

FIGURE 4
A
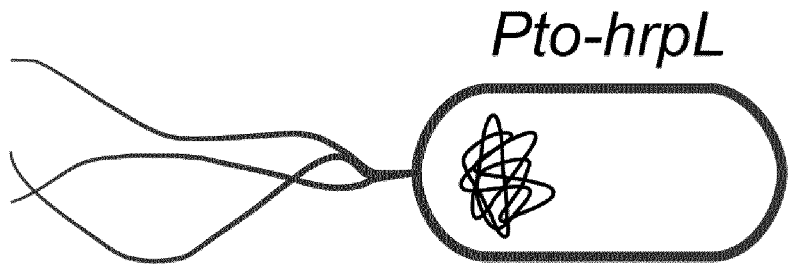
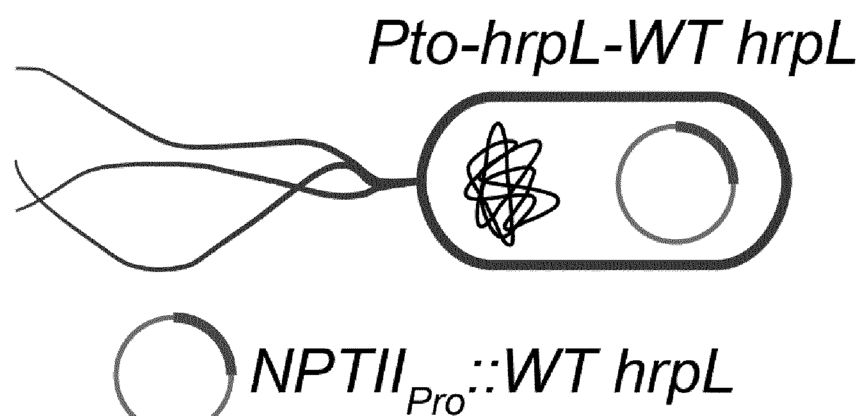
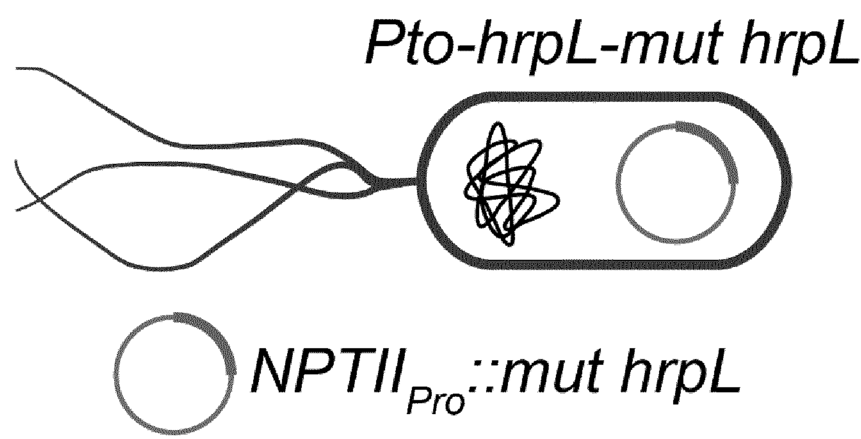

FIGURE 4 (continuation)
B
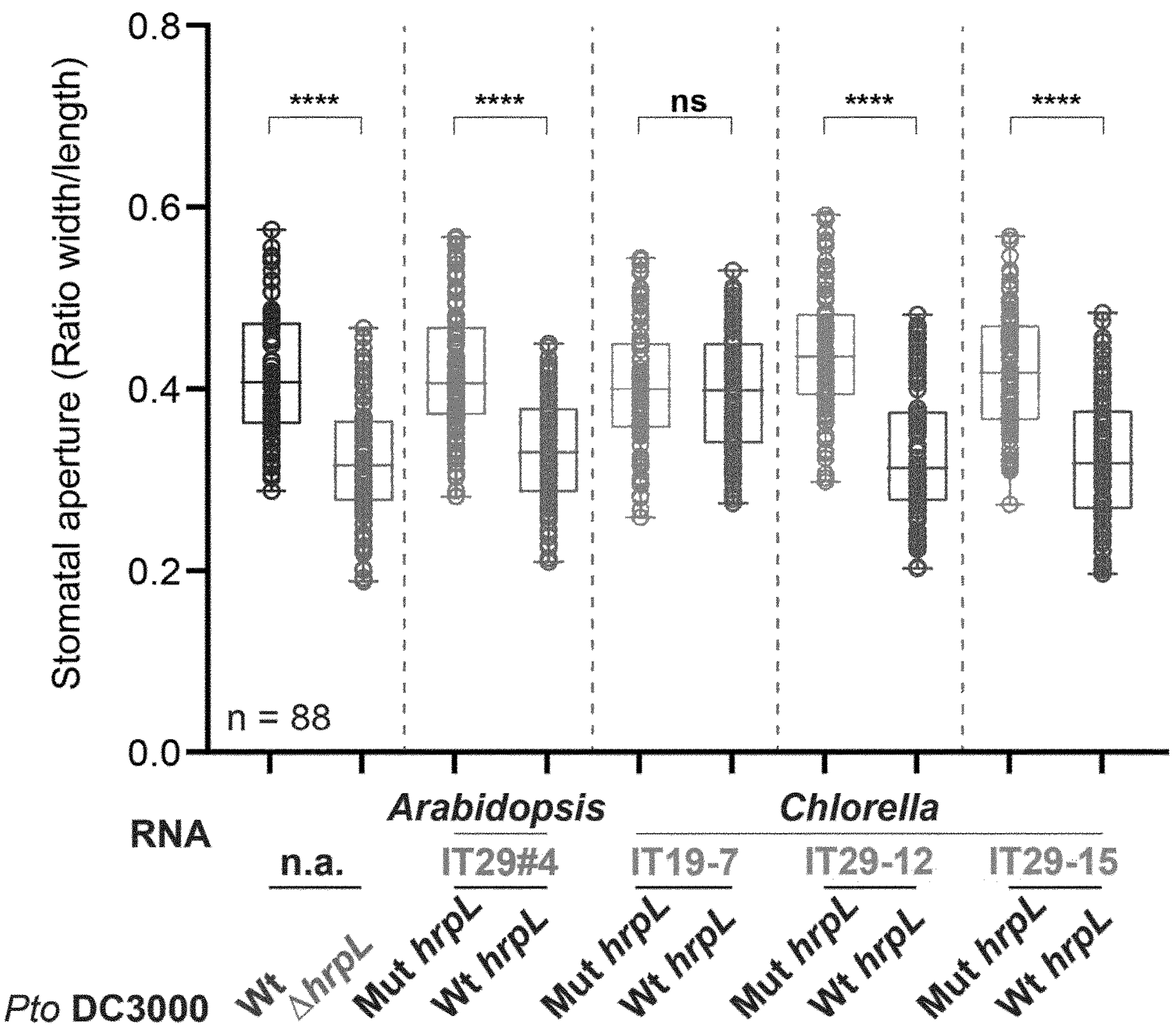

Figure 5:
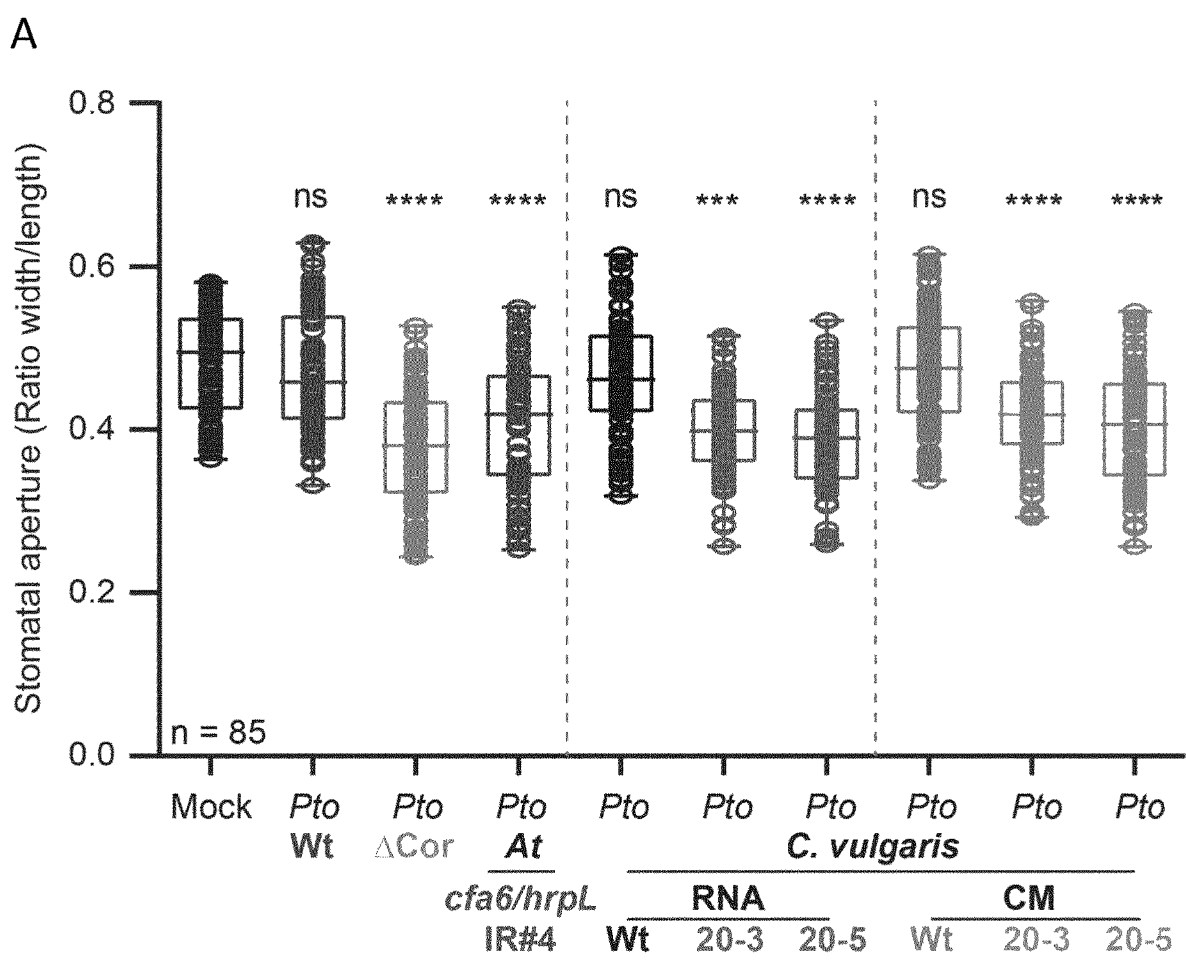

FIGURE 5 (continuation)
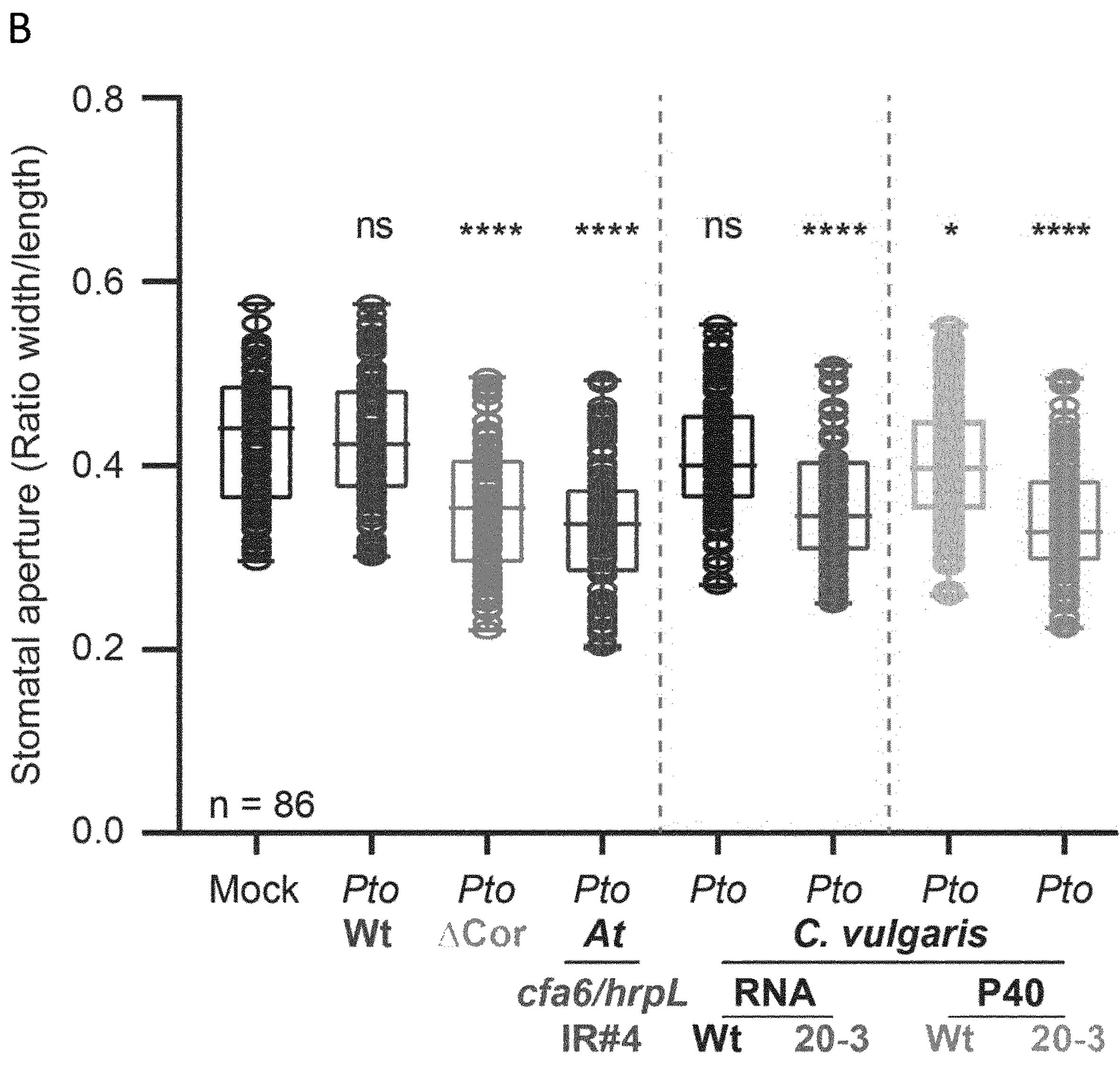

FIGURE 5 (continuation)
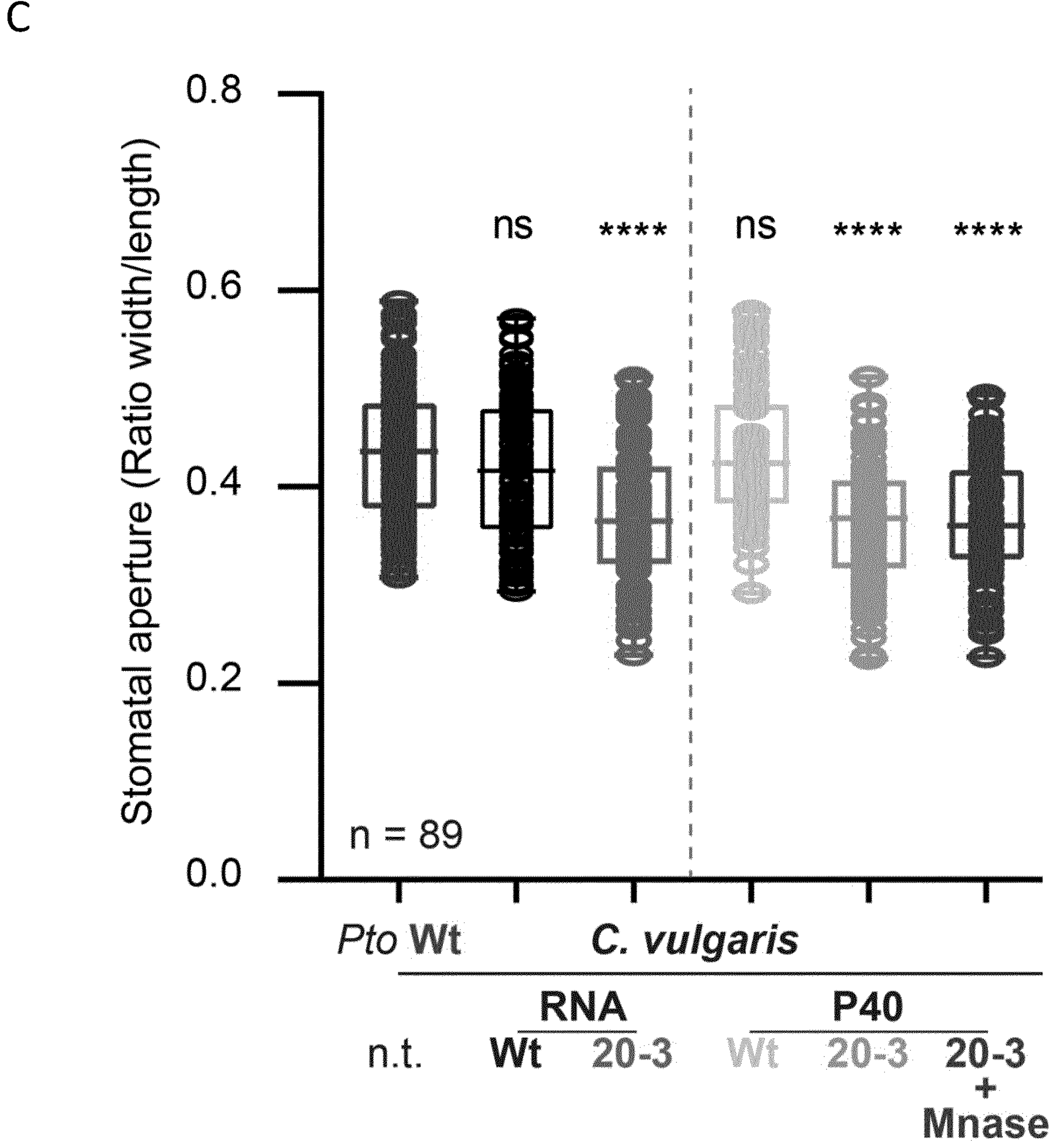

FIGURE 5 (continuation)
D
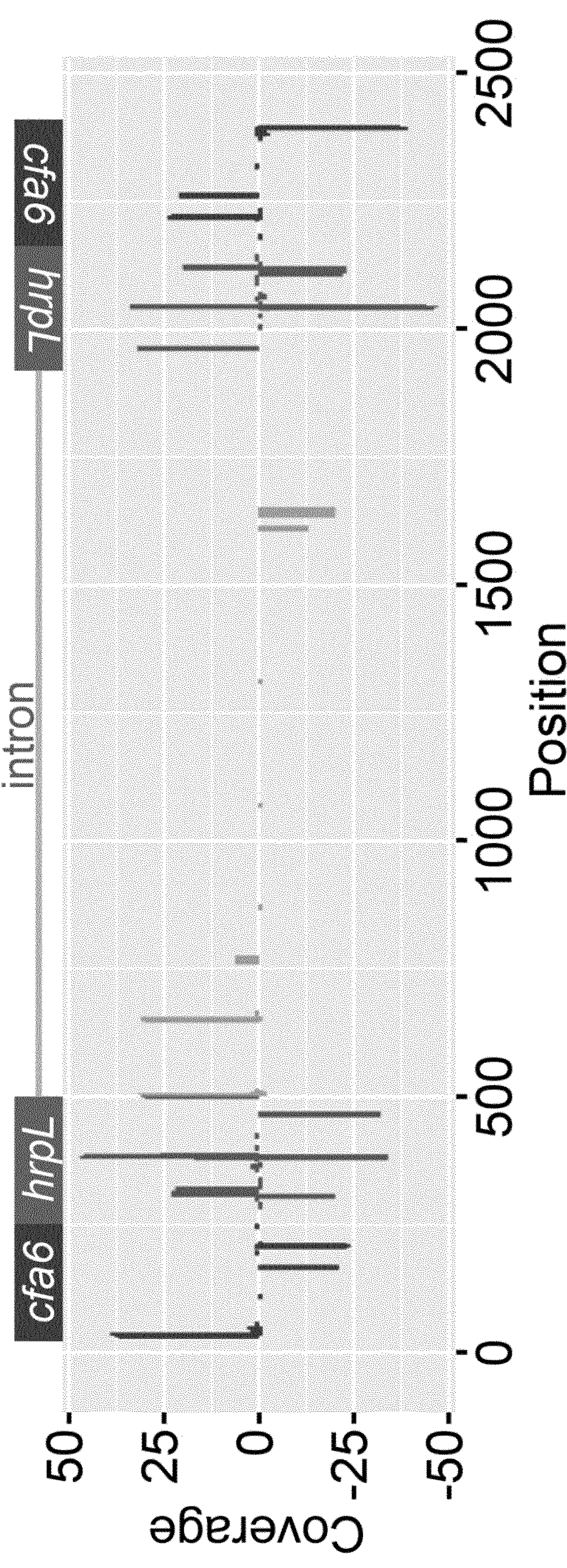

FIGURE 5 (continuation)
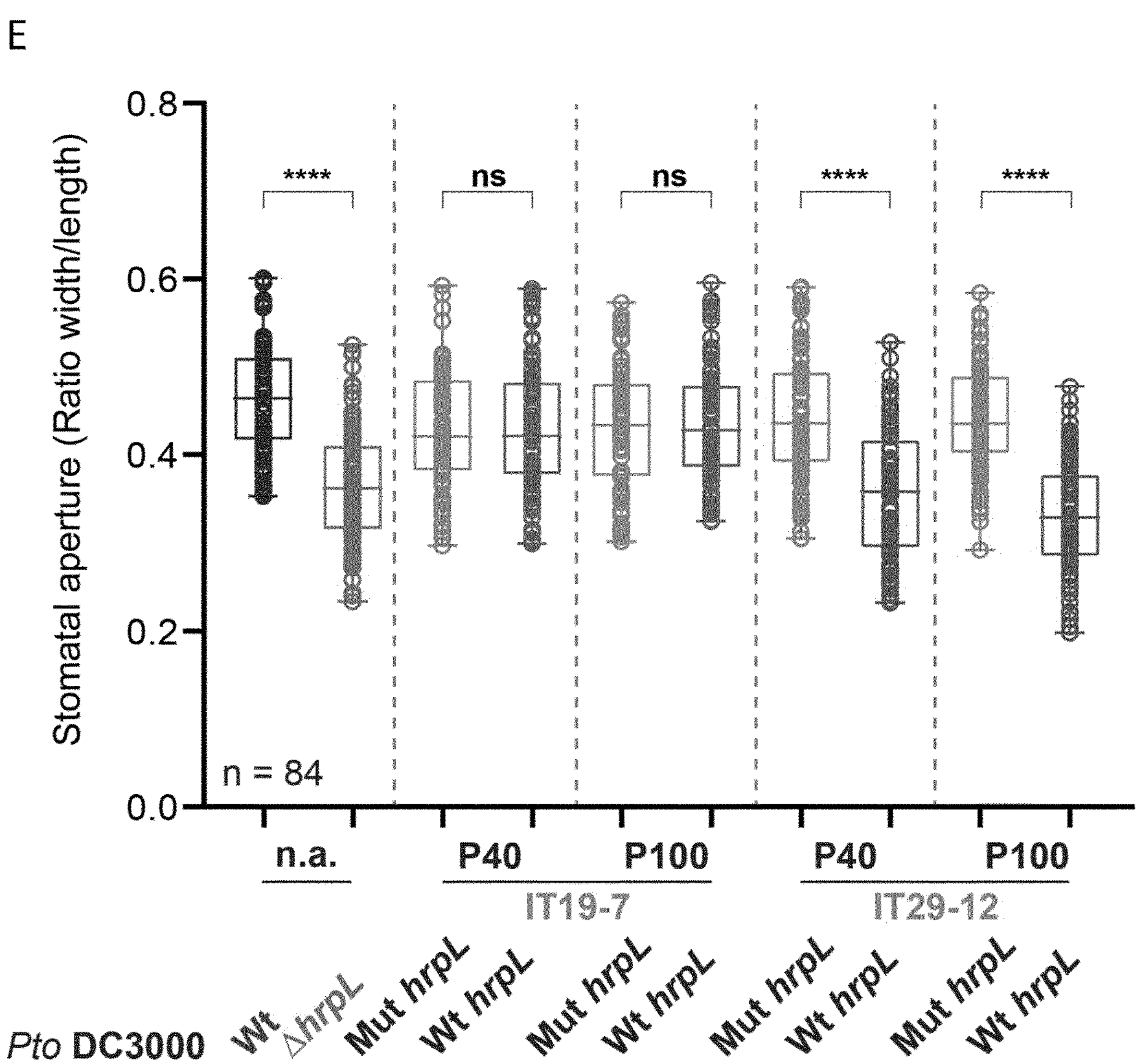

A
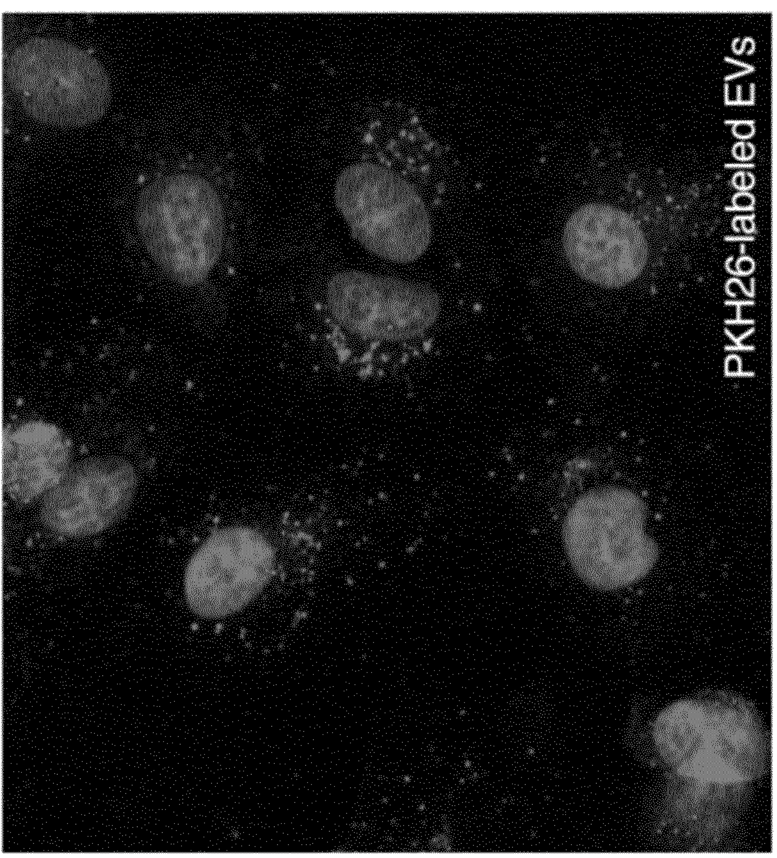
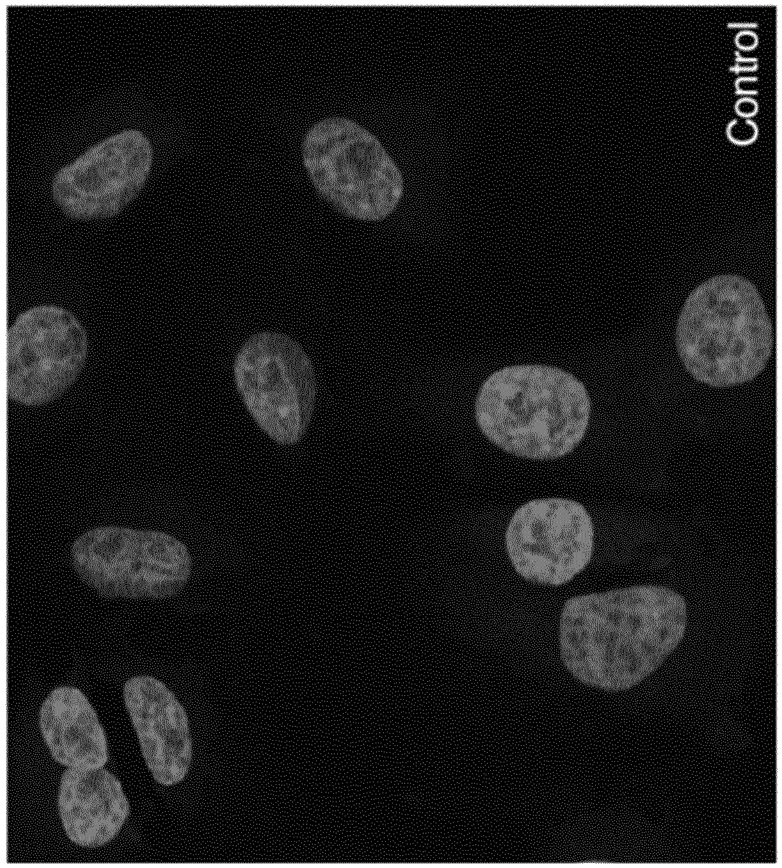

FIGURE 6 (continuation)
B
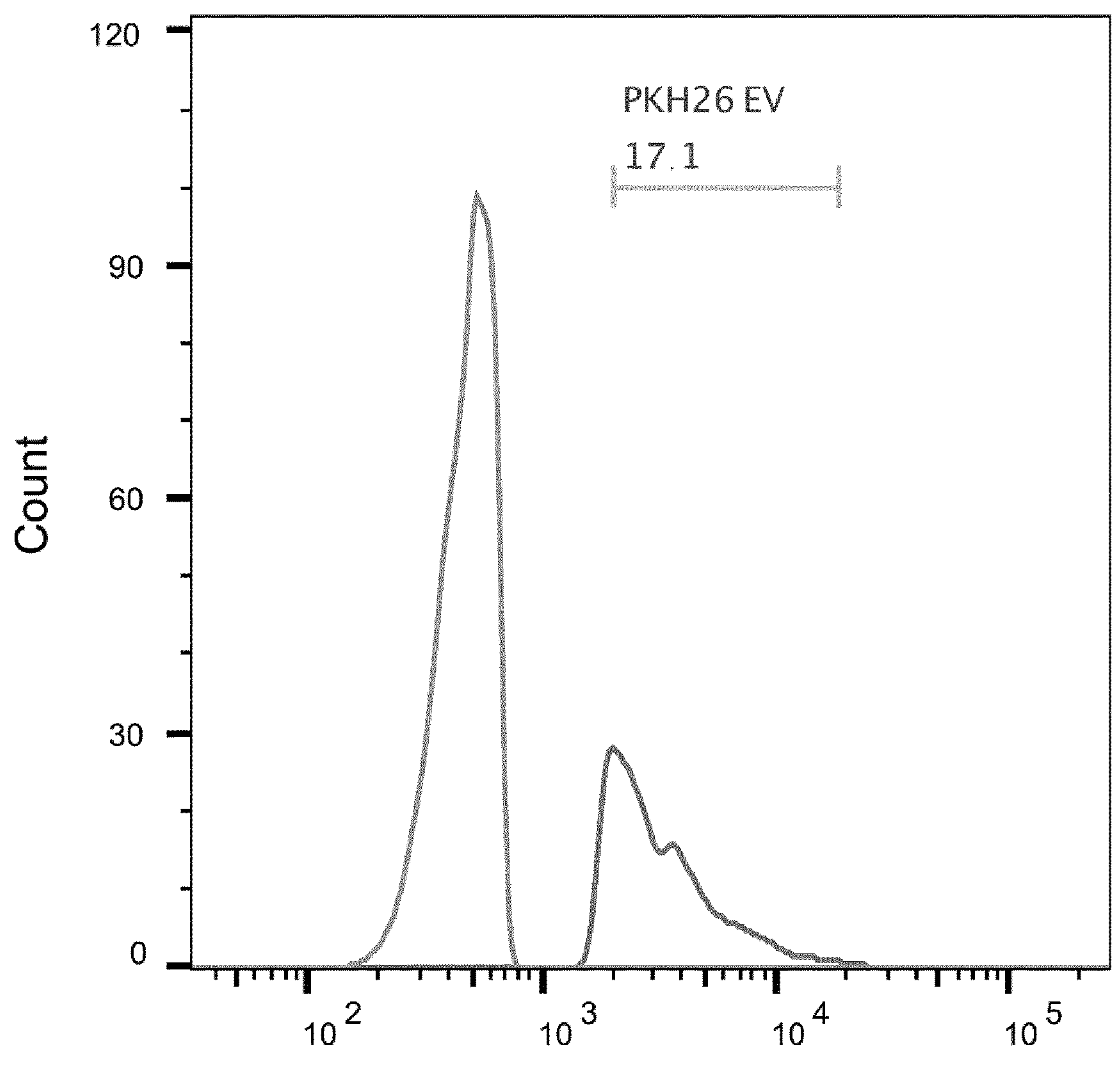

FIGURE 6 (continuation)
B
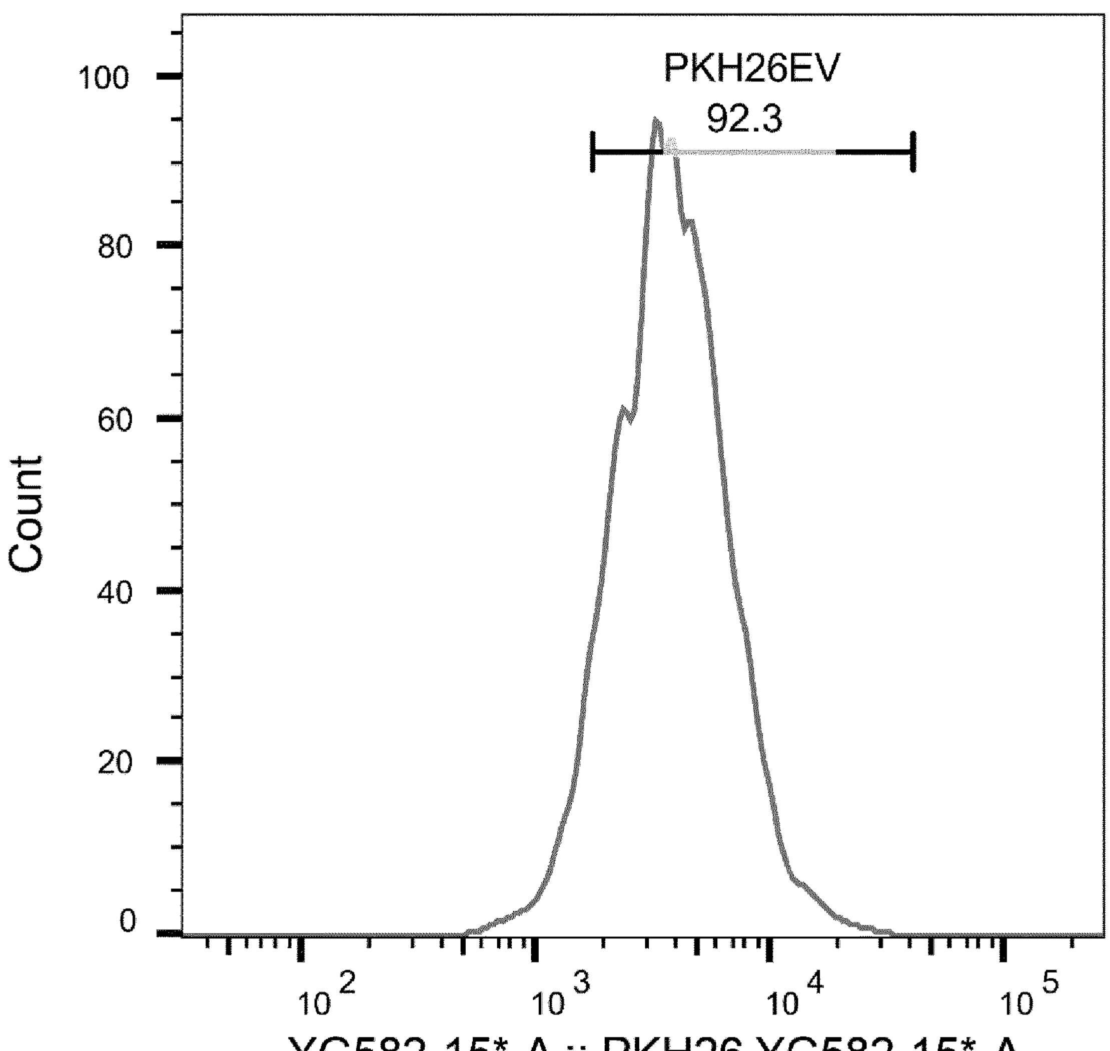

FIGURE 6 (continuation)
C
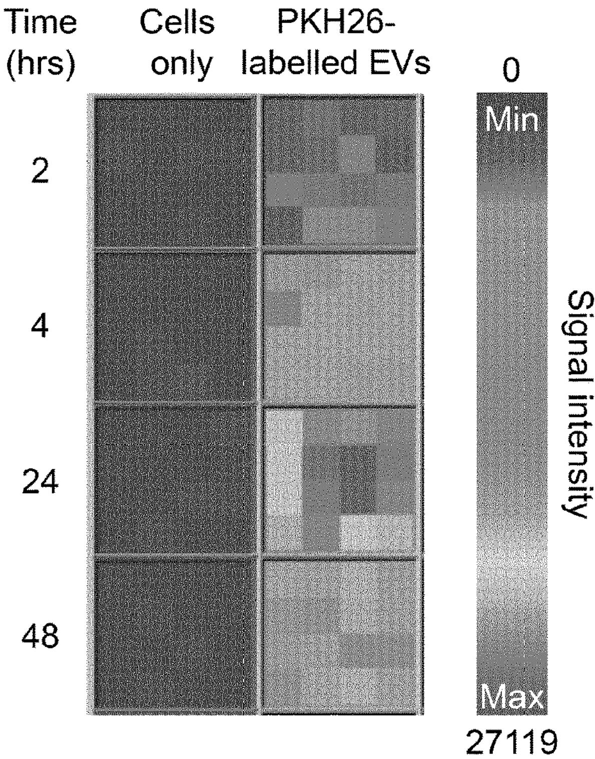
D
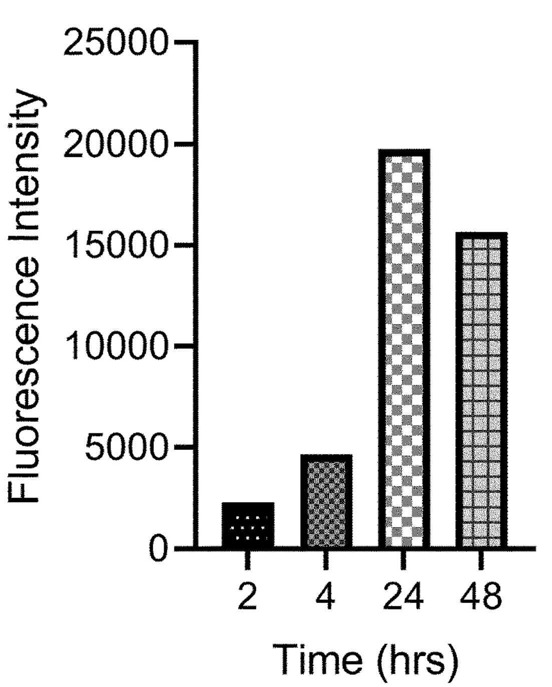

FIGURE 8
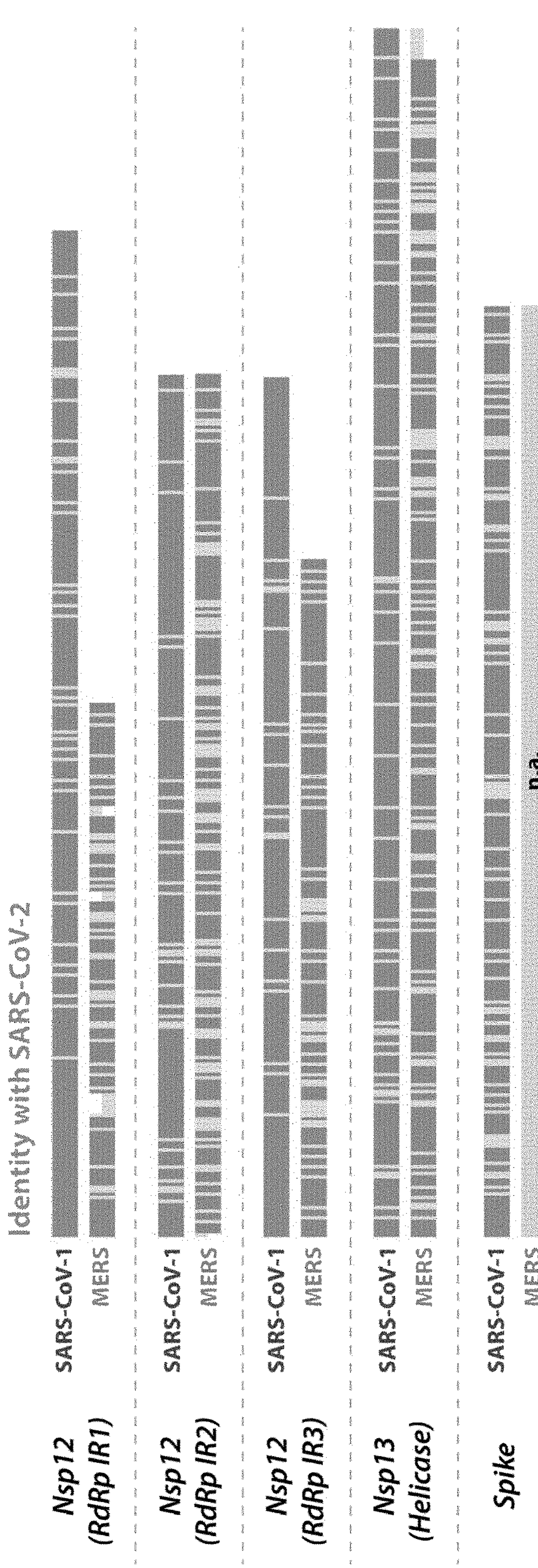
Identity with SARS-CoV-2
Nsp12 (RdRp IR1)
SARS-CoV-1
MERS
Nsp12 (RdRp IR2)
SARS-CoV-1
MERS
Nsp12 (RdRp IR3)
SARS-CoV-1
MERS
Nsp13 (Helicase)
SARS-CoV-1
MERS
Spike
SARS-CoV-1
MERS
n.a.

A

Figure 9:
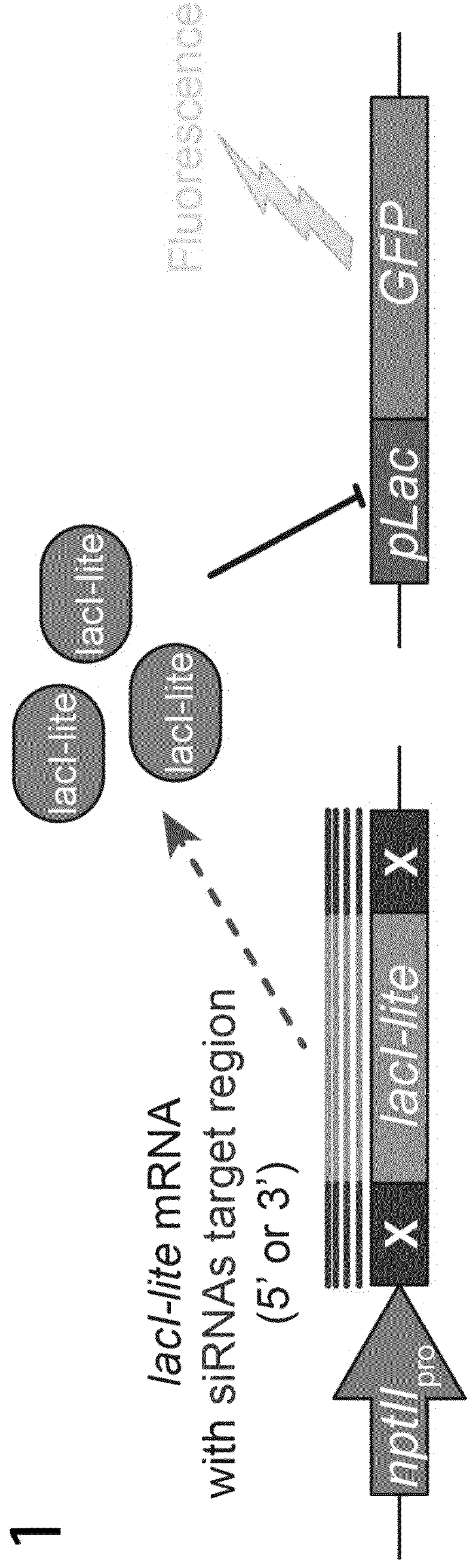

FIGURE 9 (continuation)
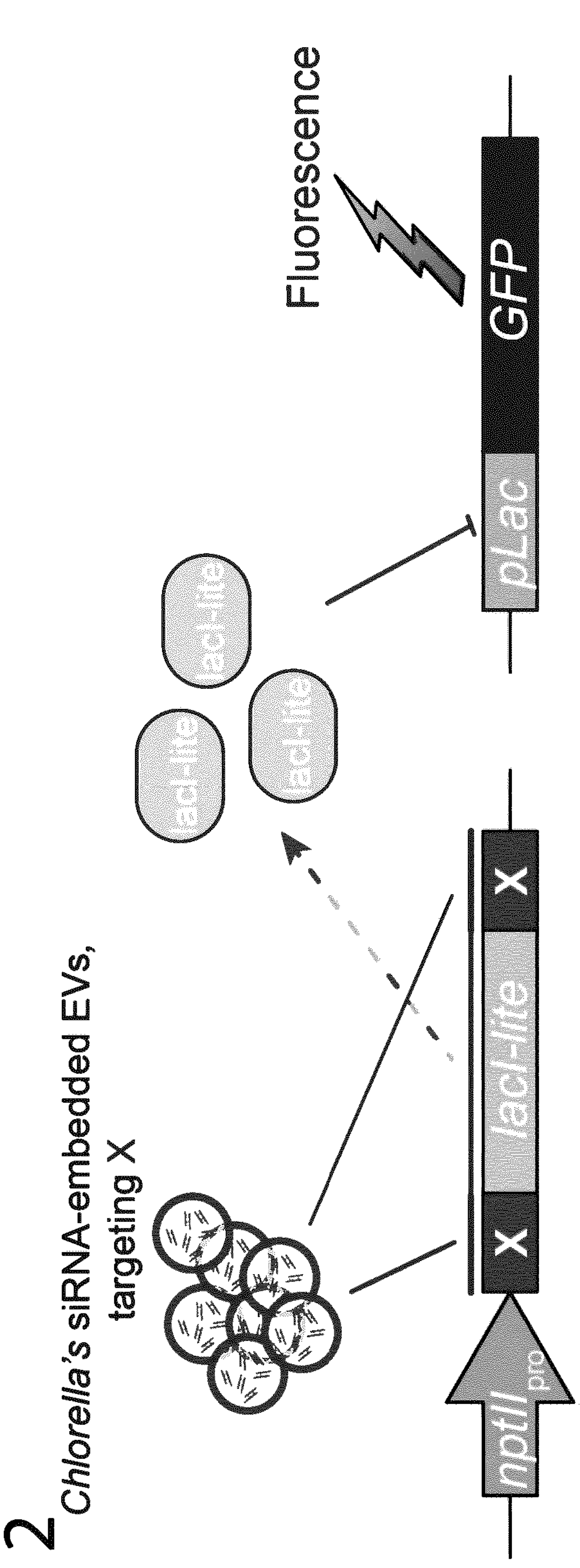

FIGURE 9 (continuation)
B
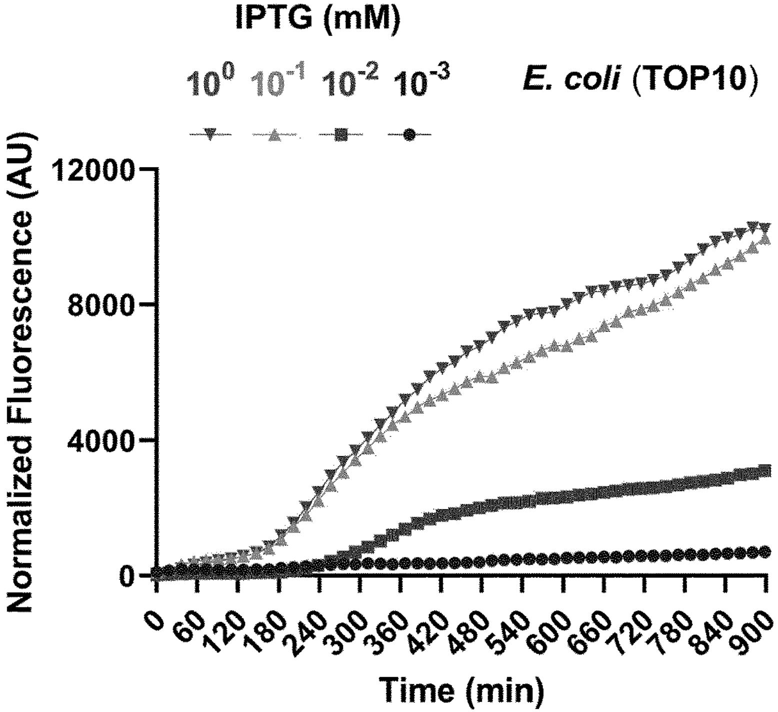
C
IPTG 5 mM *Pto* DC3000 (Wt)
Normalized Fluorescence (AU)
800
600
400
200
0
#1
#2
#3
0 60 120 180 240 300 360 420 480 540 600 660 720 780 840 900
Time (min)

FIGURE 9 (continuation)
D
1
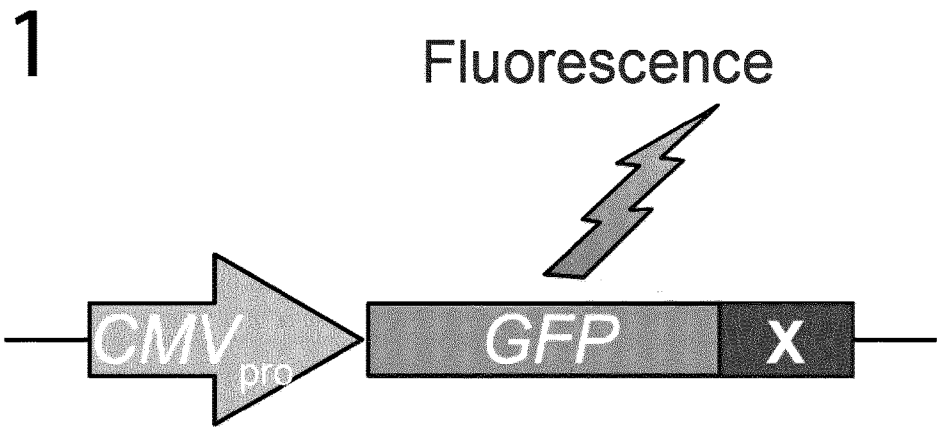
2
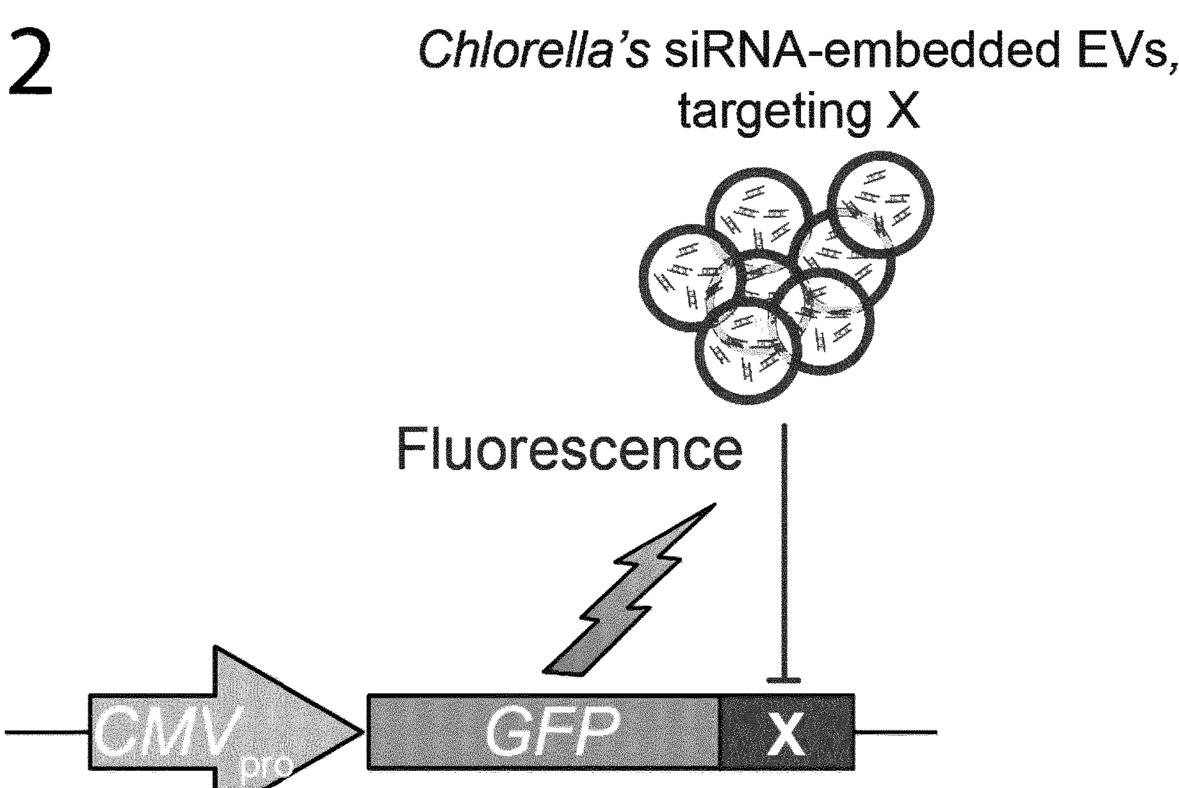

FIGURE 9 (continuation)
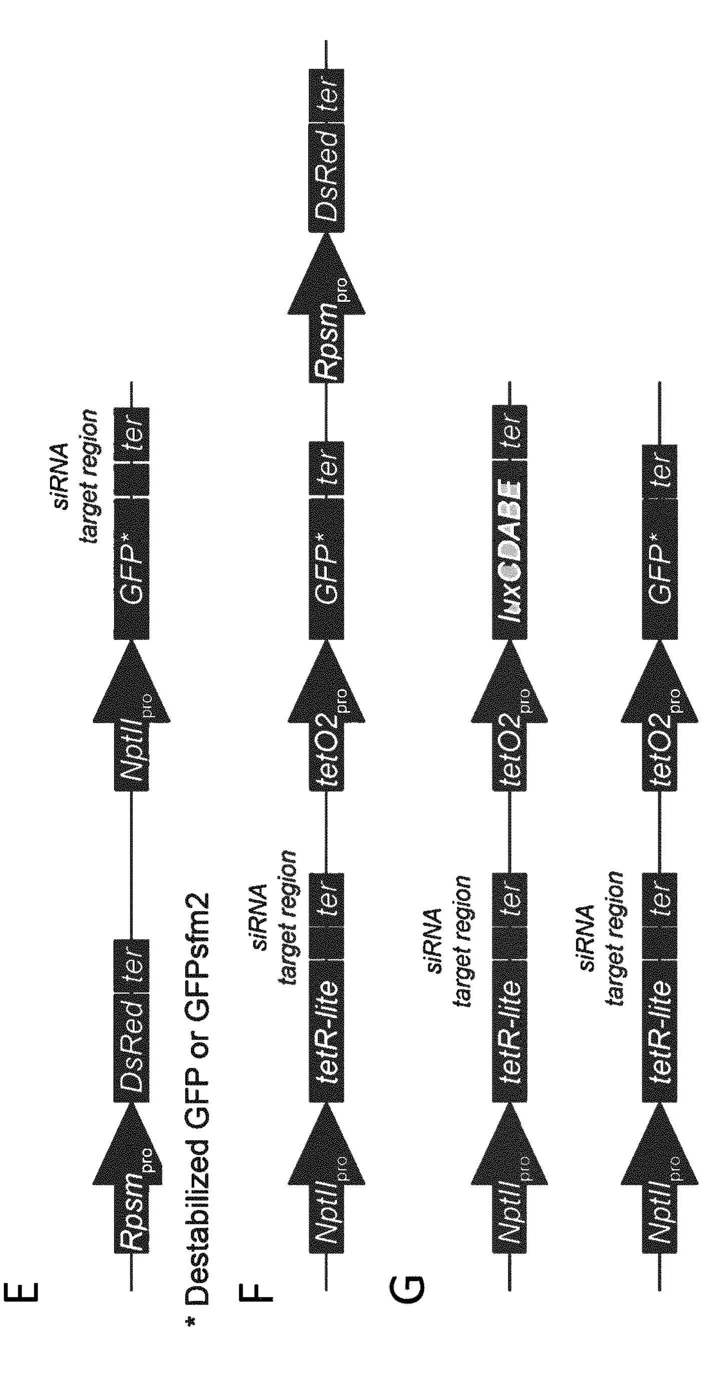

FIGURE 10
A
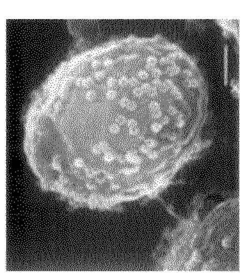
Small-scale
*Chlorella culture*
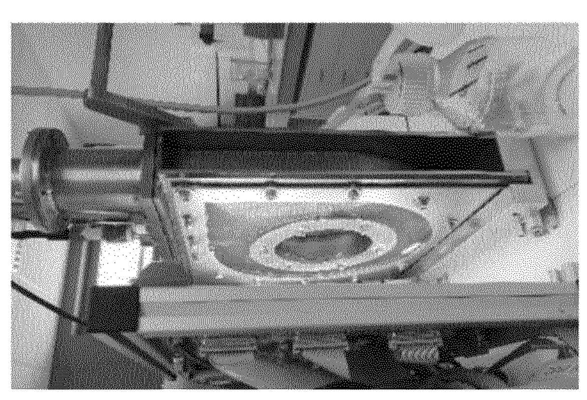
1 L PBR
(4-5 L in 3.3 days)
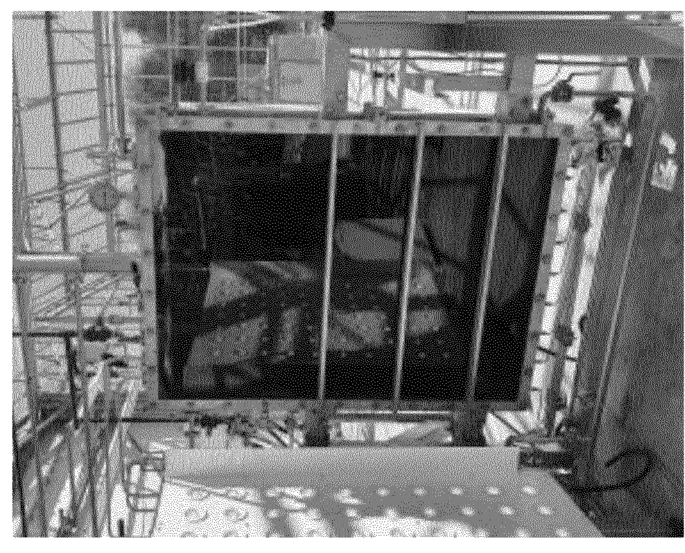
150 L PBR
(125 L of extracellular medium in 8 days)

FIGURE 10 (continuation)
B
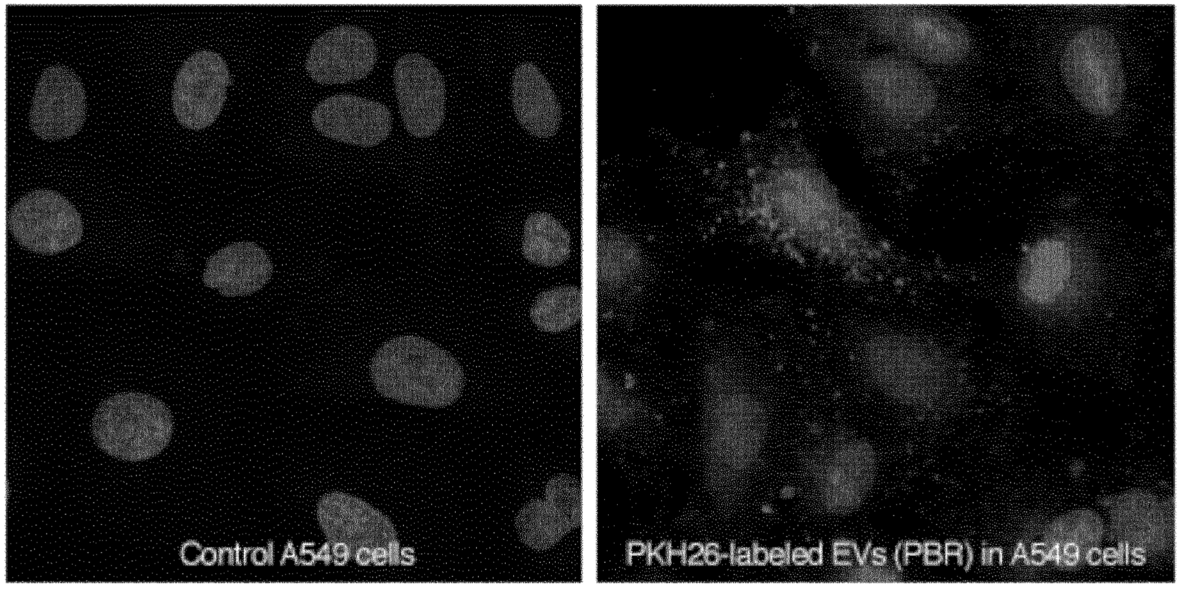
C
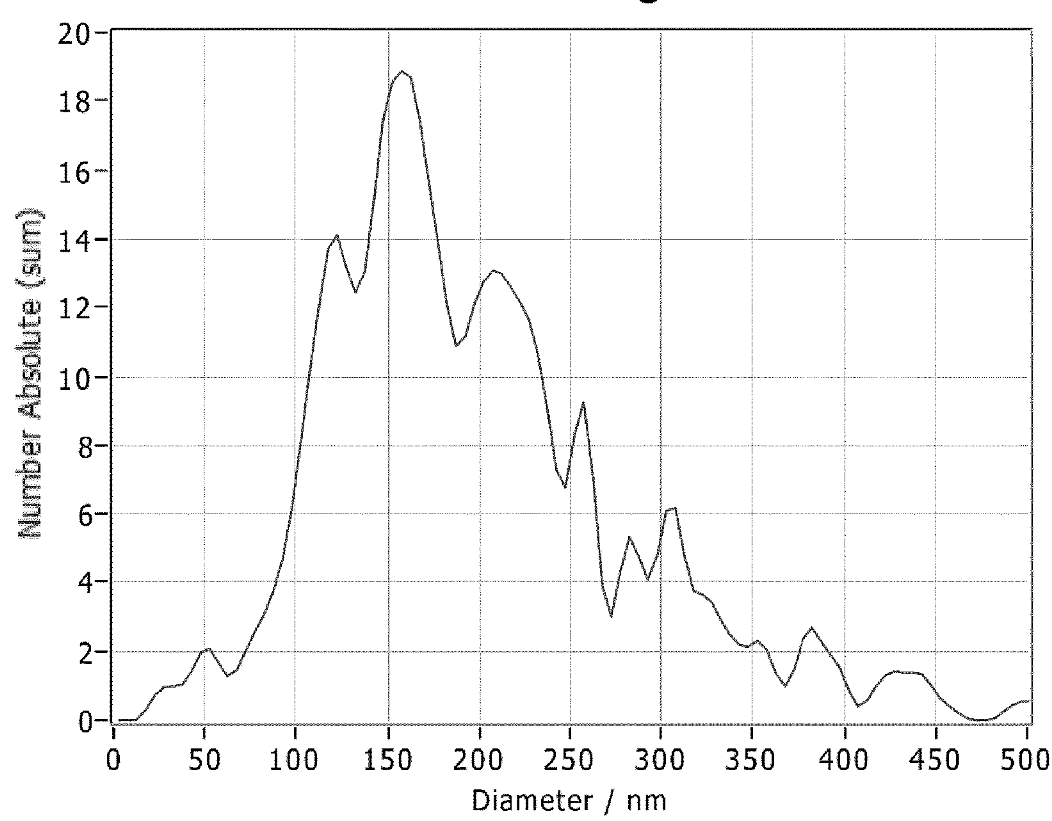

FIGURE 10 (continuation)
D
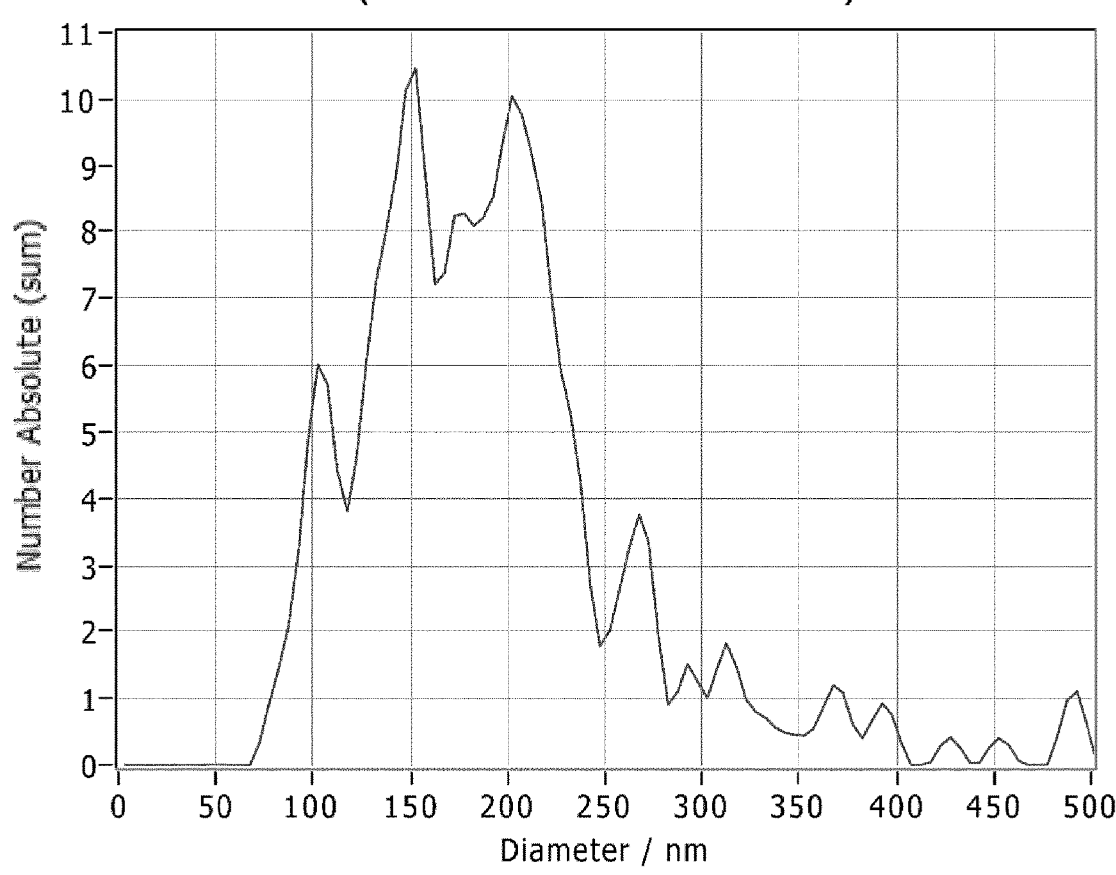

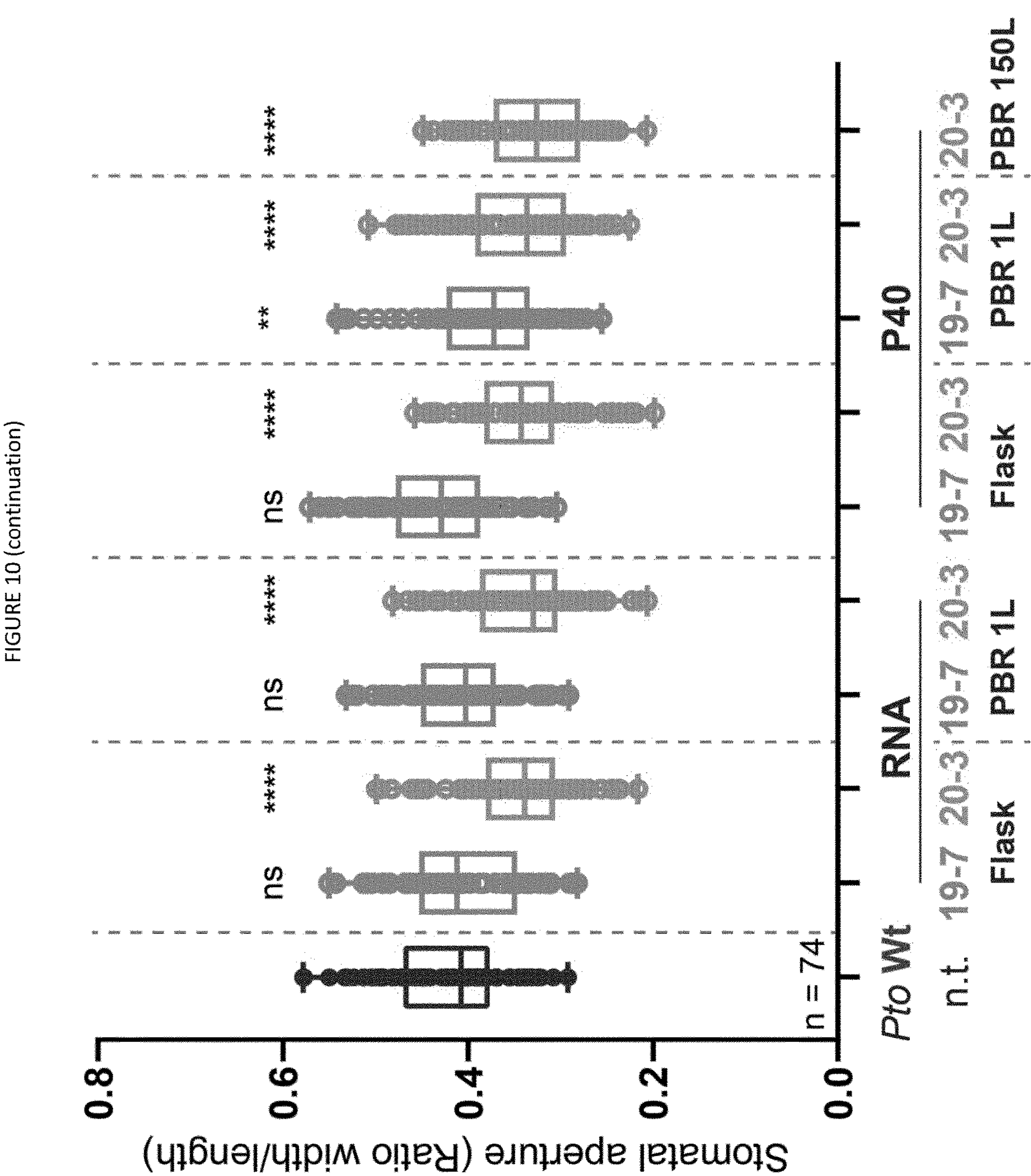
FIGURE 10 (continuation)
E

FIGURE 11
A
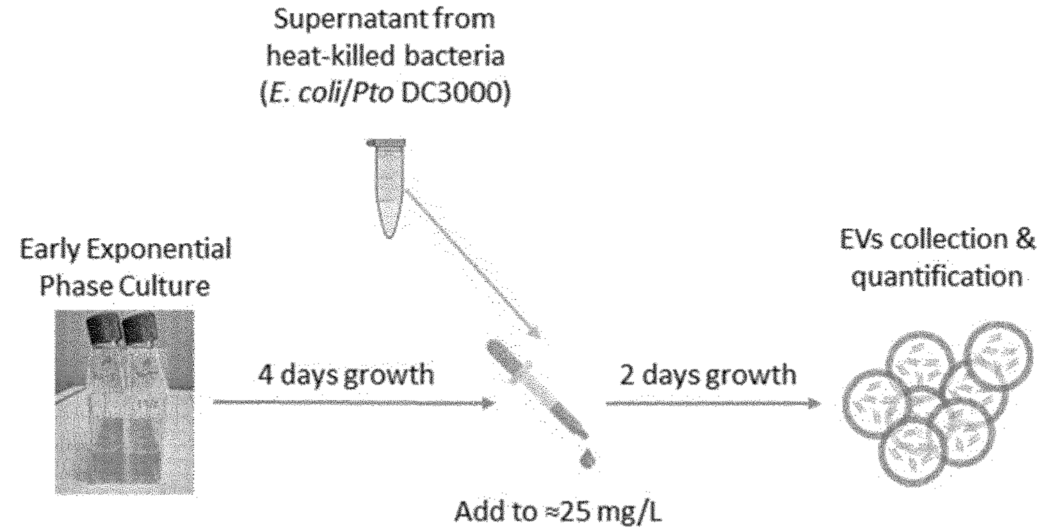
Growth conditions: No shaking, 25°C, ≈100 µmol $s^{-1}$ $m^{-2}$ white light, 14h/10h light/dark
B
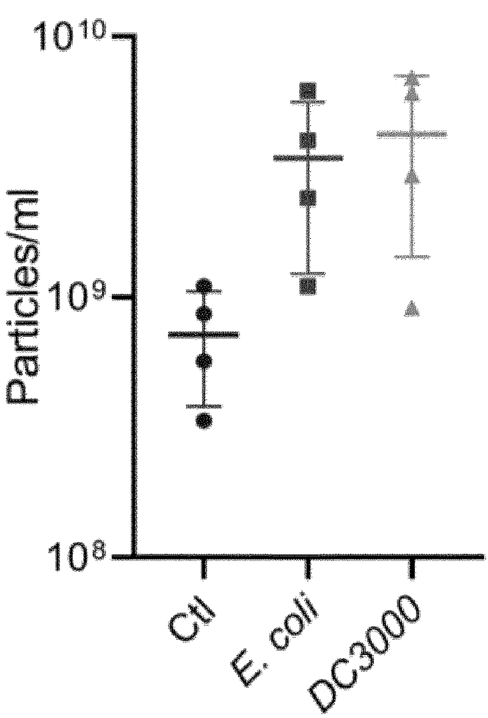

SEQUENCE LISTING

<160> NUMBER OF SEQ ID NOS: 107

<210> SEQ ID NO 1
<211> LENGTH: 1065
<212> TYPE: DNA
<213> ORGANISM: artificial
<220> FEATURE:
<223> OTHER INFORMATION: Sequence of the first arm of the Nsp1/Nsp13/Nsp4/Nsp3/Nsp5/Nsp12/Nsp14 dsRNA used to concomitantly target Nsp1, Nsp13, Nsp4, Nsp5, Nsp3, Nsp12 and Nsp14 genes from SARS-CoV-2

<400> SEQUENCE: 1
atggagagcc ttgtccctgg tttcaacgag aaaacacacg tccaactcag tttgcctgtt 60
ttacaggttc gcgacgtgct cgtacgtggc tttggagact ccgtggagga ggtcttatca 120
gaggcacgtc aacatcttaa agatggcact tgtggcttga tcgctgttgg ggcttgtgtt 180
ctttgcaatt cacagacttc attaagatgt ggtgcttgca tacgtagacc attcttatgt 240
tgtaaatgct gttacgacca tgtcatatca acatcacata aattagtctt gtctgttaat 300
ccgtatgttt gcaatgctcc atgcacactt gtgttccttt ttgttgctgc tattttctat 360
ttaataacac ctgttcatgt catgtctaaa catactgact tttcaagtga aatcatagga 420
tacaaggcta ttgatggtgg tgtcactcgt gacatagcat ctacagtgcg caccaacaaa 480
ggttactttt ggtgatgaca ctgtgataga agtgcaaggt tacaagagtg tgaatatcac 540
ttttgaactt gatgaaagga ttgataaagt acttaatgag aagtgctctg cctatacagt 600

```
tgaactcggt acagaagaag cagtggtttt agaaaaatgg cattcccatc tggtaaagtt    660

gagggttgta tggtacaagt aacttgtggt acaactacac ttaacggtct ttggcttgat    720

gacgtagttt actgtccaag acatgtgatc tgcacctctg aagacatgct ccatgttgga    780

ctgagactga ccttactaaa ggacctcatg aattttgctc tcaacataca atgctagtta    840

aacagggtga tgattatgtg taccttcctt acccagatcc atcaagaatc ctaggggccg    900

gctgttttgt agatgagtca gctgaaaatg taacaggact ctttaaagat tgtagtaagg    960

taatcactgg gttacatcct acacaggcac ctacacacct cagtgttgac actaaattca   1020

aaactgaagg tttatgtgtt gacatacctg gcatacctaa ggaca                   1065
```

```
<210> SEQ ID NO 2
<211> LENGTH: 1065
<212> TYPE: DNA
<213> ORGANISM: artificial
<220> FEATURE:
<223> OTHER INFORMATION: Sequence of the second arm of the
      Nsp1/Nsp13/Nsp4/Nsp3/Nsp5/Nsp12/Nsp14 dsRNA used to concomitantly
      target Nsp1, Nsp13, Nsp4, Nsp5, Nsp3, Nsp12 and Nsp14 genes from
      SARS-CoV-2Sequence

<400> SEQUENCE: 2

tgtccttagg tatgccaggt atgtcaacac ataaaccttc agttttgaat ttagtgtcaa     60

cactgaggtg tgtaggtgcc tgtgtaggat gtaacccagt gattacctta ctacaatctt    120

taaagagtcc tgttacattt tcagctgact catctacaaa acagccggcc cctaggattc    180

ttgatggatc tgggtaagga aggtacacat aatcatcacc ctgtttaact agcattgtat    240

gttgagagca aaattcatga ggtcctttag taaggtcagt ctcagtccaa catggagcat    300

gtcttcagag gtgcagatca catgtcttgg acagtaaact acgtcatcaa gccaaagacc    360

gttaagtgta gttgtaccac aagttacttg taccatacaa ccctcaactt taccagatgg    420

gaatgccatt tttctaaaac cactgcttct tctgtaccga gttcaactgt ataggcagag    480

cacttctcat taagtacttt atcaatcctt tcatcaagtt caaaagtgat attcacactc    540

ttgtaacctt gcacttctat cacagtgtca tcaccaaaag taacctttgt tggtgcgcac    600

tgtagatgct atgtcacgag tgacaccacc atcaatagcc ttgtatccta tgatttcact    660

tgaaaagtca gtatgtttag acatgacatg aacaggtgtt attaaataga aaatagcagc    720

aacaaaaagg aacacaagtg tgcatggagc attgcaaaca tacggattaa cagacaagac    780

taatttatgt gatgttgata tgacatggtc gtaacagcat ttacaacata agaatggtct    840

acgtatgcaa gcaccacatc ttaatgaagt ctgtgaattg caaagaacac aagccccaac    900

agcgatcaag ccacaagtgc catctttaag atgttgacgt gcctctgata agacctcctc    960

cacggagtct ccaaagccac gtacgagcac gtcgcgaacc tgtaaaacag gcaaactgag   1020

ttggacgtgt gttttctcgt tgaaaccagg gacaaggctc tccat                   1065
```

```
<210> SEQ ID NO 3
<211> LENGTH: 898
<212> TYPE: DNA
<213> ORGANISM: artificial
<220> FEATURE:
<223> OTHER INFORMATION: Sequence of the first arm of the
      E/M/N/S/Leader/TRS/3'UTR dsRNA used to concomitantly target E, M,
      N, S, subgenomic 5' leader, TRS and 3'UTR genes and regions from
      SARS-CoV-2

<400> SEQUENCE: 3
```

```
atgtactcat tcgtttcgga agagacaggt acgttaatag ttaatagcgt acttcttttt     60

cttgctttcg tggtattctt gctagttaca ctagccatcc ttactgcgct tcgattgtgt    120

gcgtactgct gcaatattgt gatcggcaga ttccaacggt actattaccg ttgaagagct    180

taaaaagctc cttgaacaat ggaacctagt aataggtttc ctattcctta catggatttg    240

tcttctacaa tttgcctatg ccaacaggaa taggtttttg tatataatta agttaatttt    300

cctctggctg tatgcatgtc tgataatgga ccccaaaatc agcgaaatgc accccgcatt    360

acgtttggtg gaccctcaga ttcaactggc agtaaccaga atggagaacg cagtggggcg    420

cgatcaaaac aacgtcggcc ccaaggttta cccaataata ctgcgtcttg gttcaccgct    480

ctcagtgcat gtttgttttt cttgttttat tgccactagt ctctagtcag tgtgttaatc    540

ttacaaccag aactcaatta ccccctgcat acactaattc tttcacacgt ggtgtttatt    600

accctgacaa agttttcaga tcctcagttt tacattcaac tcaggacttg ttcttaccgt    660

ttagaagcag gtaacaaacc aaccaacttt cgatctcttg tagatctgtt ctctaaacga    720

actccactaa actaaactca tgcagaccac acaaggcaga tgggctatat aaacgttttc    780

gcttttccgt ttacgatata tagtctactc ttgtgcagaa tgaattctcg taactacata    840

gcacaagtag atgtagttaa ctttaatctc acatagcaat ctttaatcag tgtgtaac      898
```

```
<210> SEQ ID NO 4
<211> LENGTH: 898
<212> TYPE: DNA
<213> ORGANISM: artificial
<220> FEATURE:
<223> OTHER INFORMATION: Sequence of the first arm of the
      E/M/N/S/Leader/TRS/3'UTR dsRNA used to concomitantly target E, M,
      N, S, subgenomic 5' leader, TRS and 3'UTR genes and regions from
      SARS-CoV-2

<400> SEQUENCE: 4

gttacacact gattaaagat tgctatgtga gattaaagtt aactacatct acttgtgcta     60

tgtagttacg agaattcatt ctgcacaaga gtagactata tatcgtaaac ggaaaagcga    120

aaacgtttat atagcccatc tgccttgtgt ggtctgcatg agtttagttt agtggagttc    180

gtttagagaa cagatctaca agagatcgaa agttggttgg tttgttacct gcttcgttta    240

ggtaagaaca agtcctgagt tgaatgtaaa actgaggatc tgaaaacttt gtcagggtaa    300

taaacaccac gtgtgaaaga attagtgtat gcagggggta attgagttct ggttgtaaga    360

ttaacacact gactagagac tagtggcaat aaaacaagaa aaacaaacat gcactgagag    420

cggtgaacca agacgcagta ttattgggta aaccttgggg ccgacgttgt tttgatcgcg    480

ccccactgcg ttctccattc tggttactgc cagttgaatc tgagggtcca ccaaacgtaa    540

tgcggggtgc atttcgctga ttttggggtc cattatcaga catgcataca gccagaggaa    600

aattaactta attatataca aaaacctatt cctgttggca taggcaaatt gtagaagaca    660

aatccatgta aggaatagga aacctattac taggttccat tgttcaagga gctttttaag    720

ctcttcaacg gtaatagtac cgttggaatc tgccgatcac aatattgcag cagtacgcac    780

acaatcgaag cgcagtaagg atggctagtg taactagcaa gaataccacg aaagcaagaa    840

aaagaagtac gctattaact attaacgtac ctgtctcttc cgaaacgaat gagtacat      898

<210> SEQ ID NO 5
<211> LENGTH: 1026
<212> TYPE: DNA
<213> ORGANISM: artificial
<220> FEATURE:
```

<223> OTHER INFORMATION: Sequence of the first arm of the Rpl13/eIF3e/eIF3l/eIF3F dsRNA used to concomitantly target Rpl13, eIF3e, eIF3I and eIF3F genes from Homo sapiens

<400> SEQUENCE: 5

```
ccgctccaaa ctcatcctct tccccaggaa gccctcggcc cccaagaagg gagacagttc     60

tgctgaagaa ctgaaactgg ccacccagct gaccggaccg gtcatgcccg tccggaacgt    120

ctataagaag gagaaagctc gagtcatcac tgaggaagag aagaatttca aagccttcgc    180

tagtctccgt atggcccgtg ccaacgcccg gctcttcggc atacgggcaa aaagagccaa    240

ggaagccgca gaacaggatg gatcccaggg atggtaggat gctctttgac tacctggcgg    300

acaagcatgg ttttaggcag gaatatttag atacactcta cagatatgca aaattccagt    360

acgaatgtgg gaattactca ggagcagcag aatatcttta ttttttttaga gtgctggttc    420

cagcaacaga tagaaatgct ttaagttcac tctggggaaa gctggcctct gaaatcttaa    480

tgcagaattg ggatgcagcc atggaagaca tgccaccaag catgtcctca ctggctcagc    540

tgacaacagc tgtcgtctct gggactgtga aacaggaaag cagctggccc ttctcaagac    600

caattcggct gtccggacct gcggttttga ctttgggggc aacatcatca tgttctccac    660

ggacaagcag atgggctacc agtgctttgt gagctttttt gacctgcggg atccgagcca    720

gattgacaac aatgagccct acatgaagat ccgtgctgtg gacagctacg agagacgcaa    780

cgagggtgct gcccgagtta tcgggaccct gttgggaact gtcgacaaac actcagtgga    840

ggtcaccaat tgcttttcag tgccgcacaa tgagtcagaa gatgaagtgg ctgttgacat    900

ggaatttgct aagaatatgt atgaactgca taaaaaagtt tctccaaatg agctcatcct    960

gggctggtac gctacgggcc atgacatcac agagcactct gtgctgatcc acgagtacta   1020

cagccg                                                              1026
```

<210> SEQ ID NO 6
<211> LENGTH: 1026
<212> TYPE: DNA
<213> ORGANISM: artificial
<220> FEATURE:
<223> OTHER INFORMATION: Sequence of the second arm of the Rpl13/eIF3e/eIF3l/eIF3F dsRNA used to concomitantly target Rpl13, eIF3e, eIF3I and eIF3F genes from Homo sapiens

<400> SEQUENCE: 6

```
cggctgtagt actcgtggat cagcacagag tgctctgtga tgtcatggcc cgtagcgtac     60

cagcccagga tgagctcatt tggagaaact tttttatgca gttcatacat attcttagca    120

aattccatgt caacagccac ttcatcttct gactcattgt gcggcactga aaagcaattg    180

gtgacctcca ctgagtgttt gtcgacagtt cccaacaggg tcccgataac tcgggcagca    240

ccctcgttgc gtctctcgta gctgtccaca gcacggatct tcatgtaggg ctcattgttg    300

tcaatctggc tcggatcccg caggtcaaaa aagctcacaa agcactggta gcccatctgc    360

ttgtccgtgg agaacatgat gatgttgccc ccaaagtcaa aaccgcaggt ccggacagcc    420

gaattggtct tgagaagggc cagctgcttt cctgtttcac agtcccagag acgacagctg    480

ttgtcagctg agccagtgag gacatgcttg gtggcatgtc ttccatggct gcatcccaat    540

tctgcattaa gatttcagag gccagctttc cccagagtga acttaaagca tttctatctg    600

ttgctggaac cagcactcta aaaaaataaa gatattctgc tgctcctgag taattcccac    660

attcgtactg gaattttgca tatctgtaga gtgtatctaa atattcctgc ctaaaaccat    720

gcttgtccgc caggtagtca aagagcatcc taccatccct gggatccatc ctgttctgcg    780
```

```
gcttccttgg ctctttttgc ccgtatgccg aagagccggg cgttggcacg ggccatacgg    840

agactagcga aggctttgaa attcttctct tcctcagtga tgactcgagc tttctccttc    900

ttatagacgt tccggacggg catgaccggt ccggtcagct gggtggccag tttcagttct    960

tcagcagaac tgtctccctt cttgggggcc gagggcttcc tggggaagag gatgagtttg   1020

gagcgg                                                               1026
```

```
<210> SEQ ID NO 7
<211> LENGTH: 704
<212> TYPE: DNA
<213> ORGANISM: artificial
<220> FEATURE:
<223> OTHER INFORMATION: Sequence of the first arm of the eEIF1A/eIF4A
      dsRNA used to concomitantly target eEIF1A and eEIF4A genes from H.
      sapiens

<400> SEQUENCE: 7

cctaaaagcc aaaatgggaa aggaaaagac tcatatcaac attgtcgtca ttggacacgt     60

agattcgggc aagtccacca ctactggcca tctgatctat aaatgcggtg gcatcgacaa    120

aagaaccatt gaaaaatttg agaaggaggc tgctgagatg ggaaagggct ccttcaagta    180

tgcctgggtc ttggataaac tgaaagctga gcgtgaacgt ggtatcacca ttgatatctc    240

cttgtggaaa tttgagacca gcaagtacta tgtgactatc attgatgccc caggacacag    300

agactttatc aaaaacatga ttacagggac atctcaggct gactgtgctg gatcaatggc    360

cccgatggga tggagcccga aggcgtcatc gagagtaact ggaatgagat tgttgacagc    420

tttgatgaca tgaacctctc ggagtccctt ctccgtggca tctacgcgta tggttttgag    480

aagccctctg ccatccagca gcgagccatt ctaccttgta tcaagggtta tgatgtgatt    540

gctcaagccc aatctgggac tgggaaaacg gccacatttg ccatatcgat tctgcagcag    600

attgaattag atctaaaagc cacccaggcc ttggtcctag cacccactcg agaattggct    660

cagcagatac agaaggtggt catggcacta ggagactaca tggg                     704
```

```
<210> SEQ ID NO 8
<211> LENGTH: 704
<212> TYPE: DNA
<213> ORGANISM: artificial
<220> FEATURE:
<223> OTHER INFORMATION: Sequence of the second arm of the eEIF1A/eIF4A
      dsRNA used to concomitantly target eEIF1A and eEIF4A genes from H.
      sapiens

<400> SEQUENCE: 8

cccatgtagt ctcctagtgc catgaccacc ttctgtatct gctgagccaa ttctcgagtg     60

ggtgctagga ccaaggcctg ggtggctttt agatctaatt caatctgctg cagaatcgat    120

atggcaaatg tggccgtttt cccagtccca gattgggctt gagcaatcac atcataaccc    180

ttgatacaag gtagaatggc tcgctgctgg atggcagagg gcttctcaaa accatacgcg    240

tagatgccac ggagaaggga ctccgagagg ttcatgtcat caaagctgtc aacaatctca    300

ttccagttac tctcgatgac gccttcgggc tccatcccat cggggccatt gatccagcac    360

agtcagcctg agatgtccct gtaatcatgt ttttgataaa gtctctgtgt cctggggcat    420

caatgatagt cacatagtac ttgctggtct caaatttcca caaggagata tcaatggtga    480

taccacgttc acgctcagct ttcagtttat ccaagaccca ggcatacttg aaggagccct    540

ttcccatctc agcagcctcc ttctcaaatt tttcaatggt tcttttgtcg atgccaccgc    600
```

```
atttatagat cagatggcca gtagtggtgg acttgcccga atctacgtgt ccaatgacga    660

caatgttgat atgagtcttt tcctttccca ttttggcttt tagg                     704


<210> SEQ ID NO 9
<211> LENGTH: 1052
<212> TYPE: DNA
<213> ORGANISM: artificial
<220> FEATURE:
<223> OTHER INFORMATION: Sequence of the first arm of the
      Snrpe/Naca/Kif11l/Gbf1/Srp54 dsRNA used to concomitantly target
      Snrpe, Naca, Kif11, Gbf1 and Srp54 genes from Homo sapiens

<400> SEQUENCE: 9

gggtcagaaa gtgcagaagg ttatggtgca gcccatcaac ctcatcttca gatacttaca     60

aaatagatcg cggattcagg tgtggctcta tgagcaagtg aatatgcgga tagaaggctg    120

tatcattggt tttgatgagt atatgaacct tgtattagat gatgcagaag agattcattc    180

taaaacaaag tcaagaaaac aactgggtcg gatcatgcta gatcaatttc tgccgtcctc    240

tcctgggctg gtgttggaat caccctctaa accccttgcc cctgctgatg aggatgagct    300

gctgcctctg attcccccgg aaccaatctc tgggggagtg cctttccagt cggtcctcgt    360

caacatgccc acccctaaat ctgctggaat ccctgtccca acccccctctg ccaagcaacc    420

tgttacgaaa tgcaggtggt ggtgagatgc agaccattta atttggcaga gcggaaagct    480

agcgcccatt caatagtaga atgtgatcct gtacgaaaag aagttagtgt acgaactgga    540

ggattggctg acaagagctc aaggaaaaca tacacttttg atatggtgtt tggagcatct    600

actaaacaga ttgatgttta ccgaagtgtt gtttgtccag tgcgggatcc tctgctgcat    660

agtttcggtc atctaaagga ggttttaaac agtataacag aactctcaga aattgagccc    720

aatgtattcc ttcgaccttt tctggaagtg attcgctctg aagataccac tggccctatc    780

actggactgg cactcacctc tgtcaacaag ttcctgtcct atgcactcat agatcccacc    840

caagcatacc tgtctgtctg ctcccagctt tcttgggttt cttccgacgg cgtggggcct    900

cgctaaggaa ttcccggccc ctcagggcca cggctttagc ggtgtctttt gcgagttctt    960

cgtaagtaca tcttaaagct gtcaagatgg ttctagcaga ccttggaaga aaaataacat   1020

cagcattacg ctcgttgagc aatgccacca tt                                 1052


<210> SEQ ID NO 10
<211> LENGTH: 1052
<212> TYPE: DNA
<213> ORGANISM: artificial
<220> FEATURE:
<223> OTHER INFORMATION: Sequence of the second arm of the
      Snrpe/Naca/Kif11l/Gbf1/Srp54 dsRNA used to concomitantly target
      Snrpe, Naca, Kif11, Gbf1 and Srp54 genes from Homo sapiens

<400> SEQUENCE: 10

aatggtggca ttgctcaacg agcgtaatgc tgatgttatt tttcttccaa ggtctgctag     60

aaccatcttg acagctttaa gatgtactta cgaagaactc gcaaaagaca ccgctaaagc    120

cgtggccctg aggggccggg aattccttag cgaggcccca cgccgtcgga agaaacccaa    180

gaaagctggg agcagacaga caggtatgct tgggtgggat ctatgagtgc ataggacagg    240

aacttgttga cagaggtgag tgccagtcca gtgatagggc cagtggtatc ttcagagcga    300

atcacttcca gaaaaggtcg aaggaataca ttgggctcaa tttctgagag ttctgttata    360

ctgtttaaaa cctcctttag atgaccgaaa ctatgcagca gaggatcccg cactggacaa    420

acaacacttc ggtaaacatc aatctgttta gtagatgctc caaacaccat atcaaaagtg    480
```

```
tatgttttcc ttgagctctt gtcagccaat cctccagttc gtacactaac ttcttttcgt    540

acaggatcac attctactat tgaatgggcg ctagctttcc gctctgccaa attaaatggt    600

ctgcatctca ccaccacctg catttcgtaa caggttgctt ggcagagggg gttgggacag    660

ggattccagc agatttaggg gtgggcatgt tgacgaggac cgactggaaa ggcactcccc    720

cagagattgg ttccggggga atcagaggca gcagctcatc ctcatcagca ggggcaaggg    780

gtttagaggg tgattccaac accagcccag gagaggacgg cagaaattga tctagcatga    840

tccgacccag ttgttttctt gactttgttt tagaatgaat ctcttctgca tcatctaata    900

caaggttcat atactcatca aaaccaatga tacagccttc tatccgcata ttcacttgct    960

catagagcca cacctgaatc cgcgatctat tttgtaagta tctgaagatg aggttgatgg   1020

gctgcaccat aaccttctgc actttctgac cc                                 1052
```

```
<210> SEQ ID NO 11
<211> LENGTH: 1052
<212> TYPE: DNA
<213> ORGANISM: artificial
<220> FEATURE:
<223> OTHER INFORMATION: Sequence of the first arm of the
      ACE2/TMPRSS2/Psmd1/KpnA1/IMP B1 dsRNA used to concomitantly target
      ACE2, TMPRSS2, Psmd1, KpnA1 and IMP B1 genes from Homo sapiens

<400> SEQUENCE: 11

gctgctcagt ccaccattga ggaacaggcc aagacatttt tggacaagtt taaccacgaa     60

gccgaagacc tgttctatca aagttcactt gcttcttgga attataacac caatattact    120

gaagagaatg tccaaaacat gaataatgct ggggacaaat ggtctgcctt tttaaaggaa    180

cagtccacac ttgcccaaat ggatctggag ccggatacca agtagaaaaa gtgatttctc    240

atccaaatta tgactccaag accaagaaca atgacattgc gctgatgaag ctgcagaagc    300

ctctgacttt caacgaccta gtgaaaccag tgtgtctgcc caacccaggc atgatgctgc    360

agccagaaca gctctgctgg atttccgggt ggggggccac cgaggagaaa gggaagaatg    420

cgggacctct tcaatgtcaa tgataactct gaatatgtgg aaactattat agcaaaatgc    480

attgatcact acaccaaaca atgtgtggaa aatgcagatt tgcctgaagg agaaaaaaaa    540

ccaattgacc agagattgga aggcatcgta aataaaatgt tccagcgatg tctagatgat    600

cacaagtata aacaggctat tggcattgct ctggagacag tgccagatgg aggctttcat    660

gaggctcaga ttagtaacat ggagatggca ccaggtggtg tcatcacttc tgacatgatt    720

gaaatgatat tttccaaaag cccagagcaa cagctttcag caacacagaa attcaggaag    780

ctgctttcaa aagaacctaa ccctcctatt gatgaagtta tcagcacacc aggagtagtg    840

aagcacagtc aggttgccag agttgcagct ggtctacaaa tcaagaactc tttgacatct    900

aaagatccag atatcaaggc acaatatcag cagaggtggc ttgctattga tgctaatgct    960

cgacgagaag tcaagaacta tgttttgcag acattgggta cagaaactta ccggcctagt   1020

tctgcctcac agtgtgtggc tggtattgct tg                                 1052
```

```
<210> SEQ ID NO 12
<211> LENGTH: 1052
<212> TYPE: DNA
<213> ORGANISM: artificial
<220> FEATURE:
<223> OTHER INFORMATION: Sequence of the second arm of the
      ACE2/TMPRSS2/Psmd1/KpnA1/IMP B1 dsRNA used to concomitantly target
      ACE2, TMPRSS2, Psmd1, KpnA1 and IMP B1 genes from Homo sapiens
```

<400> SEQUENCE: 12

```
caagcaatac cagccacaca ctgtgaggca gaactaggcc ggtaagtttc tgtacccaat     60
gtctgcaaaa catagttctt gacttctcgt cgagcattag catcaatagc aagccacctc    120
tgctgatatt gtgccttgat atctggatct ttagatgtca aagagttctt gatttgtaga    180
ccagctgcaa ctctggcaac ctgactgtgc ttcactactc ctggtgtgct gataacttca    240
tcaataggag ggttaggttc ttttgaaagc agcttcctga atttctgtgt tgctgaaagc    300
tgttgctctg ggcttttgga aaatatcatt tcaatcatgt cagaagtgat gacaccacct    360
ggtgccatct ccatgttact aatctgagcc tcatgaaagc ctccatctgg cactgtctcc    420
agagcaatgc caatagcctg tttatacttg tgatcatcta gacatcgctg gaacatttta    480
tttacgatgc cttccaatct ctggtcaatt ggtttttttt ctccttcagg caaatctgca    540
ttttccacac attgtttggt gtagtgatca atgcattttg ctataatagt ttccacatat    600
tcagagttat cattgacatt gaagaggtcc cgcattcttc cctttctcct cggtggcccc    660
ccacccggaa atccagcaga gctgttctgg ctgcagcatc atgcctgggt tgggcagaca    720
cactggtttc actaggtcgt tgaaagtcag aggcttctgc agcttcatca gcgcaatgtc    780
attgttcttg gtcttggagt cataatttgg atgagaaatc actttttcta cttggtatcc    840
ggctccagat ccatttgggc aagtgtggac tgttccttta aaaaggcaga ccatttgtcc    900
ccagcattat tcatgttttg gacattctct tcagtaatat tggtgttata attccaagaa    960
gcaagtgaac tttgatagaa caggtcttcg gcttcgtggt taaacttgtc caaaaatgtc   1020
ttggcctgtt cctcaatggt ggactgagca gc                                 1052
```

<210> SEQ ID NO 13
<211> LENGTH: 758
<212> TYPE: DNA
<213> ORGANISM: artificial
<220> FEATURE:
<223> OTHER INFORMATION: Sequence of the first arm of the LptH/LolA/TolB dsRNA used to concomitantly target LptH, LolA and TolB genes genes from P. aeruginosa:

<400> SEQUENCE: 13

```
atgaggttcg ttaataccct ccccccttatt ttcggtctga ctgccgccct cggcagctcc     60
atggccttgg ccctgccttc ggaccgcgaa caaccgatcc gcgtccaggc cgacagcgcc    120
gaactggacg acaagcaggg cgtcgcggtc taccgcggcg acgtcgtggt gacccagggc    180
agcaccaagc tgaccggcaa caccgtgacc ctgaagcagg acaagaacgg cgacatcgag    240
gtcgtgacct gatcatgcga ctgatccgca cgttgttcgt tgccgccctg gccatgggcg    300
cttcgctggc ccatgccgac gacagcgccg ccgtccagcg cctgaccggc ctgctgaaca    360
aggcccagac cctgaccgcg cgtttttccc agctgaccct ggacggtagc ggcacgcgcc    420
tgcaggaaac cgccggccaa ctgagcctga agcggccggg actgttccgc tggcataccg    480
atgcgccgaa cgagcaattg ctcagcatgt gagtaccctg attcgcattg cgctgttcgc    540
cctggccctg atggcaggtg ctgcgcaggc tgccgacccg ctggtgatct ccagcggtaa    600
cgaccgtgcc attcccatcg ccgtggtgcc gttcggcttc caggggggca acgtgttgcc    660
ggaagacatg tccaatatca tcggcaacga cctgcgcaac tccggctact tcgagccgct    720
gccccggcag aacatgatca gccagccggc gcaggcca                           758
```

<210> SEQ ID NO 14
<211> LENGTH: 758

<212> TYPE: DNA
<213> ORGANISM: artificial
<220> FEATURE:
<223> OTHER INFORMATION: Sequence of the second arm of the LptH/LolA/TolB dsRNA used to concomitantly target LptH, LolA and TolB genes from P. aeruginosa

<400> SEQUENCE: 14

```
tggcctgcgc cggctggctg atcatgttct gccggggcag cggctcgaag tagccggagt     60

tgcgcaggtc gttgccgatg atattggaca tgtcttccgg caacacgttg ccccccctgga   120

agccgaacgg caccacggcg atgggaatgg cacggtcgtt accgctggag atcaccagcg    180

ggtcggcagc ctgcgcagca cctgccatca gggccagggc gaacagcgca atgcgaatca    240

gggtactcac gcattgagca attgctcgtt cggcgcatcg gtatgccagc ggaacagtcc    300

cggccgcttc aggctcagtt ggccggcggt ttcctgcagg cgcgtgccgc taccgtccag    360

ggtcagctgg gaaaaacgcg cggtcagggt ctgggccttg ttcagcaggc cggtcaggcg    420

ctggacggcg gcgctgtcgt cggcatgggc cagcgaagcg cccatggcca gggcggcaac    480

gaacaacgtg cggatcagtc gcatgatcag gtcacgacct cgatgtcgcc gttcttgtcc    540

tgcttcaggg tcacggtgtt gccggtcagc ttggtgctgc cctgggtcac cacgacgtcg    600

ccgcggtaga ccgcgacgcc ctgcttgtcg tccagttcgg cgctgtcggc ctggacgcgg    660

atcggttgtt cgcggtccga aggcagggcc aaggccatgg agctgccgag ggcggcagtc    720

agaccgaaaa taagggggag ggtattaacg aacctcat                            758
```

<210> SEQ ID NO 15
<211> LENGTH: 758
<212> TYPE: DNA
<213> ORGANISM: artificial
<220> FEATURE:
<223> OTHER INFORMATION: Sequence of the first arm of the LpxA/LpxD/TolB dsRNA used to concomitantly target LpxA, LpxD and TolB genes from P. aeruginosa

<400> SEQUENCE: 15

```
atgagtttga tcgatcctcg cgccatcatc gatccgagcg ccaggctggc ggctgacgtc     60

caggtgggcc cgtggtccat cgtcggggcg gaagtggaga tcggtgaagg gacggtgatc    120

ggtccgcacg tggtgctcaa gggcccccacg aagatcggca agcacaaccg catctaccag   180

ttttccagcg tcggcgagga tactcccgac ctgaaataca agggcgagcc gacgcgcctg    240

gtgatcggtg gatcatgatg agtaccttgt cctacaccct gggccagctg gccgcgcatg    300

tcggcgcgga agtccgtggc gacgcggacc tgccaatcca gggcctggcg accttgcagg    360

aggccggacc ggctcagctg agcttcctgg ccaacccgca gtatcgcaag tacctgcccg    420

aaagccgtgc cggcgccgtc ctgctgacgg ctgccgacgc cgacgggttc gccggtaccg    480

cgctggtggt ggccaacccc taccgcatgt gagtaccctg attcgcattg cgctgttcgc    540

cctggccctg atggcaggtg ctgcgcaggc tgccgacccg ctggtgatct ccagcggtaa    600

cgaccgtgcc attcccatcg ccgtggtgcc gttcggcttc cagggggggca acgtgttgcc   660

ggaagacatg tccaatatca tcggcaacga cctgcgcaac tccggctact tcgagccgct    720

gccccggcag aacatgatca gccagccggc gcaggcca                            758
```

<210> SEQ ID NO 16
<211> LENGTH: 758
<212> TYPE: DNA
<213> ORGANISM: artificial
<220> FEATURE:

<223> OTHER INFORMATION: Sequence of the second arm of the LpxA/LpxD/TolB dsRNA used to concomitantly target LpxA, LpxD and TolB genes from P. aeruginosa

<400> SEQUENCE: 16

```
tggcctgcgc cggctggctg atcatgttct gccggggcag cggctcgaag tagccggagt     60

tgcgcaggtc gttgccgatg atattggaca tgtcttccgg caacacgttg ccccccctgga   120

agccgaacgg caccacggcg atgggaatgg cacggtcgtt accgctggag atcaccagcg   180

ggtcggcagc ctgcgcagca cctgccatca gggccagggc gaacagcgca atgcgaatca   240

gggtactcac gcatggtagg ggttggccac caccagcgcg gtaccggcga acccgtcggc   300

gtcggcagcc gtcagcagga cggcgccggc acggctttcg ggcaggtact tgcgatactg   360

cgggttggcc aggaagctca gctgagccgg tccggcctcc tgcaaggtcg ccaggccctg   420

gattggcagg tccgcgtcgc cacggacttc cgcgccgaca tgcgcggcca gctggcccag   480

ggtgtaggac aaggtactca tcatgatcca ccgatcacca ggcgcgtcgg ctcgcccttg   540

tatttcaggt cgggagtatc ctcgccgacg ctggaaaact ggtagatgcg gttgtgcttg   600

ccgatcttcg tggggccctt gagcaccacg tgcggaccga tcaccgtccc ttcaccgatc   660

tccacttccg ccccgacgat ggaccacggg cccacctgga cgtcagccgc cagcctggcg   720

ctcggatcga tgatggcgcg aggatcgatc aaactcat                            758
```

<210> SEQ ID NO 17
<211> LENGTH: 758
<212> TYPE: DNA
<213> ORGANISM: artificial
<220> FEATURE:
<223> OTHER INFORMATION: Sequence of the first arm of the secE/dnaN/gyrB dsRNA used to concomitantly target secE, dnaN and gyrB genes from P. aeruginosa

<400> SEQUENCE: 17

```
atgaatgcca aggcagaagc caaagaatca cgttttgatc tcttgaaatg gctcttggtt     60

gccgttctgg ttgtggttgc cgttgtgggc aatcagtact tttcggctca accaatcctg   120

tatcgcgttc tcggtattct cgttctggcg gtgatcgctg ctttcctggc tctgcaaacg   180

gccaaggggc aggccttctt tagtcttgct aaggaagcgc gcgtcgagat tcgcaaggtc   240

gtatggccga gatcatgcat ttcaccattc aacgcgaagc cctgttgaaa ccgctgcaac   300

tggtcgccgg cgtcgtggaa cgccgccaga cattgccggt tctctccaac gtcctgctgg   360

tggtcgaagg ccagcaactg tcgctgaccg gcaccgacct cgaagtcgag ctggttggtc   420

gcgtggtact ggaagatgcc gccgaacccg gcgagatcac cgtaccggcg cgcaagctga   480

tggacatctg caagagcctg ccgagcatat gagcgagaac aacacgtacg actcttccag   540

catcaaggtg ctgaaggggc tggatgccgt acgcaagcgc cccggcatgt acatcggcga   600

caccgacgat ggcaccggtc tgcaccacat ggtgttcgag gtggtggata actccatcga   660

cgaagcgctg gccggttact gcagcgaaat cagcatcacc atccatacgg atgagtcgat   720

cactgtccgc gacaatggac gcggtattcc ggtggata                            758
```

<210> SEQ ID NO 18
<211> LENGTH: 758
<212> TYPE: DNA
<213> ORGANISM: artificial
<220> FEATURE:
<223> OTHER INFORMATION: Sequence of the second arm of the secE/dnaN/gyrB dsRNA used to concomitantly target secE, dnaN and gyrB genes from P. aeruginosa

<400> SEQUENCE: 18

```
tatccaccgg aataccgcgt ccattgtcgc ggacagtgat cgactcatcc gtatggatgg     60
tgatgctgat ttcgctgcag taaccggcca gcgcttcgtc gatggagtta tccaccacct    120
cgaacaccat gtggtgcaga ccggtgccat cgtcggtgtc gccgatgtac atgccggggc    180
gcttgcgtac ggcatccagc cccttcagca ccttgatgct ggaagagtcg tacgtgttgt    240
tctcgctcat gcattcggca ggctcttgca gatgtccatc agcttgcgcg ccggtacggt    300
gatctcgccg ggttcggcgg catcttccag taccacgcga ccaaccagct cgacttcgag    360
gtcggtgccg gtcagcgaca gttgctggcc ttcgaccacc agcaggacgt tggagagaac    420
cggcaatgtc tggcggcgtt ccacgacgcc ggcgaccagt tgcagcggtt tcaacagggc    480
ttcgcgttga atggtgaaat gcatgatctc ggccatacga ccttgcgaat ctcgacgcgc    540
gcttccttag caagactaaa gaaggcctgc cccttggccg tttgcagagc caggaaagca    600
gcgatcaccg ccagaacgag aataccgaga acgcgataca ggattggttg agccgaaaag    660
tactgattgc ccacaacggc aaccacaacc agaacggcaa ccaagagcca tttcaagaga    720
tcaaaacgtg attctttggc ttctgccttg gcattcat                            758
```

<210> SEQ ID NO 19
<211> LENGTH: 1074
<212> TYPE: DNA
<213> ORGANISM: artificial
<220> FEATURE:
<223> OTHER INFORMATION: Sequence of the first arm of the XcpQ/ExsA/PcrV/LasR/RhlR/VqsM/RmsA dsRNA used to concomitantly target XcpQ, ExsA, PcrV, LasR, RhlR, VqsM and RmsA genes from P. aeruginosa

<400> SEQUENCE: 19

```
atgtcccagc ctttgctccg cgccctgttt gccccttcca gtcgttcgta cgttcccgcc     60
gtccttctca gcctggccct cggcatccag gcggcgcacg ccgaaaacag cggcgggaac    120
gccttcgtcc cggccggcaa ccagcaggag gatcatgcaa ggagccaaat ctcttggccg    180
aaagcagata acgtcttgtc attggaacat tccaactttc gaatacaggg taaacaagga    240
agagggcgta tatgttctgc tcgagggcga actgaccgtc caggacatcg attccacttt    300
ttgcgcatat ggaagtcaga aaccttaatg ccgctcgcga gctgttcctg gacgagctcc    360
tggccgcgtc ggcggcgcct gccagtgccg agcaggagga actgctggcc ctgttgcgca    420
gcgagcggat cgtgctggcc cacgccggcc agccgctgat gcatggcctt ggttgacggt    480
tttcttgagc tggaacgctc aagtggaaaa ttggagtgga gcgccatcct gcagaagatg    540
gcgagcgacc ttggattctc gaagatcctg ttcggcctgt tgcctaagga cagccaggac    600
tacgagaacg ccgtgcatga ggaatgacgg aggctttttg ctgtggtggg acggtttgcg    660
tagcgagatg cagccgatcc acgacagcca gggcgtgttc gccgtcctgg aaaaggaagt    720
gcggcgcctg ggcttcgatt actacgccta tggcgtgcgc cacacgaagc atggtgaccg    780
aacacatatt tgattttgaa tggcgccctc tgcagaacta tcttcgtgat cgtgatatcg    840
caataccacc ctttgcggca gaacaagagt caagaagtga cgcactttac aactggatag    900
tcagcaaggg gtattcagga tccaatgctg attctgactc gtcgggtcgg agagaccctg    960
atggtaggtg acgacgtcac cgtgacggta ctgggtgtca aagggaacca ggtgcgcatc   1020
ggcgtcaacg cgccgaagga agtcgccgta caccgggagg aaatttacca gcgc         1074
```

<210> SEQ ID NO 20
<211> LENGTH: 1074
<212> TYPE: DNA
<213> ORGANISM: artificial
<220> FEATURE:
<223> OTHER INFORMATION: Sequence of the second arm of the XcpQ/ExsA/PcrV/LasR/RhlR/VqsM/RmsA dsRNA used to concomitantly target XcpQ, ExsA, PcrV, LasR, RhlR, VqsM and RmsA genes from P. aeruginosa

<400> SEQUENCE: 20

```
gcgctggtaa atttcctccc ggtgtacggc gacttccttc ggcgcgttga cgccgatgcg     60

cacctggttc cctttgacac ccagtaccgt cacggtgacg tcgtcaccta ccatcagggt    120

ctctccgacc cgacgagtca gaatcagcat tgactcctga ataccccttg ctgactatcc    180

agttgtaaag tgcgtcactt cttgactctt gttctgccgc aaagggtggt attgcgatat    240

cacgatcacg aagatagttc tgcagagggc gccattcaaa atcaaatatg tgttcggtca    300

ccattggacg tgtggcgcac gccataggcg tagtaatcga agcccaggcg ccgcacttcc    360

ttttccagga cggcgaacac gccctggctg tcgtggatcg gctgcatctc gctacgcaaa    420

ccgtcccacc acagcaaaaa gcctccgtca ttcctcatgc ttggcgttct cgtagtcctg    480

gctgtcctta ggcaacaggc cgaacaggat cttcgagaat ccaaggtcgc tcgccatctt    540

ctgcaggatg gcgctccact ccaattttcc acttgagcgt tccagctcaa gaaaaccgtc    600

aaccaaggcc atgcaccagc ggctggccgg cgtgggccag cacgatccgc tcgctgcgca    660

acagggccag cagttcctcc tgctcggcac tggcaggcgc cgccgacgcg gccaggagct    720

cgtccaggaa cagctcgcga gcggcattaa ggtttctgac ttccatgcat gcaaaaagtg    780

gaatcgatgt cctggacggt cagttcgccc tcgagcagaa catatacgcc ctcttccttg    840

tttaccctgt attcgaaagt tggaatgttc caatgacaag acgttatctg ctttcggcca    900

agagatttgg ctccttgcat gatcctcctg ctggttgccg gccgggacga aggcgttccc    960

gccgctgttt tcggcgtgcg ccgcctggat gccgagggcc aggctgagaa ggacggcggg   1020

aacgtacgaa cgactggaag gggcaaacag ggcgcggagc aaaggctggg acat         1074
```

<210> SEQ ID NO 21
<211> LENGTH: 758
<212> TYPE: DNA
<213> ORGANISM: artificial
<220> FEATURE:
<223> OTHER INFORMATION: Sequence of the first arm of the XcpQ/PscF/PscC dsRNA used to concomitantly target XcpQ, PscF and PscC genes from P. aeruginosa

<400> SEQUENCE: 21

```
atgtcccagc ctttgctccg cgccctgttt gccccttcca gtcgttcgta cgttcccgcc     60

gtccttctca gcctggccct cggcatccag gcggcgcacg ccgaaaacag cggcgggaac    120

gccttcgtcc cggccggcaa ccagcaggag gcgcactgga cgatcaacct caaggatgcc    180

gacatccgcg aattcatcga ccagatttcc gaaatcaccg gcgagacctt cgtcgtcgac    240

ccgcgggtca gatctcagat cttctgcagg atgccttgca tcaggtcgcg cagcgcacgg    300

gtcaccgtcg agttgatgtt gtagatgacc gaccacttgt tgatcttgtg ttgcagctcg    360

gccagcagcg ccgggttgtc ggcattgtcg gtcccctgca aggccttgat cgcgtcgttg    420

acgtccttgt tcgctgcgtt ggcctgctcc ttcagggcat tggccacggt atcgagggta    480

ttccccgggt tggggttgaa tatcgcatat gcgccgcctg ctgatcggcg gactgctggc    540

gctgctgcct ggcgcggtct tgcgcgcgca gccgctggac tggcccagcc tgccttacga    600
```

```
ctatgtggcg cagggcgaaa gcctgcgcga cgtgctggcc aacttcggcg ccaactacga    660

tgcctcggtg atcgtcagcg acaaggtcaa cgaccaggtc agcggtcgct tcgacctgga    720

aagcccgcag gccttcctgc agttgatggc ctccctct                            758
```

<210> SEQ ID NO 22
<211> LENGTH: 758
<212> TYPE: DNA
<213> ORGANISM: artificial
<220> FEATURE:
<223> OTHER INFORMATION: Sequence of the second arm of the XcpQ/PscF/PscC dsRNA used to concomitantly target XcpQ, PscF and PscC genes from P. aeruginosa

<400> SEQUENCE: 22

```
agagggaggc catcaactgc aggaaggcct gcgggctttc caggtcgaag cgaccgctga     60

cctggtcgtt gaccttgtcg ctgacgatca ccgaggcatc gtagttggcg ccgaagttgg    120

ccagcacgtc gcgcaggctt tcgccctgcg ccacatagtc gtaaggcagg ctgggccagt    180

ccagcggctg cgcgcgcaag accgcgccag gcagcagcgc cagcagtccg ccgatcagca    240

ggcggcgcat gcatgatatt caaccccaac ccggggaata ccctcgatac cgtggccaat    300

gccctgaagg agcaggccaa cgcagcgaac aaggacgtca acgacgcgat caaggccttg    360

caggggaccg acaatgccga caacccggcg ctgctggccg agctgcaaca caagatcaac    420

aagtggtcgg tcatctacaa catcaactcg acggtgaccc gtgcgctgcg cgacctgatg    480

caaggcatcc tgcagaagat ctgagatctg acccgcgggt cgacgacgaa ggtctcgccg    540

gtgatttcgg aaatctggtc gatgaattcg cggatgtcgg catccttgag gttgatcgtc    600

cagtgcgcct cctgctggtt gccggccggg acgaaggcgt tcccgccgct gttttcggcg    660

tgcgccgcct ggatgccgag ggccaggctg agaaggacgg cgggaacgta cgaacgactg    720

gaaggggcaa acagggcgcg gagcaaaggc tgggacat                            758
```

<210> SEQ ID NO 23
<211> LENGTH: 758
<212> TYPE: DNA
<213> ORGANISM: artificial
<220> FEATURE:
<223> OTHER INFORMATION: Sequence of the first arm of the ExoS/ExsA/Vrf dsRNA used to concomitantly target ExoS, ExsA and Vrf genes from P. aeruginosa

<400> SEQUENCE: 23

```
atgcatattc aatcgcttca gcagagtccg tctttcgccg tcgaattgca ccaggccgcc     60

agtgggcgtt tgggacagat tgaggcccgc caggtcgcca cccccagtga agcgcagcag    120

ttggcccagc gccaggacgc gccgaagggt gaggggctgc tcgctcgctt gggtgcggca    180

ctcgtgcgtc ccttcgtggc gatcatggac tggctgggca agctgttggg ctcccacgcc    240

cgcaccggcc gatcatgcaa ggagccaaat ctcttggccg aaagcagata acgtcttgtc    300

attggaacat tccaactttc gaatacaggg taaacaagga agagggcgta tatgttctgc    360

tcgagggcga actgaccgtc caggacatcg attccacttt ttgcctggcg cctggcgagt    420

tgcttttcgt ccgccgcgga agctatgtcg taagtaccaa gggaaaggac agccgaatac    480

tctggattcc attatctgcc cagtgcatat ggtagctatt acccacacac ccaaactcaa    540

acacctagac aagctgctcg cacactgtca ccgccgccgc tacaccgcaa agagcaccat    600

catctatgcc ggcgatcgct gcgaaacgct gttcttcatc atcaagggtt cggtcaccat    660
```

```
cctcatcgag gacgacgacg gccgcgaaat gatcatcggc tacctcaaca gcggtgattt    720

cttcggcgag ctgggattgt tcgaaaagga aggcagcg                            758


<210> SEQ ID NO 24
<211> LENGTH: 758
<212> TYPE: DNA
<213> ORGANISM: artificial
<220> FEATURE:
<223> OTHER INFORMATION: Sequence of the second arm of the ExoS/ExsA/Vrf
      dsRNA used to concomitantly target ExoS, ExsA and Vrf genes from
      P. aeruginosa:

<400> SEQUENCE: 24

cgctgccttc cttttcgaac aatcccagct cgccgaagaa atcaccgctg ttgaggtagc     60

cgatgatcat ttcgcggccg tcgtcgtcct cgatgaggat ggtgaccgaa cccttgatga    120

tgaagaacag cgtttcgcag cgatcgccgg catagatgat ggtgctcttt gcggtgtagc    180

ggcggcggtg acagtgtgcg agcagcttgt ctaggtgttt gagtttgggt gtgtgggtaa    240

tagctaccat gcatactggg cagataatgg aatccagagt attcggctgt cctttccctt    300

ggtacttacg acatagcttc cgcggcggac gaaaagcaac tcgccaggcg ccaggcaaaa    360

agtggaatcg atgtcctgga cggtcagttc gccctcgagc agaacatata cgccctcttc    420

cttgtttacc ctgtattcga aagttggaat gttccaatga caagacgtta tctgctttcg    480

gccaagagat ttggctcctt gcatgatcgg ccggtgcggg cgtgggagcc caacagcttg    540

cccagccagt ccatgatcgc cacgaaggga cgcacgagtg ccgcacccaa gcgagcgagc    600

agcccctcac ccttcggcgc gtcctggcgc tgggccaact gctgcgcttc actgggggtg    660

gcgacctggc gggcctcaat ctgtcccaaa cgcccactgg cggcctggtg caattcgacg    720

gcgaaagacg gactctgctg aagcgattga atatgcat                            758


<210> SEQ ID NO 25
<211> LENGTH: 758
<212> TYPE: DNA
<213> ORGANISM: artificial
<220> FEATURE:
<223> OTHER INFORMATION: Sequence of the first arm of the ExoU/ExsA/Vrf
      dsRNA used to concomitantly target ExoU, ExsA and Vrf genes from
      P. aeruginosa

<400> SEQUENCE: 25

atgcatatcc aatcgttggg ggctactgcc tcctcgctga atcaggagcc tgtcgaaacc     60

ccgtcgcagg cagcgcataa gtccgccagc ttgcgtcagg aaccttcagg gcaaggtctc    120

ggggttgccc taaagagcac gccgggaata ctttccggga agttgccgga aagcgttagc    180

gacgtgcgtt tcagcagtcc ccaagggcaa ggggagtccc gtactctgac tgactcggca    240

gggccgcggc gatcatgcaa ggagccaaat ctcttggccg aaagcagata acgtcttgtc    300

attggaacat tccaactttc gaatacaggg taaacaagga agagggcgta tatgttctgc    360

tcgagggcga actgaccgtc caggacatcg attccacttt ttgcctggcg cctggcgagt    420

tgcttttcgt ccgccgcgga agctatgtcg taagtaccaa gggaaaggac agccgaatac    480

tctggattcc attatctgcc cagtgcatat ggtagctatt acccacacac ccaaactcaa    540

acacctagac aagctgctcg cacactgtca ccgccgccgc tacaccgcaa agagcaccat    600

catctatgcc ggcgatcgct gcgaaacgct gttcttcatc atcaagggtt cggtcaccat    660

cctcatcgag gacgacgacg gccgcgaaat gatcatcggc tacctcaaca gcggtgattt    720

cttcggcgag ctgggattgt tcgaaaagga aggcagcg                            758
```

<210> SEQ ID NO 26
<211> LENGTH: 758
<212> TYPE: DNA
<213> ORGANISM: artificial
<220> FEATURE:
<223> OTHER INFORMATION: Sequence of the second arm of the ExoU/ExsA/Vrf dsRNA used to concomitantly target ExoU, ExsA and Vrf genes from P. aeruginosa

<400> SEQUENCE: 26

```
cgctgccttc cttttcgaac aatcccagct cgccgaagaa atcaccgctg ttgaggtagc     60
cgatgatcat ttcgcggccg tcgtcgtcct cgatgaggat ggtgaccgaa cccttgatga    120
tgaagaacag cgtttcgcag cgatcgccgg catagatgat ggtgctcttt gcggtgtagc    180
ggcggcggtg acagtgtgcg agcagcttgt ctaggtgttt gagtttgggt gtgtgggtaa    240
tagctaccat gcatactggg cagataatgg aatccagagt attcggctgt cctttccctt    300
ggtacttacg acatagcttc cgcggcggac gaaaagcaac tcgccaggcg ccaggcaaaa    360
agtggaatcg atgtcctgga cggtcagttc gccctcgagc agaacatata cgccctcttc    420
cttgtttacc ctgtattcga aagttggaat gttccaatga caagacgtta tctgctttcg    480
gccaagagat ttggctcctt gcatgatcgc cgcggccctg ccgagtcagt cagagtacgg    540
gactcccctt gcccttgggg actgctgaaa cgcacgtcgc taacgctttc cggcaacttc    600
ccggaaagta ttcccggcgt gctctttagg gcaaccccga gaccttgccc tgaaggttcc    660
tgacgcaagc tggcggactt atgcgctgcc tgcgacgggg tttcgacagg ctcctgattc    720
agcgaggagg cagtagcccc caacgattgg atatgcat                            758
```

<210> SEQ ID NO 27
<211> LENGTH: 758
<212> TYPE: DNA
<213> ORGANISM: artificial
<220> FEATURE:
<223> OTHER INFORMATION: Sequence of the first arm of the LasR/RhlR/VqsM dsRNA used to concomitantly target LasR, RhlR and VqsM genes from P. aeruginosa

<400> SEQUENCE: 27

```
atggccttgg ttgacggttt tcttgagctg gaacgctcaa gtggaaaatt ggagtggagc     60
gccatcctgc agaagatggc gagcgacctt ggattctcga agatcctgtt cggcctgttg    120
cctaaggaca gccaggacta cgagaacgcc ttcatcgtcg gcaactaccc ggccgcctgg    180
cgcgagcatt acgaccgggc tggctacgcg cgggtcgacc cgacggtcag tcactgtacc    240
cagagcgtac gatcatgagg aatgacggag gctttttgct gtggtgggac ggtttgcgta    300
gcgagatgca gccgatccac gacagccagg gcgtgttcgc cgtcctggaa aaggaagtgc    360
ggcgcctggg cttcgattac tacgcctatg gcgtgcgcca cacgattccc ttcacccggc    420
cgaagaccga ggtccatggc acctatccca aggcctggct ggagcgatac cagatgcaga    480
actacggggc cgtggatccg gcgagcatat ggtgaccgaa cacatatttg attttgaatg    540
gcgccctctg cagaactatc ttcgtgatcg tgatatcgca ataccaccct ttgcggcaga    600
acaagagtca agaagtgacg cactttacaa ctggatagtc agcaaggggt attcaggaaa    660
agaaggactg aatcttggaa cttattacca tatatctgat tatggcgtga taggattggc    720
gttgctatgc gccgagaacg taggtgatat tttgaaag                            758
```

<210> SEQ ID NO 28

<211> LENGTH: 758
<212> TYPE: DNA
<213> ORGANISM: artificial
<220> FEATURE:
<223> OTHER INFORMATION: Sequence of the second arm of the LasR/RhlR/VqsM dsRNA used to concomitantly target LasR, RhlR and VqsM genes from P. aeruginosa

<400> SEQUENCE: 28

```
ctttcaaaat atcacctacg ttctcggcgc atagcaacgc caatcctatc acgccataat     60

cagatatatg gtaataagtt ccaagattca gtccttcttt tcctgaatac cccttgctga    120

ctatccagtt gtaaagtgcg tcacttcttg actcttgttc tgccgcaaag ggtggtattg    180

cgatatcacg atcacgaaga tagttctgca gagggcgcca ttcaaaatca aatatgtgtt    240

cggtcaccat gcattcgccg gatccacggc cccgtagttc tgcatctggt atcgctccag    300

ccaggccttg ggataggtgc catggacctc ggtcttcggc cgggtgaagg gaatcgtgtg    360

gcgcacgcca taggcgtagt aatcgaagcc caggcgccgc acttcctttt ccaggacggc    420

gaacacgccc tggctgtcgt ggatcggctg catctcgcta cgcaaaccgt cccaccacag    480

caaaaagcct ccgtcattcc tcatgatcgt acgctctggg tacagtgact gaccgtcggg    540

tcgacccgcg cgtagccagc ccggtcgtaa tgctcgcgcc aggcggccgg gtagttgccg    600

acgatgaagg cgttctcgta gtcctggctg tccttaggca acaggccgaa caggatcttc    660

gagaatccaa ggtcgctcgc catcttctgc aggatggcgc tccactccaa ttttccactt    720

gagcgttcca gctcaagaaa accgtcaacc aaggccat                            758
```

<210> SEQ ID NO 29
<211> LENGTH: 694
<212> TYPE: DNA
<213> ORGANISM: artificial
<220> FEATURE:
<223> OTHER INFORMATION: Sequence of the first arm of the GacA/RmsA/MvfR dsRNA used to concomitantly target GacA, RmsA and MvfR genes from P. aeruginosa

<400> SEQUENCE: 29

```
gtgattaagg tgctggtggt cgacgaccac gatctggtac gcaccggtat tacccgcatg     60

ctggccgaca tcgaaggctt gcaagtggtc ggccaggccg actgcggtga agactgtctg    120

aaactggccc gcgaactgaa gccggatgtc gtcctgatgg acgtgaagat gcccggtatc    180

ggcggcctgg aggcgacccg caagctgctg cgcagccagc ccgacatcaa ggtcgtggta    240

gtcaccgtct gatcatgctg attctgactc gtcgggtcgg agagaccctg atggtaggtg    300

acgacgtcac cgtgacggta ctgggtgtca aagggaacca ggtgcgcatc ggcgtcaacg    360

cgccgaagga agtcgccgta caccgggagg aaatttacca gcgcatccag aaagagaaag    420

atcaagagcc aaaccattaa gcatatgcct attcataacc tgaatcacgt gaacatgttc    480

ctccaggtca tcgcctccgg ttcgatttcc tccgctgcgc ggatcctgcg caagtcgcac    540

accgcggtca gctcggcggt cagcaacctg gaaatcgacc tgtgcgtgga gctggtccgt    600

cgggacggct acaaggtcga acccaccgag caggcgcttc gcctgatccc ttacatgcgc    660

agcctgctga actaccagca gctgatcggc gaca                                694
```

<210> SEQ ID NO 30
<211> LENGTH: 694
<212> TYPE: DNA
<213> ORGANISM: artificial
<220> FEATURE:
<223> OTHER INFORMATION: Sequence of the second arm of the GacA/RmsA/MvfR dsRNA used to concomitantly target GacA, RmsA and MvfR genes from P. aeruginosa

<400> SEQUENCE: 30

```
tgtcgccgat cagctgctgg tagttcagca ggctgcgcat gtaagggatc aggcgaagcg      60

cctgctcggt gggttcgacc ttgtagccgt cccgacggac cagctccacg cacaggtcga     120

tttccaggtt gctgaccgcc gagctgaccg cggtgtgcga cttgcgcagg atccgcgcag     180

cggaggaaat cgaaccggag gcgatgacct ggaggaacat gttcacgtga ttcaggttat     240

gaataggcat gcatttaatg gtttggctct tgatctttct ctttctggat gcgctggtaa     300

atttcctccc ggtgtacggc gacttccttc ggcgcgttga cgccgatgcg cacctggttc     360

cctttgacac ccagtaccgt cacggtgacg tcgtcaccta ccatcagggt ctctccgacc     420

cgacgagtca gaatcagcat gatcagacgg tgactaccac gaccttgatg tcgggctggc     480

tgcgcagcag cttgcgggtc gcctccaggc cgccgatacc gggcatcttc acgtccatca     540

ggacgacatc cggcttcagt tcgcgggcca gtttcagaca gtcttcaccg cagtcggcct     600

ggccgaccac ttgcaagcct tcgatgtcgg ccagcatgcg ggtaataccg gtgcgtacca     660

gatcgtggtc gtcgaccacc agcaccttaa tcac                                 694
```

<210> SEQ ID NO 31
<211> LENGTH: 758
<212> TYPE: DNA
<213> ORGANISM: artificial
<220> FEATURE:
<223> OTHER INFORMATION: Sequence of the first arm of the mexX/mexA/ampC dsRNA used to concomitantly target mexX, mexA and ampC genes from P. aeruginosa

<400> SEQUENCE: 31

```
atggaccggc tcgctgcgcg gctgctggcg gccctggtcg ccctattcct gctgggctgc      60

gaagaagcag cggacgccgg gaagactgcg gaggcccccg ccgaggtcgg cgtgatcgtc     120

gccaggccgg cgcctatcgg catcaccagc gagctgcccg gacgcctgga agcgtaccgc     180

caggctgaag tgcgggcgcg cgtcgccggc atcgtcaccc gtcgcctgta cgaggaaggc     240

caggacgtcc gatcatgcaa cgaacgccag ccatgcgtgt actggttccg gccctgctgg     300

tcgcgatttc ggccctttcc gggtgcggaa aaagcgaggc gccgccgccg gcgcaaacgc     360

cggaggtcgg gatcgtgacc ctggaagcgc agacggtgac cctgaatacc gagctgccgg     420

gccggaccaa tgcgttccgc atcgccgagg tgcgtcccca ggtgaacggc atcatcctca     480

agcgcctgtt caaggaaggc agcggcatat gcgcgatacc agattcccct gcctgtgcgg     540

catcgccgct tccacactgc tgttcgccac caccccggcc attgccggcg aggccccggc     600

ggatcgcctg aaggcactgg tcgacgccgc cgtacaaccg gtgatgaagg ccaatgacat     660

tccgggcctg gccgtagcca tcagcctgaa aggagaaccg cattacttca gctatgggct     720

ggcctcgaaa gaggacggcc gccgggtgac gccggaga                             758
```

<210> SEQ ID NO 32
<211> LENGTH: 758
<212> TYPE: DNA
<213> ORGANISM: artificial
<220> FEATURE:
<223> OTHER INFORMATION: Sequence of the second arm of the mexX/mexA/ampC dsRNA used to concomitantly target mexX, mexA and ampC genes from P. aeruginosa

<400> SEQUENCE: 32

```
tctccggcgt cacccggcgg ccgtcctctt tcgaggccag cccatagctg aagtaatgcg     60

gttctccttt caggctgatg gctacggcca ggcccggaat gtcattggcc ttcatcaccg    120

gttgtacggc ggcgtcgacc agtgccttca ggcgatccgc cggggcctcg ccggcaatgg    180

ccggggtggt ggcgaacagc agtgtggaag cggcgatgcc gcacaggcag gggaatctgg    240

tatcgcgcat gcatcgctgc cttccttgaa caggcgcttg aggatgatgc cgttcacctg    300

gggacgcacc tcggcgatgc ggaacgcatt ggtccggccc ggcagctcgg tattcagggt    360

caccgtctgc gcttccaggg tcacgatccc gacctccggc gtttgcgccg gcggcggcgc    420

ctcgcttttt ccgcacccgg aaagggccga aatcgcgacc agcagggccg gaaccagtac    480

acgcatggct ggcgttcgtt gcatgatcgg acgtcctggc cttcctcgta caggcgacgg    540

gtgacgatgc cggcgacgcg cgcccgcact tcagcctggc ggtacgcttc caggcgtccg    600

ggcagctcgc tggtgatgcc gataggcgcc ggcctggcga cgatcacgcc gacctcggcg    660

ggggcctccg cagtcttccc ggcgtccgct gcttcttcgc agcccagcag gaatagggcg    720

accagggccg ccagcagccg cgcagcgagc cggtccat                            758
```

```
<210> SEQ ID NO 33
<211> LENGTH: 758
<212> TYPE: DNA
<213> ORGANISM: artificial
<220> FEATURE:
<223> OTHER INFORMATION: Sequence of the first arm of the VirF/VirB/IcsA
      dsRNA used to concomitantly target VirF, VirB and IcsA genes from
      Shigella flexneri

<400> SEQUENCE: 33

atgatggata tgggacataa aaacaaaata gatataaagg ttcgcttgca taactatatt     60

attttatatg caaaaaggtg ttcaatgacg gttagctcag gcaatgaaac tttgactatc    120

gatgaagggc aaattgcttt tatagagcga aatatacaaa taaacgtctc cataaaaaaa    180

tctgatagca ttaatccatt tgagattata agccttgaca gaaatttatt attaagcatt    240

attagaataa gatcatggtg gatttgtgca acgacttgtt aagtataaag gaaggccaaa    300

agaaagagtt tacactccat tctggtaata aagtttcctt tatcaaagcc aagattcctc    360

ataaaaggat ccaagattta accttcgtca accaaaaaac gaatgtacgc gatcaagaat    420

ccctaacaga agaatcatta gccgatatca taaaaactat aaagctacaa caattcttcc    480

ctgtaatagg aagggagatt gatggcatcc cttgggagct ggtgaagatg gaatggatgc    540

gtggtatata acttcttcca acccctctca tgcatctaga actaagctac ggattaactc    600

tgatattatg attagcgcag gtcatggtgg tgctggtgat aataatgatg gtaatagttg    660

tggcggtaat ggtggtgact ctattaccgg atctgacttg tctataatca atcaaggcat    720

gattcttggt ggtagcggcg gtagcggtgc tgaccata                            758
```

```
<210> SEQ ID NO 34
<211> LENGTH: 758
<212> TYPE: DNA
<213> ORGANISM: artificial
<220> FEATURE:
<223> OTHER INFORMATION: Sequence of the second arm of the
      VirF/VirB/IcsA dsRNA used to concomitantly target VirF, VirB and
      IcsA genes from Shigella flexneri

<400> SEQUENCE: 34

tatggtcagc accgctaccg ccgctaccac caagaatcat gccttgattg attatagaca     60

agtcagatcc ggtaatagag tcaccaccat taccgccaca actattacca tcattattat    120
```

```
caccagcacc accatgacct gcgctaatca taatatcaga gttaatccgt agcttagttc    180

tagatgcatg agaggggttg gaagaagtta tataccacgc atccattcca tcttcaccag    240

ctcccaaggg gcatcatcaa tctcccttcc tattacaggg aagaattgtt gtagctttat    300

agtttttatg atatcggcta atgattcttc tgttagggat tcttgatcgc gtacattcgt    360

tttttggttg acgaaggtta aatcttggat ccttttatga ggaatcttgg ctttgataaa    420

ggaaacttta ttaccagaat ggagtgtaaa ctctttcttt tggccttcct ttatacttaa    480

caagtcgttg cacaaatcca ccatgatctt attctaataa tgcttaataa taaatttctg    540

tcaaggctta taatctcaaa tggattaatg ctatcagatt tttttatgga gacgtttatt    600

tgtatatttc gctctataaa agcaatttgc ccttcatcga tagtcaaagt ttcattgcct    660

gagctaaccg tcattgaaca ccttttttgca tataaaataa tatagttatg caagcgaacc    720

tttatatcta ttttgttttt atgtcccata tccatcat                            758
```

<210> SEQ ID NO 35
<211> LENGTH: 812
<212> TYPE: DNA
<213> ORGANISM: artificial
<220> FEATURE:
<223> OTHER INFORMATION: Sequence of the first arm of the fnbA/clfA/clfB/spa dsRNA used to concomitantly target fnbA, clfA, clfB and spa genes from S. aureus

<400> SEQUENCE: 35

```
atgggacaag acaaagaagc tgcagcatca gaacaaaaga caactacagt agaagaaaat     60

gggaattcag ctactgataa taaaacaagt gaaacacaaa caactgcaac taacgttaat    120

catatagaag aaactcaatc atataacgca acagtaacag aacaaccgtc aaacgcaaca    180

caagtaacaa ctgaagaagc gatcatgaat atgaagaaaa aagaaaaaca cgcaattcgg    240

aaaaaatcga ttggcgtggc ttcagtgctt gtaggtacgt taatcggttt tggactactc    300

agcagtaaag aagcagatgc aagtgaaaat agtgttacgc aatctgatag cgcaagtaac    360

gaaagcaaaa gtaatgattc aagtagcgtt agtgctgcac ctaagcattt acgcttttc    420

tttatgatct tgcttgcgtt ttctaaacaa tagtaatgat cctaataatg ccatcattgc    480

accaaataaa gttgcatttg tgttttcgct cttatctcct gtttctggta aagcatcagt    540

tttgtgttgt tttgatacct tattagaatg gtttacttca cctttaggat ttgatggtgc    600

tttctgttat gcttatagtt cgcgacgacg tccagctaat aacgctgcac ctaaggctaa    660

tgataatcca ccaaatacag ttgtaccgat gaatggattt tcttcaccag tttctggtaa    720

tgcttgagct ttgttagcat ctgcatggtt tgctggttgc ttcttatcaa caacaagttc    780

ttgaccaggt ttgatcatgt ttttatcagc ta                                  812
```

<210> SEQ ID NO 36
<211> LENGTH: 812
<212> TYPE: DNA
<213> ORGANISM: artificial
<220> FEATURE:
<223> OTHER INFORMATION: Sequence of the second arm of the fnbA/clfA/clfB/spa dsRNA used to concomitantly target fnbA, clfA, clfB and spa genes from S. aureus

<400> SEQUENCE: 36

```
tagctgataa aaacatgatc aaacctggtc aagaacttgt tgttgataag aagcaaccag     60

caaaccatgc agatgctaac aaagctcaag cattaccaga aactggtgaa gaaaatccat    120
```

```
tcatcggtac aactgtattt ggtggattat cattagcctt aggtgcagcg ttattagctg    180

gacgtcgtcg cgaactataa gcacaacaga aagcaccatc aaatcctaaa ggtgaagtaa    240

accattctaa taaggtatca aaacaacaca aaactgatgc tttaccagaa acaggagata    300

agagcgaaaa cacaaatgca actttatttg gtgcaatgat ggcattatta ggatcattac    360

tattgtttag aaaacgcaag caagatcata aagaaaaagc gtaagcattt aggtgcagca    420

ctaacgctac ttgaatcatt acttttgctt tcgttacttg cgctatcaga ttgcgtaaca    480

ctattttcac ttgcatctgc ttctttactg ctgagtagtc caaaaccgat taacgtacct    540

acaagcactg aagccacgcc aatcgatttt ttccgaattg cgtgtttttc ttttttcttc    600

atattcatga tcgcttcttc agttgttact tgtgttgcgt ttgacggttg ttctgttact    660

gttgcgttat atgattgagt ttcttctata tgattaacgt tagttgcagt tgtttgtgtt    720

tcacttgttt tattatcagt agctgaattc ccattttctt ctactgtagt tgtcttttgt    780

tctgatgctg cagcttcttt gtcttgtccc at                                  812
```

<210> SEQ ID NO 37
<211> LENGTH: 812
<212> TYPE: DNA
<213> ORGANISM: artificial
<220> FEATURE:
<223> OTHER INFORMATION: Sequence of the first arm of the lukF-PV/lukS-PV/lukE/lukD dsRNA used to concomitantly target lukF-PV, lukS-PV, lukE and lukD genes from S. aureus

<400> SEQUENCE: 37

```
ttagctcata ggattttttt ccttagattg agtatctatt aatttaactg tatgattttc     60

ccaatcaact tcataaattg atgtatgagt tgctctattt tcatctttat aattattacc    120

tatccagtga agttgattcc aaaagtttgt atatctatcc atttctcttt gataagtaac    180

agtaattttc gattttttttg gatctcaatt atgtcctttc actttaattt catgagtttt    240

ccagttcact tcatatttaa ctgtgtaatt tctgtttaca aatgcgttgt gtattctaga    300

tccttctaaa taactattgc catagtgtgt tgttcttcta gtagcatgag taacatccat    360

atttctgcca tacgttattt caaattcact tgtatctcct gagcgcatat gtttaagaaa    420

aaaatgttag ctgcaagttt gtcagtagga ctgattgcac ctttagcatc tccgattcaa    480

gaatctagag caaatactaa tattgaaaat attggtgatg gtgctgaagt aatcaaacgt    540

acggaggatg taagtagtaa gaaatggggc gttactcaaa atgtccaatt cgactttgta    600

aaagataaat gcatgaaaat tgaaaaatta ggcaaatcat cagttgcttc atcaattgca    660

ctgcttttgc tatcgaatac agttgatgca gctcaaaata tcacacctaa aagagagaaa    720

aaagtagatg acaaaatcac tttatacaaa acaacagcaa catctgataa tgataaattg    780

aatatttttc aaattttaac gtttaatttc at                                  812
```

<210> SEQ ID NO 38
<211> LENGTH: 812
<212> TYPE: DNA
<213> ORGANISM: artificial
<220> FEATURE:
<223> OTHER INFORMATION: Sequence of the second arm of the lukF-PV/lukS-PV/lukE/lukD dsRNA used to concomitantly target lukF-PV, lukS-PV, lukE and lukD genes from S. aureus

<400> SEQUENCE: 38

```
atgaaattaa acgttaaaat ttgaaaaata ttcaatttat cattatcaga tgttgctgtt     60

gttttgtata aagtgatttt gtcatctact tttttctctc ttttaggtgt gatattttga    120
```

```
gctgcatcaa ctgtattcga tagcaaaagc agtgcaattg atgaagcaac tgatgatttg    180

cctaattttt caattttcat gcacttatct tttacaaagt cgaattggac attttgagta    240

acgccccatt tcttactact tacatcctcc gtacgtttga ttacttcagc accatcacca    300

atattttcaa tattagtatt tgctctagat tcttgaatcg gagatgctaa aggtgcaatc    360

agtcctactg acaaacttgc agctaacatt tttttcttaa acatgcatgc tcaggagata    420

caagtgaatt tgaaataacg tatggcagaa atatggatgt tactcatgct actagaagaa    480

caacacacta tggcaatagt tatttagaag gatctagaat acacaacgca tttgtaaaca    540

gaaattacac agttaaatat gaagtgaact ggaaaactca tgaaattaaa gtgaaaggac    600

ataattgaga tccaaaaaaa tcgaaaatta ctgttactta tcaaagagaa atggatagat    660

atacaaactt ttggaatcaa cttcactgga taggtaataa ttataaagat gaaaatagag    720

caactcatac atcaatttat gaagttgatt gggaaaatca tacagttaaa ttaatagata    780

ctcaatctaa ggaaaaaaat cctatgagct aa                                  812
```

```
<210> SEQ ID NO 39
<211> LENGTH: 812
<212> TYPE: DNA
<213> ORGANISM: artificial
<220> FEATURE:
<223> OTHER INFORMATION: Sequence of the first arm of the
      HlgB/hla/tsst-1/atl dsRNA used to concomitantly target HlgB, hla,
      tsst-1 and atl genes from S. aureus

<400> SEQUENCE: 39

atgaaaatga ataaattagt caaatcatcc gttgctacat ctatggcatt attattactt     60

tctggtactg ctaatgctga aggtaaaata acaccagtca gcgtaaaaaa agtcgatgac    120

aaagttactt tatacaaaac aacagccaca gcagattctg ataaatttaa aatttcacag    180

attttaacat ttaatttcat gatcttaatt tgtcatttct tctttttccc aatcgatttt    240

atatctttct gaagaacgat ctatccattt atctttagta ttggtacctt tccaatttgt    300

tgaagtccag tgcaattggt agtcatcacg aactcgttcg tatattacat ctatatttgt    360

ttgttgtttg gatgcttttc tatccatagt aataactgta gcgagcatat gaataaaaaa    420

ttactaatga attttttat cgtaagccct ttgttgcttg cgacaatcgc tacagatttt    480

acccctgttc ccttatcatc taatcaaata atcaaaactg caaaagcatc tacaaacgat    540

aatataaagg atttgctaga ctggtatagt agtgggtctg acacttttac aaatagtgaa    600

gttttagaat gcttatttat attgtgggat gtcgaagtat ttgccgactt cgccaatttt    660

atcatagtag cctttgatga ttttagcatt gatgttagcc caatctacat ctgtagcata    720

ttggtgtgtt cctggatgtg caggattcca tctcattttg taaagtgtat tttgaccagc    780

ttttacatat gagttgccga tgaatttagc ac                                  812
```

```
<210> SEQ ID NO 40
<211> LENGTH: 812
<212> TYPE: DNA
<213> ORGANISM: artificial
<220> FEATURE:
<223> OTHER INFORMATION: Sequence of the second arm of the
      HlgB/hla/tsst-1/atl dsRNA used to concomitantly target HlgB, hla,
      tsst-1 and atl genes from S. aureus

<400> SEQUENCE: 40

gtgctaaatt catcggcaac tcatatgtaa aagctggtca aaatacactt tacaaaatga     60
```

```
gatggaatcc tgcacatcca ggaacacacc aatatgctac agatgtagat tgggctaaca    120

tcaatgctaa aatcatcaaa ggctactatg ataaaattgg cgaagtcggc aaatacttcg    180

acatcccaca atataaataa gcactctaaa acttcactat ttgtaaaagt gtcagaccca    240

ctactatacc agtctagcaa atcctttata ttatcgtttg tagatgcttt tgcagttttg    300

attatttgat tagatgataa gggaacaggg gtaaaatctg tagcgattgt cgcaagcaac    360

aaagggctta cgataaaaaa attcattagt aattttttat tcatgcattc gctacagtta    420

ttactatgga tagaaaagca tccaaacaac aaacaaatat agatgtaata tacgaacgag    480

ttcgtgatga ctaccaattg cactggactt caacaaattg gaaaggtacc aatactaaag    540

ataaatggat agatcgttct tcagaaagat ataaaatcga ttgggaaaaa gaagaaatga    600

caaattaaga tcatgaaatt aaatgttaaa atctgtgaaa ttttaaattt atcagaatct    660

gctgtggctg ttgttttgta taaagtaact ttgtcatcga cttttttttac gctgactggt    720

gttattttac cttcagcatt agcagtacca gaaagtaata ataatgccat agatgtagca    780

acggatgatt tgactaattt attcattttc at                                  812


<210> SEQ ID NO 41
<211> LENGTH: 259
<212> TYPE: DNA
<213> ORGANISM: artificial
<220> FEATURE:
<223> OTHER INFORMATION: Sequence of the first arm of the PLP dsRNA used
      to target a PLP RNA region from SARS-CoV-2

<400> SEQUENCE: 41

agaagtgcaa ggttacaaga gtgtgaatat cacttttgaa cttgatgaaa ggattgataa     60

agtacttaat gagaagtgct ctgcctatac agttgaactc ggtacagaag taaatgagtt    120

cgcctgtgtt gtggcagatg ctgtcataaa aactttgcaa ccagtatctg aattacttac    180

accactgggc attgatttag atgagtggag tatggctaca tactacttat ttgatgagtc    240

tggtgagttt aaattggct                                                 259


<210> SEQ ID NO 42
<211> LENGTH: 259
<212> TYPE: DNA
<213> ORGANISM: artificial
<220> FEATURE:
<223> OTHER INFORMATION: Sequence of the second arm of the PLP dsRNA
      used to target a PLP RNA region from SARS-CoV-2

<400> SEQUENCE: 42

agccaattta aactcaccag actcatcaaa taagtagtat gtagccatac tccactcatc     60

taaatcaatg cccagtggtg taagtaattc agatactggt tgcaaagttt ttatgacagc    120

atctgccaca acacaggcga actcatttac ttctgtaccg agttcaactg tataggcaga    180

gcacttctca ttaagtactt tatcaatcct ttcatcaagt tcaaaagtga tattcacact    240

cttgtaacct tgcacttct                                                 259


<210> SEQ ID NO 43
<211> LENGTH: 309
<212> TYPE: DNA
<213> ORGANISM: artificial
<220> FEATURE:
<223> OTHER INFORMATION: Sequence of the first arm of the 3CL dsRNA used
      to target a 3CL RNA region from SARS-CoV-2

<400> SEQUENCE: 43
```

cccatctggt aaagttgagg gttgtatggt acaagtaact tgtggtacaa ctacacttaa 60
cggtctttgg cttgatgacg tagtttactg tccaagacat gtgatctgca cctctgaaga 120
catgcttaac cctaattatg aagatttact cattcgtaag tctaatcata atttcttggt 180
acaggctggt aatgttcaac tcagggttat tggacattct atgcaaaatt gtgtacttaa 240
gcttaaggtt gatacagcca atcctaagac acctaagtat aagtttgttc gcattcaacc 300
aggacagac 309

<210> SEQ ID NO 44
<211> LENGTH: 309
<212> TYPE: DNA
<213> ORGANISM: artificial
<220> FEATURE:
<223> OTHER INFORMATION: Sequence of the second arm of the 3CL dsRNA used to target a 3CL RNA region from SARS-CoV-2

<400> SEQUENCE: 44
gtctgtcctg gttgaatgcg aacaaactta tacttaggtg tcttaggatt ggctgtatca 60
accttaagct taagtacaca attttgcata gaatgtccaa taaccctgag ttgaacatta 120
ccagcctgta ccaagaaatt atgattagac ttacgaatga gtaaatcttc ataattaggg 180
ttaagcatgt cttcagaggt gcagatcaca tgtcttggac agtaaactac gtcatcaagc 240
caaagaccgt taagtgtagt tgtaccacaa gttacttgta ccatacaacc ctcaacttta 300
ccagatggg 309

<210> SEQ ID NO 45
<211> LENGTH: 308
<212> TYPE: DNA
<213> ORGANISM: artificial
<220> FEATURE:
<223> OTHER INFORMATION: Sequence of the first arm of the Nsp10 dsRNA used to target a Nsp10 RNA region from SARS-CoV-2

<400> SEQUENCE: 45
agtgcctgcc aattcaactg tattatcttt ctgtgctttt gctgtagatg ctgctaaagc 60
ttacaaagat tatctagcta gtgggggaca accaatcact aattgtgtta agatgttgtg 120
tacacacact ggtactggtc aggcaataac agttacaccg gaagccaata tggatcaaga 180
atcctttggt ggtgcatcgt gttgtctgta ctgccgttgc cacatagatc atccaaatcc 240
taaaggattt tgtgacttaa aaggtaagta tgtacaaata cctacaactt gtgctaatga 300
ccctgtgg 308

<210> SEQ ID NO 46
<211> LENGTH: 308
<212> TYPE: DNA
<213> ORGANISM: artificial
<220> FEATURE:
<223> OTHER INFORMATION: Sequence of the second arm of the Nsp10 dsRNA used to target a Nsp10 RNA region from SARS-CoV-2

<400> SEQUENCE: 46
ccacagggtc attagcacaa gttgtaggta tttgtacata cttacctttt aagtcacaaa 60
atcctttagg atttggatga tctatgtggc aacggcagta cagacaacac gatgcaccac 120
caaaggattc ttgatccata ttggcttccg gtgtaactgt tattgcctga ccagtaccag 180
tgtgtgtaca caacatctta acacaattag tgattggttg tcccccacta gctagataat 240
ctttgtaagc tttagcagca tctacagcaa aagcacagaa agataataca gttgaattgg 300

```
caggcact                                                             308

<210> SEQ ID NO 47
<211> LENGTH: 294
<212> TYPE: DNA
<213> ORGANISM: artificial
<220> FEATURE:
<223> OTHER INFORMATION: Sequence of the first arm of the RDRP-1 dsRNA
      used to target a RDRP RNA region from SARS-CoV-2

<400> SEQUENCE: 47

taagtgcagc ccgtcttaca ccgtgcggca caggcactag tactgatgtc gtatacaggg     60

cttttgacat ctacaatgat aaagtagctg gttttgctaa attcctaaaa actaattgtt    120

gtcgcttcca agaaaaggac gaagatgaca atttaattga ttcttacttt gtagttaaga    180

gacacacttt ctctaactac caacatgaag aaacaattta taatttactt aaggattgtc    240

cagctgttgc taaacatgac ttctttaagt ttagaataga cggtgacatg gtac          294

<210> SEQ ID NO 48
<211> LENGTH: 294
<212> TYPE: DNA
<213> ORGANISM: artificial
<220> FEATURE:
<223> OTHER INFORMATION: Sequence of the second arm of the RDRP-1 dsRNA
      used to target a RDRP RNA region from SARS-CoV-2

<400> SEQUENCE: 48

gtaccatgtc accgtctatt ctaaacttaa agaagtcatg tttagcaaca gctggacaat     60

ccttaagtaa attataaatt gtttcttcat gttggtagtt agagaaagtg tgtctcttaa    120

ctacaaagta agaatcaatt aaattgtcat cttcgtcctt ttcttggaag cgacaacaat    180

tagtttttag gaatttagca aaaccagcta ctttatcatt gtagatgtca aaagccctgt    240

atacgacatc agtactagtg cctgtgccgc acggtgtaag acgggctgca ctta          294

<210> SEQ ID NO 49
<211> LENGTH: 254
<212> TYPE: DNA
<213> ORGANISM: artificial
<220> FEATURE:
<223> OTHER INFORMATION: Sequence of the first arm of the RDRP-2 dsRNA
      used to target a RDRP RNA region from SARS-CoV-2

<400> SEQUENCE: 49

actggatacc acttcagaga gctaggtgtt gtacataatc aggatgtaaa cttacatagc     60

tctagactta gttttaagga attacttgtg tatgctgctg accctgctat gcacgctgct    120

tctggtaatc tattactaga taaacgcact acgtgctttt cagtagctgc acttactaac    180

aatgttgctt ttcaaactgt caaacccggt aattttaaca aagacttcta tgactttgct    240

gtgtctaagg gttt                                                      254

<210> SEQ ID NO 50
<211> LENGTH: 254
<212> TYPE: DNA
<213> ORGANISM: artificial
<220> FEATURE:
<223> OTHER INFORMATION: Sequence of the second arm of the RDRP-2 dsRNA
      used to target a RDRP RNA region from SARS-CoV-2

<400> SEQUENCE: 50

aaacccttag acacagcaaa gtcatagaag tctttgttaa aattaccggg tttgacagtt     60

tgaaaagcaa cattgttagt aagtgcagct actgaaaagc acgtagtgcg tttatctagt    120
```

```
aatagattac cagaagcagc gtgcatagca gggtcagcag catacacaag taattcctta    180

aaactaagtc tagagctatg taagtttaca tcctgattat gtacaacacc tagctctctg    240

aagtggtatc cagt                                                      254
```

<210> SEQ ID NO 51
<211> LENGTH: 252
<212> TYPE: DNA
<213> ORGANISM: artificial
<220> FEATURE:
<223> OTHER INFORMATION: Sequence of the first arm of the RDRP-3 dsRNA used to target a RDRP RNA region from SARS-CoV-2

<400> SEQUENCE: 51

```
tgttggactg agactgacct tactaaagga cctcatgaat tttgctctca acatacaatg     60

ctagttaaac agggtgatga ttatgtgtac cttccttacc cagatccatc aagaatccta    120

ggggccggct gttttgtaga tgatatcgta aaaacagatg gtacacttat gattgaacgg    180

ttcgtgtctt tagctataga tgcttaccca cttactaaac atcctaatca ggagtatgct    240

gatgtctttc at                                                        252
```

<210> SEQ ID NO 52
<211> LENGTH: 252
<212> TYPE: DNA
<213> ORGANISM: artificial
<220> FEATURE:
<223> OTHER INFORMATION: Sequence of the second arm of the RDRP-3 dsRNA used to target a RDRP RNA region from SARS-CoV-2

<400> SEQUENCE: 52

```
atgaaagaca tcagcatact cctgattagg atgtttagta agtgggtaag catctatagc     60

taaagacacg aaccgttcaa tcataagtgt accatctgtt tttacgatat catctacaaa    120

acagccggcc cctaggattc ttgatggatc tgggtaagga aggtacacat aatcatcacc    180

ctgtttaact agcattgtat gttgagagca aaattcatga ggtcctttag taaggtcagt    240

ctcagtccaa ca                                                        252
```

<210> SEQ ID NO 53
<211> LENGTH: 284
<212> TYPE: DNA
<213> ORGANISM: artificial
<220> FEATURE:
<223> OTHER INFORMATION: Sequence of the first arm of the EndoN dsRNA used to target a EndoN (Nsp15) RNA region from SARS-CoV-2

<400> SEQUENCE: 53

```
gtgcaccact cactgtcttt tttgatggta gagttgatgg tcaagtagac ttatttagaa     60

atgcccgtaa tggtgttctt attacagaag gtagtgttaa aggtttacaa ccatctgtag    120

gtcccaaaca agctagtctt aatggagtca cattaattgg agaagccgta aaaacacagt    180

tcaattatta taagaaagtt gatggtgttg tccaacaatt acctgaaact tactttactc    240

agagtagaaa tttacaagaa tttaaaccca ggagtcaaat ggaa                     284
```

<210> SEQ ID NO 54
<211> LENGTH: 284
<212> TYPE: DNA
<213> ORGANISM: artificial
<220> FEATURE:
<223> OTHER INFORMATION: Sequence of the second arm of the EndoN dsRNA used to target a EndoN (Nsp15) RNA region from SARS-CoV-2

<400> SEQUENCE: 54

```
ttccatttga ctcctgggtt taaattcttg taaatttcta ctctgagtaa agtaagtttc     60

aggtaattgt tggacaacac catcaacttt cttataataa ttgaactgtg tttttacggc    120

ttctccaatt aatgtgactc cattaagact agcttgtttg ggacctacag atggttgtaa    180

acctttaaca ctaccttctg taataagaac accattacgg gcatttctaa ataagtctac    240

ttgaccatca actctaccat caaaaaagac agtgagtggt gcac                     284
```

<210> SEQ ID NO 55
<211> LENGTH: 289
<212> TYPE: DNA
<213> ORGANISM: artificial
<220> FEATURE:
<223> OTHER INFORMATION: Sequence of the first arm of the N dsRNA used to target a N RNA region from SARS-CoV-2

<400> SEQUENCE: 55

```
tcaccgctct cactcaacat ggcaaggaag accttaaatt ccctcgagga caaggcgttc     60

caattaacac caatagcagt ccagatgacc aaattggcta ctaccgaaga gctaccagac    120

gaattcgtgg tggtgacggt aaaatgaaag atctcagtcc aagatggtat ttctactacc    180

taggaactgg gccagaagct ggacttccct atggtgctaa caaagacggc atcatatggg    240

ttgcaactga gggagccttg aatacaccaa aagatcacat tggcacccg                289
```

<210> SEQ ID NO 56
<211> LENGTH: 289
<212> TYPE: DNA
<213> ORGANISM: artificial
<220> FEATURE:
<223> OTHER INFORMATION: Sequence of the second arm of the N dsRNA used to target a N RNA region from SARS-CoV-2

<400> SEQUENCE: 56

```
cgggtgccaa tgtgatcttt tggtgtattc aaggctccct cagttgcaac ccatatgatg     60

ccgtctttgt tagcaccata gggaagtcca gcttctggcc cagttcctag gtagtagaaa    120

taccatcttg gactgagatc tttcatttta ccgtcaccac cacgaattcg tctggtagct    180

cttcggtagt agccaatttg gtcatctgga ctgctattgg tgttaattgg aacgccttgt    240

cctcgaggga atttaaggtc ttccttgcca tgttgagtga gagcggtga                289
```

<210> SEQ ID NO 57
<211> LENGTH: 150
<212> TYPE: DNA
<213> ORGANISM: artificial
<220> FEATURE:
<223> OTHER INFORMATION: Sequence of the first arm of the E dsRNA used to target a E RNA region from SARS-CoV-2

<400> SEQUENCE: 57

```
cggaagagac aggtacgtta atagttaata gcgtacttct ttttcttgct ttcgtggtat     60

tcttgctagt tacactagcc atccttactg cgcttcgatt gtgtgcgtac tgctgcaata    120

ttgttaacgt gagtcttgta aaaccttctt                                     150
```

<210> SEQ ID NO 58
<211> LENGTH: 150
<212> TYPE: DNA
<213> ORGANISM: artificial
<220> FEATURE:
<223> OTHER INFORMATION: Sequence of the second arm of the E dsRNA used to target a E RNA region from SARS-CoV-2

<400> SEQUENCE: 58
aagaaggttt tacaagactc acgttaacaa tattgcagca gtacgcacac aatcgaagcg 60
cagtaaggat ggctagtgta actagcaaga ataccacgaa agcaagaaaa agaagtacgc 120
tattaactat taacgtacct gtctcttccg 150

<210> SEQ ID NO 59
<211> LENGTH: 315
<212> TYPE: DNA
<213> ORGANISM: artificial
<220> FEATURE:
<223> OTHER INFORMATION: Sequence of the first arm of the M dsRNA used to target a M RNA region from SARS-CoV-2

<400> SEQUENCE: 59
ggcagattcc aacggtacta ttaccgttga agagcttaaa aagctccttg aacaatggaa 60
cctagtaata ggtttcctat tccttacatg gatttgtctt ctacaatttg cctatgccaa 120
caggaatagg tttttgtata taattaagtt aattttcctc tggctgttat ggccagtaac 180
tttagcttgt tttgtgcttg ctgctgttta cagaataaat tggatcaccg gtggaattgc 240
tatcgcaatg gcttgtcttg taggcttgat gtggctcagc tacttcattg cttctttcag 300
actgtttgcg cgtac 315

<210> SEQ ID NO 60
<211> LENGTH: 315
<212> TYPE: DNA
<213> ORGANISM: artificial
<220> FEATURE:
<223> OTHER INFORMATION: Sequence of the second arm of the M dsRNA used to target a M RNA region from SARS-CoV-2

<400> SEQUENCE: 60
gtacgcgcaa acagtctgaa agaagcaatg aagtagctga gccacatcaa gcctacaaga 60
caagccattg cgatagcaat tccaccggtg atccaattta ttctgtaaac agcagcaagc 120
acaaaacaag ctaaagttac tggccataac agccagagga aaattaactt aattatatac 180
aaaaacctat tcctgttggc ataggcaaat tgtagaagac aaatccatgt aaggaatagg 240
aaacctatta ctaggttcca ttgttcaagg agcttttttaa gctcttcaac ggtaatagta 300
ccgttggaat ctgcc 315

<210> SEQ ID NO 61
<211> LENGTH: 327
<212> TYPE: DNA
<213> ORGANISM: artificial
<220> FEATURE:
<223> OTHER INFORMATION: Sequence of the first arm of the S dsRNA used to target a S RNA region from SARS-CoV-2

<400> SEQUENCE: 61
tggtttaaca ggcacaggtg ttcttactga gtctaacaaa aagtttctgc ctttccaaca 60
atttggcaga gacattgctg acactactga tgctgtccgt gatccacaga cacttgagat 120
tcttgacatt acaccatgtt cttttggtgg tgtcagtgtt ataacaccag gaacaaatac 180
ttctaaccag gttgctgttc tttatcagga tgttaactgc acagaagtcc ctgttgctat 240
tcatgcagat caacttactc ctacttggcg tgtttattct acaggttcta atgtttttca 300
aacacgtgca ggctgtttaa taggggc 327

<210> SEQ ID NO 62
<211> LENGTH: 327
<212> TYPE: DNA
<213> ORGANISM: artificial
<220> FEATURE:
<223> OTHER INFORMATION: Sequence of the second arm of the S dsRNA used to target a S RNA region from SARS-CoV-2

<400> SEQUENCE: 62
gcccctatta aacagcctgc acgtgtttga aaaacattag aacctgtaga ataaacacgc 60
caagtaggag taagttgatc tgcatgaata gcaacaggga cttctgtgca gttaacatcc 120
tgataaagaa cagcaacctg gttagaagta tttgttcctg gtgttataac actgacacca 180
ccaaaagaac atggtgtaat gtcaagaatc tcaagtgtct gtggatcacg gacagcatca 240
gtagtgtcag caatgtctct gccaaattgt tggaaaggca gaaacttttt gttagactca 300
gtaagaacac ctgtgcctgt taaacca 327

<210> SEQ ID NO 63
<211> LENGTH: 304
<212> TYPE: DNA
<213> ORGANISM: artificial
<220> FEATURE:
<223> OTHER INFORMATION: Sequence of the first arm of the 3'UTR dsRNA used to target a 3'UTR RNA region from SARS-CoV-2

<400> SEQUENCE: 63
cagaccacac aaggcagatg ggctatataa acgttttcgc ttttccgttt acgatatata 60
gtctactctt gtgcagaatg aattctcgta actacatagc acaagtagat gtagttaact 120
ttaatctcac atagcaatct ttaatcagtg tgtaacatta gggaggactt gaaagagcca 180
ccacattttc accgaggcca cgcggagtac gatcgagtgt acagtgaaca atgctaggga 240
gagctgccta tatggaagag ccctaatgtg taaaattaat tttagtagtg ctatccccat 300
gtga 304

<210> SEQ ID NO 64
<211> LENGTH: 304
<212> TYPE: DNA
<213> ORGANISM: artificial
<220> FEATURE:
<223> OTHER INFORMATION: Sequence of the second arm of the 3'UTR dsRNA used to target a 3'UTR RNA region from SARS-CoV-2

<400> SEQUENCE: 64
tcacatgggg atagcactac taaaattaat tttacacatt agggctcttc catataggca 60
gctctcccta gcattgttca ctgtacactc gatcgtactc cgcgtggcct cggtgaaaat 120
gtggtggctc tttcaagtcc tccctaatgt tacacactga ttaaagattg ctatgtgaga 180
ttaaagttaa ctacatctac ttgtgctatg tagttacgag aattcattct gcacaagagt 240
agactatata tcgtaaacgg aaaagcgaaa acgtttatat agcccatctg ccttgtgtgg 300
tctg 304

<210> SEQ ID NO 65
<211> LENGTH: 353
<212> TYPE: DNA
<213> ORGANISM: artificial
<220> FEATURE:
<223> OTHER INFORMATION: Sequence of the first arm of the Helicase dsRNA used to target a Helicase RNA region from SARS-CoV-2

<400> SEQUENCE: 65

```
gctgttgggg cttgtgttct ttgcaattca cagacttcat taagatgtgg tgcttgcata     60

cgtagaccat tcttatgttg taaatgctgt tacgaccatg tcatatcaac atcacataaa    120

ttagtcttgt ctgttaatcc gtatgtttgc aatgctccag gttgtgatgt cacagatgtg    180

actcaacttt acttaggagg tatgagctat tattgtaaat cacataaacc acccattagt    240

tttccattgt gtgctaatgg acaagttttt ggtttatata aaaatacatg tgttggtagc    300

gataatgtta ctgactttaa tgcaattgca acatgtgact ggacaaatgc tgg           353


<210> SEQ ID NO 66
<211> LENGTH: 353
<212> TYPE: DNA
<213> ORGANISM: artificial
<220> FEATURE:
<223> OTHER INFORMATION: Sequence of the second arm of the Helicase
      dsRNA used to target a Helicase RNA region from SARS-CoV-2

<400> SEQUENCE: 66

ccagcatttg tccagtcaca tgttgcaatt gcattaaagt cagtaacatt atcgctacca     60

acacatgtat ttttatataa accaaaaact tgtccattag cacacaatgg aaaactaatg    120

ggtggtttat gtgatttaca ataatagctc atacctccta agtaaagttg agtcacatct    180

gtgacatcac aacctggagc attgcaaaca tacggattaa cagacaagac taatttatgt    240

gatgttgata tgacatggtc gtaacagcat ttacaacata agaatggtct acgtatgcaa    300

gcaccacatc ttaatgaagt ctgtgaattg caaagaacac aagccccaac agc           353


<210> SEQ ID NO 67
<211> LENGTH: 627
<212> TYPE: DNA
<213> ORGANISM: artificial
<220> FEATURE:
<223> OTHER INFORMATION: Sequence of the first arm of the dnaA/dnaB/gyrB
      dsRNA used to concomitantly target the dnaA, dnaB and gyrB genes
      from P. aeruginosa

<400> SEQUENCE: 67

gtgtccgtgg aactttggca gcagtgcgtg gatcttctcc gcgatgagct gccgtcccaa     60

caattcaaca cctggatccg tcccttgcag gtcgaagccg aggcgacgaa ttgcgtgtgt    120

atgcacccaa ccgtttcgtc ctcgattggg tgaacgagaa atacctcggt cggcttctgg    180

aactgctcgg tgaacgcggg agggtcagtt gatcatgcat ttcaccattc aacgcgaagc    240

cctgttgaaa ccgctgcaac tggtcgccgg cgtcgtggaa cgccgccaga cattgccggt    300

tctctccaac gtcctgctgg tggtcgaagg ccagcaactg tcgctgaccg gcaccgacct    360

cgaagtcgag ctggttggtc gcgtggtact ggaagatgcc gccgaacccg gcgagatcac    420

catgcatgag cgagaacaac acgtacgact cttccagcat caaggtgctg aaggggctgg    480

atgccgtacg caagcgcccc ggcatgtaca tcggcgacac cgacgatggc accggtctgc    540

accacatggt gttcgaggtg gtggataact ccatcgacga agcgctggcc ggttactgca    600

gcgaaatcag catcaccatc catacgg                                        627


<210> SEQ ID NO 68
<211> LENGTH: 627
<212> TYPE: DNA
<213> ORGANISM: artificial
<220> FEATURE:
<223> OTHER INFORMATION: Sequence of the second arm of the
      dnaA/dnaN/gyrB dsRNA used to concomitantly target the dnaA, dnaB
      and gyrB genes from P. aeruginosa
```

<400> SEQUENCE: 68

```
ccgtatggat ggtgatgctg atttcgctgc agtaaccggc cagcgcttcg tcgatggagt     60

tatccaccac ctcgaacacc atgtggtgca gaccggtgcc atcgtcggtg tcgccgatgt    120

acatgccggg gcgcttgcgt acggcatcca gccccttcag caccttgatg ctggaagagt    180

cgtacgtgtt gttctcgctc atgcatggtg atctcgccgg gttcggcggc atcttccagt    240

accacgcgac caaccagctc gacttcgagg tcggtgccgg tcagcgacag ttgctggcct    300

tcgaccacca gcaggacgtt ggagagaacc ggcaatgtct ggcggcgttc cacgacgccg    360

gcgaccagtt gcagcggttt caacagggct tcgcgttgaa tggtgaaatg catgatcaac    420

tgaccctccc gcgttcaccg agcagttcca gaagccgacc gaggtatttc tcgttcaccc    480

aatcgaggac gaaacggttg ggtgcataca cacgcaattc gtcgcctcgg cttcgacctg    540

caagggacgg atccaggtgt tgaattgttg ggacggcagc tcatcgcgga gaagatccac    600

gcactgctgc caaagttcca cggacac                                        627
```

<210> SEQ ID NO 69
<211> LENGTH: 800
<212> TYPE: DNA
<213> ORGANISM: artificial
<220> FEATURE:
<223> OTHER INFORMATION: Sequence of the first arm of the rpoC/secE/SodB dsRNA used to concomitantly target the rpoC, secE and SodB genes from P. aeruginosa

<400> SEQUENCE: 69

```
tgaaagactt gcttaatctg ttgaaaaacc agggtcaaat cgaagagttc gatgccatcc     60

gtattggcct ggcttcgccc gagatgattc gttcctggtc tttcggcgaa gttaaaaagc    120

cggaaaccat caactaccgt accttcaagc cggagcgcga cggcctgttc tgcgccaaga    180

tcttcggccc ggtgaaggat tacgagtgcc tgtgcggcaa gtacaagcgc ctcaagcacc    240

gcggtgtgat ctgcgagaag tgatcatgaa tgccaaggca gaagccaaag aatcacgttt    300

tgatctcttg aaatggctct tggttgccgt tctggttgtg gttgccgttg tgggcaatca    360

gtacttttcg gctcaaccaa tcctgtatcg cgttctcggt attctcgttc tggcggtgat    420

cgctgctttc ctggctctgc aaacggccaa ggggcaggcc ttctttagtc ttgctaagga    480

agcgcgcgtc gagattcgca aggtcgtatg gccgagtcgt caagaaacaa ctcagaccac    540

gctgatcgat gcatggcttt cgaattgccg ccgctgcctt acgaaaagaa cgcccttgag    600

ccgcacattt ccgcagaaac cctggaatac caccacgaca agcaccacaa cacctacgtg    660

gtgaacctga acaacctgat cccgggcacc gagttcgaag gcaagagcct cgaagagatc    720

gtcaagagct cctccggcgg catcttcaac aacgccgccc aggtgtggaa ccacaccttc    780

tactggaact gcctgagccc                                                800
```

<210> SEQ ID NO 70
<211> LENGTH: 800
<212> TYPE: DNA
<213> ORGANISM: artificial
<220> FEATURE:
<223> OTHER INFORMATION: Sequence of the second arm of the rpoC/secE/SodB dsRNA used to concomitantly target the rpoC, secE and SodB genes from P. aeruginosa

<400> SEQUENCE: 70

```
gggctcaggc agttccagta gaaggtgtgg ttccacacct gggcggcgtt gttgaagatg     60

ccgccggagg agctcttgac gatctcttcg aggctcttgc cttcgaactc ggtgcccggg    120
```

```
atcaggttgt tcaggttcac cacgtaggtg ttgtggtgct tgtcgtggtg gtattccagg    180

gtttctgcgg aaatgtgcgg ctcaagggcg ttcttttcgt aaggcagcgg cggcaattcg    240

aaagccatgc atcgatcagc gtggtctgag ttgtttcttg acgactcggc catacgacct    300

tgcgaatctc gacgcgcgct tccttagcaa gactaaagaa ggcctgcccc ttggccgttt    360

gcagagccag gaaagcagcg atcaccgcca gaacgagaat accgagaacg cgatacagga    420

ttggttgagc cgaaaagtac tgattgccca caacggcaac cacaaccaga acggcaacca    480

agagccattt caagagatca aaacgtgatt ctttggcttc tgccttggca ttcatgatca    540

cttctcgcag atcacaccgc ggtgcttgag gcgcttgtac ttgccgcaca ggcactcgta    600

atccttcacc gggccgaaga tcttggcgca gaacaggccg tcgcgctccg gcttgaaggt    660

acggtagttg atggtttccg gctttttaac ttcgccgaaa gaccaggaac gaatcatctc    720

gggcgaagcc aggccaatac ggatggcatc gaactcttcg atttgaccct ggtttttcaa    780

cagattaagc aagtctttca                                                800
```

<210> SEQ ID NO 71
<211> LENGTH: 632
<212> TYPE: DNA
<213> ORGANISM: artificial
<220> FEATURE:
<223> OTHER INFORMATION: Sequence of the first arm of the FtsA/Can/Tsf dsRNA used to concomitantly target the FtsA, Can and Tsf genes from Shigella flexneri

<400> SEQUENCE: 71

```
atgatcaagg cgacggacag aaaactggta gtaggactgg aaattggtac cgcgaaggtt     60

gccgctttag taggggaagt tctgcccgac ggtatggtca atatcattgg cgtgggcagc    120

tgcccgtcac gtggtatgga taaaggtggg gtgaacgacc tcgaatccgt ggtcaagtgc    180

gtacaacgcg ccattgacca ggcagaattg atggcaggat ctttgtggtt ggcgtgtttc    240

agcttgaggt tggaaatccc gtgacggtaa cgttgctcaa gggtttcgcg gttggtggcg    300

gtaacatcca gatcacgcag caagccgtcg tgaatgccgt aggcccagcc gtgaatggta    360

actttctgcc cgcgtttcca cgctgattgc ataatggtgg agtggcccag gttatacacc    420

tatgctggct gaaattaccg catccctggt aaaagagctg cgtgagcgta ctggcgcagg    480

catgatggat tgcaaaaaag cactgactga agctaacggc gacatcgagc tggcaatcga    540

aaacatgcgt aagtccggtg ctattaaagc agcgaaaaaa gcaggcaacg ttgctgctga    600

cggcgtgatc aaaaccaaaa tcgacggcaa ct                                  632
```

<210> SEQ ID NO 72
<211> LENGTH: 632
<212> TYPE: DNA
<213> ORGANISM: artificial
<220> FEATURE:
<223> OTHER INFORMATION: Sequence of the second arm of the FtsA/Can/Tsf dsRNA used to concomitantly target the FtsA, Can and Tsf genes from Shigella flexneri

<400> SEQUENCE: 72

```
agttgccgtc gattttggtt ttgatcacgc cgtcagcagc aacgttgcct gctttttttcg     60

ctgctttaat agcaccggac ttacgcatgt tttcgattgc cagctcgatg tcgccgttag    120

cttcagtcag tgcttttttg caatccatca tgcctgcgcc agtacgctca cgcagctctt    180

ttaccaggga tgcggtaatt tcagccagca taggtgtata acctgggcca ctccaccatt    240
```

```
atgcaatcag cgtggaaacg cgggcagaaa gttaccattc acggctgggc ctacggcatt    300

cacgacggct tgctgcgtga tctggatgtt accgccacca accgcgaaac ccttgagcaa    360

cgttaccgtc acgggatttc caacctcaag ctgaaacacg ccaaccacaa agatcctgcc    420

atcaattctg cctggtcaat ggcgcgttgt acgcacttga ccacggattc gaggtcgttc    480

accccacctt tatccatacc acgtgacggg cagctgccca cgccaatgat attgaccata    540

ccgtcgggca gaacttcccc tactaaagcg gcaaccttcg cggtaccaat ttccagtcct    600

actaccagtt ttctgtccgt cgccttgatc at                                  632
```

```
<210> SEQ ID NO 73
<211> LENGTH: 682
<212> TYPE: DNA
<213> ORGANISM: artificial
<220> FEATURE:
<223> OTHER INFORMATION: Sequence of the first arm of the AccD/Der/Psd
      dsRNA used to concomitantly target the AccD, Der and Psd genes
      from Shigella flexneri

<400> SEQUENCE: 73

taccgggggt accactacgc cttcacgcgg cgcttcagga ttcggcgctg gcagattcat     60

caacttcgcc agaatgctcg ccagtttcag gcgcatttcc ggacgacgga cgatcatgtc    120

gatcgcgcct ttctcgatca ggaattcact gcgctggaat ctaggcggca gtttttcgcg    180

aacggtctgt tcgataacac gcggaccggc aaagccgatt aacgcttgat ctttcttgat    240

gtgcttcatc agacgcttac gtttacgcat ctgggttggc gtcagggtgt tacgcttgtt    300

cgcatacggg ttttcccctt ctttgaactg aatacgaatc ggcgatccca ttacgtccag    360

cgatttgcgg aagtagttca tcaagtagcg cttgtaggaa tcaggcaggt ctttcacctg    420

attaccgtga atcaccacaa tcggcgggat gctttttatc gtcaaccaat gggctggcgt    480

cgtgttctgc ttcgatctct tcagcaggaa gtggggcggg ttcagcgtct ggcgtaacaa    540

aggtttcggt agatactgcc agcggctggc caattttcgt gacagacagg ctttccagtt    600

gctcaaccag attcacttta cccggtgcaa acaggttgat aacggtggaa ccgagtttaa    660

agcgacccat ttcctggcct tt                                             682
```

```
<210> SEQ ID NO 74
<211> LENGTH: 682
<212> TYPE: DNA
<213> ORGANISM: artificial
<220> FEATURE:
<223> OTHER INFORMATION: Sequence of the second arm of the AccD/Der/Psd
      dsRNA used to concomitantly target the AccD, Der and Psd genes
      from Shigella flexneri

<400> SEQUENCE: 74

aaaggccagg aaatgggtcg ctttaaactc ggttccaccg ttatcaacct gtttgcaccg     60

ggtaaagtga atctggttga gcaactggaa agcctgtctg tcacgaaaat tggccagccg    120

ctggcagtat ctaccgaaac ctttgttacg ccagacgctg aacccgcccc acttcctgct    180

gaagagatcg aagcagaaca cgacgccagc ccattggttg acgataaaaa gcatcccgcc    240

gattgtggtg attcacggta atcaggtgaa agacctgcct gattcctaca agcgctactt    300

gatgaactac ttccgcaaat cgctggacgt aatgggatcg ccgattcgta ttcagttcaa    360

agaaggggaa aacccgtatg cgaacaagcg taacaccctg acgccaaccc agatgcgtaa    420

acgtaagcgt ctgatgaagc acatcaagaa agatcaagcg ttaatcggct ttgccggtcc    480

gcgtgttatc gaacagaccg ttcgcgaaaa actgccgcct agattccagc gcagtgaatt    540
```

```
cctgatcgag aaaggcgcga tcgacatgat cgtccgtcgt ccggaaatgc gcctgaaact    600

ggcgagcatt ctggcgaagt tgatgaatct gccagcgccg aatcctgaag cgccgcgtga    660

aggcgtagtg gtacccccgg ta                                             682
```

<210> SEQ ID NO 75
<211> LENGTH: 365
<212> TYPE: DNA
<213> ORGANISM: ARTIFICIAL
<220> FEATURE:
<223> OTHER INFORMATION: Sequence of the first arm of the cpsA dsRNA used to target the cpsA (Rv3484) gene from Mycobacterium tubercolosis

<400> SEQUENCE: 75

```
atggcgcgtt ctgagggcaa tcgcccacgc catcgcgctg tgcctcagcc gtcgcggatc     60

cgcaagcggc tgtcgcgggg cgttatgacg ctcgtgtcgg tggttgccct gctgatgacc    120

ggcgcagggt attgggtagc ccacggcgcg ctgggcggca tcaccatttc gcaggcccta    180

acccccgagg atccccgttc cagcggcaac aacatgaaca tcttgctcat cgggctggac    240

tcgcgcaaag accaggaagg caacgacctg ccctggtcgg tcttgaagca gctacacgcg    300

ggcgattccg acgacggcgg ctacaacacg aacacgctga tacttgtgca cgtcggtgcc    360

gatgg                                                                365
```

<210> SEQ ID NO 76
<211> LENGTH: 365
<212> TYPE: DNA
<213> ORGANISM: ARTIFICIAL
<220> FEATURE:
<223> OTHER INFORMATION: Sequence of the second arm of the cpsA dsRNA used to target the cpsA (Rv3484) gene from Mycobacterium tubercolosis

<400> SEQUENCE: 76

```
ccatcggcac cgacgtgcac aagtatcagc gtgttcgtgt tgtagccgcc gtcgtcggaa     60

tcgcccgcgt gtagctgctt caagaccgac cagggcaggt cgttgccttc ctggtctttg    120

cgcgagtcca gcccgatgag caagatgttc atgttgttgc cgctggaacg gggatcctcg    180

ggggttaggg cctgcgaaat ggtgatgccg cccagcgcgc cgtgggctac ccaataccct    240

gcgccggtca tcagcagggc aaccaccgac acgagcgtca taacgccccg cgacagccgc    300

ttgcggatcc gcgacggctg aggcacagcg cgatggcgtg ggcgattgcc ctcagaacgc    360

gccat                                                                365
```

<210> SEQ ID NO 77
<211> LENGTH: 446
<212> TYPE: DNA
<213> ORGANISM: ARTIFICIAL
<220> FEATURE:
<223> OTHER INFORMATION: Sequence of the first arm of the pcaA dsRNA used to target the pcaA (Rv0470c) gene from Mycobacterium tubercolosis

<400> SEQUENCE: 77

```
atgtccgtgc agctcacgcc gcattttgga aacgtgcaag ctcattacga cctctccgac     60

gactttttcc ggctgttctt ggaccccacc cagacctaca gctgtgccta cttcgaacgc    120

gacgacatga cgctgcagga ggcccagatc gccaagatcg acctggccct gggcaagctg    180

aacctcgaac ccgggatgac gttgctggac atcggctgcg gctggggcgc gaccatgcgg    240
```

```
cgcgccatcg agaaatacga cgtcaatgtc gtgggcctga cgttgtcgga gaaccaggcc    300

ggtcatgtcc agaaaatgtt cgaccaaatg gacacccccc gctccagacg agtgttgctg    360

gagggatggg agaaatttga cgagcccgtc gaccgcatcg tctcgatcgg cgcgttcgag    420

cacttcggcc accagcgcta ccacca                                         446


<210> SEQ ID NO 78
<211> LENGTH: 446
<212> TYPE: DNA
<213> ORGANISM: ARTIFICIAL
<220> FEATURE:
<223> OTHER INFORMATION: Sequence of the second arm of the pcaA dsRNA
      used to target the pcaA (Rv0470c) gene from Mycobacterium
      tuberculosis

<400> SEQUENCE: 78

tggtggtagc gctggtggcc gaagtgctcg aacgcgccga tcgagacgat gcggtcgacg     60

ggctcgtcaa atttctccca tccctccagc aacactcgtc tggagcgggg ggtgtccatt    120

tggtcgaaca ttttctggac atgaccggcc tggttctccg acaacgtcag gcccacgaca    180

ttgacgtcgt atttctcgat ggcgcgccgc atggtcgcgc cccagccgca gccgatgtcc    240

agcaacgtca tcccgggttc gaggttcagc ttgcccaggg ccaggtcgat cttggcgatc    300

tgggcctcct gcagcgtcat gtcgtcgcgt tcgaagtagg cacagctgta ggtctgggtg    360

gggtccaaga acagccggaa aaagtcgtcg gagaggtcgt aatgagcttg cacgtttcca    420

aaatgcggcg tgagctgcac ggacat                                         446


<210> SEQ ID NO 79
<211> LENGTH: 407
<212> TYPE: DNA
<213> ORGANISM: ARTIFICIAL
<220> FEATURE:
<223> OTHER INFORMATION: Sequence of the first arm of the icl1 dsRNA
      used to target the icl1 (Rv0467) gene from Mycobacterium
      tubercolosis

<400> SEQUENCE: 79

atgtctgtcg tcggcacccc gaagagcgcg gagcagatcc agcaggaatg ggacacgaac     60

ccgcgctgga aggacgtcac ccgcacctac tccgccgagg acgtcgtcgc cctccagggc    120

agcgtggtcg aggagcacac gctggcccgc cgcggtgcgg aggtgctgtg ggagcagctg    180

cacgacctcg agtgggtcaa cgcgctgggc gcgctgaccg gcaacatggc cgtccagcag    240

gtgcgcgccg gcctgaaggc catctacctg tcgggctggc aggtcgccgg cgatgccaac    300

ctgtccgggc acacctaccc cgaccagagc ctgtatcccg ccaactcggt gccgcaggtg    360

gtccgccgga tcaacaacgc actgcagcgc gccgaccaga tcgccaa                  407


<210> SEQ ID NO 80
<211> LENGTH: 407
<212> TYPE: DNA
<213> ORGANISM: ARTIFICIAL
<220> FEATURE:
<223> OTHER INFORMATION: Sequence of the second arm of the icl1 dsRNA
      used to target the icl1 (Rv0467) gene from Mycobacterium
      tuberculosis

<400> SEQUENCE: 80

ttggcgatct ggtcggcgcg ctgcagtgcg ttgttgatcc ggcggaccac ctgcggcacc     60

gagttggcgg gatacaggct ctggtcgggg taggtgtgcc cggacaggtt ggcatcgccg    120

gcgacctgcc agcccgacag gtagatggcc ttcaggccgg cgcgcacctg ctggacggcc    180
```

atgttgccgg tcagcgcgcc cagcgcgttg acccactcga ggtcgtgcag ctgctcccac 240
agcacctccg caccgcggcg ggccagcgtg tgctcctcga ccacgctgcc ctggagggcg 300
acgacgtcct cggcggagta ggtgcgggtg acgtccttcc agcgcgggtt cgtgtcccat 360
tcctgctgga tctgctccgc gctcttcggg gtgccgacga cagacat 407

<210> SEQ ID NO 81
<211> LENGTH: 392
<212> TYPE: DNA
<213> ORGANISM: ARTIFICIAL
<220> FEATURE:
<223> OTHER INFORMATION: Sequence of the first arm of the rip dsRNA used to target the rip (Rv2869) gene from Mycobacterium tubercolosis

<400> SEQUENCE: 81
atgatgtttg ttaccggcat tgtgctgttc gcgctcgcga tcctgatttc ggtggccctg 60
cacgaatgtg gtcacatgtg ggtcgcgcgc cgcaccggga tgaaggtacg tcgctatttc 120
gtcggctttg gccccacgtt gtggtcgacc cggcgcggcg agaccgaata cggtgtcaaa 180
gccgttccgc tgggcggctt ctgtgacatc gccggcatga ccccggtcga ggaactcgac 240
cccgacgaac gtgaccgtgc gatgtacaag caggccacct ggaagcgggt cgcagtgtta 300
ttcgccgggc ccggaatgaa cctcgctatc tgcctggtgc tgatctatgc catcgcgctg 360
gtctgggggc tgcctaacct gcatccgcca ac 392

<210> SEQ ID NO 82
<211> LENGTH: 392
<212> TYPE: DNA
<213> ORGANISM: ARTIFICIAL
<220> FEATURE:
<223> OTHER INFORMATION: Sequence of the second arm of the rip dsRNA used to target the rip (Rv2869) gene from Mycobacterium tuberculosis

<400> SEQUENCE: 82
gttggcggat gcaggttagg cagcccccag accagcgcga tggcatagat cagcaccagg 60
cagatagcga ggttcattcc gggcccggcg aataacactg cgacccgctt ccaggtggcc 120
tgcttgtaca tcgcacggtc acgttcgtcg gggtcgagtt cctcgaccgg ggtcatgccg 180
gcgatgtcac agaagccgcc cagcggaacg gctttgacac cgtattcggt ctcgccgcgc 240
cgggtcgacc acaacgtggg gccaaagccg acgaaatagc gacgtacctt catcccggtg 300
cggcgcgcga cccacatgtg accacattcg tgcagggcca ccgaaatcag gatcgcgagc 360
gcgaacagca caatgccggt aacaaacatc at 392

<210> SEQ ID NO 83
<211> LENGTH: 378
<212> TYPE: DNA
<213> ORGANISM: ARTIFICIAL
<220> FEATURE:
<223> OTHER INFORMATION: Sequence of the first arm of the fad26 dsRNA used to target the fad26 (Rv2930) gene from Mycobacterium tubercolosis

<400> SEQUENCE: 83
atgccggtga ccgaccgttc agtgccctct ttgctgcaag agagggccga ccagcagcct 60
gacagcactg catatacgta catcgactac ggatccgacc ccaagggatt tgctgacagc 120
ttgacttggt cgcaggtcta cagtcgtgca tgcatcattg ctgaagaact caagttatgc 180
gggttacccg gagatcgagt ggcggtttta gcgccacaag gactggaata tgtccttgca 240

```
ttcctgggcg cacttcaggc tggatttatc gcggttccgc tgtcaactcc acagtatggc    300

attcacgatg accgcgtttc tgcggtgttg caggattcca agccggtagc cattctcacg    360

acttcgtccg tggtaggc                                                  378
```

<210> SEQ ID NO 84
<211> LENGTH: 378
<212> TYPE: DNA
<213> ORGANISM: ARTIFICIAL
<220> FEATURE:
<223> OTHER INFORMATION: Sequence of the second arm of the fad26 dsRNA used to target the fad26 (Rv2930) gene from Mycobacterium tuberculosis

<400> SEQUENCE: 84

```
gcctaccacg gacgaagtcg tgagaatggc taccggcttg gaatcctgca acaccgcaga     60

aacgcggtca tcgtgaatgc catactgtgg agttgacagc ggaaccgcga taaatccagc    120

ctgaagtgcg cccaggaatg caaggacata ttccagtcct tgtggcgcta aaaccgccac    180

tcgatctccg ggtaacccgc ataacttgag ttcttcagca atgatgcatg cacgactgta    240

gacctgcgac caagtcaagc tgtcagcaaa tcccttgggg tcggatccgt agtcgatgta    300

cgtatatgca gtgctgtcag gctgctggtc ggccctctct tgcagcaaag agggcactga    360

acggtcggtc accggcat                                                  378
```

<210> SEQ ID NO 85
<211> LENGTH: 379
<212> TYPE: DNA
<213> ORGANISM: ARTIFICIAL
<220> FEATURE:
<223> OTHER INFORMATION: Sequence of the first arm of the hphA dsRNA used to target the hphA (Rv0475) gene from Mycobacterium tuberculosis

<400> SEQUENCE: 85

```
atggctgaaa actcgaacat tgatgacatc aaggctccgt tgcttgccgc gcttggagcg     60

gccgacctgg ccttggccac tgtcaacgag ttgatcacga acctgcgtga gcgtgcggag    120

gagactcgta cggacacccg cagccgggtc gaggagagcc gtgctcgcct gaccaagctg    180

caggaagatc tgcccgagca gctcaccgag ctgcgtgaga agttcaccgc cgaggagctg    240

cgtaaggccg ccgagggcta cctcgaggcc gcgactagcc ggtacaacga gctggtcgag    300

cgcggtgagg ccgctctaga gcggctgcgc agccagcaga gcttcgagga agtgtcggcg    360

cgcgccgaag gctacgtgg                                                 379
```

<210> SEQ ID NO 86
<211> LENGTH: 379
<212> TYPE: DNA
<213> ORGANISM: ARTIFICIAL
<220> FEATURE:
<223> OTHER INFORMATION: Sequence of the second arm of the hphA dsRNA used to target the hphA (Rv0475) gene from Mycobacterium tuberculosis

<400> SEQUENCE: 86

```
ccacgtagcc ttcggcgcgc gccgacactt cctcgaagct ctgctggctg cgcagccgct     60

ctagagcggc ctcaccgcgc tcgaccagct cgttgtaccg gctagtcgcg gcctcgaggt    120

agccctcggc ggccttacgc agctcctcgg cggtgaactt ctcacgcagc tcggtgagct    180

gctcgggcag atcttcctgc agcttggtca ggcgagcacg gctctcctcg acccggctgc    240
```

gggtgtccgt acgagtctcc tccgcacgct cacgcaggtt cgtgatcaac tcgttgacag 300
tggccaaggc caggtcggcc gctccaagcg cggcaagcaa cggagccttg atgtcatcaa 360
tgttcgagtt ttcagccat 379

<210> SEQ ID NO 87
<211> LENGTH: 815
<212> TYPE: DNA
<213> ORGANISM: ARTIFICIAL
<220> FEATURE:
<223> OTHER INFORMATION: Sequence of the first arm of the cpsA/pcaA dsRNA used to concomitantly target the cpsA (Rv3484) and pcaA (Rv0470c) genes from Mycobacterium tuberculosis

<400> SEQUENCE: 87
atggcgcgtt ctgagggcaa tcgcccacgc catcgcgctg tgcctcagcc gtcgcggatc 60
cgcaagcggc tgtcgcgggg cgttatgacg ctcgtgtcgg tggttgccct gctgatgacc 120
ggcgcagggt attgggtagc ccacggcgcg ctgggcggca tcaccatttc gcaggcccta 180
acccccgagg atccccgttc cagcggcaac aacatgaaca tcttgctcat cgggctggac 240
tcgcgcaaag accaggaagg caacgacctg ccctggtcgg tcttgaagca gctacacgcg 300
ggcgattccg acgacggcgg ctacaacacg aacacgctga tacttgtgca cgtcggtgcc 360
gatgggatca tgtccgtgca gctcacgccg cattttggaa acgtgcaagc tcattacgac 420
ctctccgacg actttttccg gctgttcttg gaccccaccc agacctacag ctgtgcctac 480
ttcgaacgcg acgacatgac gctgcaggag gcccagatcg ccaagatcga cctggccctg 540
ggcaagctga acctcgaacc cgggatgacg ttgctggaca tcggctgcgg ctggggcgcg 600
accatgcggc gcgccatcga gaaatacgac gtcaatgtcg tgggcctgac gttgtcggag 660
aaccaggccg gtcatgtcca gaaaatgttc gaccaaatgg acaccccccg ctccagacga 720
gtgttgctgg agggatggga gaaatttgac gagcccgtcg accgcatcgt ctcgatcggc 780
gcgttcgagc acttcggcca ccagcgctac cacca 815

<210> SEQ ID NO 88
<211> LENGTH: 815
<212> TYPE: DNA
<213> ORGANISM: ARTIFICIAL
<220> FEATURE:
<223> OTHER INFORMATION: Sequence of the second arm of the cpsA/pcaA dsRNA used to concomitantly target the cpsA (Rv3484) and pcaA (Rv0470c) genes from Mycobacterium tuberculosis

<400> SEQUENCE: 88
tggtggtagc gctggtggcc gaagtgctcg aacgcgccga tcgagacgat gcggtcgacg 60
ggctcgtcaa atttctccca tccctccagc aacactcgtc tggagcgggg ggtgtccatt 120
tggtcgaaca ttttctggac atgaccggcc tggttctccg acaacgtcag gcccacgaca 180
ttgacgtcgt atttctcgat ggcgcgccgc atggtcgcgc cccagccgca gccgatgtcc 240
agcaacgtca tcccgggttc gaggttcagc ttgcccaggg ccaggtcgat cttggcgatc 300
tgggcctcct gcagcgtcat gtcgtcgcgt tcgaagtagg cacagctgta ggtctgggtg 360
gggtccaaga acagccggaa aaagtcgtcg gagaggtcgt aatgagcttg cacgtttcca 420
aaatgcggcg tgagctgcac ggacatgatc ccatcggcac cgacgtgcac aagtatcagc 480
gtgttcgtgt tgtagccgcc gtcgtcggaa tcgcccgcgt gtagctgctt caagaccgac 540
cagggcaggt cgttgccttc ctggtctttg cgcgagtcca gcccgatgag caagatgttc 600
atgttgttgc cgctggaacg gggatcctcg gggttagggc cctgcgaaat ggtgatgccg 660
cccagcgcgc cgtgggctac ccaataccct gcgccggtca tcagcagggc aaccaccgac 720
acgagcgtca taacgccccg cgacagccgc ttgcggatcc gcgacggctg aggcacagcg 780
cgatggcgtg ggcgattgcc ctcagaacgc gccat 815

<210> SEQ ID NO 89
<211> LENGTH: 364
<212> TYPE: DNA
<213> ORGANISM: ARTIFICIAL
<220> FEATURE:
<223> OTHER INFORMATION: Sequence of the first arm of the dotA dsRNA used to target the dotA (lpg2686) gene from Legionella pneumophila

<400> SEQUENCE: 89
atgaataaat tagctattac ggtcctcctt tgcttttttc ctgcgcttgc actggctgaa 60
aatggagcct tgagtttcgc tcctccggca agcgatttgt ccgttgtttt tttaggtaac 120
ctatttggtg tagtcgatgg tgtattgcac ggcactggaa gccagataat gggcaatatg 180
tttggtgttt ttaactccgc tgtccttgcg ctgggcggta tcattataat gtacaccctt 240
atggtttcca ccatgaacac ggcccatgaa gggcaaatgc tcgggcaaaa atggtcttca 300
atctggattc ctcttcgctc caccttcggc ttggctttgt taatacccaa ggcatctggt 360
tatt 364

<210> SEQ ID NO 90
<211> LENGTH: 364
<212> TYPE: DNA
<213> ORGANISM: ARTIFICIAL
<220> FEATURE:
<223> OTHER INFORMATION: Sequence of the second arm of the dotA dsRNA used to target the dotA (lpg2686) gene from Legionella pneumophila

<400> SEQUENCE: 90
aataaccaga tgccttgggt attaacaaag ccaagccgaa ggtggagcga agaggaatcc 60
agattgaaga ccatttttgc ccgagcattt gcccttcatg ggccgtgttc atggtggaaa 120
ccataagggt gtacattata atgataccgc ccagcgcaag gacagcggag ttaaaaacac 180
caaacatatt gcccattatc tggcttccag tgccgtgcaa tacaccatcg actacaccaa 240
ataggttacc taaaaaaaca acggacaaat cgcttgccgg aggagcgaaa ctcaaggctc 300
cattttcagc cagtgcaagc gcaggaaaaa agcaaaggag gaccgtaata gctaatttat 360
tcat 364

<210> SEQ ID NO 91
<211> LENGTH: 369
<212> TYPE: DNA
<213> ORGANISM: ARTIFICIAL
<220> FEATURE:
<223> OTHER INFORMATION: Sequence of the first arm of the dotD dsRNA used to target the dotD (lpg2674) gene from Legionella pneumophila

<400> SEQUENCE: 91
atgaacaaca ataagattgt cataatgttt attttttcag cgcttcttgc tggttgcgct 60
ggaacaatga aatttaaaaa accacccatc aataatccaa gtgatgatgc gaccattaaa 120
ttagcagaag ctgccgtttc agtcagtgac tccatgcttg aaatggcaaa agttgaaaaa 180
gtaattactc caccaagcaa agacaatacc ttaactatac ctaatgctta taacttgcaa 240
gcaagagcca gtgtcgattg gtctggtccg attgaagaat tgactgcacg tatcgccaaa 300
gcagcacatt tcagatttcg tgttttaggc aagtcgcctt cagttccagt tttaatcagc 360
atcagtacc 369

<210> SEQ ID NO 92
<211> LENGTH: 369
<212> TYPE: DNA
<213> ORGANISM: ARTIFICIAL
<220> FEATURE:
<223> OTHER INFORMATION: Sequence of the second arm of the dotD dsRNA used to target the dotD (lpg2674) gene from Legionella pneumophila

<400> SEQUENCE: 92
ggtactgatg ctgattaaaa ctggaactga aggcgacttg cctaaaacac gaaatctgaa 60
atgtgctgct ttggcgatac gtgcagtcaa ttcttcaatc ggaccagacc aatcgacact 120
ggctcttgct tgcaagttat aagcattagg tatagttaag gtattgtctt tgcttggtgg 180
agtaattact ttttcaactt ttgccatttc aagcatggag tcactgactg aaacggcagc 240
ttctgctaat ttaatggtcg catcatcact tggattattg atgggtggtt ttttaaattt 300
cattgttcca gcgcaaccag caagaagcgc tgaaaaaaata aacattatga caatcttatt 360
gttgttcat 369

<210> SEQ ID NO 93
<211> LENGTH: 369
<212> TYPE: DNA
<213> ORGANISM: ARTIFICIAL
<220> FEATURE:
<223> OTHER INFORMATION: Sequence of the first arm of the dotC dsRNA used to target the dotC (lpg2675) gene from Legionella pneumophila

<400> SEQUENCE: 93
atgcgaaaat ttattcttag tttatctatt ttgctatcag ccctcctggt agcctgttct 60
tctcgtaatc attacgggga tactggctca ttggcaggac ttcaagctat ggctgattca 120
aaatacaccc gagctcaaaa aaaacaaaaa atgggtaaaa ttcgcgagat ggcccttaag 180
gaaaccgctt taagtgttgg cgcccaggct gggttagcct ggagagcaaa aataattgac 240
gagcaattaa acaaacaggc aaggaatctt gatgcaattt atgattttaa ttccctggtc 300
ttagagcata atattttgcc tcctgtatta cttgagggaa ggaatacttt gaatcttgca 360
gatgctcaa 369

<210> SEQ ID NO 94
<211> LENGTH: 367
<212> TYPE: DNA
<213> ORGANISM: ARTIFICIAL
<220> FEATURE:
<223> OTHER INFORMATION: Sequence of the second arm of the dotC dsRNA used to target the dotC (lpg2675) gene from Legionella pneumophila

<400> SEQUENCE: 94
ttgagcatct gcaagattca aagtattcct tccctcaagt aatacaggag gcaaaatatt 60
atgctctaag accagggaat taaaatcata aattgcatca agattccttg cctgtttgtt 120
taattgctcg tcaattattt ttgctctcca ggctaaccca gcctgggcgc caacacttaa 180
agcggtttcc ttaagggcca tctcgcgaat tttacccatt ttttgttttt tttgagctcg 240
ggtgtatttt gaatcagcca tagcttgaag tcctgccaat gagccagtat ccccgtaatg 300
attacgagaa gaacaggcta ccaggagggc tgatagcaaa atagataaac taagaataaa 360
ttttcgc 367

<210> SEQ ID NO 95
<211> LENGTH: 357
<212> TYPE: DNA
<213> ORGANISM: ARTIFICIAL
<220> FEATURE:
<223> OTHER INFORMATION: Sequence of the first arm of the dotB dsRNA used to target the dotB (lpg2676) gene from Legionella pneumophila

<400> SEQUENCE: 95

```
ctggcaacct attatagcac cagtaagtta atgtctatgg ataatattaa tttaatgccc     60

gatgagccaa ctcgtttcac tccagtattc atggacagaa tgctggagca tgcagaaagc    120

ctgaatgctt cagatataac aatccaaact ggcgaaccca tttttgcaga ggtttatgga    180

agactcctta aaattacaaa tcgacgtctt tccaatacag aattgggcga ccttattaat    240

tccatttatg gcccgaatgc cacgacacaa ttactttccg gtaaagatat agatactcat    300

tatgagtttc gacccaaccg tggtgtacgc tatcgatata gggttaacgc gactgcc       357
```

<210> SEQ ID NO 96
<211> LENGTH: 357
<212> TYPE: DNA
<213> ORGANISM: ARTIFICIAL
<220> FEATURE:
<223> OTHER INFORMATION: Sequence of the second arm of the dotB dsRNA used to target the dotB (lpg2676) gene from Legionella pneumophila

<400> SEQUENCE: 96

```
ggcagtcgcg ttaaccctat atcgatagcg tacaccacgg ttgggtcgaa actcataatg     60

agtatctata tctttaccgg aaagtaattg tgtcgtggca ttcgggccat aaatggaatt    120

aataaggtcg cccaattctg tattggaaag acgtcgattt gtaattttaa ggagtcttcc    180

ataaacctct gcaaaaatgg gttcgccagt ttggattgtt atatctgaag cattcaggct    240

ttctgcatgc tccagcattc tgtccatgaa tactggagtg aaacgagttg gctcatcggg    300

cattaaatta atattatcca tagacattaa cttactggtg ctataatagg ttgccag       357
```

<210> SEQ ID NO 97
<211> LENGTH: 261
<212> TYPE: DNA
<213> ORGANISM: ARTIFICIAL
<220> FEATURE:
<223> OTHER INFORMATION: Sequence of the first arm of the icmT dsRNA used to target the icmT (lpg0441) gene from Legionella pneumophila

<400> SEQUENCE: 97

```
atggcaggtg gattttcagc aacgagccac tggcgtgact cagcgagaag cgcgcggttt     60

tttgtagttg atgcgagggc cgcattccca atatttttat ttctaatgca tataagagta    120

tggacaggtg ttttggtctt agtttctgca attttttttg ggataattga acattatggt    180

ttcactgtcc cggttttttt acgctggctc agaagttttt tagctggttc agttagatct    240

gctagacctt ggtggagata a                                              261
```

<210> SEQ ID NO 98
<211> LENGTH: 261
<212> TYPE: DNA
<213> ORGANISM: ARTIFICIAL
<220> FEATURE:
<223> OTHER INFORMATION: Sequence of the second arm of the icmT dsRNA used to target the icmT (lpg0441) gene from Legionella pneumophila

<400> SEQUENCE: 98

```
ttatctccac caaggtctag cagatctaac tgaaccagct aaaaaacttc tgagccagcg     60
```

```
taaaaaaacc gggacagtga aaccataatg ttcaattatc ccaaaaaaaa ttgcagaaac    120

taagaccaaa acacctgtcc atactcttat atgcattaga aataaaaata ttgggaatgc    180

ggccctcgca tcaactacaa aaaaccgcgc gcttctcgct gagtcacgcc agtggctcgt    240

tgctgaaaat ccacctgcca t                                              261


<210> SEQ ID NO 99
<211> LENGTH: 301
<212> TYPE: DNA
<213> ORGANISM: ARTIFICIAL
<220> FEATURE:
<223> OTHER INFORMATION: Sequence of the first arm of the icmJ dsRNA
      used to target the icmJ (lpg0455) gene from Legionella pneumophila

<400> SEQUENCE: 99

ctgaatgtga accaaactat ggcggataat caacaacgat gtgagctaaa actaattgct     60

tcaccaggtt cctggcgttt atattctgcc agaaaaattg atgagcgatt caaatcctat    120

gagcaaaaaa tctttcagcg agataggtat acttgtcaat tttgcgggtt tcaagcccga    180

ttataccaag acatcgtgaa tctggatggt gattatacaa acaataggtt atcaaattta    240

gttacagctt gttgtttttg tgcgcaatgc tttttgttg agtcagttgg agttggtggt     300

t                                                                    301


<210> SEQ ID NO 100
<211> LENGTH: 301
<212> TYPE: DNA
<213> ORGANISM: ARTIFICIAL
<220> FEATURE:
<223> OTHER INFORMATION: Sequence of the second arm of the icmJ dsRNA
      used to target the icmJ (lpg0455) gene from Legionella pneumophila

<400> SEQUENCE: 100

aaccaccaac tccaactgac tcaacaaaaa agcattgcgc acaaaaacaa caagctgtaa     60

ctaaatttga taacctattg tttgtataat caccatccag attcacgatg tcttggtata    120

atcgggcttg aaacccgcaa aattgacaag tatacctatc tcgctgaaag atttttgct     180

cataggattt gaatcgctca tcaatttttc tggcagaata taaacgccag gaacctggtg    240

aagcaattag ttttagctca catcgttgtt gattatccgc catagtttgg ttcacattca    300

g                                                                    301


<210> SEQ ID NO 101
<211> LENGTH: 350
<212> TYPE: DNA
<213> ORGANISM: ARTIFICIAL
<220> FEATURE:
<223> OTHER INFORMATION: Sequence of the first arm of the pilD dsRNA
      used to target the pilD (lpg1524) gene from Legionella pneumophila

<400> SEQUENCE: 101

gtgtcaatga taaatgcact aataatcaat tatccatggt ttatgtattt agtcgttgga     60

ctcttttctc tagccgttgg aagtttgctt aatgtgataa tctatcgctt accaattatt    120

ttgcaggaag agtggaaaga gcaatgctgt gagctattcc atcttgaaca gcgaaaagaa    180

aaaataaaac ttaatttatt tttaccacgt tctttttgtc ctcattgtaa agcgatggtt    240

aaagcgtggc agaatattcc tctgttaagc tatattttgt taagaggacg ctgttaccaa    300

tgtgatagtc caatttcaat ccgctaccct tttgttgaga cgttgaccac               350


<210> SEQ ID NO 102
```

<211> LENGTH: 350
<212> TYPE: DNA
<213> ORGANISM: ARTIFICIAL
<220> FEATURE:
<223> OTHER INFORMATION: Sequence of the second arm of the pilD dsRNA used to target the pilD (lpg1524) gene from Legionella pneumophila

<400> SEQUENCE: 102

```
gtggtcaacg tctcaacaaa agggtagcgg attgaaattg gactatcaca ttggtaacag     60

cgtcctctta acaaaatata gcttaacaga ggaatattct gccacgcttt aaccatcgct    120

ttacaatgag gacaaaaaga acgtggtaaa aataaattaa gttttatttt ttcttttcgc    180

tgttcaagat ggaatagctc acagcattgc tctttccact cttcctgcaa aataattggt    240

aagcgataga ttatcacatt aagcaaactt ccaacggcta gagaaaagag tccaacgact    300

aaatacataa accatggata attgattatt agtgcattta tcattgacac               350
```

<210> SEQ ID NO 103
<211> LENGTH: 324
<212> TYPE: DNA
<213> ORGANISM: ARTIFICIAL
<220> FEATURE:
<223> OTHER INFORMATION: Sequence of the first arm of the ispF dsRNA used to target the ispF (lpg1363) gene from Legionella pneumophila

<400> SEQUENCE: 103

```
atgggcgcct accaatatca agcgctaaaa gtgaatggca gcattagcaa aggtgtaata     60

gaagctgatt ctgaacgcca tgcacgtcaa ttattgcgag aacaaggact aatccctact    120

caagtccaaa cattaaccca gcaacgtgct gccagcagca aaagtaaagt ttctgcggct    180

gatttggcat tactcacgag acagctggca acacttctgg ctgccggtat tcctgttgaa    240

gaatcattgc gcggggtcag cgaacaaaca gaaaaagaca aagtcagaga gcttattatc    300

ggagttcgct ctaaagtatt ggaa                                           324
```

<210> SEQ ID NO 104
<211> LENGTH: 324
<212> TYPE: DNA
<213> ORGANISM: ARTIFICIAL
<220> FEATURE:
<223> OTHER INFORMATION: Sequence of the second arm of the ispF dsRNA used to target the ispF (lpg1363) gene from Legionella pneumophila

<400> SEQUENCE: 104

```
ttccaatact ttagagcgaa ctccgataat aagctctctg actttgtctt tttctgtttg     60

ttcgctgacc ccgcgcaatg attcttcaac aggaataccg gcagccagaa gtgttgccag    120

ctgtctcgtg agtaatgcca aatcagccgc agaaacttta cttttgctgc tggcagcacg    180

ttgctgggtt aatgtttgga cttgagtagg gattagtcct tgttctcgca ataattgacg    240

tgcatggcgt tcagaatcag cttctattac acctttgcta atgctgccat tcacttttag    300

cgcttgatat tggtaggcgc ccat                                           324
```

<210> SEQ ID NO 105
<211> LENGTH: 723
<212> TYPE: DNA
<213> ORGANISM: ARTIFICIAL
<220> FEATURE:
<223> OTHER INFORMATION: Sequence of the first arm of the dotD/pilD dsRNA used to concomitantly target the dotD (lpg2674) and pilD (lpg1524) genes from Legionella pneumophila

<400> SEQUENCE: 105

-continued

```
atgaacaaca ataagattgt cataatgttt attttttcag cgcttcttgc tggttgcgct     60

ggaacaatga aatttaaaaa accacccatc aataatccaa gtgatgatgc gaccattaaa    120

ttagcagaag ctgccgtttc agtcagtgac tccatgcttg aaatggcaaa agttgaaaaa    180

gtaattactc caccaagcaa agacaatacc ttaactatac ctaatgctta taacttgcaa    240

gcaagagcca gtgtcgattg gtctggtccg attgaagaat tgactgcacg tatcgccaaa    300

gcagcacatt tcagatttcg tgttttaggc aagtcgcctt cagttccagt tttaatcagc    360

atcagtaccg atcgtgtcaa tgataaatgc actaataatc aattatccat ggtttatgta    420

tttagtcgtt ggactctttt ctctagccgt tggaagtttg cttaatgtga taatctatcg    480

cttaccaatt attttgcagg aagagtggaa agagcaatgc tgtgagctat tccatcttga    540

acagcgaaaa gaaaaaataa aacttaattt atttttacca cgttcttttt gtcctcattg    600

taaagcgatg gttaaagcgt ggcagaatat tcctctgtta agctatattt tgttaagagg    660

acgctgttac caatgtgata gtccaatttc aatccgctac ccttttgttg agacgttgac    720

cac                                                                  723
```

<210> SEQ ID NO 106
<211> LENGTH: 723
<212> TYPE: DNA
<213> ORGANISM: ARTIFICIAL
<220> FEATURE:
<223> OTHER INFORMATION: Sequence of the second arm of the dotD/pilD dsRNA used to concomitantly target the dotD (lpg2674) and pilD (lpg1524) genes from Legionella pneumophila

<400> SEQUENCE: 106

```
gtggtcaacg tctcaacaaa agggtagcgg attgaaattg gactatcaca ttggtaacag     60

cgtcctctta acaaaatata gcttaacaga ggaatattct gccacgcttt aaccatcgct    120

ttacaatgag gacaaaaaga acgtggtaaa aataaattaa gttttatttt ttcttttcgc    180

tgttcaagat ggaatagctc acagcattgc tctttccact cttcctgcaa aataattggt    240

aagcgataga ttatcacatt aagcaaactt ccaacggcta gagaaaagag tccaacgact    300

aaatacataa accatggata attgattatt agtgcattta tcattgacac gatcggtact    360

gatgctgatt aaaactggaa ctgaaggcga cttgcctaaa acacgaaatc tgaaatgtgc    420

tgctttggcg atacgtgcag tcaattcttc aatcggacca gaccaatcga cactggctct    480

tgcttgcaag ttataagcat taggtatagt taaggtattg tctttgcttg gtggagtaat    540

tactttttca actttgcca tttcaagcat ggagtcactg actgaaacgg cagcttctgc    600

taatttaatg gtcgcatcat cacttggatt attgatgggt ggttttttaa atttcattgt    660

tccagcgcaa ccagcaagaa gcgctgaaaa aataaacatt atgacaatct tattgttgtt    720

cat                                                                  723
```

<210> SEQ ID NO 107
<211> LENGTH: 1410
<212> TYPE: DNA
<213> ORGANISM: artificial
<220> FEATURE:
<223> OTHER INFORMATION: Sequence of a specific intron sequence from the Petunia Chalcone synthase gene CHSA

<400> SEQUENCE: 107

```
ggcgcgccca atcgatgatt taaatgtgta agaatttctt atgttacatt attacattca     60

acgttttatc ttaattggct cttcatttga ttgaaatttg acaattattt cttgtttttt    120
```

-continued

```
tttttgtcac actctttttg ggttggggtg gccgacgaat tgtgggaagg tagaaagagg    180
ggaggacttt tgttatactc cattagtaat tactgtttcc gtttcaattt atgtgacaat    240
atttcctttt tagtcggttc caaaagaaaa tgtcagcatt ataaacaatt taattttgaa    300
attacaattt tgccattaat aaaatgattt acaaccacaa aagtatctat gagcctgttt    360
gggtgggctt ataagcagct tattttaagt ggcttataag tcaaaaagtg acatttttg     420
agaagttaga aaatcctaac ttctcaaaaa gtagctttta agccacttat gacttataag    480
tccaaaaatt tttaagttac caaacatata ttaatgggtt tataagctta taagccactt    540
ttaagctcac ccaaacgggt tctatgtctc actttagact acaaatttta aaagtcttca    600
tttatttctt aatctccgtg gcgagtaaaa ctataacaca taaagtgaaa cggagggaat    660
aagatggagt cataaactaa tccaaatcta tactctctcc gttaatttgt tttttagttt    720
gatttggtac attaataaaa cagatttttc gaaggttata aacacagaca gatgtttccc    780
agcgagctag caaaattcca agatttctgt cgaaaattcg tgtgtttcta gctagtactt    840
gatgttatct ttaacctttt agtaattttt tgtccttttc tttctatttt tcatcttaca    900
atgaattatg agcaagttcc ttaagtagca tcacacgtga gatgtttttt atgatattga    960
ctaaatccaa tctttaccat tccttaacta gtaaaataca acacatgtta attgatacat   1020
tgcttaacac tgaggttaga aaattttaga aattagttgt ccaaatgctt tgaaattaga   1080
aatctttaat cccttatttt tttttaaaat gtttttctc actccaaaga aagagaaact    1140
gacatgaaag ctcaaaagat catgaatctt actaactttg tggaactaaa tgtacatcag   1200
aatgtttctg acatgtgaaa atgaaagctc ttaattttct tcttttattt attgagggtt   1260
tttgcatgct atgcattcaa tttgagtact ttaaagcacc tataaacact tacttacact   1320
tgccttggag tttatgtttt agtgttttct tcacatcttt tttggtcaat ttgcaggtat   1380
ttggatccta ggtgagtcta gaggcgcgcc                                    1410
```

CHLORELLA-BASED PRODUCTION OF EXTRACELLULAR VESICLE-EMBEDDED SMALL RNAS FOR PROPHYLACTIC OR THERAPEUTIC APPLICATIONS

SUMMARY OF THE INVENTION

The invention relates to a novel method to produce small RNAs targeting pathogenicity factors, essential genes and/or antimicrobial resistance genes of animal pathogens. This method also includes the production of small RNAs directed against host susceptibility factors, whose silencing, inactivation, or deletion, is known to enhance resistance towards the targeted pathogen(s). More specifically, the invention involves the expression of exogenous RNA interference (RNAi) precursor(s) in *Chlorella* cells, which in turn express and release Extracellular Vesicle (EV)-embedded and/or associated antimicrobial small RNAs. Importantly, *Chlorella* EVs protect antimicrobial small RNAs from ribonuclease-mediated digestion. They are also rapidly and efficiently internalized by human alveolar epithelial cells, highlighting their potential for delivering antimicrobial small RNAs in these cells, and for controlling respiratory infections. The invention can thus be used for prophylactic or therapeutic treatments, to reduce various infectious diseases in animals, including humans. Furthermore, because the integrity and functionality of *Chlorella* EVs remain unaltered when produced in photobioreactors, and when stored frozen, this novel method has the potential to be further exploited for the industrialization of EV-based anti-infective products.

PRIOR ART DESCRIPTION

Infectious diseases have shaped the human history and, well after the use of medicinal plants, led to the discovery of antibiotics in the late 20's by Sir Alexander Fleming. His seminal work led to the "golden era" of antibiotics discovery from 1945 to 1960. This period was followed by a sharp drop in the identification of new antibiotics, mostly because of the challenge of identifying new antimicrobial classes from natural products or synthetic molecule collections, but also because of an industrial shift in focus from discovery to chemical modifications of existing antibiotic chemical scaffolds. In addition, the significant investments required to identify and further develop a novel antibiotic was not rewarded economically due to the rapid emergence of antimicrobial resistance mechanisms. Indeed, the over-use and misuse of antibiotics, together with the strong selection pressure that these antibacterial agents exert on bacterial survival, have led to the rapid selection of multidrug-resistant bacteria, which represent nowadays a growing threat for human health. There is therefore an urgent need to control multidrug-resistant bacteria and to continuously identify novel antibiotics, or alternatives to antibiotics, if we want to manage bacterial diseases.

Viral pathogens represent also a major threat for human health. The last decades have seen the emergence of zoonotic viral pathogens due to climate change, ease of travel and change in local ecosystems, including reduced biodiversity, as well as the appearance of antiviral drug resistance (Howard et al., 2012; Strasfeld & Chou, 2010). Viral infections can have major consequences on human health, which is for instance illustrated by the 2014-2015 Ebola outbreak in West Africa that resulted in the death of more than 11,000 infected people (Kaner & Schaack, 2016). Another example is provided by the outbreak of the mosquito-transmitted Zika virus, which started in Brazil in 2015 and spread in Americas, Pacific, Asia and Africa (the last proven case being identified in the United States in 2017). Outbreaks of three coronavirus (CoV) diseases have also been observed during the last two decades. The severe acute respiratory syndrome CoV (SARS-CoV-1), the Middle East respiratory syndrome (MERS-CoV), and the SARS-CoV-2 viruses, have called global attention due to their lethal impact on the human population. For example, SARS-CoV-2, which is the causal agent of COVID-19, currently spreads at pandemic levels and has already caused more than four million deaths worldwide, along with unprecedented social and economic disruption. This highlights the necessity to identify, on a regular basis, novel solutions against human pathogens, which are estimated to cause 14 million deaths each year. It also emphasizes the need to develop versatile therapeutic platforms allowing the rapid production of targeted antimicrobials directed against any newly emerging pathogen to control an unanticipated infectious disease, now referred to as "Disease X" by the World Health Organization (WHO).

DETAILED DESCRIPTION OF THE INVENTION

Overview of the Results and the Invention

In the results below, the Inventors herein provide the first evidence that *Chlorella* cells can produce extracellular vesicles (EVs). They also demonstrate for the first time that *Chlorella* can be engineered to produce biologically active antibacterial small RNAs that are embedded into, and/or associated with EVs. More specifically, by transforming *C. vulgaris* with inverted repeat transgenes bearing sequence homology with key virulence factors from a phytopathogenic bacterium, they show that *Chlorella* EVs are competent in delivering effective small RNAs in bacterial cells, resulting in the dampening of their pathogenicity. Furthermore, they show that *Chlorella* EVs protect these antibacterial small RNAs from digestion mediated by the non-specific micrococcal nuclease. These data therefore highlight the potential of *Chlorella* EVs as vehicles of small RNAs towards bacterial pathogens. Furthermore, because plant EVs are known to deliver effective antimicrobial small RNAs in human-associated intestinal bacteria (Teng et al., 2018), but also in phytopathogenic fungi and oomycetes (Cai et al., 2018; Hou et al., 2019), it is anticipated that *Chlorella* EVs will be employed to deliver antimicrobial small RNAs in a wide spectrum of bacterial, fungal and oomycetal organisms that are pathogenic to animals, including humans.

Mammalian pathogens use sophisticated strategies to enter and replicate in host cells. For this end, they typically highjack host cell factors, referred to here as host susceptiblity factors (HSFs). To develop small RNA-based prophylactic or therapeutic approaches, by directly targeting the pathogen RNAs, or by indirectly targeting HSF mRNAs, it was essential to assess whether *Chlorella* EVs could be also internalized by human cells that will encounter, or that are already encountering, the pathogen(s) of interest. For this purpose, the inventors have investigated whether *Chlorella* EVs could be taken-up by human alveolar epithelial cells, which are relevant for various respiratory infections. Significantly, they show that *Chlorella* EVs are rapidly and efficiently internalized by these human cells. Furthermore, they have identified the EV concentration needed to optimize their cellular internalization. Collectively, these data indicate that *Chlorella* EVs are not only suitable for the delivery of small RNAs in pathogenic cells, but could be also employed for the delivery of antimicrobial small RNAs in human alveolar epithelial cells, and likely in other cells as well, to reduce infections such as respiratory infections.

Based on these findings, the inventors have further generated and characterized stable *Chlorella* transgenic lines expressing inverted repeat (IR) transgenes targeting, individually or simultaneously, large sequence regions of the SARS-CoV-2 genomic and subgenomic RNAs. In addition, they have generated *Chlorella* lines expressing IR transgenes targeting key HSFs, whose silencing, or drug-triggered inactivation, have previously been shown to restrict the replication of coronaviruses in human cells. Furthermore, the inventors have generated *Chlorella* lines expressing IR transgenes targeting genes that are essential for the fitness, pathogenicity or antibiotic resistance of various human bacterial pathogens, including *Pseudomonas aeruginosa, Staphylococcus aureus, Legionella pneumophila* and *Mycobacterium tuberculosis*. These reference *Chlorella* transgenic lines will thus be instrumental for the production of EV-embedded siRNAs with antiviral or antibacterial activities.

A pre-requisite for the industrialization of *Chlorella* EV-embedded and/or -associated small RNA products is to demonstrate that they can maintain a full integrity and functionality when produced in photobioreactors (PBRs). To address this issue, the inventors have first grown a *Chlorella* reference line producing antibacterial siRNAs in a PBR of one liter, and collected the corresponding extracellular medium, which was further stored frozen. The extracellular medium was subsequently unfreezed and subjected to filtration and ultracentrifugation, to recover purified EVs. Importantly, these *Chlorella* EVs were found to exhibit a normal size distribution and were efficiently internalized by human alveolar epithelial cells. Furthermore, the EVs integrity was equally maintained when the same *Chlorella* transgenic line was grown in a PBR of 150 liters, except that in those conditions, the yield of recovered EV particles was ~20 times increased compared to the ones collected from flasks or small PBRs. These findings indicate that the integrity and functionality of *Chlorella* EV-embedded siRNAs remain unaltered when produced in PBRs (and despite these EVs being stored frozen). The Microalgae-Induced Gene Silencing (MIGS) technology has therefore the potential to be further exploited for the production of high yields of EV-embedded antimicrobial small RNAs in pre-industrial settings.

Another pre-requisite for the possible industrialization of *Chlorella* EV-embedded and/or associated antimicrobial small RNAs, is to verify—in a rapid, reliable and cost-effective manner—the efficacy of each batch produced from PBRs. To address this issue, the inventors have designed and engineered small RNA reporter systems in bacteria and human cells, which rely on the differential fluorescence or bioluminescence signal detection in the presence of effective *Chlorella* EV-embedded antimicrobial small RNAs. These quantitative reporter systems can be easily manipulated to ensure that each batch produced is active, prior to their product manufacturing. They are also relevant to select the independent *Chlorella* lines expressing the most active EV-embedded and/or -associated small RNAs.

Based on all these discoveries, the present Inventors propose to use this MIGS technology to rapidly produce *Chlorella* EV-embedded and/or associated small RNAs directed against dedicated pathogen(s). More precisely, they propose a method to produce high yields of *Chlorella* EV-embedded and/or associated small RNAs targeting one or multiple target pathogen or HSF gene(s), by i) expressing iRNA molecules (precursors of siRNAs and miRNAs) in *Chlorella* cells, ii) collecting the EVs released by said *Chlorella* cells, iii) verifying the efficacy of *Chlorella* EV-embedded siRNAs prior to product manufacturing, and iv) delivering the concentrated or purified EV products on animal tissues, within animals (e.g. organs, body fluids), or on virally or bacterially-infected surfaces. It is noteworthy that during such production pipeline, both the extracellular medium carrying the effective EVs, or the purified EVs, can be stored frozen without major negative impact on the integrity and functionality of these EV-based anti-infective agents.

It is therefore anticipated that the MIGS technology will be extensively used for both prophylactic and therapeutical applications against a wide spectrum of animal pathogens, including human pathogens. This approach will have a major impact on public health, especially in the management of viral, fungal, oomycetal and/or bacterial infections.

The following features and advantages of the methods of the invention are worth to be mentioned.

1) *Chlorella* is an Ideal Biological System for the Production of Endogenous and Heterologous Molecules:

*Chlorella* belongs to a group of green microalgae (Chlorophyta, Trebuxiophyceae) able to adapt and grow in a variety of conditions. *Chlorella* is easy to maintain in laboratory conditions, possesses a simple life cycle, a haploid genome and metabolic pathways similar to higher plants (Blanc et al., 2010). It also possesses the capacity to grow in auto-, hetero- or mixo-trophic conditions with high growth rates (Zuniga et al., 2016). The metabolic flexibility, the ease of maintenance and growth are features that enable *Chlorella* to be exploited as industrial production scaffold in PBRs for a variety of molecules of interest. In particular, *Chlorella* cells can be easily transformed with a disarmed *Agrobacterium tumefaciens* (Cha et al., 2012), and stable transformed transgenic lines can be selected within a 2 months period. This exceptionally rapid selection process positions *Chlorella* as an ideal biological system to produce within a short timeframe any construct of interest. This feature is notably valuable in the context of outbreak or pandemic situations, as *Chlorella* can be exploited to rapidly produce vectorized small RNAs against virulence factors, essential genes and/or antimicrobial resistance genes from any pathogen(s) of interest (which can nowadays be sequenced within a few days).

To summarize, the possibility to rapidly transform *Chlorella* with a transgene of interest, and to obtain large volumes of *Chlorella* extracellular media from PBRs, shows that this green microalga is suitable for the industrial production of dedicated EV-embedded and/or -associated antimicrobial small RNAs.

2) The MIGS Technology is Highly Versatile and Sequence-Specific.

The MIGS technology relies on the stable expression of inverted repeat, artificial miRNAs or sense-antisense, transgenes in *Chlorella*, which will be processed into siRNAs or miRNAs by the endogenous Dicer-like enzyme, or other endogenous RNases, and further internalized into EVs. The MIGS technology also relies on the production of RNAi precursors from recombinant viruses that can infect *Chlorella* cells and likewise generate high yields of small RNA populations through Virus-Induced Gene Silencing (VIGS), as previously described in plants (Bally et al., 2018). These transgene- and viral-based RNAi precursors can notably be designed in such a way that they will target one or multiple genes of interest and trigger their selective silencing. This feature is particularly valuable for controlling the replication of one or multiple pathogens, while having no side effects on commensal microbes or the animal organism.

3) The MIGS Technology can be Used to Produce Antimicrobial Small RNA Populations, Likely Conferring Durable Disease Resistance.

*Chlorella* can be employed to produce small RNA populations targeting up to 1500 bp long regions from a single gene or up to a dozen genes. This is distinct from individual siRNAs classically used in animals or humans, which are designed to target specific ~20-22 nt long sequences. It is noteworthy that, such as plants, *Chlorella* is able to express long dsRNAs without triggering cell toxicity. This is an important distinction from mammalian cell-based systems that often trigger potent inflammation upon detection of long dsRNAs, which are sensed as viral replication intermediates and induce a potent interferon response through the RIG-I-like Receptor (RLR) signaling pathways (Fan & Jin, 2019). *Chlorella* is thus well-suited to produce small RNAs covering large portions of microbial gene(s), thereby maximizing the chance of detecting a potent silencing effect towards the targeted microbial gene(s). Furthermore, by targeting long sequence regions, the microbe will unlikely be able to mutate all along the targeted region, thereby resulting in long-lasting protection effects against the targeted pathogen(s). This is particularly relevant in the case of RNA viruses, which usually have high mutation rates (e.g., influenza virus). The MIGS technology is thus expected to overcome the recurrent problem of pathogen-directed escaping mutations and is therefore expected to confer durable disease resistance.

4) The MIGS Technology is Effective Against Prokaryotic Cells, which is not the Case of Other Platforms Producing Long dsRNAs.

The present inventors have previously reported that the exogenous application of siRNAs can target, in a sequence-specific manner, virulence factors in bacterial pathogens (Singla-Rastogi, Navarro, PCT/EP2019/072169, PCT/EP2019/072170). By contrast, long dsRNAs were not active in this process, suggesting that they are either not taken-up by, or not active in, bacterial cells. This is a major distinction from environmental RNAi previously reported in nematodes and plant herbivores, which exclusively relies on long dsRNAs (Bolognesi et al., 2012; Ivashuta et al., 2015; Whangbo et al., 2008), or in fungi and oomycetes, which is dependent on both small RNAs and long dsRNAs (Koch et al., 2016; Wang et al., 2016). By producing small RNA species, the MIGS technology has therefore the potential to be exploited as a new production scaffold of antibacterial agents, which is not the case of other biological systems currently used to produce long dsRNAs as fungicides, insecticides or nematicides for agricultural applications. The MIGS technology can also be employed to selectively target genes from commensal bacteria to enhance their beneficial effects for humans. MIGS is therefore a unique RNAi production scaffold technology that can be exploited towards prokaryotic cells, and likely many other unrelated microbes or parasites.

5) Such as Plant EVs, *Chlorella* EVs are Expected to be More Stable than Mammalian EVs and Potentially Non-Toxic/Non-Immunogenic.

Companies working in the field of RNAi therapeutics are usually using synthetic vectors/siRNAs, which can have toxicity effects. The present biological system involves the production of *Chlorella* EVs, which resemble plant nanovesicles that have previously been shown to be non-toxic, non-immunogenic and stable (Wang et al., 2013; Zhang et al., 2017). The toxicity profile of EVs from *Chlorella* is thus expected to be safe—they have notably no impact on cell viability, as shown in Example 10 below. In addition, it is expected that *Chlorella* EVs will be more stable than mammalian EVs in the host organism, such as their plant counterparts (Wang et al., 2013; Zhang et al., 2017).

Definitions

The present method/use can be performed either in vivo or in vitro. By "in vitro", it is herein meant that the steps of the claimed methods or uses are conducted using biological components (e.g., human cell lineages) that have been isolated from their usual host organisms or that are directly grown in in vitro media.

By "in vivo", it is herein meant that the steps of the claimed methods or uses are conducted using whole organisms, for example whole individuals.

As used herein, the term "functional interfering RNA" (functional iRNA) refers to an RNA molecule capable of inducing the process of sequence-specific silencing of at least one gene. In particular, said functional interfering RNA molecule can be either i) a small interfering RNA, well-known in the art as small or short interfering RNA (siRNA) molecule (simplex or duplex), or a precursor thereof; or ii) a microRNA (miRNA) molecule (simplex or duplex) or a precursor thereof.

RNAi is a conserved gene regulatory mechanism that promotes antiviral resistance in plants, flies, worms and mammals (Guo et al., 2019). The core mechanism of antiviral silencing involves the recognition and processing of viral double-stranded RNAs (dsRNAs) by the RNAse III enzyme DICER, leading to the production of 20-25 nt long short interfering RNA (siRNA) duplexes. These siRNA duplexes subsequently bind to a central component of the RNA Induced Silencing Complex (RISC), namely the Argonaute (AGO) protein, and one strand, the guide, remains bound to AGO to silence post-transcriptionally viral complementary transcripts. Recent studies have shown that plant and/or animal endogenous small RNAs can additionally directly target virulence or essential genes from fungi, bacteria and oomycete pathogens, supporting a broader role of RNAi in trans-kingdom gene regulation during host-pathogen interactions (Cai et al., 2019; Guo et al., 2019; Hou et al., 2019).

The term "precursor of siRNA" or "siRNA precursor" herein refers to an RNA molecule which can be directly or indirectly processed into siRNA duplex(es) in *Chlorella* cells (or *Chlorella* extracts). Examples of siRNA precursors that can be directly processed include long double-stranded RNAs (long dsRNAs), while examples of siRNA precursors that can be indirectly processed include long single-stranded RNAs (long ssRNAs) that can be used as template for the production of processable long dsRNAs.

The term "precursor of miRNA" or "miRNA precursor" herein refers to an RNA molecule which can be processed into miRNA duplex(es) in *Chlorella* cells (or *Chlorella* extracts).

Examples of miRNA precursors include primary miRNA precursors (pri-miRNAs) and pre-miRNAs, comprising a hairpin loop.

Of note, plasmids or vectors and other DNA constructs or viral vectors encoding said precursor molecules are also encompassed in the definition of "functional interfering RNA".

For targeting multiple genes, the method of the invention can use i) a mixture of several different iRNAs which altogether target multiple genes of interest or ii) a chimeric iRNA targeting several different genes of interest or iii) a mixture of any of these chimeric iRNAs.

In one particular embodiment, the method/use of the invention comprises the introduction of one or several long functional iRNAs into *Chlorella* cells as precursors, and these cells will produce the small RNAs (such as siRNAs or miRNAs) that can be further formulated and used to prevent pathogenic infections.

These long functional iRNAs can be long single-stranded RNA molecules (named hereafter as "long ssRNAs"). These long ssRNAs may be produced by an RNA virus that can infect *Chlorella* cells, and further converted into long dsRNA molecules during viral replication (as replicative intermediates). The resulting viral dsRNA is subsequently processed into siRNAs by the *Chlorella* DCL enzyme.

As used herein, the term "long ssRNAs" designates single-stranded structures containing a single-strand of at least 50 bases, more preferably of 80 to 3000 bases. Long ssRNAs may contain 80 to 3000 bases when produced by a *Chlorella* transgene, but preferably contain 80 to bases when produced by a recombinant RNA virus.

These long functional iRNAs can also be double-stranded RNA molecules (named hereafter as "long dsRNAs"). These long dsRNAs act as miRNA or siRNA precursors and can be processed into miRNAs or siRNAs in *Chlorella* cells, thanks to the DCL proteins encoded by *Chlorella* genomes (see EXAMPLE 2).

As used herein, the term "long dsRNAs" designates double-stranded structures containing a first (sense strand) and a second (antisense) strand of at least 50 base pairs, more preferably of 80 to base pairs.

The results of the present inventors show that, in *Chlorella* cells, long dsRNAs can be efficiently processed into effective small RNAs (EXAMPLE 5). Such long dsRNAs are advantageously chimeric dsRNAs, i.e., they bear sequence homologies to multiple genes.

The long functional iRNA used in the method of the invention is preferably a long dsRNA that is cleavable by the DCL enzyme in *Chlorella* cells so as to generate miRNAs or siRNAs.

These long dsRNAs can be generated from a hairpin structure, through sense-antisense transcription constructs, or through VIGS. More precisely, they may comprise bulges, loops or wobble base pairs to modulate the activity of the dsRNA molecule so as to mediate efficient RNA interference in the target cells. The complementary sense and antisense regions of these long dsRNA molecules may be connected by means of nucleic acid-based or non-nucleic acid-based linker(s). These long dsRNAs may also comprise one duplex structure and one loop structure to form a symmetric or asymmetric hairpin secondary structure.

In a particular embodiment, the precursor of the invention can target individual SARS-CoV-2 viral regions of ~350 bp and have for example the following sequences (see EXAMPLE 11): IR-PLP=SEQ ID NO: 41-42; IR-3CL=SEQ ID NO: 43-44; IR-NSP10=SEQ ID NO: 45-46; IR-RDRP-1=SEQ ID NO: 47-48; IR-RDRP-2=SEQ ID NO: 49-50; IR-RDRP-3=SEQ ID NO: 51-52; IR-EndoN=SEQ ID NO: 53-54; IR-N==SEQ ID NO: 55-56; IR-E=SEQ ID NO: 57-58; IR-M=SEQ ID NO: 59-60; IR-S=SEQ ID NO: 61-62; IR-3'UTR=SEQ ID NO: 63-64; and IR-Hel=SEQ ID NO: 65-66.

They can furthermore simultaneously target several SARS-CoV-2 viral regions of ~150-250 bp or HSF genes and have for example the following sequences: IR-NSP1/NSP4/NSP3/PLP/3CL/NSP12/NSP13/NSP14=SEQ ID NO: 1-2; IR-S/E/M/N/leader-TRS/3'UTR=SEQ ID NO: 3-4; IR-Rp113a/eIF3ee/F3i/eIF3f=SEQ ID NO: 5-6; IR-eIF4A/eEF1a=SEQ ID NO: 7-8; IR-Snrpe/Naca/Kif11/Gbf1/Srp54a=SEQ ID NO: 9-10; and IR-ACE2/TMPRSS2/Psmd1/IMPα/IMPβ1=SEQ ID NO: 11-12.

In another particular embodiment (see EXAMPLE 12), the precursor of the invention can target essential genes from *P. aeruginosa*, including LptH, LolA, TolB, LpxA, LpxD, dnaA, dnaN, gyrB, rpoC, secE and sodB, and have the following sequences: IR-LptH/LolA/TolB=SEQ ID NO: 13-14; IR-LpxA/LpxD/TolB=SEQ ID NO: 15-16; IR-dnaA/dnaB/gyrB=SEQ ID NO: 67-68; IR-rpoC/secE/SodB=SEQ ID NO: 69-70; and IR-secE/dnaN/gyrB=SEQ ID NO: 17-18.

In another particular embodiment, the precursor of the invention can target key virulence genes from *P. aeruginosa*, including genes involved in the regulation and/or assembly of type II or type III secretion systems, XcpQ, PscF, PscC, PcrV, PcrR, ExoS, ExoU, ExsA, Vrf, the quorum sensing signaling factors LasR, RhlR, MvfR, VqsM, the GAC signaling components GacA, RsmA, with the following sequences: IR-XcpQ/ExsA/PcrV/LasR/RhlR/VqsM/RmsA=SEQ ID NO: 19-20; IR-XcpQ/PscF/PscC=SEQ ID NO: 21-22; IR-ExoS/ExsA/Vrf=SEQ ID NO: 23-24; IR-ExoU/ExsA/Vrf=SEQ ID NO: 25-26; IR-LasR/RhlR/VqsM=SEQ ID NO: 27-28; and IR-GacA/RmsA/MvfR=SEQ ID NO: 29-30.

In another particular embodiment, the precursor of the invention can target key antibiotic resistance genes from *P. aeruginosa*, including mexX, mexA and ampC, and have the following sequence: IR-mexX/mexA/ampC=SEQ ID NO: 31-32.

In another particular embodiment, the precursor of the invention can target essential genes of *Shigella flexneri*, including FtsA, Can, Tsf, AccD, Der, Psd and have the following sequences: IR-FtsA/Can/Tsf=SEQ ID NO: 71-72 and IR-AccD/Der/Psd=SEQ ID NO: 73-74.

In another particular embodiment, the precursor of the invention can target virulence genes of *Shigella flexneri*, including VirF, VirB, IcsA with the construct IR-VirF/VirB/IcsA=SEQ ID NO: 33-34, and virulence genes of *Staphylococcus aureus*, including the genes encoding the surface bound proteins fnbA, clfA, clfB, spa, atl, the leukotoxins lukF-PV, lukS-PV, lukE, lukD, HlgB, the alpha hemolysin hla, and the toxic shock syndrome toxin-1 tsst-1, with the constructs: IR-fnbA/clfA/clfB/spa=SEQ ID NO: 35-36; IR-lukF-PV/lukS-PV/lukE/lukD=SEQ ID NO: 37-38; and IR-HlgB/hla/tsst-1/atl=SEQ ID NO:39-40.

In another particular embodiment, the precursor of the invention can target virulence genes of *Mycobacterium tuberculosis*, including cspA, pcaA, icl1, rip, fad26, hphA using the constructs: IR-cpsA=SEQ ID NO: 75-76; IR-pcaA SEQ ID NO: 77-78; IR-icl1 SEQ ID NO:79-80; IR-rip SEQ ID NO:81-82; IR-fad26 SEQ ID NO:83-84; IR-hphA=SEQ ID NO:85-86; and IR-cpsA/pcaA=SEQ ID NO:87-88.

In another particular embodiment, the precursor of the invention can target virulence genes of *Legionella pneumophila*, including dotA, dotB, dotC, dotD, icmT, icmJ, pilD, and ispF using the constructs: IR-dotA=SEQ ID NO: 89-90; IR-dotD=SEQ ID NO: 91-92; IR-dotC=SEQ ID NO:93-94; IR-dotB=SEQ ID NO:95-96; IR-icmT=SEQ ID NO:97-98; IR-icmJ=SEQ ID NO:99-100; IR-pilD SEQ ID NO:101-102; IR-ispF=SEQ ID NO:103-104; and IR-dotD/pilD=SEQ ID NO:105-106.

The present invention targets the use of any of these siRNA precursors of SEQ ID NO:1-106 to produce a population of functional small iRNAs in *Chlorella* cells.

As demonstrated in the examples of the present application, the introduction of dsRNAs into *Chlorella* cells triggers the production of small RNA molecules that are embedded into, and/or associated with, EVs and protected from ribonuclease-mediated digestion (EXAMPLES 2-8). More precisely, the *Chlorella* cells of the invention are able to produce functional small iRNAs such as siRNAs or miRNAs. These small RNAs have a short size, which is less than 50 base pairs, preferably comprised between 10 and 30 base pairs. More particularly, the functional small iRNAs produced by *Chlorella* cells contain mainly 18 base pairs or 15 base pairs (cf. EXAMPLE 4 and FIG. 2).

These small RNAs can be formulated in pharmaceutical or cosmetical compositions, e.g., into topic compositions or into sprayable liquid compositions (see below). In this case, the said compositions containing the said small RNAs can be administered directly to tissues or to contaminated surfaces.

In one particularly preferred embodiment, the functional interfering small RNA of the invention is a “siRNA”, which designates either a “siRNA duplex” or a “siRNA simplex”. These duplex or simplex siRNAs are preferably 15 or 18 nucleotides in size. They are therefore shorter than plant-produced siRNAs that are typically 21 or 24 nucleotides in size or mammalian-produced siRNAs that are typically ~22 nucleotides in size. The functional small RNAs of the invention that are generated by *Chlorella* cells are therefore distinct from those produced by plants and other eukaryotic cells.

More specifically, the term “siRNA duplex” designates double-stranded structures or duplex molecules containing a first (sense) and a second (antisense) strand of at least 10 base pairs, and preferably of less than 20 base pairs; preferably, said antisense strand comprises a region of at least 10 contiguous nucleotides that are complementary to a transcript of the targeted gene. In a preferred embodiment, these molecules contain precisely 15 to 18 base pairs, as shown in the experimental part below. These siRNA duplexes can be produced from long dsRNA precursors that are processed by the *Chlorella* DCL enzyme.

As used herein, the term “siRNA simplex” or “mature siRNA” designates simplex molecules (also known as “single-stranded” molecules) that originate from the siRNA duplex but have been matured in the RISC machinery of a microalgae cell and are loaded in the *Chlorella* AGO protein and/or associated with other RNA-binding proteins. They have a short size, which is less than 50 bases, preferably between 10 and 30 bases, more preferably between 10 and 18 bases, even more preferably between 15 and 18 bases. In a particular embodiment, they contain precisely either 15 or 18 bases.

In another embodiment, the functional iRNA of the invention is a “miRNA”, which designates either a “miRNA duplex” or a “miRNA simplex”. In a preferred embodiment, the iRNAs of the invention are double-stranded miRNAs.

More specifically, the term “miRNA duplex” designates double-stranded structures or duplex molecules containing a first (sense) and a second (antisense) strand of at least 10 base pairs, preferably of at least 15 base pairs; preferably, said antisense strand comprises a region of at least 10 contiguous nucleotides that are complementary to a transcript of the targeted gene. These miRNA duplexes may also contain bulges. These miRNA duplexes can be produced from miRNA precursors that are processed by the *Chlorella* DCL enzyme. As the duplex siRNAs, they have a short size which is less than 50 base pairs, preferably comprised between 10 and 35 base pairs. More particularly, the small miRNAs produced by *Chlorella* cells contain mainly 18 base pairs. They can also contain 15 base pairs (cf. EXAMPLE 4 and FIG. 2).

As used herein, the term “miRNA simplex” or “mature miRNA” designates simplex molecules (also known as “single-stranded” molecules) that originate from the miRNA duplex but have been matured in the RISC machinery of a microalgae cell and are loaded in the *Chlorella* AGO protein and/or associated with other RNA-binding proteins. These simplex miRNAs typically contain between 10 and 18 nucleotides, even more preferably between 15 and 18 nucleotides. In a particular embodiment, they contain precisely either 15 or 18 nucleotides.

Methods to design iRNAs such as long dsRNAs that can be converted into siRNA/miRNA are available in the art and can be used to obtain the sequence of the precursors of the invention.

The inventors herein show (EXAMPLES 2-8) that it is possible to use long double-stranded inverted repeat constructs in order to (i) transform *Chlorella* cells efficiently and (ii) have them produce functional small iRNAs that can dampen pathogenicity, said small iRNAs being embedded into EVs, which protect these RNA entities from ribonuclease-mediated digestion (see FIG. 5C).

As used herein, the term “sequence homology” refers to sequences that have sequence similarity, i.e., a sufficient degree of identity or correspondence between nucleic acid sequences. In the context of the invention, two nucleotide sequences share “sequence homology” when at least about 80%, alternatively at least about 81%, alternatively at least about 82%, alternatively at least about 83%, alternatively at least about 84%, alternatively at least about 85%, alternatively at least about 86%, alternatively at least about 87%, alternatively at least about 88%, alternatively at least about 89%, alternatively at least about 90%, alternatively at least about 91%, alternatively at least about 92%, alternatively at least about 93%, alternatively at least about 94%, alternatively at least about 95%, alternatively at least about 96%, alternatively at least about 97%, alternatively at least about 98%, alternatively at least about 99% of the nucleotides are similar.

Conversely, nucleotide sequences that have “no sequence homology” are nucleotide sequences that have a degree of identity of less than about 10%, alternatively of less than about 5%, alternatively of less than 2%.

Preferably, the similar or homologous nucleotide sequences are identified by using the algorithm of Needleman and Wunsch. Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By “equivalent program” is intended any sequence comparison program that, for any two sequences in question, generates an alignment having identical nucleotide residue matches and an identical percent sequence identity when compared to the corresponding alignment generated by GAP Version 10.

Production Methods of the Invention

In a first aspect, the present invention is drawn to a method for producing functional interfering small RNAs, said method comprising at least the steps of:

a) transforming *Chlorella* cells with a siRNA or miRNA precursor comprising a fragment of at least one target gene, and b) cultivating said *Chlorella* cells in appropriate conditions so that they express said precursor and release EV-embedded functional small iRNAs targeting said gene fragment.

The terms "interfering small RNA" and "siRNA or miRNA precursor" have been defined above, in the definition section.

In a preferred embodiment, said siRNA or miRNA precursor is a long single- or double-stranded RNA molecule. In a more preferred embodiment, said siRNA or miRNA precursor is a long double-stranded RNA molecule, said molecule comprising a fragment of at least one target gene, or a complementary sequence thereof.

As explained above, *Chlorella* cells can be transformed by large nucleotide constructs. More precisely, the targeted fragment contained in the said precursor can have a large size, e.g., up to 3000 bp.

The "fragment" contained in the precursor of the invention can in fact contain one or several portion(s) of one single gene, or several portions of several genes (see the EXAMPLES 11 and below). After transformation, the *Chlorella* cells will then produce siRNA populations targeting one or various portions from a single gene or from several genes. This is a clear advantage over other iRNA producer cells, as covering large portions of microbial gene(s) maximizes the chance of trigerring an effective silencing effect towards the targeted microbial gene(s) or HSF genes, and reduces the chance that the microbe acquires resistance against the small iRNA population (to do so, it will have to mutate all along the small RNA targeted portions), thereby resulting in long-lasting protection effects against the targeted pathogen(s). It is also possible to design and use a precursor that contains one or more portions of genes from several pathogens.

In a particular embodiment, the fragment of the target gene(s) contained in the precursor of the invention comprises between 50 and 3000 bp, preferably between 100 bp and 2000 bp, more preferably between 500 bp and 1500 bp.

Particular "target genes" are described below, in the appropriate sections.

Useful *Chlorella* Genus

*Chlorella* is a genus of single-celled green algae belonging to the division Chlorophyta. It is spherical in shape, about 2 to 10 m in diameter, and is without flagella. It contains the green photosynthetic pigments chlorophyll-a and -b in its chloroplast. In ideal conditions it multiplies rapidly, requiring only carbon dioxide, water, light, and a small amount of minerals to grow. Due to the elevated protein, vitamin, mineral and pigment contents, various *Chlorella* cells are currently used as food complement for humans and livestock.

The *Chlorella* cells used in the method of the invention can be of any *Chlorella* species. In particular, they can be any cells that are currently used as food complement for humans and livestock (Safi C. et al., 2014). In a particular embodiment, they can belong to the species: *Chlorella ellipsoidea, Chlorella pyrenoidosa, Chlorella sorokiniana, Chlorella vulgaris* or *Chlorella variabilis.*

In a preferred embodiment, the *Chlorella* cells used in the method of the invention are from the vulgaris species. As the other *Chlorella* cells, *C. vulgaris* cells are able to adapt and grow in a variety of conditions. They are easy to maintain in laboratory conditions, possess a simple life cycle, a haploid genome and metabolic pathways similar to higher plants. They also possess the capacity to grow in auto-, hetero- or mixo-trophic conditions with high growth rates (de Andrade et al., 2017). The metabolic flexibility, the ease of maintenance and growth are features that enable *C. vulgaris* to be exploited as industrial production scaffold in photobioreactors (PBRs) for a variety of molecules of interest (Lin et al., 2013; Blanc et al., 2010).

In a first step of the method of the invention, the siRNA or miRNA precursor of the invention is introduced in the selected *Chlorella* cells. Said siRNA or miRNA precursor will be processed into siRNA or miRNA duplexes by using the *Chlorella* DCL enzyme and other small RNA processing factors. Said small RNAs duplexes and/or mature small RNA guides (i.e., loaded into AGOs) are thereafter released in the extracellular medium, or at the surface of the *Chlorella* cells, embedded into, and/or associated with, EVs. As demonstrated in the examples below (EXAMPLES 5 and 7 and FIG. 5), the virulence of bacterial cells is decreased when placed in contact with *Chlorella* EVs containing antibacterial small RNAs.

The term "introduced" in the context of inserting a nucleic acid into a cell, means "transfection" or "transformation" or "transduction", and includes reference to the incorporation of a nucleic acid into a eukaryotic cell where the nucleic acid may be stably incorporated into the genome of the cell (e.g., chromosome, plasmid), or transiently expressed (e.g., transient delivery of a gene construct via *Agrobacterium tumefaciens*, an infection with a recombinant virus).

The expression of the iRNAs of the invention in the host *Chlorella* cell may be transient or stable. Stable expression refers in particular to the preparation of transgenic *Chlorella* cell lineages using conventional techniques.

By way of non-limitative examples, step a) of the method of the invention can be performed by using electroporation, projectile bombardment, PEG-mediated protoplast transformation, virus-mediated transformation, conjugation, *Agrobacterium*-mediated transformation, and the like. These transformation methods are described e.g. in Kim et al., 2002; Cha et al., 2012; Lin et al., 2013; Yang et al., 2015; Bai et al., 2013; Niu et al., 2011; Chien et al., 2012; Run et al., 2016.

In a preferred embodiment, step a) of the method of the invention involves the delivery of the gene construct into *Chlorella* cells by means of *Agrobacterium tumefaciens*. This technique is well-known and do not need to be explained (Cha et al., 2012; Lin et al., 2013).

In a particular embodiment, the method of the invention comprises introducing into *Chlorella* cells one or several dsRNAs targeting one or multiple genes of different parasites, such as viruses, fungi, oomycetes, bacteria, insects or nematodes. In this embodiment, the EVs are directed to an essential gene, to a virulence gene or an antimicrobial/antiparasitic resistance gene of several pathogens or parasites.

Such methods are useful for concomitant prevention or treatment of diseases caused by several pathogens and/or parasites. They can be carried out using EVs containing chimeric iRNAs carrying sequence homologies with different pathogenic/parasitic genes, or a cocktail of EVs that have been produced separately, some containing iRNAs bearing homologies to genes of one pathogen/parasite, and others containing iRNAs bearing homologies to genes from several pathogens/parasites.

In a second step, the transformed *Chlorella* cells containing the precursor of the invention are cultivated so as to express said precursor and secrete functional small iRNAs targeting said gene fragment.

In this step, one can use classical conditions well-known in the art for cultivating *Chlorella* cells (Kim et al., 2002; Cha et al., 2012; Lin et al., 2013; Yang et al., 2015; Bai et al., 2013; Niu et al., 2011; Chien et al., 2012; Run et al., 2016). A standard cultivating method is described in EXAMPLE 1 below.

The present inventors herein show that, like for plant cells, it is possible to enhance the yield of EVs production by cultivating the *Chlorella* cells in conditions of biotic stresses, for example by challenging *Chlorella* cells with plant defense elicitors or defense-related phytohormones such as Salicylic Acid (SA). As disclosed in EXAMPLE 16 below, it is possible to enhance the yield of the *Chlorella* EVs by treating cells with supernatants of heat-killed bacteria, such as *E. coli* K12 TOP10 or Pto DC3000 cells. The rationale for using supernatants from heat-killed bacterial cells is that these supernatants should contain cocktails of molecules, including MAMPs/PAMPs, which could be sensed by yet-unknown *Chlorella* Pattern Recognition Receptors (PRRs), thereby resulting in enhanced EVs production and/or secretion as found in plants.

The inventors have found that the production of EVs by *Chlorella* can be increased several times by such treatments, as plant EVs do. Consequently, it is proposed that some biotic stresses can thus be employed to increase *Chlorella* EVs production and/or secretion. A preferred treatment is to use the supernatants from heat-killed bacteria, that can be easily produced and in a cost-effective manner, and have been found suitable for enhancing the production of *Chlorella* EVs (EXAMPLE 16 and FIG. 11).

In one preferred embodiment, the small RNAs of the invention are isolated as free RNA molecules. These RNA molecules can be used directly for prophylactic or therapeutic purposes (see EXAMPLES 5 and 7).

In this embodiment, the methods of the invention further comprise the step of recovering the expressed small iRNAs from the cultivated *Chlorella* cells.

Isolating intact RNA contained within *Chlorella* cells requires four steps: 1) Disruption of the *Chlorella* cells; 2) Inactivation of endogenous ribonuclease (RNase) activity; 3) Denaturation of nucleoprotein complexes; and 4) Removal of contaminating DNA and proteins. The most important step is the immediate inactivation of endogenous RNases that are released from membrane-bound organelles when cells are disrupted. RNA purification methods typically use silica membrane-based, resin-based and magnetic options for nucleic acid binding, and incorporate DNase treatment to remove contaminating genomic DNA. Purified RNA is then eluted from the solid support.

RNA is notoriously susceptible to degradation and RNases are ubiquitous. Many commercially available RNA purification methods include specific chemicals to inactivate RNases present in cell or tissue lysates, and may also include RNase inhibitors to safeguard against RNA degradation throughout the procedure. Any of these methods can be used to recover the small RNAs of the invention.

In another preferred embodiment, the small RNAs of the invention are not used as free RNA molecules, but they are embedded into extracellular vesicles (EVs). The present inventors have indeed shown that *Chlorella* cells can produce EVs which are in a size range that is similar to the one of plant exosomes, and that these EVs are rapidly and efficiently taken-up by human alveolar epithelial cells, in which they presumably deliver their small iRNAs content and further trigger their silencing effect (see EXAMPLE 9). These *Chlorella* derived iRNA-containing EVs can be used for prophylactic or therapeutic purposes, as mammalian and plant-derived EVs are.

In this particularly preferred embodiment, the method of the invention further comprises the step of recovering the Extracellular Vesicles (EV) released by *Chlorella* cells in the extracellular medium.

In the context of the invention, recovering EVs can be done by any conventional means described in the art. Isolation and purification means are for example discussed in literature (Colao I L. et al. 2018). Downstream processing for efficient purification can be used to enrich EVs from cell culture media, e.g., by size-exclusion (based on typica diameters), sedimentation force or flotation density, precipitation-based methods and affinity-based capture. While differential ultracentrifugation can be used, other purification methods will be preferred, such as filtration or chromatic separation. Tangential-flow filtration is more promising, due to tight and reproducible size distributions and the ease with which processes can be scaled. Immunoaffinity methods can also be adjusted to the particular EVs of the invention.

EVs Obtained by the Method of the Invention

Extracellular Vesicles (EVs) are nanosized, membrane-bound vesicles that are released into the extracellular space and transport cargoes towards recipient cells. Mammalian EVs are in part composed of exosomes, which are formed by the fusion between multivesicular bodies (MVBs) and the plasma membrane, in which MVBs release vesicles whose diameters range from 40 to 150 nanometers (O'Brien et al., 2020). During the last decade, mammalian exosomes have been extensively characterized as vehicles of miRNAs. Interestingly, emerging evidence indicates that plant-derived EVs can also operate as carriers of miRNAs in mammalian cells and organs (Wang et al., 2013; Zhang et al., 2017). These lipid-based particles are more stable in the organism than their mammalian counterparts. Furthermore, they present the advantage of being non-toxic and non-immunogenic (Yang & Merlin, 2020), which is not always the case of synthetic nanoparticles classically used as vectors of small RNAs in therapeutic approaches.

In another aspect, the present invention is drawn to the Extracellular Vesicles (EVs) obtained by the method of the invention, as disclosed above. These EVs contain a population of functional small iRNAs targeting one or several region(s) in the target gene(s) of interest. Interestingly, antibacterial small iRNAs can be detected from Mnase-treated *Chlorella* EVs (see EXAMPLE and FIG. 5).

As shown in EXAMPLE 3 and FIG. 1, the present inventors were able to characterize the *Chlorella* EVs by Nanoparticle Tracking Analysis (NTA) and through labeling of lipid-based extracellular particles. This first analysis revealed that *Chlorella* EVs are in a size range between and 200 nm. Further transmission electron microscopy (TEM) unveiled the presence of round shaped particles with an apparent lipidic bilayer and a ~130 nm mean diameter.

The results of the inventors (EXAMPLE 2 and table 2) also show that the EVs produced by the *Chlorella* cells are not likely to contain tetraspanin in their membrane, since the *Chlorella* genome and transcriptome do not contain such factors. Yet, tetraspanin 8 is known to be present on plant EVs (Cai et al., 2018). Therefore, the EVs produced by *Chlorella* cells are different from those produced by plants.

The results of the present inventors show that these EVs can rapidly and efficiently be taken-up by human cells such as human alveolar epithelial cells (EXAMPLE 9), where they can deliver the functional iRNAs contained, as plant or mammalian EVs can do.

In a preferred embodiment, the EVs of the invention preferably contain a population of functional small iRNAs, preferably of 10 to 18 base pairs, that targets several regions in one or several viral gene(s). Accordingly, these EVs can be used as anti-viral agents.

For example, these anti-viral EVs can contain a population of functional small iRNAs, preferably of 10 to 18 base pairs, that targets one or several regions of one or several viral gene(s) that are critical for the replication or the pathogenicity of the SARS-CoV-2 virus.

In another preferred embodiment, the EVs of the invention preferably contain a population of functional small iRNAs, preferably of 10 to 18 base pairs, that targets several regions in one or several bacterial gene(s). Accordingly, these EVs can be used as anti-bacterial agents.

For example, these anti-bacterial EVs can contain a population of functional small iRNAs, preferably of 10 to 18 base pairs, that targets a virulence factor or viability or antibiotic resistant gene of a pathogenic bacterium such as *Pseudomonas aeruginosa, Staphylococcus aureus, Shigella flexneri, Legionella pneumophila, Mycobacterium tuberculosis.*

As explained above, purification of EVs can be performed by various methods. While differential ultracentrifugation can be used, other purification methods will be preferred for industrial purposes, such as filtration, chromatic separation, or affinity-purification methods.

Pharmaceutical Compositions of the Invention

Besides its natural antimicrobial defensive role, iRNA has been extensively used as a prospective tool for innovative anti-infectious approaches. For example, multiple studies conducted on human or monkey cells have shown that synthetic siRNAs exhibit antiviral effects against SARS-CoV-1, which is closely related to SARS-CoV-2, and was responsible for the SARS epidemic in 2002/2003 (Asha et al., 2018). Besides restricting viral replication in vitro, synthetic siRNAs have also been shown to trigger protection in vivo against various viral respiratory infections in mice, macaques and even humans (Tompkins et al., 2004; Ge et al., 2004; Bitko et al., 2005; Li et al., 2005; DeVincenzo et al., 2010; Asha et al., 2018). For example, intranasal delivery of synthetic siRNAs directed against SARS-CoV-1 RNAs significantly reduces viral titer, infection-induced fever and acute diffuse alveoli damage in Rhesus macaques (Li et al., 2005). Therefore, the use of anti-SARS-CoV-2 siRNAs represents a promising approach to defeat COVID-19.

Also, it is noteworthy that the small RNAs of the invention contained within the natural Extracellular Vesicles (EVs) of the invention are protected from ribonuclease-mediated digestion (EXAMPLE 7). iRNA-containing EVs can therefore be used efficiently and longlastingly in pharmaceutical compositions as a therapeutic tool against target pathogens.

In a further aspect, the present invention is thus drawn to pharmaceutical compositions containing, as active principle, the EVs of the invention. More precisely, they contain an effective amount of the *Chlorella*-derived EVs as defined above.

By "effective amount", it is herein meant an amount that has been shown to have an antipathogenic effect (e.g., an antibacterial or antiviral effect) in a test such as described in the examples below. In in vitro applications where isolated cells are to be treated, this amount is preferably comprised between 0.05 and 100 pM, preferably between 0.05 and 10 pM, of EVs containing effective small RNAs. In in vivo applications where whole animals (in particular human beings) are to be treated, this amount is preferably comprised between 0.05 and 100 nM, preferably between 0.05 and 10 nM, of EVs containing effective small RNAs.

The therapeutic compositions of the invention can be formulated in a suitable and/or environmentally acceptable carrier. Such carriers can be any material that the individual to be treated can tolerate. Furthermore, the carrier must be such that the composition remains effective at controlling the infection. Examples of such carriers include water, saline, Ringer's solution, dextrose or other sugar solutions, Hank's solution, and other aqueous physiologically balanced salt solutions, phosphate buffer, bicarbonate buffer and Tris buffer.

These compositions may furthermore contain a surface-active agent, an inert carrier, a preservative, a humectant, a feeding stimulant, an attractant, an encapsulating agent, a binder, an emulsifier, a dye, a UV protectant, a buffer, a flow agent, etc. It can also contain other active principles, such as insecticides, fungicides, bactericides, nematicides, molluscicides or acaricides. These agents can be combined with carriers, surfactants or adjuvants customarily employed in the art of formulation, or other components to facilitate product handling and application. Suitable carriers and adjuvants can be solid or liquid and correspond to the substances ordinarily employed in formulation technology, e.g., natural or regenerated mineral substances, solvents, dispersants, wetting agents, tackifiers, or binders.

In a preferred embodiment, the invention is a liquid sprayable composition. It can then easily be applied on tissues or on clothes or on any material that can be in contact with pathogens, as a preventing measure or as a treatment to get rid of an infection. It can also be easily inhaled for preventing nasally acquired infections.

In another preferred embodiment, the composition of the invention is formulated as a pill, for example in a slow-release pill, that can be easily swallowed by animals and humans to act on gut mucosa or other internal tissues.

In another preferred embodiment, the composition of the invention is formulated as a cream, lotion, or gel, that can conveniently be applied on skin or hair tissues.

More generally, it is possible to add EVs of the invention in cosmetic products in order to prevent infections from occuring or to enhance the growth of a beneficial microbe.

Therapeutic Methods and Uses of the Invention

In another aspect of the invention, the present invention is drawn to therapeutic methods involving the use of the EVs of the invention. These EVs can be used for treating any parasitic infection and/or infectious disease in an animal.

Said parasitic infection and/or infectious disease can be caused e.g., by a virus, a bacterium, a fungus, an oomycete, or any other pathogens or parasites.

The EVs of the invention can target a gene of said pathogen and/or a gene of the diseased subject/host, if this gene is known to facilitate the infection.

In a preferred embodiment, said infectious disease affects tissues and/or organs having contact with the external environment, such as the hair, the nail, the gut, the respiratory tract, the digestive tract, the eyes, the skin, wounds, vaginal mucosa, urinary tract, auditory tract, of said subject.

In the context of the invention, the EVs of the invention or the compositions comprising them can be delivered to the animal tissues by various means (orally, topically, systemically, etc.).

The EVs of the invention can be added in an external composition such as a spray or a cream or a pill.

In one embodiment, the composition of the invention is applied externally to an animal tissue (i.e., by spraying the composition or by applying a lotion, a gel, a cream on said tissue), to protect the individual from a pathogenic infection.

The composition of the invention can also be applied on any tissue that can be in contact with a pathogen. This tissue is preferably chosen in the group consisting of: skin, hair, mucosa, nail, gut, wound, eyes, etc.

Preferably, said animal is of the genus: *Homo sapiens, Canis lupus, Felis catus, Equus caballus, Bos taurus, Ovis aries, Capra hircus, Sus scrofa, Gallus gallus, Meleagris gallopavo, Anser anser, Anas platyrhynchos, Oryctolagus cuniculus, Apis mellifera, Salmo salar* and *Penaeus vannamei—Penaeus monodon*. It can be a healthy animal hosting beneficial bacteria, or a sick animal already infected by a pathogen.

More preferably, said animal is a human being.

It can be a healthy human hosting beneficial bacteria, or a sick human already infected by a pathogen.

The treatment method of the invention includes oral, topic and systemic administration of the EVs of the invention. Nasal and intravenous administration can also be contemplated.

Another aspect of the invention relates to the use of the EVs as defined above, or therapeutic compositions containing them, for preparing a medicament intended to treat an infectious disease, or to prevent an infection from developing.

The EVs of the invention are useful for silencing genes in any microbes. Examples of target microbes are now disclosed.

Pathogenic Bacteria

The EVs of the invention are useful for silencing genes in any pathogen: pathogenic or non-pathogenic bacteria; Gram-positive or Gram-negative bacteria, virus, fungus, oomycetes, or other parasites associated with animal organisms.

In a preferred embodiment, said pathogen is a human pathogenic bacterium.

Non-limitative examples of human pathogenic bacteria, which can be targeted using the EVs of the invention include: *Actinomyces israelii, Bacillus anthracis, Bacillus cereus, Bacteroides fragilis, Bordetella pertussis, Borrelia* sp. (*burgdorferi, garinii, afzelii, recurrentis, crocidurae, duttonii, hennsii* etc), *Brucella* sp. (*abortus, canis, melitensis*, suis), *Campylobacter jejuni, Chlamydia* sp. (*pneumoniae, trachomatis*), *Chlamydophila psittaci, Clostridium* sp. (*botulinum, difficile, perfringens, tetani*), *Corynebacterium diphtheriae, Ehrlichia* sp. (*canis, chaffeensis*), *Enterococcus* (*faecalis, faecium*), *Escherichia coli* O157:H7, *Francisella tularensis, Haemophilus influenza, Helicobacter pylori, Klebsiella pneumoniae, Legionella pneumophila, Leptospira* sp., *Listeria monocytogenes, Mycobacterium* sp. (*leprae, tuberculosis*), *Mycoplasma pneumoniae, Neisseria* (*gonorrhoeae, meningitidis*), *Pseudomonas aeruginosa, Porphyromonas gingivalis, Nocardia asteroides, Rickettsia rickettsii, Salmonella* sp. (*typhi, typhimurium*), *Shigella* sp. (*sonnei, dysenteriae*), *S. flexneri, Staphylococcus* (*aureus, epidermidis, saprophyticus*), *Streptococcus* sp. (*agalactiae, mutans, pneumoniae, pyogenes, viridans*), *Tannerella forsythia, Treponema pallidum, Vibrio cholerae*, and *Yersinia pestis*.

In a preferred embodiment, the EVs of the invention are useful for silencing genes in pathogenic Gram-negative bacteria, for example proteobacteria including *Escherichia coli* (*E. coli*), *Salmonella, Shigella*, or other Enterobacteriaceae, *Pseudomonas, Moraxella, Helicobacter, Stenotrophomonas*, Bdellovibrio, acetic acid bacteria, *Legionella*, etc. Medically relevant gram-negative bacilli include a multitude of species. Some of them cause primarily respiratory problems (*Klebsiella pneumoniae, Legionella pneumophila, Pseudomonas aeruginosa*), primarily urinary problems (*Escherichia coli, Proteus mirabilis, Enterobacter cloacae, Serratia marcescens*), and primarily gastrointestinal problems (*Helicobacter pylori, Salmonella enteritidis, Salmonella typhi, Shigella flexneri, Shigella sonnei, Shigella dysenteriae, Shigella boydii*). The EVs of the invention can be used to limit or prevent an infection due to any of these bacteria.

Beneficial Bacteria

In a particular embodiment, the herein described technology is also useful to control the expression of genes from beneficial bacteria in order to enhance their multiplication and/or their beneficial effects for the host animals.

In other words, the EVs of the invention can also be used for promoting the replication of beneficial (commensal) bacteria by inhibiting genes that negatively regulate directly or indirectly bacterial growth. The EVs of the invention can for example target genes that negatively regulate the survival of beneficial (commensal/symbiotic) bacteria, or genes that prevent their invasion in and association with the host, or genes negatively controlling their carbohydrate metabolism and uptake (knocking-down such genes resulting in an increased bacterial titer).

Preferably, said beneficial commensal or symbiotic bacteria are chosen in the group consisting of. *Actinomyces naeslundii, Veillonella dispar, Faecalibacterium prausnitzii*, Enterobacteriaceae, *Bacteroides thetaiotaomicron, Escherichia coli* K12, *Bifidobacterium* sp. (*longum, bifidum, adolescentis, dentium, breve, themophilum*), *Eggerthella lenta, Bacteroides* sp. (*xylanisolvens, thetaiotaomicron, fragilis, vulgatus, salanitronis*), *Parabacteroides distasonis, Faecalibacterium prausnitzii, Ruminococcus* sp. (*bromii, champanellensis*, SRI 5), *Streptococcus* (*parasanguinis, salivarius, thermophilus, suis, pyogenes, anginosus*), *Lactococcus* (*lactis, garvieae*), *Enterococcus* (*faecium, faecalis, casseliflavus, durans, hirae, Melissococcus plutonius, Tetragenococcus halophilus, Lactobacillus* sp. (*casei, ruminis, delbrueckii, buchneri, reuteri, fermentum, pentosus, amylovorus, salivarius*), *Pediococcus* (*pentosaceus, claussenii*), *Leuconostoc* (*mesenteroides, lactis, carnosum, gelidum, citreum*), *Weissella* (*thailandensis, koreensis*), *Oenococcus oeni, Paenibacillus* sp. (*terrae, polymyxa, mucilaginosus*, Y412MC10), *Thermobacillus composti, Brevibacillus brevis, Bacillus* (*amyloliquefaciens, subtilis, licheniformis, atrophaeus, weihenstephanensis, cereus, thuringiensis, coagulans, megaterium, selenitireducens*), *Geobacillus thermodenitrificans, Lysinibacillus sphaericus, Halobacillus halophilus, Listeria* sp., *Streptomyces* sp., *Eubacterium* (*rectale, eligens, siraeum*), *Clostridium saccharolyticum*, and butyrate-producing bacteria (SS3/4 and SSC/2).

The present invention therefore relates to the EVs of the invention for use for promoting beneficial effects of beneficial commensal or symbiotic bacteria in a subject in need thereof.

In such an embodiment, the EVs of the invention should have sequence homologies with beneficial bacterial genes but no sequence homology to pathogenic genomes, with the host genome or with other genomes of host colonizers and/or mammals that feed on the host organism.

Targeted Virus

The EVs of the invention are also useful for silencing viral genes. In this case, they contain small RNAs that have a portion which is complementary to a fragment of a viral transcript, so as to trigger its degradation and/or reduce production of the cognate viral protein.

In a preferred embodiment, said virus can infect humans. It is for example chosen in the group consisting of. Ebola virus, Hepatitis C Virus (HCV), Hepatitis B Virus (HBV), Chikungunya virus (CHIKV), Human Immunodeficiency Virus (HV), Zika virus (ZIKV), coronaviruses, influenza A virus, Human Papilloma Virus (HPV), etc.

Other Pathogens

The EVs of the invention are also useful for silencing genes in fungal pathogens, said fungus being for example chosen in the group consisting of: *Aspergillus fumigatus, Aspergillus flavus, Blastomyces, Candida albicans, Candida auris, Coccidioides, Criptococcus neoformans, Criptococcus gattii, Histoplasma capsulatum, Pneumoicystis jirovecii, Sporothrix schenckii, Stachybotrys chartarum, Talaromyces marneffei*, and *Trichophyton rubrum.*

Chimeric EVs of the Invention

For protecting subjects against diseases caused by several bacterial pathogens, the method of the invention advantageously uses functional EVs carrying sequence homologies with more than one pathogen (hereafter referred to as "chimeric EVs").

In this embodiment, the small RNAs contained in the EVs of the invention can target several genes of several pathogens or parasites. These "chimeric EVs" are not specific to one pathogen but can affect the growth of several pathogens (e.g., a bacterium and a virus, a bacterium and a fungus, two different bacteria, or three different viruses, etc. . . . ).

All the embodiments proposed above for the EVs, the iRNAs, the vectors, and the transformation methods are herewith encompassed and do not need to be repeated.

When the EVs of the invention target several pathogens or parasites, the pharmaceutical composition of the invention can concomitantly treat or prevent the diseases caused by these different pathogens/parasites.

In a preferred embodiment, the EVs of the invention contain chimeric iRNAs inhibiting at least one gene encoding a virulence factor or an essential gene of bacterial cells as defined above, together with at least one other gene encoding a virulence factor or an essential gene of other pathogens or parasites known to be sensitive to host-induced gene silencing. It can be also a gene required for the biosynthesis of toxic secondary metabolites from non-bacterial pathogens or parasites.

In another preferred embodiment, the therapeutic applications of the invention use: (i) EVs containing one or more iRNAs targeting a widespread sequence region of an essential or virulence gene that is conserved in a large set of pathogens or (ii) EVs containing one or more iRNAs targeting genes that are essential or virulence factors from unrelated pathogens. Such particular embodiment confers broad-spectrum protection towards multiple pathogens.

The EVs of the invention are useful for silencing any genes in any microbes. Examples of target genes are now disclosed.

Target Bacterial Genes

For anti-bacterial applications, the EVs of the invention should contain effective small RNAs having a sufficient sequence homology with at least one bacterial gene in order to induce sequence-specific silencing of said at least one gene. In addition, to prevent unwanted off-target effects, the sequence homology of the dsRNAs, miRNAs or small RNA species contained in said EVs with the eukaryotic host genome or other genomes of beneficial bacteria, host colonizers and/or mammals that feed on the host organism should be quasi-inexistent (if not absent).

According to the invention, the term "bacterial gene" refers to any gene in bacteria including (natural) protein-coding genes or non-coding genes, present naturally in bacteria and artificial genes introduced in bacteria by recombinant DNA technology. Said target bacterial genes are either specific to a given bacterial species or conserved across multiple bacterial species. Preferably, it shares no homology with any gene of the eukaryotic host genome, host colonizers and/or mammals that feed on the host organism. This avoids collateral effects on the animal host, beneficial bacteria associated with the host, host colonizers and/or animals that feed on the host organism.

In a preferred embodiment, said at least one bacterial gene is a bacterial virulence factor or an essential gene for bacteria or an antibiotic resistance gene.

As used herein, the term "essential gene for bacteria" refers to any bacterial gene that is essential for bacterial cell viability. These genes are absolutely required to maintain bacteria alive, provided that all nutrients are available. It is thought that the absolutely required number of essential genes for bacteria is about 250-500 in number. The identification of such essential genes from unrelated bacteria is now becoming relatively easily accessible through the use of transposon sequencing approaches. These essential genes encode proteins to maintain a central metabolism, replicate DNA, ensure proper cell division, translate genes into proteins, maintain a basic cellular structure, and mediate transport processes into and out of the cell. In the context of the invention, the iRNAs of the invention can for example target the essential genes LptH, LolA, TolB, LpxA, LpxD, dnaA, dnaN, gyrB, rpoC, secE and sodB, essential genes involved in amino acid synthesis (AroA, LysC, CysH, GalU), transpeptidases (PbpA, PbpB, PbpC), genes encoding components of bacterial transcriptional machinery (e.g., sigma 70, sigma 54), genes encoding structural components of bacterial cell walls (peptidoglycan biosynthesis genes), genes that are critical for cell division (e.g., FtsZ, FtsA, FtsN, FtsK, FtsI, FtsW), structural homologs of actin (e.g., MreB, Mbl), other crucial genes such as ZipA, ZapA, TolA, TolB, TolQ, TolR, Pal, Min CD, actin-related genes (MreB and Mld).

As used therein, the term "virulence gene" refers to any bacterial gene that has been shown to play a critical role for at least one of the following activities: pathogenicity, disease development, colonization of a specific host tissues or host cell environment, etc. All these activities help the bacteria to grow and/or promote disease symptoms in the host, although they are not essential for their survival in vitro.

In the context of the invention, the EVs of the invention target for example structural genes of secretion systems including the type II or III secretion system (e.g., PscC, PscJ, PscN, XcpQ, PcrV; PcrR), structural genes of the type IV secretion system (e.g., VirB1, VirD4), genes encoding the GAC signaling-related components (GacA, RsmA), structural genes of the type VI secretion system (e.g., TssM, TssJ, TssB TssC, TssE, VgrG, Hcp), genes of the dot/icm system (DotC, DotD, DotF, DotG and DotH), transcriptional regulators or type III secreted effectors (ExoS, ExoU, exsA, VirF, VirB), the Vrf gene encoding the cAMP-dependent DNA-binding protein, adhesins (e.g., IcsA), quorum sensing-related genes (e.g. LasR, RhlR, MvfR, VqsM, LuxS, Luxl-LuxR), genes encoding surface bound proteins (fnbA, clfA, clfB, spa, atl), leukotoxins (lukF-PV, lukS-PV, lukE, lukD, HlgB), the alpha hemolysin hla, and the toxic shock syndrome toxin-1 tsst-1.

The EVs of the invention can also inhibit the expression of an antibiotic resistance gene in order to render bacteria sensitive to said antibiotic treatment.

These antibiotic resistance genes are for example: bacterial efflux pump genes (Arc, Ptr, Nor, Mep, Cme types), genes of the four molecular classes of beta-lactamases: class A (e.g., TEM, SHV, GES types), class B (e.g., metallo beta-lactamases VIM, NDM), class C (e.g. AmpC type), class D (OXA type). Non-limitative examples of antibiotic resistance genes include: VIM-1, VIM-2, VIM-3, VIM-5, CasE, OXA-28, OXA-14, OXA-19, OXA-145, PER-1, TEM-116, and GES-9, as well as other vital genes that lead to lethality of the bacterium when these genes are deleted or inactivated in the microorganism and those listed in the The Comprehensive Antibiotic Resistance Database 2017 (or CARD 2017).

In a preferred embodiment, said virulence factor gene or bacterial viability gene or antibiotic resistant gene is therefore chosen in the group consisting of: LptH, LolA, TolB, LpxA, LpxD, XcpQ, PcrV, PcrR, Vrf, dnaA, dnaN, gyrB, rpoC, secE, sodB, ExoS, ExoU, exsA, LasR, RhlR, MvfR, VqsM, GacA, RsmA, VirF, VirB, IcsA, fnbA, clfA, cpfB, spa, atl, lukF-PV, lukS-PV, lukE, lukD, HlgB, hla, tsst-1, mexX, mexA, ampC, PscC, PscJ, PscN, VirB1, VirD4, TssM, TssJ, TssB TssC, TssE, VgrG, Hcp, DotC, DotD, DotF, DotG, DotH, LuxS, LuxlLuxR, AroA, LysC, CysH, GalU, PbpA, PbpB, PbpC, Pigma70, Sigma 54, Arc, Ptr, Nor, Mep, Cme, TEM, SHV, GES, VIM, NDM, mexX, mexA, AmpC, VIM-1, VIM-2, VIM-3, VIM-5, Case, OXA-28, OXA-14, OXA-19, OXA-145, PER-1, TEM-ii6, GES-9, FtsZ, FtsA, FtsN, FtsK, FtsI, FtsW, ZipA, ZapA, TolA, TolB, TolQ, ToIR, Pal, MinCD, MreB and Mld.

In anti-bacterial applications, the EVs of the invention have advantageously sequence homologies with essential genes for the viability or virulence genes from bacterial pathogen species but no sequence homology with commensal bacteria genomes. Such advantageous embodiment of the method avoids collateral effects on the commensal bacteria present in the host.

Particular useful sequences targeting some of these genes are provided in the EXAMPLE 12 below, and in the SEQ ID NO: 13-32 and 57-70 for *P. aeruginosa*, SEQ ID NO:71-74 and 33-34 for *S. flexneri*, SEQ ID NO:35-40 for *S. aureus*, SEQ ID NO: 75-88 for *Mycobacterium tuberculosis*, and in SEQ ID NO:89-106 for *Legionella pneumophila* (see the details of these useful sequences in Table 1).

Target Viral Genes

The genes targeted by the small RNAs contained in the EVs of the invention are for example: the NP, VP35, VP40, GP, VP30, VP24, and/or L (RdRp) genes from the Ebola Virus, the preS1, PreS2, C, P, S and X genes from the HBV, the 5' UTR, C, E1, E2, 2, 3, 4B, 5A, 5B and/or 3' UTR genes and regions from the HCV, the C, prM, E, NS1, NS2A, NS2B, NS3, NS4B and/or NS5 genes from the ZIKV, the 5'cap, nsP1, nsP2, nsP3, nsP4, C, E3, E2, 6K and E1 genes from CHIKV, the 5' LTR, gag, pol, vif, vpr, vpu, tat, rev, env, nef and/or 3'LTR genes and regions from HV, the PB2, PB, PA, HA, NP, NA and/or M genes from Influenza Viruses, the E1, E2, E4, E5, E6, E7, L1 and/or L2 genes from HPV.

Particular useful sequences targeting SARS-CoV-2 viral regions are provided in the EXAMPLE below, and in the SEQ ID NO: 41-46 (individual genes) and in SEQ ID NO:1-12 (multiple genes) (see the details of these useful sequences in Table 1).

In Vitro Antibiotic Antiviral Methods and Uses of the Invention

In another aspect, the present invention relates to an in vitro method for inhibiting the expression of at least one gene in a target pathogenic cell, said method comprising the step of in vitro contacting said target pathogenic cell with one or more of the EVs of the invention or with compositions comprising same.

In other words, the present invention relates to the in vitro use of the EVs of the invention, or of a composition comprising same, for inhibiting the expression of at least one gene in a pathogenic cell, wherein said target pathogenic cell is contacted directly with said EVs or with said composition.

By "inhibiting the expression of at least one gene", it is herein meant that the expression of said gene is reduced, i.e., the mRNA or protein levels of the target sequence is statistically lower than the mRNA level or protein level of the same target sequence in an appropriate control which is exposed to control small RNAs targeted unrelated genes. In particular, reducing the mRNA polynucleotide level and/or the polypeptide level of the target gene according to the invention results in reaching less than 60%, less than 50%, less than 40%, less than 30%, less than 20%, less than 10%, or less than 5% of the mRNA polynucleotide level, or the level of the polypeptide encoded thereby, of the same target sequence in an appropriate control. Methods to assay the expression level of the RNA transcript, the expression level of the polypeptide encoded by the targeted gene, or the activity of said polynucleotide or polypeptide are well-known in the art. A reporter system has also been developped by the inventors (see below).

In this aspect, any type of bacteria can be targeted. Pathogenic bacteria that infect animal (including human) hosts, or beneficial (e.g., symbiotic or commensal) bacteria that provide a beneficial effect for animal (including human) host can be targeted, as described above.

This method is of particular interest for inhibiting or limiting the pathogenicity and growth of a pathogen in vitro, on a surface or in a sample.

In another embodiment, this method can also be used for promoting the replication of beneficial bacteria by inhibiting genes that negatively regulate directly or indirectly bacterial growth, as described above.

In another embodiment, it is also possible to use this method for restoring the sensitivity of bacterial cells to an antibiotic compound by targeting a gene that is involved in the bacterial resistance to said antibiotic compound.

Restoring Antibiotic Sensitivity with the Pharmaceutical Compositions of the Invention In another aspect, the inventors propose to use the EVs of the invention for restoring the sensitivity of bacterial cells to an antibiotic compound, by targeting a gene that is involved in the bacterial resistance to said antibiotic compound.

The compositions of the invention may be applied simultaneously or in succession with other compounds. In particular, the compositions of the invention may be applied with antibiotic compounds, especially when the iRNAs they carry target an antibiotic resistance gene.

In this case, the composition of the invention may be supplied as a "kit of parts", comprising the EVs of the invention (the small RNAs defined above) and the corresponding bactericidal compound in a separate container.

Thus, in a further aspect, the present invention therefore relates to a pharmaceutical kit containing:

a) *Chlorella*-derived EVs of the invention, containing small interfering RNA inhibiting specifically an antibiotic resistance gene, or a therapeutic composition containing same, as disclosed above, and
b) an antibiotic compound.

The present invention also targets the use of such pharmaceutical kit for treating and/or preventing a bacterial infection in a subject in need thereof and treating methods using same.

In another aspect, the present invention relates to a combination product comprising: a) *Chlorella*-derived EVs of the invention, containing small interfering RNA inhibiting specifically an antibiotic resistance gene, or a therapeutic composition containing same, as disclosed above, and b) an antibiotic compound, for use for simultaneous, separated or staggered use for preventing and/or treating a bacterial infection in a subject in need thereof.

In a preferred embodiment, said EVs are administered before said antibiotic compound, preferably one week before, more preferably one day before.

In these kits and products, said antibiotic resistance gene is preferably chosen from: VIM-1, VIM-2, VIM-3, VIM-5, CasE, OXA-28, OXA-14, OXA-19, OXA-145, PER-1, TEM-116, and GES-9.

By "antibiotic compound", it is meant a compound that is used or proposed for killing bacteria.

Classical antibiotic compounds that are used in the therapeutic field are for example copper-based bactericides or secondary metabolites derived from macro- and micro-organisms. These include but are not restricted to Aminoglycosides, Carbapenems, Ceftazidime (3rd generation), Cefepime (4th generation), Ceftobiprole (5th generation), Ceftolozane tazobactam, Fluoroquinolones, Piperacillin tazobactam, Ticarcillin clavulanic acid, Amikacin, Gentamicin, Kanamycin, Neomycin, Netilmicin, Tobramycin, Paromomycin, Streptomycin, Spectinomycin, Geldenamycin, herbimycin, Rifaximin, Ertapenem, Doripenem, Imipenem, Meropenem, Cefadroxil, Cefazolin, Cephradine, Cephapirin, Cephalothin, Cefalexin, Cefaclor, Cefoxitin, Cefotetan, Cefamandole, Cefmetazole, Cefonicid, Loracarbef, Cefprozil, Cefuroxime, Cefixime, Cefdinir, Cefditoren, Cefoperazone, Cefotaxime, Cefpodoxime, Ceftazidime, Ceftibuten, Ceftizoxime, Moxalactam, Ceftriaxone, Cephalosporins, Cefepime, Cephalosporins, Ceftaroline fosamil, Ceftobiprole, Glycopeptides, Teicoplanin, Vancomycin, Telavancin, Dalbavancin, Oritavancin, Lincosamides(Bs), Clindamycin, Lincomycin, Lipopeptide, Daptomycin, Macrolides(Bs), Azithromycin, Clarithromycin, Erythromycin, Roxithromycin, Telithromycin, Spiramycin, Fidaxomicin, Monobactams, Aztreonam, Nitrofurans, Furazolidone, Nitrofurantoin(Bs), Oxazolidinones(Bs), Linezolid, Posizolid, Radezolid, Torezolid, Penicillins, Amoxicillin, Ampicillin, Azlocillin, Dicloxacillin, Flucloxacillin, Mezlocillin, Methicillin, Nafcillin, Oxacillin, Penicillin G, Penicillin, Piperacillin, Temocillin, Ticarcillin, Penicillin combinations, Amoxicillin clavulanate, Ampicillin sulbactam, Piperacillin tazobactam, Ticarcillin clavulanate, Polypeptides, Bacitracin, Colistin, Polymyxin B, Quinolones Fluoroquinolones, Ciprofloxacin, Enoxacin, Gatifloxacin, Gemifloxacin, Levofloxacin, Lomefloxacin, Moxifloxacin, Nadifloxacin, Nalidixic acid, Norfloxacin, Ofloxacin, Trovafloxacin, Grepafloxacin, Sparfloxacin, Temafloxacin, Sulfonamides(Bs), Mafenide, Sulfacetamide, Sulfadiazine, Silver sulfadiazine, Sulfadimethoxine, Sulfamethizole, Sulfamethoxazole, Sulfanilimide (archaic), Sulfasalazine, Sulfisoxazole, Trimethoprim-Sulfamethoxazole (Co-trimoxazole) (TMP-SMX), Sulfonamidochrysoidine (archaic), Tetracyclines (Bs), Demeclocycline, Doxycycline, Metacycline, Minocycline, Oxytetracycline, Tetracycline, Clofazimine, Dapsone, Capreomycin, Cycloserine, Ethambutol(Bs), Ethionamide, Isoniazid, Pyrazinamide, Rifampicin, Rifabutin, Rifapentine, Streptomycin, Arsphenamine, Chloramphenicol(Bs), Fosfomycin, Fusidic acid, Metronidazole, Mupirocin, Platensimycin, Quinupristin Dalfopristin, Thiamphenicol, Tigecycline(Bs), Tinidazole, Trimethoprim(Bs) etc.

Preferably, the target bacteria are then chosen in the group consisting of: *Actinomyces israelii, Bacillus anthracis, Bacillus cereus, Bacteroides fragilis, Bordetella pertussis, Borrelia* sp. (*burgdorferi, garinii, afzelii, recurrentis, crocidurae, duttonii*, hennsii etc), *Brucella* sp. (*abortus, canis, melitensis*, suis), *Campylobacter jejuni, Chlamydia* sp. (*pneumoniae, trachomatis*), *Chlamydophila psittaci, Clostridium* sp. (botulinum, *difficile, perfringens, tetani*), *Corynebacterium diphtheriae, Ehrlichia* sp. (*canis, chaffeensis*), *Enterococcus* (*faecalis, faecium*), *Escherichia coli* O157:H7, *Francisella tularensis, Haemophilus influenza, Helicobacter pylori, Klebsiella pneumoniae, Legionella pneumophila*, Leptospira sp., *Listeria monocytogenes, Mycobacterium* sp. (*leprae*, tuberculosis), *Mycoplasma pneumoniae, Neisseria* (*gonorrhoeae, meningitidis*), *Pseudomonas aeruginosa, Porphyromonas gingivalis, Nocardia asteroides, Rickettsia rickettsii, Salmonella* sp. (*typhi, typhimurium*), *Shigella* sp. (*sonnei, dysenteriae*), *Staphylococcus* (*aureus, epidermidis, saprophyticus*), *Streptococcus* sp. (*agalactiae, mutans, pneumoniae, pyogenes, viridans*), Tannerella forsythia, *Treponema pallidum, Vibrio cholerae, Yersinia pestis* etc.

The amount of EVs to be used typically depends on the number of bacteria and on the type of bacteria that are targeted. In in vitro applications where isolated cells are to be treated, this amount is preferably comprised between 0.05 and 100 pM, preferably between 0.05 and 10 pM, of EVs containing effective small RNAs. In in vivo applications where whole animals (in particular human beings) are to be treated, this amount is preferably comprised between 0.05 and 100 nM, preferably between 0.05 and 10 nM, of EVs containing effective small RNAs.

Preferably, said subject is an animal of the genus: *Homo sapiens, Canis lupus, Felis catus, Equus caballus, Bos taurus, Ovis aries*, Capra hircus, *Sus scrofa, Gallus gallus, Meleagris gallopavo*, Anser anser, Anas platyrhynchos, Oryctolagus *cuniculus*.

Transgenic *Chlorella* Cells of the Invention

The *Chlorella* cells transformed with the iRNAs of the invention and able to generate the small RNAs of the invention are hereafter designated as "transgenic *Chlorella* cells of the invention" or "recombinant *Chlorella* cells of the invention" or "host cells of the invention".

These producer cells can be of any *Chlorella* species. In particular, they can be any cells that are currently used as food complement for humans and livestock. In a particular embodiment, they can belong to the species: *Chlorella* ellipsoidea, *Chlorella pyrenoidosa, Chlorella sorokiniana, Chlorella vulgaris* or *Chlorella variabilis.*

In another aspect, the present invention relates to an isolated *Chlorella* cell or to a transgenic *Chlorella* stably or transiently expressing at least one functional iRNA of the invention. It also relates to an isolated *Chlorella* cell containing a DNA or a viral vector containing the precursor of the invention. Said *Chlorella* cell may be a genetically modified cell obtained by transformation with said DNA construct or vector.

Examples of transformation processes are *Agrobacterium*-mediated transformation or shot-gun-mediated transformation, as described above.

All the embodiments proposed above for the *Chlorella* cells, the iRNAs, the precursor, the vectors, and the transformation methods are herewith encompassed and do not need to be repeated.

Methods to generate such transgenic *Chlorella* are disclosed in the example part below (EXAMPLE 1). They contain the steps of:

i) transforming a *Chlorella* cell with a DNA vector expressing at least one long functional interfering RNA of the invention, as explained above, or, ii) infecting a *Chlorella* cell with a virus, preferably selected from RNA viruses able to infect *Chlorella* cells, engineered to express at least one functional interfering RNA of the invention from their genomes, for a sufficient time (typically 3 to 8 days) for the *Chlorella* cell to stably or transiently express a significant amount of small RNAs.

By "significant amount", it is herein meant an amount that has been shown to have an antimicrobial effect in a test such as described above. In in vitro applications where isolated cells are to be treated, this amount is preferably comprised between 0.05 and 100 pM, preferably between 0.05 and 10 pM, of EVs containing effective small RNAs. In in vivo applications where whole animals (in particular human beings) are to be treated, this amount is preferably comprised between 0.05 and 100 nM, preferably between 0.05 and 10 nM, of EVs containing effective small RNAs.

In particular, said transgenic *Chlorella* is capable of host-induced gene silencing of a pathogen (e.g., a virus or a bacterium), and contains an expressible iRNA, capable of down-regulating or suppressing the expression of at least one gene of said pathogen.

In another aspect, the present invention relates to a target transgenic *Chlorella* cell stably or transiently expressing the small RNAs described above. In one embodiment, said target transgenic *Chlorella* contains the precursors of the invention, described above.

More precisely, the invention relates to recombinant *Chlorella* cells containing and expressing a siRNA or miRNA precursor comprising a fragment of at least one target gene, said *Chlorella* cells releasing EV-embedded functional small iRNAs targeting said gene fragment.

In one preferred embodiment, said at least one target gene is an oomycete gene, a viral gene, a bacterial gene, or a fungus gene or a gene of any other pathogens or parasite.

In one preferred embodiment, said *Chlorella* cells is chosen from: *Chlorella* ellipsoidea, *Chlorella pyrenoidosa, Chlorella sorokiniana, Chlorella vulgaris* or *Chlorella variabilis.*

In a further aspect, the present invention is also drawn to pharmaceutical compositions containing, as active principles, the transgenic *Chlorella* cells stably or transiently expressing the small RNAs described above. More precisely, these pharmaceutical compositions advantageously contain an effective amount of the transgenic *Chlorella* cells that are able to produce the small RNAs of the invention in situ, once applicated on the target subject. In this aspect, the biomass of *Chlorella* cells can serve as a dietary supplement, more preferably as a pet food supplement. It is preferably used as a veterinary treatment, as disclosed above in the part entitled "therapeutic methods and uses of the invention".

To obtain a high yield of these transgenic cells or to enhance the ability of these transgenic cells to produce EVs, it is possible to follow the recommendations disclosed above in the specific part entitled "production methods of the invention". They apply here, mutatis mutandis, and need not be repeated.

As disclosed previously, these compositions can be formulated in a suitable and/or environmentally acceptable carrier. Such carriers can be any material that the individual to be treated can tolerate. Furthermore, the carrier must be such that the composition remains effective at controlling the infection. Examples of such carriers include water, saline, Ringer's solution, dextrose or other sugar solutions, Hank's solution, and other aqueous physiologically balanced salt solutions, phosphate buffer, bicarbonate buffer and Tris buffer.

Platform of the Invention

In a final aspect, the invention relates to a versatile platform for producing high throughput amount of functional EV-embedded interfering small RNAs, said platform using the recombinant *Chlorella* cells as defined above.

By "versatile", it is meant that this platform is able to adapt or be adapted to many different functions or activities, generating modulators of a number of different pathogens, in a rapid manner.

This platform is called "MIGS platform". It is useful for producing high amounts of siRNA populations targeting up to 1500 bp long regions in up to a dozen genes. These siRNAs are thus effective against any pathogens, which can not easily set resistance mechanisms. They are embedded in extracellular vesicles that are known to be very stable and non-toxic/non-immunogenic. All the advantages of this platform have been highlighted above.

The inventors have also generated tools for rapidly evaluating the biological activity of each P40 or P100 fraction batch produced from transformed *Chlorella* reference lines. More precisely, they engineered bacteria (here the *Escherichia coli* K12 strain) to express a reporter system that exhibits a differential siRNA targeted reporter gene expression when EV-embedded siRNAs are internalized and active in bacterial cells.

Five different reporter systems are herein proposed:

A first reporter system family is based on the plasmid expression of a bipartite cassette composed of a first construct expressing a short-lived variant of the transcriptional repressor, namely LacI-lite, carrying in its 5' or 3' ends the antimicrobial siRNA target region of interest, and a second construct composed of an intermediate stability variant of the GFP (Andersen et al., 1998; Elowitz & Leibler., 2000), whose transcriptional activity is directed by the pLac promoter and regulated by the lacO operator (FIG. 9A). In the absence of EV-embedded and/or associated small RNAs, LacI-lite proteins should be constitutively produced in bacteria and in turn shut-down the expression of the GFP, resulting in an absence of GFP fluorescence signal. By contrast, when a given small RNA population is internalized and active in bacterial cells, the silencing of LacI-lite results in the derepression of the GFP expression, leading to the detection of GFP fluorescence signal (FIG. 9A). Of note, other systems than LacI-lacO can also be used for the same purpose, such as the TetR-lite tetO2 or cI-lite PR systems. The bipartite reporter system in destination plasmids can be assembled with backbones adapted for expression and replication in both *E. coli* and Pto DC3000. It is then possible to introduce a small RNA target sequence specific to a target gene (here for example the Pto DC3000 gene fusA) at the 3' end of the LacI-lite repressor. The transformed bacterial cells can be incubated with IPTG the $OD_{600}$ and GFP fluorescence can be measured. The GFP fluorescence of the +IPTG conditions can be normalized using the −IPTG and a chloramphenicol control, in order to determine the correct induction kinetics once the background signal was removed.

A second reporter system can be generated a GFP-based reporter by assembling the strong constitutive promoter pCMV to a GFP transgene fused to a small RNA target sequence at the 3' end of the coding sequence (FIG. 9D). This reporter can be further transfected into human cells treated with the candidate EVs population and the silencing of the GFP protein can be further monitored by different approaches including western blot analysis at 24- and 48-hours post treatments.

A third reporter system family relies on the plasmid-based expression of a cassette composed of a first construct constitutively expressing a non-targeted DsRed reporter that is used as an internal control for normalization, and a second construct carrying a destabilized GFP reporter, containing in its downstream region (or upstream region) the antimicrobial siRNA target region of interest (FIG. 9E). When expressed in bacteria (e.g., *E. coli*), this system will result in a specific decrease in GFP expression and fluorescence signal upon internalization of a given effective EV-embedded siRNA population.

A fourth reporter system family is based on the plasmid expression of a tripartite cassette composed of a first construct expressing a short-lived variant of the transcriptional repressor, namely TetR-lite, carrying in its downstream region the antimicrobial siRNA target region of interest, a second construct composed of an intermediate stability variant of the GFP (Andersen et al., 1998; Elowitz & Leibler, 2000), whose transcriptional activity is controlled by the tetO2 (or tetO1) operator, and a third construct expressing a non-targeted DsRed reporter, which serves as internal control for normalization (FIG. 9F). In the absence of EV-embedded small RNA, TetR-lite proteins should be constitutively produced in bacteria and in turn shut-down the expression of the GFP, resulting in an absence of GFP fluorescence signal (only the fluorescence of the DsRed reporter should be detected). By contrast, when a given siRNA population is internalized and active in bacterial cells, the silencing of TetR-lite results in the derepression of the GFP expression, leading to the detection of GFP fluorescence signal.

A fifth family of reporter system relies on the plasmid-based expression of a bipartite cassette composed of a first construct expressing a short-lived variant of the transcriptional repressor, namely TetR-lite, carrying in its downstream region (or upstream region) the antimicrobial siRNA target region of interest and a second construct composed of the GFP (Andersen et al., 1998; Elowitz & Leibler, 2000), or a bioluminescence reporter (e.g., the *Photorhabdus luminescens* operon luxCDABE (Meighen, 1991), whose transcriptional activity is controlled by the tetO2 (or tetO1) operator (FIG. 9G). When a given siRNA population is internalized and active in bacterial cells, the silencing of TetR-lite results in the derepression of the GP or luxCDABE operon expression, leading to the detection of GFP fluorescence or bioluminescence signals. Of note, other systems than TetR-tetO2 could also be used for the same purpose, such as the lacI-lite/lacO or cl-lite/λPR systems.

These reporter systems are also part of the invention and will be instrumental to validate the biological activities or EV-embedded siRNA batches prior product manufacturing.

In addition to the above arrangements, the invention also comprises other arrangements, which will emerge from the description that follows, which refers to exemplary embodiments of the subject of the present invention, with reference to the attached drawings and Table of sequences in which:

TABLE 1

Sequence details on the tools used in the examples

| SEQ ID NO: | Name/details |
|---|---|
| 1 | Sequence of the first arm of the Nsp1/Nsp13/Nsp4/Nsp3/Nsp5/Nsp12/Nsp14 dsRNA used to concomitantly target Nsp1, Nsp13, Nsp4, Nsp5, Nsp3, Nsp12 and Nsp14 genes from SARS-CoV-2 |
| 2 | Sequence of the second arm of the Nsp1/Nsp13/Nsp4/Nsp3/Nsp5/Nsp12/Nsp14 dsRNA used to concomitantly target Nsp1, Nsp13, Nsp4, Nsp5, Nsp3, Nsp12 and Nsp14 genes from SARS-CoV-2 |
| 3 | Sequence of the first arm of the E/M/N/S/Leader/TRS/3'UTR dsRNA used to concomitantly target E, M, N, S, subgenomic 5' leader, TRS and 3'UTR genes and regions from SARS-CoV-2 |
| 4 | Sequence of the first arm of the E/M/N/S/Leader/TRS/3'UTR dsRNA used to concomitantly target E, M, N, S, subgenomic 5' leader, TRS and 3'UTR genes and regions from SARS-CoV-2 |
| 5 | Sequence of the first arm of the Rpl13/eIF3e/eIF3l/eIF3F dsRNA used to concomitantly target Rpl13, eIF3e, eIF3i and eIF3F genes from *Homo sapiens* |
| 6 | Sequence of the second arm of the Rpl13/eIF3e/eIF3l/eIF3F dsRNA used to concomitantly target Rpl13, eIF3e, eIF3i and eIF3F genes from *H. sapiens* |
| 7 | Sequence of the first arm of the eEIF1A/eIF4A dsRNA used to concomitantly target eEIF1A and eEIF4A genes from *H. sapiens* |
| 8 | Sequence of the second arm of the eEIF1A/eIF4A dsRNA used to concomitantly target eEIF1A and eEIF4A genes from *H. sapiens* |
| 9 | Sequence of the first arm of the Snrpe/Naca/Kif11l/Gbf1/Srp54 dsRNA used to concomitantly target Snrpe, Naca, Kif11, Gbf1 and Srp54 genes from *H. sapiens* |
| 10 | Sequence of the second arm of the Snrpe/Naca/Kif11l/Gbf1/Srp54 dsRNA used to concomitantly target Snrpe, Naca, Kif11, Gbf1 and Srp54 genes from *H. sapiens* |
| 11 | Sequence of the first arm of the ACE2/TMPRSS2/Psmd1/KpnA1/IMPBβ1 dsRNA used to concomitantly target ACE2, TMPRSS2, Psmd1, KpnA1 and IMPBβ1 genes from *H. sapiens* |
| 12 | Sequence of the second arm of the ACE2/TMPRSS2/Psmd1/KpnA1/IMPBβ1 dsRNA used to concomitantly target ACE2, TMPRSS2, Psmd1, KpnA1 and IMPBβ1 genes from *H. sapiens* |
| 13 | Sequence of the first arm of the LptH/LolA/TolB dsRNA used to concomitantly target LptH, LolA and TolB genes genes from *P. aeruginosa*: |
| 14 | Sequence of the second arm of the LptH/LolA/TolB dsRNA used to concomitantly target LptH, LolA and TolB genes from *P. aeruginosa* |
| 15 | Sequence of the first arm of the LpxA/LpxD/TolB dsRNA used to concomitantly target LpxA, LpxD and TolB genes from *P. aeruginosa* |
| 16 | Sequence of the second arm of the LpxA/LpxD/TolB dsRNA used to concomitantly target LpxA, LpxD and TolB genes from *P. aeruginosa* |

TABLE 1-continued

| Sequence details on the tools used in the examples | |
|---|---|
| SEQ ID NO: | Name/details |
| 17 | Sequence of the first arm of the secE/dnaN/gyrB dsRNA used to concomitantly target secE, dnaN and gyrB genes from *P. aeruginosa* |
| 18 | Sequence of the second arm of the secE/dnaN/gyrB dsRNA used to concomitantly target secE, dnaN and gyrB genes from *P. aeruginosa* |
| 19 | Sequence of the first arm of the XcpQ/ExsA/PcrV/LasR/RhlR/VqsM/RmsA dsRNA used to concomitantly target XcpQ, ExsA, PcrV, LasR, RhlR, VqsM and RmsA genes from *P. aeruginosa* |
| 20 | Sequence of the second arm of the XcpQ/ExsA/PcrV/LasR/RhlR/VqsM/RmsA dsRNA used to concomitantly target XcpQ, ExsA, PcrV, LasR, RhlR, VqsM and RmsA genes from *P. aeruginosa* |
| 21 | Sequence of the first arm of the XcpQ/PscF/PscC dsRNA used to concomitantly target XcpQ, PscF and PscC genes from *P. aeruginosa* |
| 22 | Sequence of the second arm of the XcpQ/PscF/PscC dsRNA used to concomitantly target XcpQ, PscF and PscC genes from *P. aeruginosa* |
| 23 | Sequence of the first arm of the ExoS/ExsA/Vrf dsRNA used to concomitantly target ExoS, ExsA and Vrf genes from *P. aeruginosa* |
| 24 | Sequence of the second arm of the ExoS/ExsA/Vrf dsRNA used to concomitantly target ExoS, ExsA and Vrf genes from *P. aeruginosa*: |
| 25 | Sequence of the first arm of the ExoU/ExsA/Vrf dsRNA used to concomitantly target ExoU, ExsA and Vrf genes from *P. aeruginosa* |
| 26 | Sequence of the second arm of the ExoU/ExsA/VrfdsRNA used to concomitantly target ExoU, ExsA and Vrf genes from *P. aeruginosa* |
| 27 | Sequence of the first arm of the LasR/RhlR/VqsM dsRNA used to concomitantly target LasR, RhlR and VgsM genes from *P. aeruginosa* |
| 28 | Sequence of the second arm of the LasR/RhlR/VqsM dsRNA used to concomitantly target LasR, RhlR and VqsM genes from *P. aeruginosa* |
| 29 | Sequence of the first arm of the GacA/RmsA/MvfR dsRNA used to concomitantly target GacA, RmsA and MvfR genes from *P. aeruginosa* |
| 30 | Sequence of the second arm of the GacA/RmsA/MvfR dsRNA used to concomitantly target GacA, RmsA and MvfR genes from *P. aeruginosa* |
| 31 | Sequence of the first arm of the mexX/mexA/ampC dsRNA used to concomitantly target mexX, mexA and ampC genes from *P. aeruginosa* |
| 32 | Sequence of the second arm of the mexX/mexA/ampC dsRNA used to concomitantly target mexX, mexA and ampC genes from *P. aeruginosa* |
| 33 | Sequence of the first arm of the VirF/VirB/IcsA dsRNA used to concomitantly target VirF, VirB and IcsA genes from *Shigella flexneri* |
| 34 | Sequence of the second arm of the VirF/VirB/IcsA dsRNA used to concomitantly target VirF, VirB and IcsA genes from *Shigella flexneri* |
| 35 | Sequence of the first arm of the fnbA/clfA/clfB/spa dsRNA used to concomitantly target fnbA, clfA, clfB and spa genes from *S. aureus* |
| 36 | Sequence of the second arm of the fnbA/clfA/clfB/spa dsRNA used to concomitantly target fnbA, clfA, clfB and spa genes from *S. aureus* |
| 37 | Sequence of the first arm of the lukF-PV/lukS-PV/lukE/lukD dsRNA used to concomitantly target lukF-PV, lukS-PV, lukE and lukD genes from *S. aureus* |
| 38 | Sequence of the second arm of the lukF-PV/lukS-PV/lukE/lukD dsRNA used to concomitantly target lukF-PV, lukS-PV, lukE and lukD genes from *S. aureus* |
| 39 | Sequence of the first arm of the HlgB/hla/tsst-1/atl dsRNA used to concomitantly target HlgB, hla, tsst-1 and atl genes from *S. aureus* |
| 40 | Sequence of the second arm of the HlgB/hla/tsst-1/atl dsRNA used to concomitantly target HlgB, hla, tsst-1 and atl genes from *S. aureus* |
| 41 | Sequence of the first arm of the PLP dsRNA used to target a PLP RNA region from SARS-CoV-2 |
| 42 | Sequence of the second arm of the PLP dsRNA used to target a PLP RNA region from SARS-CoV-2 |
| 43 | Sequence of the first arm of the 3CL dsRNA used to target a 3CL RNA region from SARS-CoV-2 |
| 44 | Sequence of the second arm of the 3CL dsRNA used to target a 3CL RNA region from SARS-CoV-2 |
| 45 | Sequence of the first arm of the Nsp10 dsRNA used to target a Nsp10 RNA region from SARS-CoV-2 |
| 46 | Sequence of the second arm of the Nsp10 dsRNA used to target a Nsp10 RNA region from SARS-CoV-2 |
| 47 | Sequence of the first arm of the RDRP-1 dsRNA used to target a RDRP RNA region from SARS-CoV-2 |
| 48 | Sequence of the second arm of the RDRP-1 dsRNA used to target a RDRP RNA region from SARS-CoV-2 |
| 49 | Sequence of the first arm of the RDRP-2 dsRNA used to target a RDRP RNA region from SARS-CoV-2 |
| 50 | Sequence of the second arm of the RDRP-2 dsRNA used to target a RDRP RNA region from SARS-CoV-2 |
| 51 | Sequence of the first arm of the RDRP-3 dsRNA used to target a RDRP RNA region from SARS-CoV-2 |
| 52 | Sequence of the second arm of the RDRP-3 dsRNA used to target a RDRP RNA region from SARS-CoV-2 |
| 53 | Sequence of the first arm of the EndoN dsRNA used to target an EndoN (Nsp15) RNA region from SARS-CoV-2 |

TABLE 1-continued

| SEQ ID NO: | Name/details |
|---|---|
| | Sequence details on the tools used in the examples |
| 54 | Sequence of the second arm of the EndoN dsRNA used to target an EndoN (Nsp15) RNA region from SARS-CoV-2 |
| 55 | Sequence of the first arm of the N dsRNA used to target a N RNA region from SARS-CoV-2 |
| 56 | Sequence of the second arm of the N dsRNA used to target a N RNA region from SARS-CoV-2 |
| 57 | Sequence of the first arm of the E dsRNA used to target an E RNA region from SARS-CoV-2 |
| 58 | Sequence of the second arm of the E dsRNA used to target an E RNA region from SARS-CoV-2 |
| 59 | Sequence of the first arm of the M dsRNA used to target a M RNA region from SARS-CoV-2 |
| 60 | Sequence of the second arm of the M dsRNA used to target a M RNA region from SARS-CoV-2 |
| 61 | Sequence of the first arm of the S dsRNA used to target a S RNA region from SARS-CoV-2 |
| 62 | Sequence of the second arm of the S dsRNA used to target a S RNA region from SARS-CoV-2 |
| 63 | Sequence of the first arm of the 3'UTR dsRNA used to target a 3'UTR RNA region from SARS-CoV-2 |
| 64 | Sequence of the second arm of the 3'UTR dsRNA used to target a 3'UTR RNA region from SARS-CoV-2 |
| 65 | Sequence of the first arm of the Helicase dsRNA used to target a Helicase RNA region from SARS-CoV-2 |
| 66 | Sequence of the second arm of the Helicase dsRNA used to target a Helicase RNA region from SARS-CoV-2 |
| 67 | Sequence of the first arm of the dnaA/dnaB/gyrB dsRNA used to concomitantly target the dnaA, dnaB and gyrB genes from *P. aeruginosa* |
| 68 | Sequence of the second arm of the dnaA/dnaN/gyrB dsRNA used to concomitantly target the dnaA, dnaB and gyrB genes from *P. aeruginosa* |
| 69 | Sequence of the first arm of the rpoC/secE/SodB dsRNA used to concomitantly target the rpoC, secE and SodB genes from *P. aeruginosa* |
| 70 | Sequence of the second arm of the rpoC/secE/SodB dsRNA used to concomitantly target the rpoC, secE and SodB genes from *P. aeruginosa* |
| 71 | Sequence of the first arm of the FtsA/Can/Tsf dsRNA used to concomitantly target the FtsA, Can and Tsf genes from *Shigella flexneri* |
| 72 | Sequence of the second arm of the FtsA/Can/Tsf dsRNA used to concomitantly target the FtsA, Can and Tsf genes from *Shigella flexneri* |
| 73 | Sequence of the first arm of the AccD/Der/Psd dsRNA used to concomitantly target the AccD, Der and Psd genes from *Shigella flexneri* |
| 74 | Sequence of the second arm of the AccD/Der/Psd dsRNA used to concomitantly target the AccD, Der and Psd genes from *Shigella flexneri* |
| 75 | Sequence of the first arm of the cpsA dsRNA used to target the cpsA (Rv3484) gene from *Mycobacterium tuberculosis* |
| 76 | Sequence of the second arm of the cpsA dsRNA used to target the cpsA (Rv3484) gene from *Mycobacterium tuberculosis* |
| 77 | Sequence of the first arm of the pcaA dsRNA used to target the pcaA (Rv0470c) gene from *Mycobacterium tuberculosis* |
| 78 | Sequence of the second arm of the pcaA dsRNA used to target the pcaA (Rv0470c) gene from *Mycobacterium tuberculosis* |
| 79 | Sequence of the first arm of the icl1 dsRNA used to target the icl1 (Rv0467) gene from *Mycobacterium tuberculosis* |
| 80 | Sequence of the second arm of the icl1 dsRNA used to target the icl1 (Rv0467) gene from *Mycobacterium tuberculosis* |
| 81 | Sequence of the first arm of the rip dsRNA used to target the rip (Rv2869) gene from *Mycobacterium tuberculosis* |
| 82 | Sequence of the second arm of the rip dsRNA used to target the rip (Rv2869) gene from *Mycobacterium tuberculosis* |
| 83 | Sequence of the first arm of the fad26 dsRNA used to target the fad26 (Rv2930) gene from *Mycobacterium tuberculosis* |
| 84 | Sequence of the second arm of the fad26 dsRNA used to target the fad26 (Rv2930) gene from *Mycobacterium tuberculosis* |
| 85 | Sequence of the first arm of the hbhA dsRNA used to target the hbhA (Rv0475) gene from *Mycobacterium tuberculosis* |
| 86 | Sequence of the second arm of the hbhA dsRNA used to target the hbhA (Rv0475) gene from *Mycobacterium tuberculosis* |
| 87 | Sequence of the first arm of the cpsA/pcaA dsRNA used to concomitantly target the cpsA (Rv3484) and pcaA (Rv0470c) genes from *Mycobacterium tuberculosis* |
| 88 | Sequence of the second arm of the cpsA/pcaA dsRNA used to concomitantly target the cpsA (Rv3484) and pcaA (Rv0470c) genes from *Mycobacterium tuberculosis* |
| 89 | Sequence of the first arm of the dotA dsRNA used to target the dotA (lpg2686) gene from *Legionella pneumophila* |
| 90 | Sequence of the second arm of the dotA dsRNA used to target the dotA (lpg2686) gene from *Legionella pneumophila* |
| 91 | Sequence of the first arm of the dotD dsRNA used to target the dotD (lpg2674) gene from *Legionella pneumophila* |

TABLE 1-continued

| Sequence details on the tools used in the examples | |
|---|---|
| SEQ ID NO: | Name/details |
| 92 | Sequence of the second arm of the dotD dsRNA used to target the dotD (lpg2674) gene from *Legionella pneumophila* |
| 93 | Sequence of the first arm of the dotC dsRNA used to target the dotC (lpg2675) gene from *Legionella pneumophila* |
| 94 | Sequence of the second arm of the dotC dsRNA used to target the dotC (lpg2675) gene from *Legionella pneumophila* |
| 95 | Sequence of the first arm of the dotB dsRNA used to target the dotB (lpg2676) gene from *Legionella pneumophila* |
| 96 | Sequence of the second arm of the dotB dsRNA used to target the dotB (lpg2676) gene from *Legionella pneumophila* |
| 97 | Sequence of the first arm of the icmT dsRNA used to target the icmT (lpg0441) gene from *Legionella pneumophila* |
| 98 | Sequence of the second arm of the icmT dsRNA used to target the icmT (lpg0441) gene from *Legionella pneumophila* |
| 99 | Sequence of the first arm of the icmJ dsRNA used to target the icmJ (lpg0455) gene from *Legionella pneumophila* |
| 100 | Sequence of the second arm of the icmJ dsRNA used to target the icmJ (lpg0455) gene from *Legionella pneumophila* |
| 101 | Sequence of the first arm of the pilD dsRNA used to target the pilD (lpg1524) gene from *Legionella pneumophila* |
| 102 | Sequence of the second arm of the pilD dsRNA used to target the pilD (lpg1524) gene from *Legionella pneumophila* |
| 103 | Sequence of the first arm of the ispF dsRNA used to target the ispF (lpg1363) gene from *Legionella pneumophila* |
| 104 | Sequence of the second arm of the ispF dsRNA used to target the ispF (lpg1363) gene from *Legionella pneumophila* |
| 105 | Sequence of the first arm of the dotD/pilD dsRNA used to concomitantly target the dotD (lpg2674) and pilD (lpg1524) genes from *Legionella pneumophila* |
| 106 | Sequence of the second arm of the dotD/pilD dsRNA used to concomitantly target the dotD (lpg2674) and pilD (lpg1524) genes from *Legionella pneumophila* |
| 107 | Sequence of a specific intron sequence from the *Petunia Chalcone* synthase gene CHSA |

FIGURE LEGENDS

FIG. 1. Scattering and fluorescence NTA analyses of *Chlorella* EVs

- A) Size distribution of overall *Chlorella* particles from P40 fractions, determined through scattering analysis (using the Particle Metrix ZetaView system).
- B) Size distribution of overall *Chlorella* particles from P100 fractions, determined through scattering analysis (using the Particle Metrix ZetaView system).
- C) Transmission electron microscopy (TEM) images of P100 *Chlorella* EVs.
- D) Size distribution of P100 *Chlorella* EVs (n=609) measured from TEM images.
- E) Size distribution of PKH26-labeled *Chlorella* particles from P40 fractions (using the Particle Metrix ZetaView system). The measurements were performed using the 488 nm laser.

FIG. 2. Phylogenetic analysis of *Chlorella variabilis* AGO and DCL proteins and RNA-sequencing analysis of small RNAs from a *Chlorella vulgaris* reference transgenic line

- A) NJ trees (1000 bootstraps) including 111 AGO and 77 DCL sequences, respectively, from plants, animals, fungi and algae. The position of the *C. variabilis* AGO and DCL proteins are shown. The trees are midpoint rooted.
- B) Comparative size distribution profile between the *Arabidopsis* IR-CFA6/HRPL #4 and the *Chlorella* reference transgenic line IT20-3 small RNAs. The most aboundant small RNA population from *Chlorella* is of 18 nt long, whilst in *Arabidopsis* they are of 21 and 24 nt long. It is also noteworthy that *Chlorella* and *Arabidopsis* exhibit minor peaks of small RNA species at 15 and 16 nt, respectively. Two biological replicates are shown separately in this analysis.

FIG. 3. *Chlorella vulgaris* can be engineered to produce active small RNAs targeting the Pto DC3000 virulence factors cfa6 and hrpL

- A) Schematic representation of the IT20 construct designed to express small RNAs targeting the Pto DC3000 cfa6 and hrpL mRNAs under the control of the constitutive Cauliflower Mosaic Virus (CaMV) 35S promoter. The chimeric 504 bp region targeting the two virulence genes has been cloned in sense (B module) and antisense (D module) orientations using the Green Gate assembly strategy.
- B) Stomatal reopening assay at 3 hours post-infection (hpi) on *Arabidopsis* (Col-0 accession) leaf sections incubated with water (Mock) or total RNAs (20 μg) from *Arabidopsis thaliana* (At), wild type *Chlorella* or transgenic *Chlorella* lines expressing the IR-CFA6/HRPL transgene. Leaves were incubated with wild type (Pto/Pto Wt) or mutant Pto DC3000 strains (of note, Pto ΔCor, is deleted of the cfa6 gene and is thus altered in the reopening of stomata). N, total number of analyzed stomata. Statistical analyses were performed using 2way ANOVA and compared with the mock condition (p-value: ns>0.05; *<0.001; **<0.0001).
- C) Coverage of small RNAs reads showing the total count of mapped reads across the IR-CFA6/HRPL inverted repeat (on both the minus and plus strands). The reads in black map to the cfa6 sequence region, while the reads in dark grey map to the hrpL sequence region.

FIG. 4. *Chlorella* artificial small RNAs directed against Pto DC3000 hrpL transcripts are causal for the suppression of hrpL-mediated stomatal reopening function.

A) Schematic representation of the Pto DC3000 ΔhrpL strain along with the complementation strains generated upon transformation with the plasmids encoding WT hrpL or mut hrpL respectively, under the control of the constitutive promoter NPTII.

B) Stomatal reopening assay at 3 hpi on *Arabidopsis* (Col-0) leaf sections incubated with total RNAs (20 μg) from *Arabidopsis thaliana* (At) or *Chlorella* transgenic lines expressing the IR-HRPL construct (*Arabidopsis*, clone IT29 #4; *Chlorella*, clones IT29 #12 an IT29 #15) or the control IR-CYP51 construct (*Chlorella*, IT19 #7). Stomatal reopening response was assessed as described in FIG. 3B.

FIG. 5. Stomatal reopening assays using concentrated media (CM) and P40 fractions from transgenic *Chlorella vulgaris* lines A) Stomatal reopening assay at 3 hpi on *Arabidopsis* (Col-0) leaf sections incubated with water (Mock), total RNA (20 μg) or concentrated media (CM) from *Chlorella* transgenic lines (IT20 #3 and IT20 #5) and wild type (Wt) lines. Total RNA (20 μg) from the *Arabidopsis* IR-CFA6/HRPL #4 reference line was also used as a control. Leaf sections were inoculated with Pto DC3000 Wt or mutant strains. N, total number of analyzed stomata. Statistical analyses were performed using 2way ANOVA and compared with the mock condition (p-value: ns>0.05; *<0.001; **<0.0001).

B) as in A) except that the P40 fraction from the IT20 #3 line was used for this assay. RNA extracts from the same *Chlorella* transgenic line were also used as a positive control. N, total number of analyzed stomata. Statistical analyses were performed using 2way ANOVA and compared with the mock condition (p-value: ns>0.05; *<0.001; **<0.0001).

C) as in B) but the P40 fractions were subjected to a 30' incubation at 37° C. in the presence or absence of 300 U/ml of Mnase. The digestion reaction was blocked by adding EGTA, at a final concentration of 20 mM.

D) Coverage of small RNAs reads from the P100 fraction sample computed as the total count of mapped reads across the IR-CFA6/HRPL inverted repeat is depicted and includes both the plus and minus strands of the construct. The reads in black map to the cfa6 sequence region, while the reads in dark grey map to the hrpL sequence region.

E) Stomatal reopening assay performed using the Pto DC3000 ΔhrpL bacteria complemented either with the Wt or the Mut hrpL versions. Both P40 and P100 EVs fractions from the *Chlorella* IR-HRPL (IT29 #12) and IR-CYP51 (IT19 #7) lines were treated with the Mnase as described, before performing the assay. Stomatal reopening response was assessed as described in A).

FIG. 6. Internalization of PKH26-labeled *Chlorella* EVs in A549 and A549-ACE2 cells analyzed by confocal fluorescence microscopy, flow cytometry and microplate reader A) Confocal fluorescence microscopy pictures of A549 cells incubated or not with PKH26-labeled *Chlorella* EVs from the P40 fraction. In blue, the DAPI staining of the nuclear genomic DNA; in red, the PKH26 staining of the lipidic membrane of *Chlorella* EVs. Similar results were obtained in A549-ACE2 cells (not shown).

B) Flow cytometry quantification of PKH26-labeled *Chlorella* EVs internalization in A549-ACE2 cells. Cells were incubated with 0.06 pM or 0.5 pM of PKH26-labeled EVs and fluorescence internalization measured on 5,000 cells. Data analysis was performed with the FlowJo 10.7 software. Similar results were obtained when 50,000 human cells were analyzed (not shown).

C) Raw fluorescence data showing the kinetics of DiR-labeled EVs internalization in A549-ACE2 cells over a 48 hours timecourse experiment. Pixels represent discrete section of the well showing the spatial distribution of the NIR intensity in each well.

D) Kinetics of DiR-labeled EVs internalization in A549-ACE2 cells over a 48 hours timecourse experiment. Bars represent the net intensity of NIR fluorescence signal at the different time points.

Figure 7:
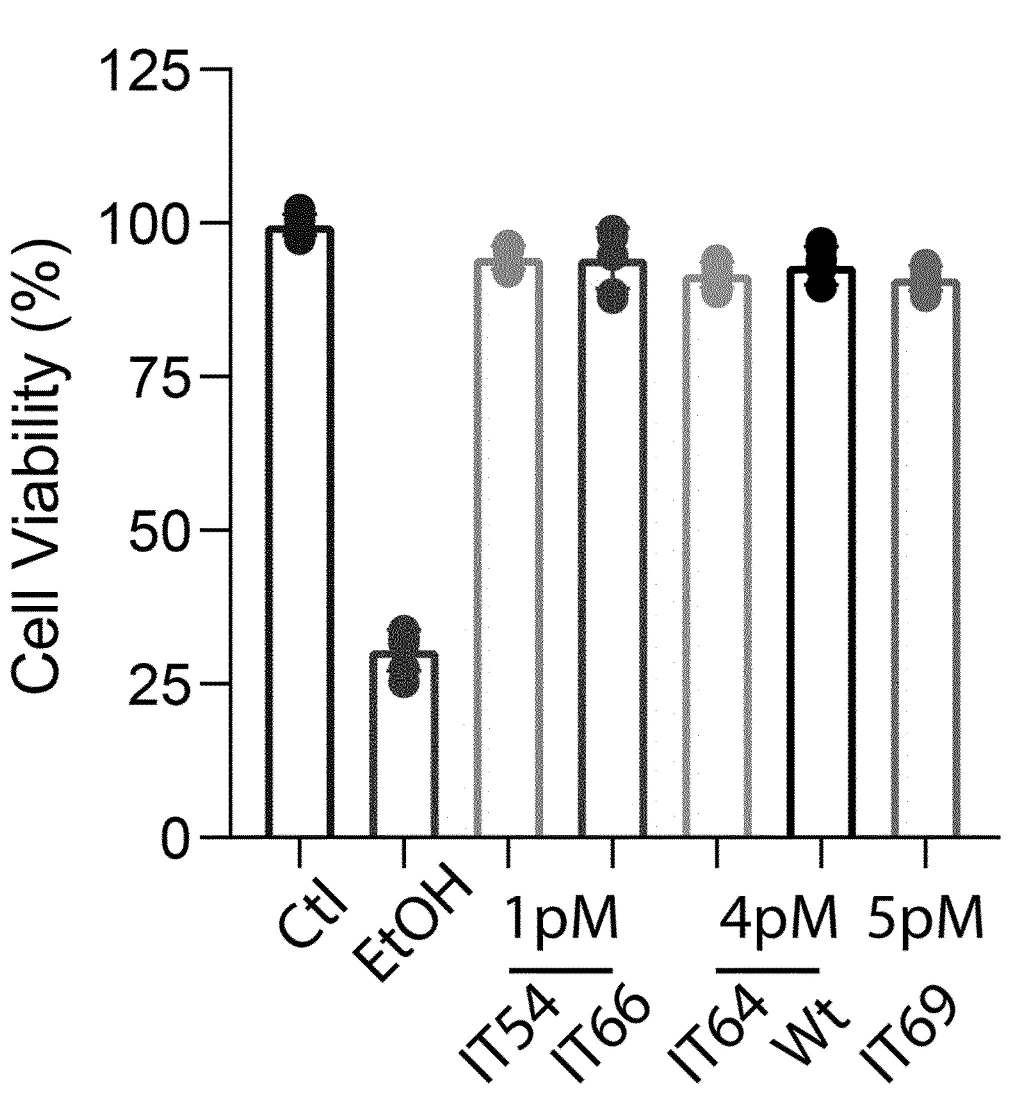

FIG. 7. Cell viability after treatment with different amounts of *Chlorella* EVs from different transgenic lines The cell viability was determined through a bioluminescent assay that quantifies the amount of ATP released by the viable cells in the medium. Untreated (Ctl) and 20% EtOH treated cells (EtOH) were used as controls. Wt correspond to strain, IT54 expresses an IR construct targeting the SARS-CoV-2 (SC2) RdRp transcript; IT64 targets simultaneously the following SC2 transcripts: Nsp14, Nsp13, Nsp12, Nsp5, Nsp4, Nsp3, Nsp1; IT66 targets 4 human transcripts: Rp113, eIF3e, eIF3i, eIF3f; IT69 targets the transcripts of the LUC transgene.

FIG. 8. Schematic representation of the Nsp12, Nsp13 and Spike IR sequence conservation among SARS-CoV-2, SARS-CoV-1 and MERS viruses The IR regions used to generate the constructions targeting the SARS-CoV-2 (SC2) genes Nsp12, Nsp13 and Spike were aligned with the corresponding sequences from the SARS-CoV-(SC1) and MERS viruses. Overall, the similarity between SC1 and SC2 ranges around 75-92%, whilst MERS-SC2 is around 67-71% over the considered regions. n.a.: the selected IR region from the SC2 virus yielded no significant similarity with the MERS Spike DNA sequence.

FIG. 9. Schematic representation of the reporter systems that will be used to monitor EV-embedded siRNA activity in bacterial cells A) Schematic representation of the bipartite cassette designed to detect a specific gain of GFP expression upon treatment with a given EV-embedded siRNA population. The system is composed of a first construct that includes a short-lived variant of a transcriptional repressor, such as the depicted lacI-lite, which contains a siRNA target region of interest in its downstream region (or potentially in its upstream region), driven by a constitutive promoter (e.g., the nptII promoter sequence depicted here as an example) and a downstream terminator sequence (e.g., the SoxR terminator sequence); and a second construct that includes a destabilized GFP reporter sequence (e.g., the intermediate stability GFP variant gpf-aav sequence (Campbell-Valois et al., 2014; Elowitz & Leibler, 2000)), whose transcriptional activity is controlled by the lacO operator in a pLac promoter, and is composed of a downstream terminator sequence (e.g., the SoxR terminator sequence). In normal conditions, the GFP expression is repressed by the presence of the LacI-lite repressor (1). Silencing of such a repressor, triggered by EV-contained small RNAs targeting the regulatory region "X", releases the inhibition allowing GFP expression (2).

B) Kinetics of the fluorescence induction mediated by different concentrations of IPTG on *E. coli* TOP10 cells containing the R37 construct. This construct has a small RNAs targeted region corresponding to the Pto DC3000 genefusA cloned at the 3' end of the lacI gene. The GFP fluorescence obtained by subtracting the fluorescence values of the −IPTG and the +Chloramphenicol conditions was used as control. The fluorescence and $OD_{600}$ (not shown) were monitored in a Tecan Infinite 200 plate reader system, by means of specific filters performing data acquisition every 5' for 15 hours at 37° C.

C) Kinetics of the fluorescence induction mediated by the IPTG on Pto DC3000 Wt cells containing the R37 construct. The GFP fluorescence obtained by subtracting the fluorescence values of the−IPTG and the +Chloramphenicol conditions was used as control. The fluorescence and $OD_{600}$ (not shown) were monitored in a Tecan Infinite plate reader system, by means of specific filters performing data acquisition every 5' for 15 hours at 28° C.

D) Schematic representation of the reporter system designed to detect a specific loss of GFP expression upon treatment with a given EV-embedded siRNA population. The system is composed of a cassette expressing the GFP under the control of the constitutive promoter pCMV. The GFP is fused at its 3' end with a small RNAs target sequence (X). In normal conditions, the GFP is continuously expressed (1). Treatment with EV-contained small RNAs targeting the regulatory region "X" triggers GFP mRNA degradation and reduction of the protein levels that can notably be monitored by Western blot analysis (2).

E) Schematic representation of the first dual reporter family cassette designed to detect a specific decrease in GFP expression upon treatment with a given EV-embedded siRNA population. The dual reporter cassette is composed of a first DsRed reporter construct driven by a constitutive promoter (e.g., the Rpsm promoter sequence depicted here as an example) and a downstream terminator sequence (e.g. the TonB terminator sequence depicted here as an example); a second construct composed of a destabilized GFP reporter version (e.g., the GFPsmf2 sequence carrying a degradation tag in its downstream region or the intermediate stability GFP variant gpf-aav sequence (Campbell-Valois et al., 2014; Elowitz & Leibler, 2000) that contains the siRNA target sequence region of interest cloned in its downstream region (or upstream, not shown), driven by a constitutive promoter (e.g., the NPTII promoter sequence depicted here as an example), with a downstream terminator sequence (e.g., the SoxR terminator sequence depicted here as an example).

F) Schematic representation of the second tripartite cassette designed to detect a specific gain of GFP expression upon treatment with a given EV-embedded siRNA population. The tripartite cassette is composed of a first construct that includes a short-lived variant of a transcriptional repressor, such as the depicted TetR-lite, which contains a siRNA target region of interest in its downstream region (or eventually in its upstream region, not shown), driven by a constitutive promoter (e.g., the NPTII promoter sequence depicted here as an example) and a downstream terminator sequence (e.g. the SoxR terminator sequence depicted here as an example); a second construct that includes a destabilized GFP reporter sequence (e.g., the GFPsmf2 sequence carrying a degradation tag in its downstream region or the intermediate stability GFP variant gpf-aav sequence (Campbell-Valois et al., 2014; Elowitz & Leibler, 2000)), whose transcriptional activity is controlled by the tetO2 operator, and composed of a downstream terminator sequence (e.g., the soxR or tonB terminator sequences depicted here as an example); a third construct that includes a DsRed reporter sequence driven by a constitutive promoter (e.g., the Rpsm promoter sequence depicted here as an example) and a downstream terminator sequence (e.g., the TonB terminator sequence depicted here as an example).

G) Schematic representation of the third bipartite cassette designed to detect a specific gain of a reporter gene expression upon treatment with a given EV-embedded siRNA population. The bipartite cassette is composed of a first construct that includes a short-lived variant of a transcriptional repressor, such as the depicted TetR-lite, which contains a siRNA target region of interest in its downstream region (or eventually in its upstream region, not shown), driven by a constitutive promoter (e.g., the NPTII promoter sequence depicted here as an example), and a downstream terminator sequence (e.g., the SoxR terminator sequence depicted here as an example); a second construct that includes a destabilized GFP reporter sequence (e.g., the GFPsmf2 sequence carrying a degradation tag in its downstream region or the intermediate stability GFP variant gpf-aav sequence (Campbell-Valois et al., 2014; Elowitz & Leibler, 2000)) or a bioluminescence reporter (e.g., the the *Photorhabdus luminescens* operon luxCDABE (Meighen, 1991)), whose transcriptional activity is controlled by the tetO2 operator, and composed of a downstream terminator sequence (e.g., the soxR or tonB terminator sequence depicted here as an example).

FIG. 10. The cultivation of a reference *Chlorella* line in photobioreactors does not affect the quality and functionality of the corresponding EVs fractions A) Transgenic *Chlorella*, such as the IT20 #3 reference line, can be easily cultivated in photobioreactors (PBRs) of different sizes, from 1 to 150 L PBRs (AlgoSolis, Saint Nazaire, France).

B) Confocal fluorescence microscopy pictures of A549 cells treated or not with PKH26-labeled *Chlorella* EVs from the P40 fraction of 1 L cultures. In blue, the DAPI staining of the nuclear genomic DNA; in red, the PKH26 staining of the EVs lipidic membrane.

C) Size distribution, in the range 0-500 nm, of *Chlorella* particles from P40 factions obtained from a 150 L PBR cultures determined through scattering analysis (using the Particle Metrix ZetaView system).

D) Size distribution, in the range 0-500 nm, of PKH26-labeled *Chlorella* particles from P40 fractions obtained from a 150 L PBR culture using the Particle Metrix ZetaView system. The measurements were performed using the 488 nm laser.

E) Stomatal reopening assay performed using total RNAs and P40 fractions from the reference IT20 #3 and the control IT19 #7 lines. Samples were prepared using cell biomass and medium from different production systems as depicted. Stomatal reopening response was assessed as previously described.

FIG. 11. Treatment with supernatants of heat-killed bacteria improves *Chlorella* EVs production and/or secretion A) Scheme of the treatment to increment EVs production. A freshly diluted *Chlorella* culture is left to grow to early stationary phase (2 to $4\times10^6$ cells/ml). The culture is then treated with the equivalent of 25 mg/ml of supernatants from heat-killed *E. coli* and Pto DC3000 cells resuspended in water. After two days, the P100 fractions from the different treatments (untreated, +*E. coli* and +Pto DC3000) are collected and quantified. The total number of *Chlorella* cells is also determined to check possible effects on the microalgae growth.

(B) Particle concentration in the P100 fractions of the untreated (Ctl), +*E. coli* and +Pto DC3000 (DC3000) cultures. N=4 independent biological replicates.

EXAMPLES

Example 1: Materials and Methods

*Chlorella vulgaris* Material and Growth Conditions

The wild type *C. vulgaris* strain UTEX265 was kept in BG11, 1% agar plates and grown in autotrophic conditions in a Sanyo MLR-351 growth chamber. Environmental conditions were set at 25° C., 14 h/10 h photoperiod and about 100 $\mu mol/m^2/s$ of light intensity. Transgenic *Chlorella* lines were kept in the same condition using plates containing 20 μg/ml of Hygromycin. Liquid culture was started by inoculating a single colony in BG11 (pH 7) in aerated 25 $cm^2$ plastic flasks with no agitation and then regularly diluted once or twice per week (dilution ratio 1:10) in order to reach the final volume (200-800 ml split in several aerated 75 $cm^2$ flasks). Culture density was assessed by using a Malassez chamber. To assess culture axenicity, routine contamination tests were perfomed by adding 1 ml of culture to BG11 supplemented with peptone. The mixture was kept in the dark for 3 weeks and bacterial growth followed by microscopic observation. *Chlorella* production in the 150 L PBR was carried out under continuous light cycle regime, with a light intensity increasing from 150 to 400 $\mu mol/m^2/s$ of white light to cope with the growing cell density in the PBR, a mean temperature of 22.9±6° C. and a fixed pH at 8. In those standard growth conditions, the transgenic *Chlorella* cells reached a maximum culture density of about 1.1 g/L after 8 days. Cell-free medium collection was performed by two successive rounds of centrifugation at 3600 g, for a gross cell precipitation, and 4000 g to remove all the remaining cells.

Bioinformatics, Sequence Conservation and Phylogenetic Analyses

To identify sequences belonging to the vesicle and extracellular vesicle biogenesis or functions, candidate human and plant sequences were used as query for BLASTP analyses on the NCBI and JGI (*Chlorella variabilis*) databases. The first 10 hits were retained and used for local alignments with the query sequence. The best candidates (i.e., the ones with the highest sequence similarity) were also analyzed on the Pfam (http://pfam.xfam.org/) and SMART (http://smart.embl-heidelberg.de/) databases and using the PHMMEVIER search (https://www.ebi.ac.uk/Tools/hmmer/search/phmmer) in order to compare the protein domain composition with the query. The *Chlorella* proteins showing high sequence similarity and a conserved domain composition were considered as "putative orthologs".

For *C. vulgaris* analyses, the transcriptome of the UTEX 395 strain was used (Guarnieri et al., 2018) to perform local blastp and blastn searches. The retrieved sequences were analyzed for similarity and domain architecture as described.

For *Chlorella* AGO and DCL phylogenetic analysis, the protein sequences of AGO and DCL of *Homo sapiens* and *Arabidopsis thaliana* were used as queries for BLASTP analyses against the *Chlorella variabilis* genome (JGI). The protein sequences for plant, animal and fungal AGOs (Murphy et al., 2008) and DCL (Mukherjee et al., 2013; Gao et al., 2014) were obtained from the literature. A total of 111 AGO and 77 DCL proteins were retained after preliminary alignments to eliminate the divergent sequences. Protein domain architecture was analyzed to unambiguously identify AGO and DCL proteins similar to the canonical ones. The sequence alignments were manually trimmed to keep only the most conserved regions for the analysis corresponding to 288 aa for AGO and 436 aa for DCL. MEGA X software was used to perform the NJ phylogenies and the trees edited using FigTree 1.4.

Generation of Constructs for Small RNAs Production in *Chlorella*

Inverted repeat constructs designed to produce artificial small RNAs targeting specific regions (140-400 bp) of virulence and essential genes from various bacterial plant pathogens were generated using the Green Gate assembly strategy. The gene specific or chimeric targeted regions were cloned as "B" (sense) and "D" (antisense) modules and assembled in expression constructs. All the generated hairpins contained a specific intron sequence from the *Petunia* Chalcone synthase gene CHSA (SEQ ID NO: 107) and were under the control of Cauliflower Mosaic Virus (CaMV) 35S promoter, including a Hygromycin resistance cassette. The chimeric cfa6-hrpL construct (IT20) has been previously described (PCT/EP2019/072169, PCT/EP2019/072170). The precise target regions of the expression constructs assembled to target genes from the human pathogenic bacteria *P. aeruginosa, S. flexneri, S. aureus, L. pneumophila* and *M. tuberculosis* are shown in the following table:

| Construct | Target Genes | Species | Targeted region | | |
|---|---|---|---|---|---|
| IT13 | dnaA-dnaN-gyrB | *P. aeruginosa* | 1-210 - dnaA | 1-207 - dnaN | 1-202 - gyrB |
| IT14 | rpoC-secE-sodB | | 2-261 - rpoC | 1-283 - secE | 1-247 - sodB |
| IT16 | xcpQ-pscF-pscC | | 1-230 - xcpQ | 1-219 - pscF | 1-222 - pscC |
| IT18 | xcpQ-exsA-hphA | | 1-230 - xcpQ | 1-226 - exsA | 1-198 - hphA |
| IT32 | dnaN | | 1-207 - dnaN | — | — |
| IT37 | secE | | 1-283 - secE | — | — |
| IT38 | secE-dnaN-gyrB | | 1-283 - secE | 1-207 - dnaN | 1-202 - gyrB |
| IT21 | ftsA-can-tsf | *S. flexneri* | 1-217 - ftsA | 4-200 - can | 2-207 - tsf |
| IT26 | accD-der-psd IR | | 25-251 - accD | 10-226 - der | 14-243 - psd |
| IT27 | virF-virB-icsA IR | | 105-324 - virF | 1-229 - virB | 469-694 - icsA |
| IT76 | cpsA | *M. tuberculosis* | 1-365 | — | — |

-continued

| Construct | Target Genes | Species | Targeted region | | |
|---|---|---|---|---|---|
| IT77 | pcaA | | 1-446 | — | — |
| IT78 | icl1 | | 1-407 | — | — |
| IT79 | rip | | 1-392 | — | — |
| IT80 | fad26 | | 1-378 | — | — |
| IT81 | hphA | | 1-379 | — | — |
| IT82 | cpsA-pcaA | | 1-365 - cpsA | 1-446 - pcaA | — |
| IT83 | dotA | *L. pneumophila* | 1-364 | — | — |
| IT85 | dotD | | 1-369 | — | — |
| IT86 | dotC | | 1-369 | — | — |
| IT88 | dotB | | 1-357 | — | — |
| IT89 | icmT | | 1-261 | — | — |
| IT90 | icmJ | | 1-301 | — | — |
| IT91 | pilD | | 1-350 | — | — |
| IT92 | ispF | | 1-324 | — | — |
| IT93 | dotD-pilD | | 1-369 - dotD | 1-350 - pilD | — |

The SARS-CoV-2 specific expression constructs target the following regions of the viral genome:

| Construct | Gene/Region | Species | Target region |
|---|---|---|---|
| IT50 | PLP (Nsp3) IR | SARS-CoV-2 | 2715-2973 |
| IT51 | 3CL (Nsp5) IR | | 10034-10342 |
| IT52 | Nsp10 IR | | 12997-13304 |
| IT53 | RdRp IR1 | | 13436-13729 |
| IT54 | RdRp IR2 | | 14426-14677 |
| IT55 | RdRp IR3 | | 15790-16040 |
| IT56 | EndoN IR | | 19919-20202 |
| IT57 | N IR | | 28386-28674 |
| IT58 | E IR | | 26216-26365 |
| IT59 | M IR | | 26480-26794 |
| IT60 | S IR | | 23146-23472 |
| IT61 | 3'UTR IR | | 29528-29831 |
| IT62 | Hel (Nsp13) IR | | 16192-16544 |

The chimeric anti-viral (SARS-CoV-2) and anti-HSF (*H sapiens*) constructs simultaneously target the following regions of the viral RNA or human transcripts:

| | Construct | | | | |
|---|---|---|---|---|---|
| | IT64 Chimera1 | IT65 Chimera2 | IT66 Chimera3 | IT67 Chimera4 | IT68 Chimera5 |
| | Species | | | | |
| | SARS-CoV-2 | | *H. sapiens* | | |
| Target region | 18036-18180 - Nsp14 | 26241-26380 - E | 411-670 - Rpl13 | 79-298 - Snrpe | 95-295 - Ace2 |
| | 16233-16390 - Nsp13 | 26521-26687 - M | 335-579 - eIF3e | 2024-2228 - Naca | 1138-1349 - Tmprss2 |
| | 15831-15973 - Nsp12 | 28270-28438 - N | 722-960 - eIF3i | 305-510 - Kif11 | 413-630 - Psmd1 |
| | 10051-10198 - Nsp5 | 21559-21679 - S | 322-591 - eIF3f | 367-564 - Gbf1 | 376-572 - KpnA1 |
| | 8590-8730 - Nsp4 | 3-70 - Leader 5' | — | 117-323 - Srp54 | 472-679 - KpnB1 |
| | 2716-2863 - Nsp3 | 29527-29693 - 3'UTR | — | — | — |
| | 262-419 - Nsp1 | — | — | — | — |

All the chimeric constructs were obtained through simultaneous ligation of the different DNA fragments into a "B" Green Gate module and specific oligonucleotides were used to generate and clone the antiparallel strand as a "D" module. All the plasmids were verified by restriction analysis, Sanger sequencing and then introduced into the *Agrobacterium tumefaciens* C58C1 strain by electroporation.

Generation of *C. vulgaris* Transgenic Lines

*C. vulgaris* genetic transformation was performed using a disarmed *A. tumefaciens* strain. In more details, $5\times10^6$ total cells from an exponentially growing culture were plated on BG11 agar plates and grown under normal light irradiance for 5 days. *A. tumefaciens* carrying the appropriate inverted repeat construct was pre-inoculated the day before the transformation either from glycerol stock or from a LB plate at 28° C., 180 rpm shaking. The day of the transformation, 5 mL of the *A. tumefaciens* pre-inoculum was used to seed 50 ml of LB and grown up to $OD_{600}$=0.8-1.2. At the right optical density, the bacteria were collected, washed and resuspended in induction medium (BG11, pH 5.6, acetosyringone 100 μM) at $OD_{600}$=0.5. *Chlorella* cells were gently scraped form the plates, resuspended in 200 μl of bacteria and co-cultivated for 2 days on induction medium agar plates in the dark at 25° C. After the co-cultivation, the cells were harvested, put in 7 ml of BG11 supplemented with 50 μg/mL of TIM or Cefotaxime and left in the dark for 2 days at 25° C. Finally, the cells were collected and plated onto BG11 agar plates supplemented with 20 μg/ml of Hygromycin and 50 μg/ml of Ticarcillin disodium/clavulanate potassium (TIM, T0190, Duchefa) or Cefotaxime (C7039, Merck). After 2 days in the dark, the plates were exposed to light. After 2-3 weeks, 20-30 colonies were plated on fresh BG11 agar plates with 20 μg/ml of Hygromycin.

Selection and Identification of *C. vulgaris* Transgenic Lines

To identify the clones carrying the expression construct, gDNA from the transformant colonies was collected as follows. A few *Chlorella* cells were scraped with a sterile plastic tip from the colonies growing on agar plates and put in 10 μl of HotShot5 lysis buffer (150 mM NaOH, 0.1 mM EDTA, 1% Triton X-100). The mix was incubated for 10' at RT and boiled for 15' at 95° C. The lysate was then diluted by adding 100 μl of $H_2O$ and 1-5 μl used as template for a PCR reaction using IT-specific oligonucleotides. The wild type strain was included as negative control and the corresponding IT plasmid (5 ng per reaction) as positive control.

Total RNA Extraction (*Chlorella*)

50-800 ml of liquid *Chlorella* culture ($5\times10^6$-$1\times10^7$ cells/ml) were harvested by centrifugation (Beckman rotor JS5.3, 5000 g, 15', 18° C.), the pellet washed in 1×PBS and flash frozen in liquid nitrogen. The frozen pellet was ground to a fine powder in liquid nitrogen, using a mortar and pestle. Total RNA extraction was performed using Tri-Reagent (Sigma, St. Louis, MO) according to manufacturer's instructions using about 100 mg of powder.

*Chlorella* EVs Fraction Purification

To isolate *Chlorella* EVs, two cell-free medium concentration/purification strategies were employed: by centrifugal concentration (Pall macrosep 100 kDa devices) or tangential flow filtration (Sartorius VivaFlow 50R 100 kDa device). For the first approach, the BG11 collected after cell separation was further centrifuged (Beckman rotor JS5.3, 5000 g, 10', 18° C.) to eliminate all residual cells. The supernatant was then filtered using Pall Macrosep 100 kDa devices (MAP100C37) according to manufacturer's instructions. The recovered concentrated medium (CM) was then passed through 0.45 μm filters and stored at 4° C. before performing further purification steps. For the second strategy, the BG11 collected after cell separation was further centrifuged (Beckman rotor JA18, 10000 g, 10', 4° C.) and vacuum-filtered onto 0.65 μm Whatman paper filters, to eliminate all residual cells. The supernatant was then filtered using the Sartorius VivaFlow 50R 100 kDa system (VF05H4) according to manufacturer's instructions. The recovered concentrated medium (CM) was then passed through 0.45 μm filters and used to purify *Chlorella* EVs. Starting from the CM, the P40 fraction was obtained by ultracentrifugation at 40000 g and the P100 fraction at 100000 g, for 1 hour at 4° C., in a Sorvall WX 80 Ultracentrifuge (ThermoFisher). After centrifugation, the supernatant was discarded and the purified EVs pellet, either from P40 or P100 purifications, resuspended in 1 ml of filtered 1×PBS and filtered using a 0.22 μm filter. For sample quality analysis, 1/200 of the EVs sample was processed using a Nanoparticle Tracking system (ParticleMetrix ZetaView). To estimate the amount of exosome-like EVs in the sample, the particles were labeled using the PKH26 dye.

To recover the P40 fraction from the cell-free extracellular medium of 150 L PBR a modified protocol of ultrafiltration and ultracentrifugation was employed. At first, two rounds of vacuum filtration on Millipore Glass Fiber Prefilters AP25 (2 μm) were performed. Then, the sample was centrifuged at 5000 g (10', 4° C.) followed by a second vacuum filtration on MF-Millipore 0.65 μm filters, required to eliminate the suspended organic matter still present in the cell-free medium. The clarified medium was then processed as described above to purify the P40 fraction by centrifugal filtration and ultracentrifugation.

*Chlorella* EVs Production Improvement Using Bacterial Supernatants

A fresh (4 days old max) Wt *Chlorella* culture was diluted and split in 3 different 75 $cm^2$ aerated flasks with 50 ml of culture at ≈$5\times10^5$ cells/ml. The flasks were left to reach the end of the exponential phase, ≈3/4 days in our conditions, at $2/4\times10^6$ cells/ml before starting the treatment with the bacterial supernanatant. The bacteria, both *E. coli* K12, TOP10 and Pto DC3000 Wt, were scraped from plates at confluent growth, the recovered pellet resuspended in 300 μl of $H_2O$ and weigthed before being heat inactivated for 15' at 95° C. The inactivated bacteria were spun down by centrifugation and the supernatant diluted to a concentration of 10 μg of pellet/100 μl. The *Chlorella* cultures were treated with the bacterial supernatant to a final concentration of pg/100 ml and then put back in the incubator, in standard conditions (25° C., 14/10 light/dark, no shaking), for 48 hours. At the end of the incubation, the *Chlorella* cells were counted using a Malassez chamber to verify that the treatment did not affect the cell growth. Then, the P100 fractions were prepared as described (Sartorius Vivaflow 50R 100 kDa) and analyzed by NTA profiling.

Labeling of EVs with PKH26 or DiR Dyes

For EV labeling with the PKH26 dye (Sigma), the P40 fraction and an ultracentrifuge tube containing the same volume of BG11 medium were brought up to 1 ml with diluent C. Then, 6 μl of PKH26 dye were added to both tubes according to the manufacturer's protocol. The samples were mixed continuously for 30" and incubated 5'. After the incubation at room temperature, 2 ml of 1% BSA in PBS were added and completed up to a volume of 8.5 ml with BG11. Before the precipitation, 1.5 ml of a 0.931M Glucose solution was carefully stratified at the bottom of the ultracentrifugation tube. The sample was ultracentrifuged at 190000 g for 2 hours, 4° C. and all the supernatant carefully discarded. The resulting pellet was washed with 1×PBS at 100000 g for 30' at 4° C. The labeled EVs were syringe-filtered through a 0.45 μm filter before further processing (NTA analysis or internalization experiments).

For DiR labeling, a working solution at 1 mg/ml in 100% Ethanol of the dye was prepared and 5 μl of this solution added to 1 ml of freshly prepared P40 fraction to a final concentration of 5 μM. The sample was incubated 1 hour at 37° C. and then centrifuged at 100000 g for 30' at 4° C. The resulting pellet was washed with 1×PBS at 100000 g for 30', 4° C. to remove the free dye and finally resuspended in 1 ml of 1×PBS. The labeled EVs were passed through a 0.45 m filter before use.

EV Internalization Analyses (Flow Cytometry and Microplate Reader) Internalization of PKH26-labeled EVs was assessed by flow cytometry. A549-ACE2 cells incubated with PKH26-labeled EVs were washed 5 times with 1×PBS. After the final wash, the cells were treated with Trypsin-EDTA 1× for 5' at 37° C. to detach them from the flask. After collection, the cells were centrifuged 3' at 200 g, washed twice with 1×PBS, resuspended in 200 μl BSA 0.5% in PBS 1× and placed on ice before analysis. For each sample, between 5000 and 50000 cells were processed and sorted using the appropriate fluorescent channel. Data were analyzed using the FlowJo 10.7 software.

DiR-labeled cells internalization kinetics were analyzed by using a microplate reader. A549-ACE2 cells, 50000 cells per test, were incubated with 0.5 μM of DiR-labelled EVs ($3\times10^8$ particles/ml). DiR fluorescence was measured after 2, 4, 24 and 48 hours of incubation in a TECAN Infinite 200 microplate reader with the following settings: Excitation 750 nm, Emission nm, gain 255. Data were exported and analyzed on Excel.

Confocal Microscopy Observation of Labeled EVs

For microscopic observation, A549-ACE2 cells were grown onto polylysine-treated coverslips hours before the treatment. The following day, the cells were incubated with PHK26-labeled EVs and fixed after 4 hours of incubation using 4% PFA for 15' at RT. After 3 washes with 1×PBS, 10 μl of DAPI (2 μg/ml) were added and the cells incubated 5' at RT in the dark. The sample was finally washed 3 times with 1×PBS, the coverslips mounted to a slide and stored at 4° C. in the dark before the microscopic observation. Confocal pictures of the cells were acquired using a Leica SP5 microscopy and the images treated with ImageJ 1.53c.

Stomatal Reopening Assay

Plants (4/5 weeks old, 8 h/16 h light/dark photoperiod) were kept under light (100 $\mu E/m^2/s$) before subjecting them to any treatment to ensure full expansion of stomata. Intact young leaf sections, at least 6 per condition, were immersed in water or bacterial suspension (at a concentration of $10^8$ cfu/ml, $OD_{600}$=0.2). One hour prior to the bacterial infection, the sections were treated with either the EVs (from ≈10 pM) or total RNAs (20 μg). After 3 hours of infection with the bacteria, the leaf sections were labeled 10' with Propidium Iodide (10 ng/ml in $H_2O$) washed 5' in $H_2O$ and observed under SP5 laser scanning confocal microscope. For each condition, 10-15 pictures were taken from different leaf surface regions. From the pictures, at least 60 stomata per condition were manually measured using ImageJ 1.53c to obtain their width and length. The width/length ratio was calculated using excel and statistical analysis performed using the 2way ANOVA test.

For Mnase protection assay, before incubation with the leaf sections, the samples were treated by incubating them for 30' at 37° C. in the presence or absence of 300 U/ml of Mnase. The reaction was stopped by adding EGTA to a final concentration of 20 mM before using the samples for the stomatal reopening assay.

Generation of Constructs to Detect Small RNAs Activity in Bacteria and Eukaryotic Cells To detect small RNAs activity from total RNA extracts or purified EVs samples, gain-of-function lacI-based reporter constructs were generated using the Green gate approach. All the elements of the reporter system were cloned in different Green gate modules using the repressilator plasmids as template for PCR amplification (Elowitz and Leibler, 2000). The strategy aimed in the assembly of two different cassettes in the same construction: one constitutively expressing the LacI repressor fused to a siRNAs target sequence either at its 5' or 3' end (cassette C-F), and one expressing a GFP reporter gene only in absence of the LacI repressor (cassette A-B). To this end, the pLac (with RBS) promoter was cloned as A module, the destabilized GFPaav with the tRrnB T1 terminator as B module, the constitutive pNPTII promoter (with RBS) as C module, the LacI-lite destabilized repressor as modules D and E, the small RNAs target region as modules D and E, and the tRrnB T1 terminator as module F. The construct R37, bearing the fusA target region at the 3' end of the LacI gene, was selected to test the kinetics of GFP induction in *E. coli* TOP10 cells using the lacI inhibitor IPTG.

| | Green Gate Modules | | | | | |
|---|---|---|---|---|---|---|
| Construct | A | B | C | D/E | | F |
| R37 | pLac (100 bp) | GFPaav::tRrnB T1 (903 bp) | pNPTII (142 bp) | LacI-lite (1125 bp) | fusA IR (83 bp) | tRrnB T1 (140 bp) |

For the reporter system in eukaryotic cells, loss of fluorescence systems were assembled in the pDEST FHA plasmid (Invitrogen Gateway), fused with an EGFP. Approximately 100 bps of small RNA target regions flanked by AscI and BstBI restriction sites were cloned at the 3' end of the EGFP gene under the expression of pCMV promoter containing the same sites generating the following reports (see table below).

| Construct | 3'UTR siRNA target sites | Size (bp) |
|---|---|---|
| pKS35 | IT66 (Rpl13) | 89 |
| pKS36 | IT69 (LUC) | 90 |

-continued

| Construct | 3'UTR siRNA target sites | Size (bp) |
|---|---|---|
| pKS37 | IT64 (Nsp14) | 90 |
| pKS38 | IT54 (RdRp IR2) | 99 |
| pKS39 | Rab7a | 85 |
| pKS40 | IT66 (eIF3e) | 85 |
| pKS41 | IT66 (eIF3f) | 91 |
| pKS42 | IT66 (eIF3i) | 89 |
| pKS43 | IT57 (N) | 91 |
| pKS44 | FusA | 90 |
| pKS45 | Hrpl | 98 |
| pKS46 | Hrpl Mutated | 90 |

Detection of Small RNAs Activity Using Bacterial Reporter Systems

To test the reporter constructs in bacterial cells, *E. coli* TOP10 cells carrying the R37 construct were inoculated O/N at 37° C., 180 rpm, in LB supplemented with 50 μg/ml of Spectinomycin. The following day, an overday culture was performed for 4-5 hours in the same conditions, by inoculating 1:1000 of the O/N culture in fresh medium. At the end of the preculture, the $OD_{600}$ was measured and the culture serially diluted to reach $OD_{600}$=0.02. A total of 180 μl of diluted culture was put in technical duplicates in a 96-well plate to perform kinetics in a TECAN Infinite Pro plate reader. The cells were treated with 20 μl of LB containing either different IPTG concentrations (from 1 to 0.001 mM) (+IPTG condition), 25 μg/ml of Chloramphenicol (background control) or LB diluted with $H_2O$ (−IPTG condition). The $OD_{600}$ and the GFP fluorescence were simultaneously measured at each time point (5') over 12-16 hours kinetics by means of specific filters in the plate reader. At the end of the kinetics, the $OD_{600}$ values were analyzed to confirm the correct cell growth over the time course. The GFP fluorescence was normalized as follows: the mean values of the technical replicates from the +IPTG treatments was subtracted from the means of the control Chloramphenicol wells and -IPTG conditions.

Cell Viability Assay on EVs-Treated A549-ACE2 Cells

For cell viability assay, 25000 A549-ACE2 cells were plated in 96 well plates in triplicates and incubated for 24 hours with 100 μl of medium containing different EVs concentrations. Untreated cells, wells with only medium (to measure the background luminescence) and cells treated with Ethanol 20% for 20 minutes at RT (positive control of a toxic compound) were used as controls. For the luminescence reading, 100 μl of CellTiter-Glo 2.0 Luminescent Cell Viability Assay reagent were added per well (Promega). The samples were mixed for 2' on an orbital shaker and incubated for 10' at RT. The samples were transferred to a Grenier 96 well white bottom plate and the luminecence value read using a Berthold Technologies Luminometer (Tristar LB941). Data was exported and analysed on Excel and the percentage viability calculated relative to untreated cells for each replicate (3 technical replicate per test).

Small RNA Sequencing and Data Mining

Custom libraries for up to 43 nucleotides for small RNAs sequencing of total and EV-derived RNAs from the P100 fraction of the *Chlorella* reference line IT20-3 (IR cfa6/hrpL) were constructed and sequenced by Fasteris®. Reads adaptors were trimmed using the UMI library v0.2.3 (https://github.com/CGATOxford/UMI-tools). Low quality reads were filtered-out based on a base-call threshold of Q20 (99% base call accuracy). In order to represent the small RNA production from the cfa6/hrpL hairpin, we selected a subset of read size comprised between 10 and 25 nucleotides for further analyses and graphical representation. Reads were mapped to the IR cfa6/hrpL sequence using bowtie (Langmead et al., 2009), allowing zero mismatches. We then used an inhouse R script to load aligned reads from the '.bam' files, and represent reads abundance on both extremities of the cfa6/hrpL haipin using the GenomicAlignments package (https://github.com/Bioconductor/GenomicAlignments).

Transmission Electron Microscopy Observation of *Chlorella* EVs

For transmission electron microscopy, a droplet of purified EVs (2 to 10 µl at $10^9$ to $10^{11}$ particles/ml) was deposited on formvar/carbon coated grids for 20'. After the incubation, the excess sample was removed and the grids fixed with 2% paraformaldehyde/10% glutaraldehyde in 0.1 M PBS (pH 7.4) for 20' at RT. After 6 1' washes in $H_2O$, the samples were contrasted with Uranyl acetate in Methylcellulose (4% Uranyl acetate in $H_2O$/Methylcellulose, ratio 1:9) for 10'.

At the end of the incubation period, the excess contrast was removed and the grid air-dried before visualization. Electron micrographs were acquired on a Tecnai Spirit electron microscope (Thermo Fisher, Eindhoven, The Netherlands) equipped with a 4 k CCD camera.

Example 2: *Chlorella* Microalgae Possess Both Highly Conserved EV Biogenesis Factors as Well as Plant-Related EV Factors To determine whether *Chlorella* could be exploited as scaffold for EV-embedded and/or -associated small RNA production, we have first investigated the possible presence of core components required for EVs biogenesis and functions in its genome or transcriptome. To this end, we have conducted an in silico comparative analysis using available genomes and transcriptomes of *Chlorella variabilis* NC64a, *Chlorella vulgaris* UTEX 395, *Saccharomyces cerevisiae, Homo sapiens* and *Arabidopsis thaliana*. Results from this analysis revealed that *C. variabilis* encodes putative orthologs of the ESCRT-I, ESCRT-II and ESCRT-III complexes and of the plant FREE1/FYVE1-like protein, a plant-specific ESCRT essential for intracellular vesicle biogenesis (Table 2, Kolb et al., 2015). By analyzing the *C. vulgaris* UTEX 395 transcriptome we were also able to identify most of the typical ESCRT factors involved in EVs biogenesis. Surprisingly, we did not identify canonical ESCRT-O-related proteins (e.g., human STAM1/2) in the genome of *C. variabilis*, although a single transcript encoding such a putative factor was retrieved in the transcriptome of *C. vulgaris*. However, the low sequence similarity between the human and the *C. vulgaris* proteins suggests that the *Chlorella* ESCRT-0 complex is more likely composed of different and yet-unknown factors. Another intriguing observation is the apparent absence of tetraspanin in the *Chlorella* genome and transcriptome: searches using specific candidates (e.g., human CD63) or the tetraspanin domain (PF00335) against Pfam or JGI protein domain databases failed to identify such factors—which are known to be present in both plants and mammals. The absence of tetraspanin factor was observed also in other green algae (Wang et al., 2012) and, whilst this protein family is considered present in all multicellular organisms, in unicellular species data show a more complex scenario of gene gain and loss that needs further investigations.

TABLE 2

Comparison of the factors encoding ESCRT complexes and other microvesicle-related proteins in Yeast, Human, Plant and *Chlorella*

| Regulators | Yeast (Sc) | Human (Hs) | Plant (At) | *C. variabilis* (NC64a) | *C. vulgaris* (UTEX 395) |
|---|---|---|---|---|---|
| ESCRT-0 and Equivalent | VPS27 | HRS | — | x | — |
| | Hse1 | STAM1, 2 | — | x | Transcript_contig_56508 |
| | — | — | FREE1/FYVE1 | XP_005846966 | Transcript_contig_54179 |
| | — | — | PROS | x | — |
| ESCRT-0 functional analogs | GGA 1, 2 | GGA 1, 2, 3 | — | x | — |
| | — | TOM1, L1, L2, L3 | TOL1 to TOL9 | x | — |
| ESCRT-I | VPS23 | TSG101 | VPS23A/ELC | XP_005843934 | Transcript_contig_53739 |
| | — | — | VPS23B | XP_005843933 | — |
| | VPS28 | hVPS28 | VPS28-1/-2 | XP_005846911 | Transcript_contig_61269 |
| | — | — | — | — | Transcript_contig_68519 |
| | VPS37 | VPS37 A, B, C, D | VPS37-1/-2 | XP_005846305 | Transcript_contig_56274 |
| | MVB12 | hMVB12 A, B | — | x | — |
| | UBAP1 | — | — | x | — |
| ESCRT-II | VPS22 | EAP30 | VPS22 | XP_005846063 | Transcript_contig_57148 |
| | VPS25 | EAP20 | VPS25 | XP_005851443 | Transcript_contig_3694 |
| | VPS36 | EAP45 | VPS36 | XP_005844559 | — |
| ESCRT-III | VPS20 | CHMP6 | VPS20-1 | XP_005848234 | — |
| | SNF7 (VPS32) | CHMP4 A, B, C | SNF7-1/-2 | XP_005850888 | Transcript_contig_59252 |
| | — | — | | x | Transcript_contig_59300 |
| | — | — | | x | Transcript_contig_55347 |
| | VPS24 | CHMP3 | VPS24-1/-2 | XP_005846960 | Transcript_contig_59620 |
| | VPS2 | CHMP2 A/B | VPS2-1/-2/-3 | XP_005849915 | Transcript_contig_67861 |
| | — | — | | XP_005851546 | Transcript_contig_54164 |
| | Did2 | CHMP1/5/1A/1B | CHMP1A/B | x | — |
| | VPS60 | CHMP5 | VPS60-1/-2 | XP_005849964 | Transcript_contig_53967 |
| | IST1 | — | ISTL1 | XP_005842806 | Transcript_contig_89181 |
| | Cmp7 | CHMP7 | CHMP7 | x | — |

TABLE 2-continued

Comparison of the factors encoding ESCRT complexes and other microvesicle-related proteins in Yeast, Human, Plant and *Chlorella*

| Regulators | Yeast (Sc) | Human (Hs) | Plant (At) | *C. variabilis* (NC64a) | *C. vulgaris* (UTEX 395) |
|---|---|---|---|---|---|
| Other ESCRT-related proteins | BRO1 | ALIX | BRO1/ALIX | XP_005850236 | Transcript_contig_474* |
| | — | — | Bro1L1, L2 | | Transcript_contig_55676* |
| | Doa4 | AMSH | AMSH1, 2, 3 | XP_005850797 | Transcript_contig_58892 |
| ESCRT Independent | NMASE2 | — | — | x | — |
| | Rab27A/B | Rab27A/B | — | ✓ | ✓ |
| | — | — | EXO70E2 | XP_005849494 | Transcript_contig_57551 |
| VPS4 and accessory proteins | VPS4 | VPS4/SKD1 | VPS4/SKD1 | XP_005847253 | Transcript_contig_54972 |
| | | | | XP_005845860 | Transcript_contig_56834 |
| | VTA1 | LIP5 | LIP5 | XP_005852259 | Transcript_contig_59235 |
| Microvesicles-related | ARF1/ARF6 | ARF1/ARF6 | — | ✓ | ✓ |
| | RAC1 | RAC1 | — | ✓ | ✓ |
| | RHOA | RHOA | — | XP_005847786 | — |
| Other EVs markers | — | — | Syn121/PEN1 | XP_005845633 | Transcript_contig_54538 |
| | HSP70 | HSP70 | HSP70 | ✓ | ✓ |
| | — | Tetraspanin(s) | | x | — |

✓ = several potential candidates
x = not identified by blast search
*= probably part of the same transcript By contrast, potential ESCRT-independent EVs biogenesis factors, like Rab GTPases (e.g., orthologs of human Rab27a and Rab27b, which control different steps of exosome secretion (Ostrowski et al., 2010)), were recovered in *Chlorella*. Furthermore, we retrieved putative orthologs of the syntaxin PENETRATION1 (PEN1), which has recently been characterized as an exosome marker in both *Arabidopsis* and *Nicotiana benthamiana* (Rutter and Innes, 2017; Zhang et al., 2020). In addition to this factor, we were also able to identify homologs of other plant EV markers like the HSP70 and BRO/ALIX (Table 2). Overall, our data indicate that *Chlorella* microalgae possess conserved EV-related factors, shared between humans, yeasts and plants, but also EV-related factors that have so far been exclusively recovered from plant genomes. They also suggest that the mechanisms of *Chlorella* EVs biogenesis and functions are more closely related to the ones from plants than from yeasts or humans.

Example 3: The Extracellular Medium of *Chlorella vulgaris* Contains EVs that are in a Size Range Between 50 and 200 nm To determine whether *Chlorella* could produce EVs, and to characterize these lipid-based vesicles, we next decided to adapt protocols that have been previously used for the isolation and purification of *Arabidopsis* leaf apoplastic EVs (Rutter and Innes, 2017; PCT/EP2019/072169, PCT/EP2019/072170). Briefly, cell-free culture medium from *Chlorella* grown in flasks was first concentrated using 100 kDa MWCO Pall membranes by centrifugation, or 100 kDa Sartorius VivaFlow 50R tangential filtration devices, in order to obtain a concentrated medium (30-50×) to be used for EVs purification. The resulting concentrated medium, referred to as "C", was further subjected to ultracentrifugation at a centrifugation speed of 40000 g, 4° C., to separate *Chlorella* EVs from the secreted proteins/polysaccharides, as previously reported in *Arabidopsis* (Rutter and Innes, 2017). The latter purification step leads to the recovery of a fraction referred to as the "P40 fraction". Alternatively, a "P100 fraction" was also obtained through a CM ultracentrifugation step at 100000 g, 4° C. Nanoparticle tracking analysis (NTA) of these fractions revealed the presence of particle populations with sizes ranging between 50 to 350 nm, and with a more discrete and abundant particle population centered around nm (FIG. 1A, B for P40 and P100, respectively). To further confirm these results and get more insights into the morphology of these *Chlorella* EVs, the P100 fraction was analyzed by transmission electron microscopy (TEM). The latter analysis unveiled the presence of round shaped particles with an apparent lipidic bilayer, a morphology that resembles mammalian and plant EVs (FIG. 1C, Rutter and Innes, 2017; Zhang et al., 2020; Noble et al., 2020). Size measurement revealed the presence of heterogenous particles with a ~130 nm mean diameter, suggesting that the particles detected through NTA do correspond to *Chlorella* EVs (FIG. 1D). Further labeling of the P40 fraction with the lipophilic dye PKH26, which uses aliphatic tails to anchor into lipid bilayer (Fick et al., 1995; Askenasy et al., 2002), and that is classically used to label mammalian exosomes for fluorescence imaging (Chuo et al., 2018), revealed that the vast majority of particles that are above 200 nm in size are not lipid-based particles (FIG. 1E). Based on this fluorescence imaging coupled with TEM and NTA analyses, we conclude that *Chlorella* EVs, which are in a size range between 50 and 200 nm, can be recovered from the cell-free culture medium of flasks. To date, these results provide the first evidence supporting the presence of *Chlorella* EVs in a cell-free culture medium.

Example 4: *Chlorella* Cells Produce Small RNAs, Suggesting that the RNAi Machinery Present in this Microalga is Functional In algae and microalgae, the presence of small RNAs and/or of RNAi activity has been demonstrated in a few species from several different lineages, including Rhodophyta, Chlorophyta, Haptophyta, Stramenopiles and Dinoflagellata (Cerutti et al., 2011). Although the *Chlorella* genome contains a simple RNAi machinery composed of single DCL and AGO proteins (Cerrutti et al. 2011), which we found phylogenetically related to their plant counterparts (FIG. 2A), there is currently no evidence indicating that this green alga could produce small non-coding RNAs. To test this possibility, we performed small RNA-sequencing (sRNA-seq) from total RNAs extracted from *C. vulgaris* cells. As a control, we also used sRNA-seq datasets that we had previously generated from total RNAs extracted from

*Arabidopsis* adult leaf tissues. Intriguingly, we found that the major small RNA population produced by *C. vulgaris* was 18 nt in size, which is very different from the two main 21 and 24 nt long small RNA species typically recovered from *Arabidopsis* and other plant species (FIG. 2B). Furthermore, we noticed that *C. vulgaris* and *A. thaliana* can additionally produce minor peaks of 15 and 16 nt long small RNAs, respectively (FIG. 2B). Given that Dicer acts as a molecular ruler and cuts the dsRNA substrate at a precise length that is determined by the distance between the PAZ and the RNAse III domains (Zhang et al., 2004), it is possible that the structure of the *Chlorella* DCL enzyme exhibits distinct features compared to the one of plant DCL enzymes, which would favour the production of shorter small RNA species. Alternatively, or additionally, other RNAse III enzymes, which were also retrieved from *Chlorella* genome and transcriptome (Table 3), or other biogenesis factors, could contribute to this process. Altogether, these data provide evidence indicating that *Chlorella* can produce small RNA species, with distinct size classes compared to the ones previously reported in plants. They also suggest that *Chlorella* is equipped with a functional machinery for small RNA biogenesis.

TABLE 3

Putative RNAse III and DCL-like factors identified by blast searches in *C. variabilis* and *C. vulgaris*

| Factor | *C. variabilis* (NC64a) | *C. vulgaris* (UTEX 395) |
|---|---|---|
| DCL-like | XP_005849661 | Transcript_contig_56994* |
| | — | Transcript_contig_79877* |
| | — | Transcript_contig_64095 |
| RNAse III | XP_005851019 | Transcript_contig_78810 |
| | XP_005848456 | Transcript_contig_60223 |
| | XP_005845370 | Transcript_contig_55978 |
| | XP_005849661 | Transcript_contig_68382 |

*Potentially part of the same transcript

Example 5: *Chlorella* can be Engineered to Produce Small RNAs with Antimicrobial Activity Previous studies demonstrated that the exogenous administration of small RNAs and/or long dsRNAs can be effective against eukaryotic pathogenic/parasitic (micro)organisms including fungi, oomycetes, insects and nematodes (Ivashuta et al., 2015; Wang et al., 2016; Koch et al., 2016; Wang & Jin., 2017; Wang et al., 2017). Environmental RNAi can also occur against pathogenic bacteria and relies on small RNA entities rather than on long dsRNAs (Singla-Rastogi & Navarro, PCT/EP2019/072169, PCT/EP2019/072170). Based on these studies, and on the ability of *C. vulgaris* to produce small RNA species (EXAMPLE 4), we reasoned that we could make use of this biological system to produce antimicrobial small RNAs. To test this possibility, *C. vulgaris* was stably transformed with an inverted repeat (IR) transgene carrying sequence homology with two major virulence factors of *Pseudomonas syringae* pv. tomato strain DC3000 (Pto DC3000), which is a Gram negative bacterium previously shown to be sensitive to environmental RNAi (Singla-Rastogi & Navarro, PCT/EP2019/072169, PCT/EP2019/072170, FIG. 3A). The first targeted virulence factor is the coronafacic acid polyketide synthase I (cfa6) gene, which encodes a major structural component of the phytotoxin coronatine (COR) (Brooks et al., 2004). The second one is hrpL, which encodes an alternative sigma factor that is known to directly control the expression of type III-secretion system associated genes, and to indirectly regulate the expression of COR biosynthesis genes (Fouts et al., 2002; Sreedharan et al., 2006). Interestingly, when stably expressed in *Arabidopsis*, the IR-CFA6/HRPL inverted repeat is efficiently processed by endogenous plant DCLs into anti-Cfa6 and anti-HrpL siRNAs, which in turn target the cfa6 and hrpL genes in Pto DC3000, along with the dampening of its pathogenicity during infection (Singla-Rastogi & Navarro, PCT/EP2019/072169, PCT/EP2019/072170). Importantly, some of these phenotypes are fully recapitulated upon exogenous administration of total RNAs from these transgenic plants, which contain effective anti-cfa6 and anti-hrpL siRNAs (Singla-Rastogi & Navarro, PCT/EP2019/072169, PCT/EP2019/072170). In particular, the exogenous application of these RNA extracts suppresses the ability of Pto DC3000 to trigger stomatal opening, a major virulence response employed by this bacterium to enter through stomata and colonize inner leaf tissues (Melotto et al., 2006; PCT/EP2019/072169, PCT/EP2019/072170).

By using the same stomatal reopening readout, which is highly sensitive to anti-Cfa6 and anti-HrpL siRNAs, we found that RNA extracts derived from the five independent *Chlorella* IT20 lines tested, which express the IR-CFA6/HRPL transgene, suppressed stomatal reopening events (FIG. 3B). Importantly, these phenotypes were comparable to the one observed in the presence of RNA extracts derived from the control *Arabidopsis* IR-CFA6/HRPL #4 plants, and mimicked the impaired stomatal reopening phenotype detected in response to a P to DC3000 mutant strain unable to produce COR (FIG. 3B). Furthermore, because this phenotype is known to be dependent on anti-cfa6 and anti-hrpL siRNAs, but not on unprocessed IR-CFA6/HRPL transcripts (Singla-Rastogi & Navarro, PCT/EP2019/072169, PCT/EP2019/072170), our data suggest that *Chlorella* IR-CFA6/HRPL lines are likely competent for producing antibacterial small RNA species. Accordingly, small RNAs mapping to the IR-CFA6/HRPL inverted transgene transcripts were recovered from the *Chlorella* IR-CFA6/HRPL IT20 #3 reference line (FIG. 3C). It is also noteworthy that these small RNAs were produced from both the cfa6 and hrpL regions of the inverted repeat transcripts, with an enhanced accumulation of small RNAs corresponding to the hrpL region (FIG. 3C). Collectively, these data provide evidence that *Chlorella* can be engineered to produce small RNAs exhibiting antibacterial activity.

Example 6: *Chlorella* Artificial Small RNAs Directed Against the Virulence Factor hrpL are Causal for the Suppression of hrpL-Mediated Stomatal Reopening Function To determine whether *Chlorella* artificial small RNAs could be causal for the observed antibacterial activity, we next took advantage of previously described recombinant bacteria expressing a small RNA-resilient version of the hrpL gene (Singla-Rastogi & Navarro, PCT/EP2019/072169, PCT/EP2019/072170). This mutated version of the hrpL gene contains as many silent mutations as possible in the small RNA targeted region, in order to alter the binding of anti-hrpL small RNAs to hrpL mRNAs, whilst producing wild type HrpL proteins. Both the mutant and Wt versions of the hrpL gene were cloned in a plasmid, under the control of the neomycin phosphotransferase H (NPTII) promoter, and further transformed in the Pto DC3000 ΔhrpL strain, which is deleted of the hrpL gene and thus fully impaired in its ability to reopen stomata (Singla-Rastogi & Navarro, PCT/EP2019/072169, PCT/EP2019/072170, FIG. 4A). It is noteworthy that the resulting recombinant bacteria, referred to as Pto DC3000 ΔhrpL WT hrpL and mut hrpL, were previously shown to restore the ability of the Pto DC3000 ΔhrpL strain to reopen stomata, indicating that both transgenes are functional (Singla-Rastogi & Navarro, PCT/EP2019/072169, PCT/EP2019/072170). These recombinant bacteria were subsequently used in a stomatal reopening assay in the presence of total RNA extracts from the *Arabidopsis* IR-HRPL #4 line or the *Chlorella* IT29 #12, IT29 #15 lines, which express from the *Chlorella* genome an IR-HRPL inverted repeat that specifically targets the hrpL gene. As controls, we used the Pto DC3000 Wt and ΔhrpL strains as well as total RNAs from the IT19 #7 reference line, which expresses from the *Chlorella* genome an IR-CYP51 inverted repeat that does not exhibit sequence homology with the Pto DC3000 genome, but instead targets three cytochrome P450 lanosterol C-14α-demethylase (CYP51) genes of the fungal phytopathogen *Fusarium graminearum* (Koch et al., 2013). We found that the bacteria complemented with the hrpL Wt gene were sensitive to RNA extracts derived from the two independent *Chlorella* IT29 #12 and IT29 #15 lines, but also from the control *Arabidopsis* IR-HRPL #4 line, as manifested by an altered ability of these bacteria to reopen stomata (FIG. 4B). By contrast, these recombinant bacteria reopened stomata in the presence of RNA extracts derived from the *Chlorella* IT19 #7 reference line (FIG. 4B), supporting a specific effect of anti-hrpL small RNAs in this phenomenon. Importantly, we found that the bacteria complemented with the mutated hrpL gene were fully resistant to RNA extracts derived from the two independent *Chlorella* IT29 lines and the control *Arabidopsis* IR-HRPL #4 line, allowing normal stomatal reopening phenotypes (FIG. 4B). The latter data indicate that the suppression of stomatal reopening phenotype is not due to potential off-target effects of these anti-hrpL small RNAs, but rather caused by their targeting effects over the hrpL transcript sequence. They also indicate that anti-hrpL small RNAs, produced from either *Chlorella* or *Arabidopsis* transgenic lines, are causal for the suppression of hrpL-mediated stomatal reopening function. The results reported in EXAMPLES 5 and 6 provide thus a proof-of-concept demonstrating that *Chlorella* can be engineered to produce effective antibacterial small RNAs acting in a sequence-specific manner.

Example 7: EVs from *Chlorella* IR-CFA6/HRPL Transgenic Lines Exhibit Antibacterial Activity Previous studies have reported that plant EVs can deliver biologically active antimicrobial small RNAs in fungal, oomycetal and bacterial cells (Cai et al., 2018; Teng et al., 2018; Hou et al. 2019; PCT/EP2019/072169, PCT/EP2019/072170), thereby reducing their pathogenicity. To investigate whether this phenomenon holds also true for antimicrobial small RNAs embedded in, and/or associated with, *Chlorella* EVs, we first collected the cell-free medium from two independent *Chlorella* IT20 lines, which express the IR-CFA6/HRPL transgene, and further used an ultrafiltration method designed to retain particles that are above 30-90 nm. The resulting concentrated medium (CM), corresponding to a 30-50 times concentrate of the original *Chlorella* medium, was additionally filtered using a 0.45 μm sterilized filter to eliminate possible bacterial contaminants derived from the ultrafiltration process. The antibacterial activities of the CM were further analyzed using a stomatal reopening assay, and RNA extracts from the corresponding *Chlorella* IT20 cells, and from the *Arabidopsis* IR-CFA6/HRPL #4 plants, were included in the assay as positive controls. Interestingly, the CM from the two independent *Chlorella* IT20 lines suppressed stomatal reopening events, to the same extent as total RNA extracts derived from the same producing cells or from the *Arabidopsis* IR-CFA6/HRPL #4 plants (FIG. 5A). These results suggest that the *Chlorella* IT20 lines could produce extracellular EVs—bigger than 30-90 nm—containing anti-cfa6 and/or anti-hrpL small RNAs. Consistent with this idea, we found that the P40 fraction from the reference *Chlorella* IT20 #3 line was fully competent in suppressing Pto DC3000-induced stomatal reopening, to the same extent as total RNAs from *Chlorella* cells or from the *Arabidopsis* IR-CFA6/HRPL #4 plants (FIG. 5B). We conclude that EVs from *Chlorella* IT20 lines are likely loaded and/or associated with anti-cfa6 and anti-hrpL small RNAs, which must be delivered into Pto DC3000 cells to trigger the detected antibacterial effect.

We have previously shown that plant EVs protect antibacterial small RNAs from digestion mediated by the non-specific Micrococcal nuclease (Mnase) (Singla-Rastogi & Navarro, PCT/EP2019/072169, PCT/EP2019/072170). Here, to determine whether *Chlorella* EVs could share similar features, we treated the P40 fraction from the IT20 #3 reference line with Mnase and further used it in a stomatal reopening assay. In more details, the samples were incubated for 30' at 37° C. in the presence or absence of 300 U/ml of Mnase. At the end of this incubation period, EGTA, at a final concentration of 20 mM, was added to inhibit Mnase activity, and the samples were further used for stomatal reopening assay. Significantly, we found that the P40 fraction treated with Mnase remained fully capable of suppressing Pto DC3000-induced stomatal reopening, such as the untreated P40 fraction used as control (FIG. 5C). These data suggest that anti-cfa6 and anti-hrpL small RNAs are protected from ribonuclease-mediated digestion when embedded into, and/or associated with, *Chlorella* EVs. Consistent with this hypothesis, we were able to detect through sRNA-seq analysis both anti-cfa6 and anti-hrpL small RNA reads from Mnase-treated EV samples produced by the *Chlorella* IT20 #3 reference line (FIG. 5D).

Based on these overall results, we propose that EV-associated anti-cfa6 and anti-hrpL small RNAs produced by the *Chlorella* IT20 #3 line are intravesicular and/or extra-vesicular but likely associated with ribonucleoprotein complexes, and thus protected from RNAses.

Example 8: *Chlorella* EV-Embedded and or -Associated Small RNAs Directed Against hrpL are Causal for the Suppression of hrpL-Mediated Stomatal Reopening Function To confirm that antibacterial small RNAs are the bioactive cargoes, and to compare the antibacterial potential of both the P40 and P100 fractions, we performed a stomatal reopening assay with the Pto DC3000 ΔhrpL Wt hrpL and Mut hrpL bacteria described in EXAMPLE 4. The P40 and P100 fractions were collected from the *Chlorella* IT19 #7(IR-CYP51) and IT29 #12 (IR-HRPL) reference lines and treated with Mnase, as previously described, using the untreated Pto DC3000 Wt and ΔhrpL strains as controls. As observed using the total RNA extracts in EXAMPLE 4, only the bacteria complemented with the Wt hrpL gene were sensitive to EVs from the *Chlorella* IT29 #12 reference line, with the P40 and P100 fractions showing similar antibacterial effects (FIG. 5E). By contrast, these recombinant bacteria reopened stomata in the presence of the Mnase-treated P40 and P100 fractions derived from the *Chlorella* IT19 #7 line (FIG. 5E), supporting a specific effect of EV-embedded and/or -associated anti-hrpL small RNAs. Importantly, the recombinant bacteria expressing the hrpL mutant version were fully refractory to the suppression of stomatal reopening effects mediated by the Mnase-treated P40 and P100 fractions produced by the *Chlorella* IT29 #12 reference line (FIG. 5B). These data support a causal role for EV-embedded and/or -associated anti-hrpL small RNAs in suppressing the ability of Pto DC3000 to reopen stomata. They also indicate that *Chlorella* EVs likely deliver anti-hrpL small RNAs in Pto DC3000 cells to target the hrpL gene in a sequence-specific manner, thereby suppressing bacterial-triggered stomatal reopening.

Example 9: *Chlorella* EVs are Efficiently Internalized by Human Alveolar Epithelial Cells A vast number of mammalian pathogens uses sophisticated strategies to enter and replicate in host cells. Furthermore, it is now well-established that various pathogens hijack host cellular factors in order to replicate in their hosts. The development of RNAi-based prophylactic or therapeutic approaches, either directly directed against pathogen transcripts, or indirectly against host susceptibility factor(s), therefore relies on the delivery of small RNAs in host cells that will encounter, or that are already encountering, the targeted pathogen(s). Mammalian EVs are particularly valuable in that respect, because they can deliver effective small RNAs in various cell types and organs (O'Brien et al., 2020). Interestingly, plant EVs can also be taken-up by mammalian cells and deliver siRNAs in recipient cells. For instance, the tropism of grapefruit-derived nanovesicles has been established in different human cell types, including A549 human alveolar epithelial cells, in which the delivery of siRNAs has been demonstrated (Wang et al., 2013; Zhang et al., 2016). Furthermore, these lipid-based particles were notably recovered in the lungs and brain of mice upon their intranasal administration (Wang et al., 2013), suggesting that these vectors can also operate in vivo for the delivery of RNAi-based molecules. Here, we have investigated whether *Chlorella* EVs could similarly be taken-up by human cells. For this purpose, we used the A549 cell line, which is notably relevant for *Pseudomonas aeruginosa* infection, but also A549-ACE2 cells, which overexpress the angiotensin-converting enzyme 2 (ACE2) receptor that is critical for SARS-CoV-2 entry in host cells (Hoffman et al., 2020). We first labeled *Chlorella* EVs from P40 fractions with PKH26, and further incubated them with A549 and A549-ACE2 cells for hours. After multiple washes, the control cells and cells incubated with the PKH26-labeled *Chlorella* EVs were fixed and stained with DAPI, which binds to adenine-thymine rich regions in DNA and thus stains cell nuclei. Confocal analyses revealed a clear red fluorescence signal from PKH26-labeled EVs in human cells, providing a first evidence that *Chlorella* EVs can be internalized by A549 and A549-ACE2 cells (FIG. 6A, data not shown). We next quantified PKH26-labeled *Chlorella* EV uptake events using a Fluorescence-activated cell sorting (FACS) approach. At 4 hours after incubation of PKH26-labeled *Chlorella* EVs at a concentration of 0.06 μM, we found that 17% of A549-ACE2 cells took-up these lipid particles (FIG. 6B, left panel). Importantly, these uptake events occurred in ~92% of A549-ACE2 cells when a concentration of 0.5 μM of PKH26-labeled *Chlorella* EVs was used in the same conditions (FIG. 6B, right panel), and similar results were found in A549 cells (data not shown). Collectively, these data do not only demonstrate that *Chlorella* EVs are efficiently taken-up by A549 and A549-ACE2 cells, but also provide us with the optimal concentration needed to ensure that most of the targeted human alveolar epithelial cells will take-up the antimicrobial siRNA vectors in in vitro infection assays.

We further investigated the timeframe of *Chlorella* EV internalization events by human alveolar epithelial cells. For this purpose, *Chlorella* EVs were labeled with the near infrared (NIR) lipophilic 1,1'-Dioctadecyl-3,3,3',3'-Tetramethylindotricarbocyanine Iodide (DiR) dye and incubated with A549 and A549-ACE2 cells for 2 h, 4 h, 24 h and 48 h. After washing of the human cells, their NIR fluorescence emission was analyzed using a microplate fluorometer. Interestingly, the NIR fluorescence signal was already detected at 2 hours post-incubation of DIR-labeled EVs, highlighting the rapid internalization of *Chlorella* EVs by A549 or A549-ACE2 cells (FIG. 6C/D, data not shown). Furthermore, we noticed that, from one experiment to the other, the peak of NIR fluorescence intensity was observed either at 8 or 24 hours after EV treatments (FIG. 6C/D, data not shown). These results indicate that the maximal EV internalization events by A549 and A549-ACE2 cells must occur between those timepoints. These EVs uptake kinetics are notably valuable to optimize the design of EV treatments in in vitro infections assays.

Example 10: *Chlorella* EVs do not Alter the Viability of Human Alveolar Epithelial Cells In order to exploit the MIGS technology for the future development of small RNA-based therapeutics, it is important to assess the impact of microalgae EVs on the immunogenicity and/or their toxicity in mammalian cells or organisms. Several studies have already explored these issues in human cells and in mice treated with plant EVs, but no information is currently available for microalgae EVs (Garaeva et al., 2021; Maji et al., 2017). We thus performed a cell viability assay on A549-ACE2 cells by incubating cell cultures in the presence of different concentrations of *Chlorella* EVs from wild type and transgenic lines expressing small RNAs targeting either SARS-CoV-2 genes (IT54, IT64), human genes (IT66, see EXAMPLE 1 for details) or, as a control, the luciferase gene (IT69). It is noteworthy that, based on the results obtained in FIG. 6, the concentrations chosen for the cell viability assay should result in the uptake of a significant amount of *Chlorella* EVs by the whole targeted human cell population. After 24 hours of EVs incubation with A549-ACE2 cells, the cell viability was determined through a bioluminescent assay that quantifies the amount of ATP released by the viable cells in the medium, using untreated and ethanol (EtOH)-treated cells as controls. Importantly, while the EtOH treatment triggered an expected ~70% reduction in the number of viable cells, we did no detect any effect of the different populations of *Chlorella* EVs on the cell viability of A549-ACE2 cells (FIG. 7). Collectively, these results indicate that *Chlorella* EVs do not alter the viability of human alveolar epithelial cells.

Example 11: Generation of Stable *Chlorella* Lines Expressing Inverted Repeat Transgenes Directed Against SARS-CoV-2 RNAs or HSF mRNAs To produce *Chlorella* EV-embedded and/or -associated small RNAs against SARS-CoV-2, we have generated 20 inverted repeat constructs and transformed all of them in *Chlorella vulgaris* using *Agrobacterium*-mediated transformation. More specifically, 16 viral sequence regions are targeted, which span the genomic and subgenomic RNAs of the SARS-CoV-2. For example, we decided to target viral regions corresponding to the RNA-dependent RNA polymerase (RdRP) and the Spike regions, from which two synthetic siRNAs were previously designed to restrict SARS-CoV-1 replication in Rhesus macaques (FIG. 8, Li et al., 2005). As another example, we are targeting the leader sequence, whose siRNA-directed silencing is known to suppress the transcription of all subgenomic RNAs from SARS-CoV-1, resulting in a strong compromised viral replication in mammalian cells (Li et al., 2005). It is also important to note that several of these viral regions exhibit sequence conservation with other coronavirus sequences, and have therefore the potential of triggering cross-protection against various coronaviruses, including harmful coronaviruses that will be emerging in the future. These *Chlorella* transgenic lines might thus be valuable for future repurposing approaches against other coronaviruses. To support this hypothesis, we provide here sequence alignments of the targeted regions of SARS-CoV-2 RdRP and Helicase with the RdRP and the Helicase sequences of SARS-CoV-1 and MERS, which exhibit extensive sequence similarities (FIG. 8). A sequence alignment of the targeted region of the SARS-CoV-2 Spike with the Spike sequence of SARS-CoV-1 is also depicted in FIG. 8 to highlight the high sequence similarities between those viral regions.

The following IR constructs target individual SARS-CoV-2 viral regions of ~350 bp (they contain the intron of SEQ ID NO: 107, apart from the target sequences):

IR-PLP, SEQ ID NO: 41-42;
IR-3CL, SEQ ID NO: 43-44;
IR-NSP10, SEQ ID NO: 45-46;
IR-RDRP-1, SEQ ID NO: 47-48;
IR-RDRP-2, SEQ ID NO: 49-50;
IR-RDRP-3, SEQ ID NO: 51-52;
IR-EndoN, SEQ ID NO: 53-54;
IR-N, SEQ ID NO: 55-56;
IR-E, SEQ ID NO: 57-58;
IR-M, SEQ ID NO: 59-60;
IR-S, SEQ ID NO: 61-62;
IR-3'UTR, SEQ ID NO: 63-64; and
IR-Hel, SEQ ID NO: 65-66.

The following chimeric IR constructs target concomitantly multiple SARS-CoV-2 viral regions of ~150 bp each (they contain the intron of SEQ ID NO: 107, apart from the target sequences):

IR-NSP1/NSP4/NSP3/PLP/3CL/NSP12/NSP13/NSP14, SEQ ID NO: 1-2; and
IR-S/E/M/N/leader-TRS 3'UTR, SEQ ID NO: 3-4

It is noteworthy that, when stably expressed in *Chlorella vulgaris*, these chimeric IR transgenes should produce long dsRNAs that will likely be processed all along through the processive activity of the *Chlorella* DCL enzyme, and/or other *Chlorella* RNase III, thereby giving rise to small RNA populations targeting simultaneously multiple SARS-CoV-2 RNAs. This principle is supported by previous data, notably showing that a similar IR structure triggers the concomitant production of antibacterial siRNA populations against two bacterial virulence factors when stably expressed in *Arabidopsis* (Singla-Rastogi & Navarro, PCT/EP2019/072169, PCT/EP2019/072170).

In addition, we chose to target 16 host factors, referred to here as Host-Susceptibility Factors (HSFs), which have recently been shown to be essential for coronaviruses to establish their life cycle in human cells (V'kovski et al., 2019; Hoffman et al., 2020; Siddiqui et al., 2020; Gordon et al., 2020). In particular, we aim to simultaneously target the translational factors Rp113a, eIF3e, eIF3i and eIF3f, which are essential for active translation proximal to replication complexes of coronaviruses (V'kovski et al., 2019). Importantly, the silencing of each of these host factors has been shown to drastically reduce the replication of a recombinant MHV coronavirus in human cells (V'kovski et al., 2019), and might similarly prevent SARS-CoV-2 replication in human cells. This targeting strategy is particularly relevant because coronaviruses are known to highjack the host translational machinery to achieve replication in their hosts (V'kovski et al., 2019; Gordon et al., 2020). In addition, we are concomitantly targeting mRNAs for the eukaryotic initiation factor-4A (eIF4A) and the translation elongation factor-1A (eEF1A). The rationale for targeting these factors is supported by the fact that the Food and Drug Administration (FDA)-approved eIF4A inhibitor, i.e., zotatifin, and eEF1A inhibitors, i.e., ternatin-4 or aplidin/plitidepsin, can efficiently restrict SARS-CoV-2 infectivity in human cells and are currently used in clinical trials to treat patients against COVID-19 (Gordon et al., 2020). Furthermore, we are targeting host factors that are essential for (i) vesicle trafficking and coronavirus replication in human cells (Snrpe, Naca, Kifl1, Gbf1 and Srp54a) (V'kovski et al., 2019), (ii) the entry of SARS-CoV-2 in human cells (ACE2, TMPRSS2) (Hoffman et al., 2020), and (iii) the 20S and 26S proteasome functions, which are required for the replication of a recombinant MHV coronavirus in human cells (V'kovski et al., 2019). Finally, based on the efficient in vitro reduction in SARS-CoV-2 replication upon administration of ivermectin (Siddiqui et al., 2020), which inhibits viral import of unrelated viruses, notably by inhibiting IMPα1 and IMP31 functions, we have decided to target these additional HSF mRNAs.

The following chimeric IR constructs target concomitantly multiple HSF region of ~150 bp each (they contain the intron of SEQ ID NO: 107, apart from the target sequences):

IR-Rp113a/eIF3e/eIF3i/eIF3f, SEQ ID NO: 5-6;
IR-eIF4A/eEF1a, SEQ ID NO: 7-8;
IR-Snrpe/Naca/Kif1/Gbf1/Srp54a, SEQ ID NO: 9-10; and
IR-ACE2/TMPRSS2/Psmd1/IMPα/IMP β1 SEQ ID NO: 11-12.

Example 12: Generation of Stable *Chlorella* Lines Expressing IR Transgenes Directed Against Virulence and Essential Genes from *Pseudomonas aeruginosa, Shigella flexneri, Mycobacterium tuberculosis, Legionella Pneumophila*, and *Staphylococcus aureus*

To produce *Chlorella* EV-embedded small RNAs that might be ultimately used as RNAi-based prophylactic or therapeutic agents against bacteria, we are generating IR constructs and stably expressed them in *Chlorella vulgaris* using *Agrobacterium*-mediated transformation. More specifically, we are targeting the essential genes from *P. aeruginosa*, including LptH, LolA, TolB, LpxA, LpxD, dnaA, dnaB, dnaN, gyrB, rpoC, secE and sodB, using the following constructs (all of them containing the intron of SEQ ID NO:107, apart from the target sequences):

IR-LptH/LolA/TolB, SEQ ID NO: 13-14;
IR-LpxA/LpxD/TolB, SEQ ID NO: 15-16;
IR-dnaA/dnaB/gyrB, SEQ ID NO: 67-68;
IR-rpoC/secE/SodB, SEQ ID NO: 69-70; and
IR-secE/dnaN/gyrB, SEQ ID NO: 17-18.

We are also targeting the essential genes of *Shigella flexneri*, including FtsA, Can, Tsf, AccD, Der, Psd using the constructs:

IR-FtsA/Can/Tsf, SEQ ID NO: 71-72 and

IR-AccD Der Psd, SEQ ID NO: 73-74.

The same approach has been also used for the production of *Chlorella* EV-embedded small RNAs directed against key virulence genes from *P. aeruginosa*, including genes involved in the regulation and/or assembly of type II or type III secretion systems, XcpQ, PscC, PcrV, ExoS, ExoU, ExsA, Vrf, the quorum sensing signaling factors LasR, RhlR, MvfR, VqsM, the GAC signaling components GacA and RsmA, by using the following constructs:

IR-XcpQ/ExsA/PcrV/LasR/RhlR/VqsM/RmsA, SEQ ID NO: 19-20;

IR-XcpQ/PscF/PscC, SEQ ID NO: 21-22;

IR-ExoS/exsA/Vrf, SEQ ID NO: 23-24;

IR-ExoU/ExsA/Vrf, SEQ ID NO: 25-26;

IR-LasR/RhlR/VqsM, SEQ ID NO: 27-28; and

IR-GacA/RmsA/MvfR, SEQ ID NO: 29-30.

We are additionally using this approach for the production of *Chlorella* EV-embedded small RNAs directed against key antibiotic resistance genes from *P. aeruginosa*, including mexX, mexA and ampC, by using the following construct:

IR-mexX/mexA/ampC SEQ ID NO: 31-32.

We are also targeting the virulence genes of *Shigella flexneri*, including VirF, VirB, IcsA using the constructs IR-VirF VirB IcsA, SEQ ID NO: 33-34, and the virulence genes of *Staphylococcus aureus*, including the genes encoding surface bound proteins fnbA, clfA, clfB, spa, atl, the leukotoxins lukF-PV, lukS-PV, lukE, lukD, HlgB, the alpha hemolysin hla, and the toxic shock syndrome toxin-1 tsst-1, by using the constructs:

IR-fnbA/clfA/clfB/spa, SEQ ID NO: 35-36;

IR-lukF-PV/lukS-PV/lukE/lukD, SEQ ID NO: 37-38; and

IR-HlgB/hla/tsst-1/atl, SEQ ID NO:39-40.

We are also targeting the virulence genes of *Mycobacterium tuberculosis*, including cspA, pcaA, icl1, rip, fad26, hphA using the constructs:

IR-cpsA, SEQ ID NO: 75-76;

IR-pcaA, SEQ ID NO: 77-78;

IR-icl1, SEQ ID NO:79-80;

IR-rip, SEQ ID NO:81-82;

IR-fad26, SEQ ID NO: 83-84;

IR-hphA, SEQ ID NO: 85-86; and

IR-cpsA/pcaA, SEQ ID NO: 87-88.

We are also targeting the virulence genes of *Legionella pneumophila*, including dotA, dotB, dotC, dotD, icmT, icmJ, pilD, and ispF using the constructs:

IR-dotA, SEQ ID NO: 89-90;

IR-dotD, SEQ ID NO: 91-92;

IR-dotC, SEQ ID NO:93-94;

IR-dotB, SEQ ID NO:95-96;

IR-icmT, SEQ ID NO:97-98;

IR-icmJ, SEQ ID NO:99-100;

IR-pilD, SEQ ID NO:101-102;

IR-ispF, SEQ ID NO:103-104; and

IR-dotD/pilD, SEQ ID NO:105-106;

Example 13: Design and Generation of Reporter Systems to Rapidly and Reliably Detect the Biological Activity of EV-Contained Small RNAs Produced from *Chlorella* Transgenic Lines 13.1. To validate the biological activity of EVs produced from *Chlorella* transgenic lines expressing antimicrobial small RNAs, we have developed two types of reporter systems in bacterial cells and human cells. Both reporter systems are expected to exhibit a differential reporter gene expression when EV-embedded and/or associated small RNAs are internalized by the recipient cells.

The first reporter system family is based on the plasmid expression of a bipartite cassette composed of a first construct expressing a short-lived variant of the transcriptional repressor, namely LacI-lite, carrying in its 5' or 3' ends the antimicrobial siRNA target region of interest, and a second construct composed of an intermediate stability variant of the GFP (Andersen et al., 1998; Elowitz & Leibler., 2000), whose transcriptional activity is directed by the pLac promoter and regulated by the lacO operator (FIG. 9A). In the absence of EV-embedded and/or associated small RNAs, LacI-lite proteins should be constitutively produced in bacteria and in turn shut-down the expression of the GFP, resulting in an absence of GFP fluorescence signal. By contrast, when a given small RNA population is internalized and active in bacterial cells, the silencing of LacI-lite results in the derepression of the GFP expression, leading to the detection of GFP fluorescence signal (FIG. 9A). Of note, other systems than LacI-lacO could also be used for the same purpose, such as the TetR-lite tetO2 or cI-lite PR systems. We assembled the bipartite reporter system in destination plasmids with backbones adapted for expression and replication in both *E. coli* and Pto DC3000. In both cases, we introduced a small RNA target sequence specific to the Pto DC3000 gene fusA at the 3' end of the LacI-lite repressor, giving the R37 construct. As a first characterization step, we made use of the Isopropyl β-d-1-thiogalactopyranoside (IPTG) ability to directly inhibit the LacI protein, in order to test the reporter system and its sensitivity once transformed in bacteria. We therefore incubated *E. coli* TOP10 bacterial cells transformed with the R37 construct with different IPTG concentrations, from $10^{-3}$ to 1 mM, and continuously measured both the $OD_{600}$ and GFP fluorescence over a 15 hours kinetic experiment. The GFP fluorescence of the +IPTG conditions was normalized using the−IPTG and a chloramphenicol control, in order to determine the correct induction kinetics once the background signal was removed. The analysis revealed that an IPTG concentration of 0.1 mM was sufficient to trigger the GFP induction already after 60', with a sharp fluorescence increase starting after about 2-3 hours of incubation (FIG. 9B). Interestingly, neither the presence of the reporter nor of the IPTG itself affected the bacterial growth rate over the kinetics, as shown by $OD_{600}$ measurements (data not shown). After generating a Pto DC3000 compatible vector with the R37 construct, we performed the same IPTG test in this bacterial phytopathogen. The normalized GFP fluorescence revealed that the reporter system was active and responded to the IPTG induction also in this *Pseudomonas* species starting from 2-3 hours of incubation (FIG. 9C). However, we noticed that the overall GFP levels were lower compared to the ones detected in *E. coli* cells.

For the second reporter system, we generated a GFP-based reporter by assembling the strong constitutive promoter pCMV to a GFP transgene fused to a small RNA target sequence at the 3' end of the coding sequence (FIG. 9D). This reporter is further transfected into human cells treated with the candidate EVs population and the silencing of the GFP protein is further monitored by different approaches including western blot analysis at 24- and 48-hours post treatments.

We have furthermore engineered other bacteria (including the *Escherichia coli* K12 strain) to express dual reporter systems that can exhibit a differential siRNA targeted reporter gene expression when EV-embedded siRNAs are internalized in bacterial cells.

A first reporter system family relies on the plasmid-based expression of a cassette composed of a first construct constitutively expressing a non-targeted DsRed reporter that is used as an internal control for normalization, and a second construct carrying a destabilized GFP reporter, containing in its downstream region the antimicrobial siRNA target region of interest (FIG. 9E). When expressed in bacteria (e.g., *E. coli*), this system is predicted to result in a specific decrease in GFP expression and fluorescence signal upon internalization of a given EV-embedded siRNA population.

A second dual reporter system family is based on the plasmid expression of a tripartite cassette composed of a first construct expressing a short-lived variant of the transcriptional repressor, namely TetR-lite, carrying in its downstream region the antimicrobial siRNA target region of interest, a second construct composed of an intermediate stability variant of the GFP (Andersen et al., 1998; Elowitz & Leibler., 2000), whose transcriptional activity is controlled by the tetO2 operator, and a third construct expressing a non-targeted DsRed reporter, which serves as an internal control for normalization (FIG. 9F). In the absence of EV-embedded small RNAs, TetR-lite proteins should be constitutively produced in bacteria and in turn shut-down the expression of the GFP, resulting in an absence of GFP fluorescence signal (only the fluorescence of the DsRed reporter should be detected). By contrast, when a given siRNA population is internalized and active in bacterial cells, the silencing of TetR-lite results in the derepression of the GFP expression, leading to the detection of GFP fluorescence signal.

A third family of reporter system relies on the plasmid-based expression of a bipartite cassette composed of a first construct expressing a short-lived variant of the transcriptional repressor, namely TetR-lite, carrying in its downstream region the antimicrobial siRNA target region of interest and a second construct composed of an intermediate stability variant of the GFP (Andersen et al., 1998; Elowitz & Leibler., 2000), or a bioluminescence reporter (e.g., the *Photorhabdus luminescens* operon luxCDABE (Meighen, 1991), whose transcriptional activity is controlled by the tetO2 operator (FIG. 9G). When a given siRNA population is internalized and active in bacterial cells, the silencing of TetR-lite results in the derepression of the GFP or luxCDABE operon expression, leading to the detection of GFP fluorescence or bioluminescence signals. Of note, other systems than TetR-tetO2 could also be used for the same purpose, such as the lacI-lite/lacO or cl-lite/PR systems.

Overall, we have generated five reporter system families that will allow us to quantify the biological activities of EV-contained small RNAs in a rapid and reliable manner.

Example 14: *Chlorella* EVs Produced in Photobioreactors Maintain their Integrity and Ability to be Taken-Up by A549 and A549-ACE2 Cells A prerequisite for the development of MIGS-derived applications, is to verify that *Chlorella* EVs maintain their integrity and functionality when produced in photobioreactors (PBRs). To address this issue, the reference *Chlorella* IT20 #3 transgenic line, expressing the IR-CFA6/HRPL transgene, was grown under continuous light conditions (270 μmol/m$^2$/s) in a 1 L PBR for 3.3 days (FIG. 10A). It is noteworthy that the growth rate of this line was comparable to the one achieved with a wild type *Chlorella vulgaris* strain grown in the same PBR conditions, indicating that the expression of the inverted repeat transgene seems not to alter the fitness of this microalgae (data not shown). This is an important distinction from mammalian cell lines that trigger a potent inflammatory response upon sensing of long dsRNAs by RIG-I-like receptors (RLRs) (Fan & Jin, 2019). The extracellular medium from the above *Chlorella* IT20 #3 culture was further collected and separated from microalgae cells using a low-speed centrifugation method—two rounds of centrifugation at 3000 to 4000 g for to 15 min. *Chlorella* EVs were further purified using the ultrafiltration and ultracentrifugation methods described in EXAMPLE 3, and the resulting P40 fractions were analyzed by NTA. We found that the size distribution of EVs was similar to the one retrieved from the same *Chlorella* line grown in flask conditions (data not shown). Furthermore, when comparable volumes of cell-free media recovered from flask and PBR conditions were analyzed, we detected a similar number of PKH26-positive exosome-like particles, ranging from 3.7×10$^7$ to 3.8×10$^8$ particles per ml, from 1 liter of collected extracellular medium. To further analyze the functionality of *Chlorella* EVs recovered from PBRs, we next monitored their ability to be taken-up by A549 and A549-ACE2 human cells. The P40 fractions from the cell-free medium collected from PBRs were labeled with the PKH26 dye, incubated with A549 or A549-ACE2 cells, and further analyzed by confocal microscopy as described in EXAMPLE 7. Importantly, we found that these *Chlorella* EVs were clearly detected within A549 and A549-ACE2 cells, as observed with PKH26-positive EVs derived from the P40 fractions of *Chlorella* grown in flasks (FIGS. 6A, 10B). Altogether, these data indicate that the integrity and functionality of *Chlorella* EVs are maintained when produced in small PBRs.

Example 15. *Chlorella* EV-Contained Antibacterial Small RNAs can be Relatively Easily Produced and Purified from the Extracellular Medium of a 150 L PBR without Altering their Yield, Integrity and Functionality We next wanted to verify whether the scaling-up from a few liters of production (laboratory) up to a few m$^3$ (pre-industrial) would not impact the yield nor the integrity of *Chlorella* EVs. To test this, we grew the reference *Chlorella* IT20 #3 line in a 150 L PBR, as detailed in EXAMPLE (FIG. 10A). The NTA analysis revealed that, despite the presence in the original sample of suspended organic matter, the size distribution of *Chlorella* EVs was well centered around 150 nm diameter, with ~70% of the sample being in a size range between 100 and 200 nm and the rest were above 200 nm (FIG. 10C). Further PKH26-labeling of the P40 fractions recovered from the 150 L PBR, followed by a NTA analysis in a fluorescence mode, exhibited a size distribution similar to the one observed when a NTA analysis was conducted from unlabeled P40 fractions in a scattering mode (FIG. 10C/D). This result suggests that the detected particles from unlabeled P40 fractions are likely lipid-based EVs. Interestingly, the particle concentration obtained from 5 L of cell-free medium was quite high: 3.3×10$^{10}$ particles/ml, corresponding to ~60 μM in ~2.5 ml. In comparison, the production of EVs obtained from several flasks (~800 ml of cell-free medium), usually yield ~0.5 pM (3×10$^8$ particles/ml) in 1 ml. Therefore, *Chlorella* EVs production in a 150 L PBR is ~20 times more productive than in flasks. Collectively, these data indicate that *Chlorella* EVs recovered from a 150 L PBR exhibit a normal size distribution. They also show that a ~20-fold increase in EVs yield can be obtained in such PBRs, even when standard growth conditions were used. It is therefore anticipated that the EVs yield will be relatively easily enhanced by optimizing the growth conditions and subsequent pre-filtration, filtration and purification steps.

Finally, we evaluated the biological activity of the *Chlorella* EV-embedded and/or -associated small RNAs obtained from the 150 L PBR culture. To this aim, we compared total RNAs and P40 fractions from different production systems, (flask, 1 L and 150 L PBRs) of both the IT20 #3 (IR-CFA6/HRPL) and IT19 #7 (IR-CYP51) lines in a stomatal reopening assay, as described in EXAMPLE 5. This comparative analysis revealed that both the total RNAs and P40 fractions from the *Chlorella* IT20 #3 line have similar antibacterial effects, inhibiting Pto DC3000-triggered stomatal reopening, independently of the production method employed (FIG. 10E).

Our results therefore provide a proof-of-concept demonstrating that *Chlorella* EV-contained antibacterial small RNAs can be relatively easily produced and purified from the extracellular medium of a 150 L PBR without altering their yield, integrity and functionality.

Example 16. Optimization of EVs Production and or Secretion Through Treatments of *Chlorella* Cultures with Supernatants from Heat-Killed Bacteria Our data from *Chlorella* cultures grown in different conditions (flask vs PBRs) suggest that the growth conditions—as the ones used in the 150 L PBR—can elevate the yield of purified EVs (EXAMPLE 15). Besides growth conditions, there are emerging data indicating that abiotic and biotic stresses can promote EVs production and/or secretion from eukaryotic cells (Collett et al., 2018; Nakase et al., 2021). For example, specific temperature conditions or viral infections were shown to trigger an enhanced EVs release from cells (Bewicke et al., 2017; Schatz et al., 2017). Furthermore, a heightened plant EVs secretion was found in response to *Pseudomonas syringae* infection, as well as upon treatment with salicylic acid (Rutter & Innes, 2017), which is a phytohormone known to promote disease resistance against (hemi)biotrophic phytopathogens (Durrant & Dong, 2004). In addition, we detected an increased plant EVs secretion and/or biogenesis in response to the bacterial Microbe- or Pathogen-Associated Molecular Pattern (MAMP/PAMP) flagellin peptide flg22, which is sensed by the Pattern Recognition Receptor (PRR) Flagellin Sensing 2 (FLS2) and triggers plant immune signaling (Gomez-Gomez & Boller, 2000; Zipfel et al., 2004; Navarro et al., 2004; data not shown). To determine whether *Chlorella* EVs secretion and/or biogenesis could be similarly enhanced in response to biotic stresses, we decided to work with cultures in early stationary phase to obtain enough biomass and maximize the eventual positive effect of biotic stresses over EVs production and/or release. The *Chlorella* cultures were further treated with supernatants from heat-killed *E. coli* K12 TOP10 or Pto DC3000 Wt cells and then set in standard growth conditions, to avoid the risk of applying multiple stresses at the same time, which could alter *Chlorella* growth and/or EVs production/secretion. The rationale for using supernatants from heat-killed bacterial cells was that they should contain cocktails of molecules, including MAMPs/PAMPs, which could be sensed by yet-unknown *Chlorella* PRRs, thereby resulting in enhanced EVs production and/or secretion as found in plants. After 2 days of incubation, we quantified the cells and the purified EVs (FIG. 11A). Interestingly, although the treatments did not significantly affect *Chlorella* growth over the 2 days of incubation (data not shown), a to 7 times increment in the yield of purified EVs was detected upon treatment with either bacterial supernatant compared to the control condition (FIG. 111B). These biotic stresses can thus be employed to increase *Chlorella* EVs production and/or secretion. Given that supernatants from heat-killed bacteria can be easily produced and in a cost-effective manner, our findings reveal promising conditions that might be suitable for enhancing the production of *Chlorella* EVs in large PBRs.

BIBLIOGRAPHIC REFERENCES

Andersen, J. B., Sternberg, C., Poulsen, L. K., Bjorn, S. P., Givskov, M., & Molin, S. (1998). New unstable variants of green fluorescent protein for studies of transient gene expression in bacteria. *Applied and environmental microbiology,* 64(6), 2240-2246.

Asha K., Kumar P., Sanicas M., Meseko C., Khanna M., & Kumar B. (2018). Advancements in Nucleic Acid Based Therapeutics against Respiratory Viral Infections. Journal of Clinical Medicine, 8(1), 1-24. 10.3390/jcm8010006

Askenasy, N., & Farkas, D. L. (2002). Optical imaging of PKH-labeled hematopoietic cells in recipient bone marrow in vivo. *Stem cells* (Dayton, Ohio), 20(6), 501-513.

Bai, L. L., Yin, W. B., Chen, Y. H., Niu, L. L., Sun, Y. R., Zhao, S. M., Yang, F. Q., Wang, R. R., Wu, Q., Zhang, X. Q., & Hu, Z. M. (2013). A new strategy to produce a defensin: stable production of mutated NP-1 in nitrate reductase-deficient *Chlorella* ellipsoidea. *PloS one,* 8(1), e54966.

Bally, J., Jung, H., Mortimer, C., Naim, F., Philips, J. G., Hellens, R., Bombarely, A., Goodin, M. M., & Waterhouse, P. M. (2018). The Rise and Rise of *Nicotiana benthamiana*: A Plant for All Reasons. *Annual review of phytopathology,* 56, 405-426.

Bewicke-Copley, F., Mulcahy, L. A., Jacobs, L. A., Samuel, P., Akbar, N., Pink, R. C., & Carter, D. (2017). Extracellular vesicles released following heat stress induce bystander effect in unstressed populations. *Journal of extracellular vesicles,* 6(1), 1340746. https://doi.org/10.1080/20013078.2017.1340746.

Bitko, V., Musiyenko, A., Shulyayeva, O., & Barik, S. (2005). Inhibition of respiratory viruses by nasally administered siRNA. *Nature medicine,* 11(1), 50-55.

Blanc, G., Duncan, G., Agarkova, I., Borodovsky, M., Gurnon, J., Kuo, A., Lindquist, E., Lucas, S., Pangilinan, J., Polle, J., Salamov, A., Terry, A., Yamada, T., Dunigan, D. D., Grigoriev, I. V., Claverie, J. M., & Van Etten, J. L. (2010). The *Chlorella variabilis* NC64A genome reveals adaptation to photosymbiosis, coevolution with viruses, and cryptic sex. *The Plant cell,* 22(9), 2943-2955.

Bolognesi, R., Ramaseshadri, P., Anderson, J., Bachman, P., Clinton, W., Flannagan, R., Ilagan, O., Lawrence, C., Levine, S., Moar, W., Mueller, G., Tan, J., Uffman, J., Wiggins, E., Heck, G., & Segers, G. (2012). Characterizing the mechanism of action of double-stranded RNA activity against western corn rootworm (*Diabrotica virgifera virgifera* LeConte). *PloS one,* 7(10), e47534.

Brooks, D. M., Hernindez-Guzmin, G., Kloek, A. P., Alarcon-Chaidez, F., Sreedharan, A., Rangaswamy, V., Penaloza-Vizquez, A., Bender, C. L., & Kunkel, B. N. (2004). Identification and characterization of a well-defined series of coronatine biosynthetic mutants of *Pseudomonas syringae* pv. tomato DC3000. Molecular plant-microbe interactions: MPMI, 17(2), 162-174.

Cai, Q., Qiao, L., Wang, M., He, B., Lin, F. M., Palmquist, J., Huang, S. D., andJin, H. (2018b). Plants send small RNAs in extracellular vesicles to fungal path-ogen to silence virulence genes. Science360, 1126-112

Campbell-Valois, F. X., Schnupf, P., Nigro, G., Sachse, M., Sansonetti, P. J., & Parsot, C. (2014). A fluorescent reporter reveals on/off regulation of the *Shigella* type III secretion apparatus during entry and cell-to-cell spread. *Cell host & microbe,* 15(2), 177-189.

Cerutti, H., Ma, X., Msanne, J., & Repas, T. (2011). RNA-mediated silencing in Algae: biological roles and tools for analysis of gene function. *Eukaryotic cell,* 10(9), 1164-1172.

Cha, T. S., Yee, W., & Aziz, A. (2012). Assessment of factors affecting *Agrobacterium*-mediated genetic transformation of the unicellular green alga, *Chlorella vulgaris*. World journal of microbiology & biotechnology, 28(4), 1771-1779.

Chien, L. F., Kuo, T. T., Liu, B. H., Lin, H. D., Feng, T. Y., Huang, C. C. (2012). Solar-to-bioH(2) production enhanced by homologous overexpression of hydrogenase in green alga *Chlorella* sp. DT, Int. J. Hydrog. Energy 37 (2012) 17738-17748.

Chuo, S. T., Chien, J. C., & Lai, C. P. (2018). Imaging extracellular vesicles: current and emerging methods. *Journal of biomedical science,* 25(1), 91.

Colao, I. L., Corteling, R., Bracewell, D., & Wall, I. (2018). Manufacturing Exosomes: A Promising Therapeutic Platform. *Trends in molecular medicine,* 24(3), 242-256.

Collett G. P., Redman C. W., Sargent I. L., Vatish M. Endoplasmic reticulum stress stimulates the release of extracellular vesicles carrying danger-associated molecular pattern (DAMP) molecules. Oncotarget. 2018; 9: 6707-6717.

de Andrade, C. J., de Andrade, L. M. (2017). An overview on the application of genus *Chlorella* in bio-technological processes. J Adv Res Biotech 2(1):1-9. DOI:

DeVincenzo, J., Lambkin-Williams, R., Wilkinson, T., Cehelsky, J., Nochur, S., Walsh, E., Meyers, R., Gollob, J., & Vaishnaw, A. (2010). A randomized, double-blind, placebo-controlled study of an RNAi-based therapy directed against respiratory syncytial virus. *Proceedings of the National Academy of Sciences of the United States of America,* 107(19), 8800-8805.

Durrant W E, Dong X. Systemic acquired resistance. Annu Rev Phytopathol. 2004; 42:185-209. doi: 10.1146/annurev.phyto.42.040803.140421. PMID: 15283665.

Elowitz, M. B., & Leibler, S. (2000). A synthetic oscillatory network of transcriptional regulators. *Nature,* 403(6767), 335-338.

Fan, X., & Jin, T. (2019). Structures of RIG-I-Like Receptors and Insights into Viral RNA Sensing. *Advances in experimental medicine and biology,* 1172, 157-188.

Fick, J., Barker, F. G., 2nd, Dazin, P., Westphale, E. M., Beyer, E. C., & Israel, M. A. (1995). The extent of heterocellular communication mediated by gap junctions is predictive of bystander tumor cytotoxicity in vitro. *Proceedings of the National Academy of Sciences of the United States of America,* 92(24), 11071-11075.

Fouts, D. E., Abramovitch, R. B., Alfano, J. R., Baldo, A. M., Buell, C. R., Cartinhour, S., Chatterjee, A. K., D'Ascenzo, M., Gwinn, M. L., Lazarowitz, S. G., Lin, N. C., Martin, G. B., Rehm, A. H., Schneider, D. J., van Dijk, K., Tang, X., & Collmer, A. (2002). Genomewide identification of *Pseudomonas syringae* pv. tomato DC3000 promoters controlled by the HrpL alternative sigma factor. *Proceedings of the National Academy of Sciences of the United States of America,* 99(4), 2275-2280.

Gao, Z., Wang, M., Blair, D., Zheng, Y., & Dou, Y. (2014). Phylogenetic analysis of the endoribonuclease Dicer family. *PloS one,* 9(4), e95350.

Garaeva, L., Kamyshinsky, R., Kil, Y. et al. Delivery of functional exogenous proteins by plant-derived vesicles to human cells in vitro. Sci Rep 11, 6489 (2021). https://doi.org/10.1038/s41598-021-85833-y.

Ge Q, Filip L, Bai A, Nguyen T, Eisen H N, Chen J. Inhibition of influenza virus production in virus-infected mice by RNA interference. *Proc Natl Acad Sci USA.* 2004; 101(23):8676-8681. doi:10.1073/pnas.0402486101

Gómez-Gömez L, Boller T. FLS2: an LRR receptor-like kinase involved in the perception of the bacterial elicitor flagellin in *Arabidopsis*. Mol Cell. 2000 June; 5(6):1003-11. doi: 10.1016/s1097-2765(00)80265-8. PMID: 10911994.

Gordon, D. E., Jang, G. M., Bouhaddou, M., Xu, J., Obernier, K., O'Meara, M. J., Guo, J. Z., Swaney, D. L., Tummino, T. A., Huttenhain, R., Kaake, R. M., Richards, A. L., Tutuncuoglu, B., Foussard, H., Batra, J., Haas, K., Modak, M., Kim, M., Haas, P., Polacco, B. J., . . . Krogan, N. J. (2020). A SARS-CoV-2-Human Protein-Protein Interaction Map Reveals Drug Targets and Potential Drug-Repurposing. *bioRxiv: the preprint server for biology,* 2020.03.22.002386.

Guarnieri, M. T., Levering, J., Henard, C. A., Boore, J. L., Betenbaugh, M. J., Zengler, K., & Knoshaug, E. P. (2018). Genome Sequence of the Oleaginous Green Alga, *Chlorella vulgaris* UTEX 395. Frontiers in bioengineering and biotechnology, 6, 37. https://doi.org/10.3389/fbioe.2018.00037.

Guo, Z., Li, Y., & Ding, S. W. (2019). Small RNA-based antimicrobial immunity. *Nature reviews. Immunology,* 19(1), 31-44.

Hoffmann, M., Kleine-Weber, H., Schroeder, S., Kruger, N., Herrler, T., Erichsen, S., Schiergens, T. S., Herrler, G., Wu, N. H., Nitsche, A., Müller, M. A., Drosten, C., & Pohlmann, S. (2020). SARS-CoV-2 Cell Entry Depends on ACE2 and TMPRSS2 and Is Blocked by a Clinically Proven Protease Inhibitor. *Cell,* 181(2), 271-280.e8.

Hou, Y., Zhai, Y., Feng, L., Karimi, HZ., Rutter, B. D., Zeng, L., Choi, D. S., Zhang, B., Gu, W., Chen, X., et al. (2019). A *Phytophthora* Effector SuppressesTrans-Kingdom RNAi to Promote Disease Susceptibility. Cell Host Microbe 25, 153-165.e5

Howard, C. R., & Fletcher, N. F. (2012). Emerging virus diseases: can we ever expect the unexpected?. *Emerging microbes & infections,* 1(12), e46.

Ivashuta, S., Zhang, Y., Wiggins, B. E., Ramaseshadri, P., Segers, G. C., Johnson, S., Meyer, S. E., Kerstetter, R. A., McNulty, B. C., Bolognesi, R., & Heck, G. R. (2015). Environmental RNAi in herbivorous insects. *RNA* (New York, N. Y.), 21(5), 840-850.

Kaner, J., & Schaack, S. (2016). Understanding Ebola: the 2014 epidemic. *Globalization and health,* 12(1), 53.

Kim, D. H., Kim, Y. T., Cho, J. J., Bae, J. H., Hur, S. B., Hwang, I., & Choi, T. J. (2002). Stable integration and functional expression of flounder growth hormone gene in transformed microalga, *Chlorella* ellipsoidea. *Marine biotechnology* (New York, N. Y.), 4(1), 63-73.

Koch, A. et al. Host-induced gene silencing of cytochrome P450 lanosterol C14alpha-demethylase-encoding genes confers strong resistance to Fusarium species. *Proc Natl Acad Sci USA* 110, 19324-9 (2013).

Koch, A., Biedenkopf, D., Furch, A., Weber, L., Rossbach, O., Abdellatef, E., Linicus, L., Johannsmeier, J., Jelonek, L., Goesmann, A., Cardoza, V., McMillan, J., Mentzel, T., & Kogel, K. H. (2016). An RNAi-Based Control of *Fusarium graminearum* Infections Through Spraying of Long dsRNAs Involves a Plant Passage and Is Controlled by the Fungal Silencing Machinery. *PLoSpathogens,* 12(10), e1005901.

Kolb, C., Nagel, M. K., Kalinowska, K., Hagmann, J., Ichikawa, M., Anzenberger, F., Alkofer, A., Sato, M. H., Braun, P., & Isono, E. (2015). FYVE1 is essential for vacuole biogenesis and intracellular trafficking in *Arabidopsis. Plant physiology,* 167(4), 1361-1373.

Langmead, B., Trapnell, C., Pop, M., Salzberg, S. L., 2009. Ultrafast and memory-efficient alignment of short DNA sequences to the human genome. Genome Biol. 10, R25.

Li, B. J., Tang, Q., Cheng, D., Qin, C., Xie, F. Y., Wei, Q., Xu, J., Liu, Y., Zheng, B. J., Woodle, M. C., Zhong, N., & Lu, P. Y. (2005). Using siRNA in prophylactic and therapeutic regimens against SARS coronavirus in Rhesus macaque. *Nature medicine,* 11(9), 944-951.

Lin, H. D., Liu, B. H., Kuo, T. T., Tsai, H. C., Feng, T. Y., Huang, C. C., & Chien, L. F. (2013). Knockdown of PsbO leads to induction of HydA and production of photobiological H2 in the green alga *Chlorella* sp. DT. *Bioresource technology,* 143, 154-162.

Maji S, Yan I K, Parasramka M, Mohankumar S, Matsuda A, Patel T. In vitro toxicology studies of extracellular vesicles. *J Appl Toxicol.* 2017 March; 37(3):310-318. doi: 10.1002/jat.3362. Epub 2016 Jul. 20. PMID: 27435060.

Meighen E. A. (1991). Molecular biology of bacterial bioluminescence. *Microbiological reviews,* 55(1), 123-142.

Melotto M, Underwood W, Koczan J, Nomura K, He S Y. Plant stomata function in innate immunity against bacterial invasion. *Cell.* 2006; 126(5):969-980. doi:10.1016/j.cell.2006.06.054

Mukherjee, K., Campos, H., & Kolaczkowski, B. (2013). Evolution of animal and plant dicers: early parallel duplications and recurrent adaptation of antiviral RNA binding in plants. *Molecular biology and evolution,* 30(3), 627-641.

Murphy D., Dancis B., Brown J. R. (2008). The evolution of core proteins involved in microRNA biogenesis. BMC Evol. Biol. 8:92. 10.1186/1471-2148-8-92

Nakase, I., Ueno, N., Matsuzawa, M., Noguchi, K., Hirano, M., Omura, M., Takenaka, T., Sugiyama, A., Bailey Kobayashi, N., Hashimoto, T., Takatani-Nakase, T., Yuba, E., Fujii, I., Futaki, S. and Yoshida, T. (2021), Environmental pH stress influences cellular secretion and uptake of extracellular vesicles. FEBS Open Bio, 11: 753-767. https://doi.org/10.1002/2211-5463.13107.

Navarro L, Zipfel C, Rowland O, Keller I, Robatzek S, Boller T, Jones J D. The transcriptional innate immune response to flg22. Interplay and overlap with Avr gene-dependent defense responses and bacterial pathogenesis. Plant Physiol. 2004 June; 135(2):1113-28. doi: 10.1104/pp. 103.036749. Epub 2004 Jun. 4. PMID: 15181213; PMCID: PMC514144.

Navarro, L. and Singla-Rastogi, M. (2020). RNA-Based Biocontrol Methods to Protect Plants Against Pathogenic Bacteria and/or Promote Beneficial Effects of Symbiotic and Commensal Bacteria. WO/2020/035619, PCT/EP2019/072169

Navarro, L. and Singla-Rastogi, M. (2020). RNA-Based Therapeutic Methods to Protect Animals Against Pathogenic Bacteria and/or Promote Beneficial Effects of Symbiotic and Commensal Bacteria. WO/2020/035620, PCT/EP2019/072170

Niu, Y. F., Zhang, M. H., Xie, W. H., Li, J. N., Gao, Y. F., Yang, W. D., Liu, J. S., & Li, H. Y. (2011). A new inducible expression system in a transformed green alga, *Chlorella vulgaris*. Genetics and molecular research: *GMR,* 10(4), 3427-3434.

Noble J M, Roberts L M, Vidavsky N, Chiou A E, Fischbach C, Paszek M J, Estroff L A, Kourkoutis L F. Direct comparison of optical and electron microscopy methods for structural characterization of extracellular vesicles. J Struct Biol. 2020 Apr. 1; 210(1):107474. doi: 10.1016/j.jsb.2020.107474. Epub 2020 Feb. 4. PMID: 32032755; PMCID: PMC7067680.

O'Brien, K., Breyne, K., Ughetto, S., Laurent, L. C., & Breakefield, X. O. (2020). RNA delivery by extracellular vesicles in mammalian cells and its applications. *Nature reviews. Molecular cell biology,* 1-22. Advance online publication.

Ostrowski, M., Carmo, N. B., Krumeich, S., Fanget, I., Raposo, G., Savina, A., Moita, C. F., Schauer, K., Hume, A. N., Freitas, R P., Goud, B., Benaroch, P., Hacohen, N., Fukuda, M., Desnos, C., Seabra, M. C., Darchen, F., Amigorena, S., Moita, L. F., & Thery, C. (2010). Rab27a and Rab27b control different steps of the exosome secretion pathway. *Nature cell biology,* 12(1), 19-13.

Run, C., Fang, L., Fan, J., Fan, C., Luo, Y., Hu, Z., Li, Y. (2016). Stable nuclear transformation of the industrial alga *Chlorella pyrenoidosa*, Algal Research 17 (2016) 196-201

Rutter, B. D., & Innes, R. W. (2017). Extracellular Vesicles Isolated from the Leaf Apoplast Carry Stress-Response Proteins. *Plant physiology,* 173(1), 728-741.

Safi, C., Zebib, B., Merah, O., Pontalier, P.-Y., Vaca-Garcia, C. (2014). Morphology, composition, production, processing and applications of *Chlorella vulgaris*: A review. Renewable and Sustainable Energy Reviews, Volume 35, July 2014, Pages 265-278.

Schatz D, Rosenwasser S, Malitsky S, Wolf S G, Feldmesser E, Vardi A. Communication via extracellular vesicles enhances viral infection of a cosmopolitan alga. Nat Microbiol. November; 2(11):1485-1492. doi: 10.1038/s41564-017-0024-3. Epub 2017 Sep. 18. PMID: 28924189.

Siddiqi, H. K., & Mehra, M. R. (2020). COVID-19 illness in native and immunosuppressed states: A clinical-therapeutic staging proposal. *The Journal of heart and lung transplantation: the official publication of the International Society for Heart Transplantation,* 39(5), 405-407.

Sreedharan, A., Penaloza-Vazquez, A., Kunkel, B. N., & Bender, C. L. (2006). CorR regulates multiple components of virulence in *Pseudomonas syringae* pv. tomato DC3000. *Molecular plant-microbe interactions: MPMI,* 19(7), 768-779.

Strasfeld, L., & Chou, S. (2010). Antiviral drug resistance: mechanisms and clinical implications. *Infectious disease clinics of North America,* 24(2), 413-437.

Teng, Y., Ren, Y., Sayed, M., Hu, X., Lei, C., Kumar, A., Hutchins, E., Mu, J., Deng, Z., Luo, C., et al. (2018). Plant-Derived Exosomal MicroRNAs Shape the Gut Microbiota. Cell Host Microbe 24, 637-652.e8.

Tompkins, S. M., Lo, C. Y., Tumpey, T. M., & Epstein, S. L. (2004). Protection against lethal influenza virus challenge by RNA interference in vivo. *Proceedings of the National Academy of Sciences of the United States of America,* 101(23), 8682-8686.

V'kovski, P., Gerber, M., Kelly, J., Pfaender, S., Ebert, N., Braga Lagache, S., Simillion, C., Portmann, J., Stalder, H., Gaschen, V., Bruggmann, R., Stoffel, M. H., Heller, M., Dijkman, R, & Thiel, V. (2019). Determination of host proteins composing the microenvironment of coronavirus replicase complexes by proximity-labeling. *eLife,* 8, e42037.

Wang, M., & Jin, H. (2017). Spray-Induced Gene Silencing: a Powerful Innovative Strategy for Crop Protection. *Trends in microbiology,* 25(1), 4-6.

Wang, M., Thomas, N., & Jin, H. (2017). Cross-kingdom RNA trafficking and environmental RNAi for powerful innovative pre- and post-harvest plant protection. *Current opinion in plant biology,* 38, 133-141.

Wang F, Vandepoele K, Van Lijsebettens M. Tetraspanin genes in plants. Plant Sci. July; 190:9-15. doi: 10.1016/j.plantsci.2012.03.005. Epub 2012 Mar. 23. PMID: 22608515.

Wang, M., Weiberg, A., Lin, F. M., Thomma, B. P., Huang, H. D., & Jin, H. (2016). Bidirectional cross-kingdom RNAi and fungal uptake of external RNAs confer plant protection. *Nature plants,* 2, 16151.

Wang, Q., Zhuang, X., Mu, J., Deng, Z. B., Jiang, H., Zhang, L., Xiang, X., Wang, B., Yan, J., Miller, D., & Zhang, H. G. (2013). Delivery of therapeutic agents by nanoparticles made of grapefruit-derived lipids. *Nature communications,* 4, 1867.

Whangbo, J. S., & Hunter, C. P. (2008). Environmental RNA interference. *Trends in genetics: TIG,* 24(6), 297-305.

Yang, B., Liu, J., Liu, B., Sun, P., Ma, X., Jiang, Y., Wei, D., Chen, F. (2015). Development of a stable genetic system for *Chlorella vulgaris*—a promising green alga for C02 biomitigation, Algal Res. 12 (2015) 134-141.

Yang, C., & Merlin, D. (2020). Can naturally occurring nanoparticle-based targeted drug delivery effectively treat inflammatory bowel disease? *Expert opinion on drug delivery,* 17(1), 1-4.

Zhang, J., Qiu, Y., & Xu, K. (2020). Characterization of GFP-AtPEN1 as a marker protein for extracellular vesicles isolated from *Nicotiana benthamiana* leaves. Plant signaling & behavior, 15(9), 1791519.

Zhang, M., Viennois, E., Xu, C., & Merlin, D. (2016). Plant derived edible nanoparticles as a new therapeutic approach against diseases. *Tissue barriers,* 4(2), el 134415.

Zuñiga, C., Li, C. T., Huelsman, T., Levering, J., Zielinski, D. C., McConnell, B. O., Long, C. P., Knoshaug, E. P., Guarnieri, M. T., Antoniewicz, M. R., Betenbaugh, M. J., & Zengler, K. (2016). Genome-Scale Metabolic Model for the Green Alga *Chlorella vulgaris* UTEX 395 Accurately Predicts Phenotypes under Autotrophic, Heterotrophic, and Mixotrophic Growth Conditions. *Plant physiology,* 172(1), 589-602.

Zhang H, Kolb F A, Jaskiewicz L, Westhof E, Filipowicz W. Single processing center models for human Dicer and bacterial RNase III. Cell. 2004 Jul. 9; 118(1):57-68. doi: 10.1016/j.cell.2004.06.017. PMID: 15242644.

Zipfel C, Robatzek S, Navarro L, Oakeley E J, Jones J D, Felix G, Boller T. Bacterial disease resistance in Arabidopsis through flagellin perception. *Nature.* 2004 Apr. 15; 428(6984):764-7. doi: 10.1038/nature02485. PMID: 15085136.

Zuniga, C., Li, C. T., Huelsman, T., Levering, J., Zielinski, D. C., McConnell, B. O., Long, C. P., Knoshaug, E. P., Guarnieri, M. T., Antoniewicz, M. R., Betenbaugh, M. J., & Zengler, K. (2016). Genome-Scale Metabolic Model for the Green Alga *Chlorella vulgaris* UTEX 395 Accurately Predicts Phenotypes under Autotrophic, Heterotrophic, and Mixotrophic Growth Conditions. *Plant physiology,* 172(1), 589-602.

The invention claimed is:

1. A method for producing functional interfering small RNAs, said method comprising at least the steps of:

a) transforming *Chlorella* cells with a short interfering RNA (siRNA) or microRNA (miRNA) precursor comprising at least one fragment of at least one target gene, and b) cultivating said *Chlorella* cells in appropriate conditions so that they express said precursor and release extracellular vesicles (EV)-embedded functional small interfering RNAs (iRNAs) targeting said at least one gene fragment.

2. The method of claim 1, wherein said siRNA or miRNA precursor is a long single- or double-stranded RNA molecule.

3. The method of claim 1, wherein said at least one fragment of at least one target gene comprises between 50 and 3000 bp.

4. The method of claim 1, further comprising the step of recovering said small iRNAs from said *Chlorella* cells.

5. The method of claim 1, further comprising the step of recovering the Extracellular Vesicles (EVs) released by said *Chlorella* cells in the extracellular medium.

6. The method of claim 1, wherein said target gene is an oomycete gene, a viral gene, a bacterial gene, or a fungus gene.

7. The method of claim 1, wherein said siRNA precursor has a sequence chosen among SEQ ID NO:1-106.

8. A method to produce a population of functional small iRNAs in *Chlorella* cells, said method comprising at least the steps of:

a) transforming *Chlorella* cells with a siRNA precursor of SEQ ID NO: 1-106, and b) cultivating said *Chlorella* cells in appropriate conditions so that they express said precursor and release extracellular vesicles (EV)-embedded functional small iRNAs.

* * * * *